(12) United States Patent
Rovner et al.

(10) Patent No.: US 12,241,062 B2
(45) Date of Patent: Mar. 4, 2025

(54) MAMMALIAN CELLS AND METHODS FOR ENGINEERING THE SAME

(71) Applicant: 64-X, Inc., San Francisco, CA (US)

(72) Inventors: Alexis Rovner, San Francisco, CA (US); Gaurab Chakrabarti, Houston, TX (US); David Thompson, Brookline, MA (US); Gregory Sieczkiewicz, Wellesley, MA (US)

(73) Assignee: 64-X, Inc., San Francisco, CA (US)

( * ) Notice: Subject to any disclaimer, the term of this patent is extended or adjusted under 35 U.S.C. 154(b) by 0 days.

(21) Appl. No.: 18/492,069

(22) Filed: Oct. 23, 2023

(65) Prior Publication Data

US 2024/0076655 A1    Mar. 7, 2024

Related U.S. Application Data

(63) Continuation of application No. 18/023,909, filed as application No. PCT/US2021/048741 on Sep. 1, 2021.

(60) Provisional application No. 63/111,238, filed on Nov. 9, 2020, provisional application No. 63/073,365, filed on Sep. 1, 2020.

(51) Int. Cl.
*C12N 15/10* (2006.01)
*C12N 15/86* (2006.01)

(52) U.S. Cl.
CPC ..... *C12N 15/1082* (2013.01); *C12N 15/1065* (2013.01); *C12N 15/86* (2013.01); *C12N 2740/15044* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | |
|---|---|---|
| 2016/0208243 A1 | 7/2016 | Zhang et al. |
| 2020/0270632 A1 | 8/2020 | Roy et al. |
| 2020/0392479 A1* | 12/2020 | Blainey ........... C12N 1/205 |
| 2021/0128642 A1* | 5/2021 | Kenny ........... A61K 31/575 |
| 2021/0277418 A1 | 9/2021 | Sah et al. |
| 2024/0052341 A1 | 2/2024 | Rovner et al. |

FOREIGN PATENT DOCUMENTS

| | | |
|---|---|---|
| CA | 3123875 A1 | 7/2020 |
| CN | 102/174576 A | 9/2011 |
| WO | WO-2008/060510 A2 | 5/2008 |
| WO | WO-2009/146179 A1 | 12/2009 |
| WO | WO-2013/163628 A2 | 10/2013 |
| WO | WO-2014/040370 A1 | 3/2014 |
| WO | WO-2014/134412 A1 | 9/2014 |
| WO | WO-2016/073990 A2 | 5/2016 |
| WO | WO-2017/181162 A1 | 10/2017 |
| WO | WO-2017/184768 A1 | 10/2017 |
| WO | WO-2019/055878 A2 | 3/2019 |
| WO | WO-2020/139892 A1 | 7/2020 |
| WO | WO-2022/051418 A1 | 3/2022 |
| WO | WO-2023/167860 A1 | 9/2023 |

OTHER PUBLICATIONS

Adachi, K. et al., Drawing a high-resolution functional map of adeno-associated virus capsid by massively parallel sequencing, Nature Communications, 5(3075): pp. 1-14 (2014).
International Search Report for PCT/US2021/048741, 4 pages (Jan. 10, 2022).
Pekrun, K. et al., Using a barcoded AAV capsid library to select for novel clinically relevant gene therapy vectors, bioRxiv, pp. 1-50 (2019).
Written Opinion for PCT/US2021/048741, 8 pages (Jan. 10, 2022).
Benson, D. A. et al., GenBank, Nucl. Acids Res., 41(10.1093):D36-D42 (2013).
Boshart, M. et al., A very strong enhancer is located upstream of an immediate early gene of human cytomegalovirus, Cell, 41(2):521-530, (1985).
Briner, A. E. et al., Guide RNA functional modules direct Cas9 activity and orthogonality, Molecular Cell, 56(2):333-339, (2014).
Deltcheva, E. et al., CRISPR RNA maturation by trans-encoded small RNA and host factor RNase III, Nature, 471(7340):602-607 (2011).
Ferretti, J. J. et al., Complete genome sequence of an M1 strain of *Streptococcus pyogenes*, Proc. Natl. Acad. Sci. U.S.A., 98(8):4658-4663 (2001).
Jiang, W. et al., RNA-guided editing of bacterial genomes using CRISPR-Cas systems, Nat Biotechnol., 31(3):233-239 (2013).
Jinek, et al., A Programmable Dual-RNA-Guided DNA Endonuclease in Adaptive Bacterial Immunity, Science, 337(6096):816-821, (2012).
Langmead, B. and Salzberg, S. L., Fast gapped-read alignment with Bowtie 2, Nature Methods, 9(4):357-359, (2012).
Li, W. et al., MAGeCK enables robust identification of essential genes from genome-scale CRISPR/Cas9 knockout screens, Genome Biology, 15(12):554, (2014).
Love, M. I., et al., Moderated estimation of fold change and dispersion for RNA-seq data with DESeq2, Genome Biology, 15(12):550, (2014).
Manservigi, et al., HSV Recombinant Vectors for Gene Therapy, Open Virol J., 4:123-156 (2010).
Myers, E. W. and Miller, W., Approximate matching of regular expressions, Bulletin of Mathematical Biology, 51(1):5-37 (1989).

(Continued)

*Primary Examiner* — Christopher M Gross
(74) *Attorney, Agent, or Firm* — Choate, Hall & Stewart LLP; Brenda Herschbach Jarrell; Mandeep Kaur

(57) ABSTRACT

The present disclosure provides mammalian cell lines for expression of viral vectors, and methods of making and using the same. Provided methods employ use of identifiers that are capable of being packaged into a viral vector to select and/or identify mammalian cell lines with engineered sequences associated with beneficial characteristics for viral vectors production. Exemplary viral vectors include AAV vectors.

20 Claims, 17 Drawing Sheets

(56) References Cited

OTHER PUBLICATIONS

Pearson, W. R. and Lipman, D. J., Improved tools for biological sequence comparison, PNAS, 85(8):2444-2448, (1988).
Pelletier, J., et al., Cap-independent translation of poliovirus mRNA is conferred by sequence elements within the 5' noncoding region, Mol. Cell. Biol., 8(3):1103-1112, (1988).
Proudfoot, N. J. et al., Integrating mRNA processing with transcription, Cell, 108(4):501-512, (2002).
Velculescu, V. E., et al., Serial analysis of gene expression, Science, 270(5235):484-487 (1995).
Zetsche, B. et al., Cpf1 is a single RNA-guided endonuclease of a class 2 CRISPR-Cas system, Cell, 163(3):759-771 (2015).
Zolotukhin, S, et al., Recombinant adeno-associated virus purification using novel methods improves infectious titer and yield, Gene Therapy, 6(6):973-985 (1999).
Adachi, K. et al., Drawing a high-resolution functional map of adeno-associated virus capsid by massively parallel sequencing, Nat Commun., 5:3075 (2014).
Bossin, H. Junonia coenia Densovirus-Based Vectors for Stable Transgene Expression in Sf9 Cells: Influence of the Densovirus Sequences on Genomic Integration, Journal of Virology, 77(20):11060-11071 (2003).
International Search Report for PCT/US2023/014125, 3 pages (May 19, 2023).
Pekrun, K. et al., Using a barcoded AAV capsid library to select for clinically relevant gene therapy vectors, JCI Insight, 4(22):e131610 (2019).
Written Opinion for PCT/US2023/014125, 8 pages (May 19, 2023).

\* cited by examiner

FIG. 3

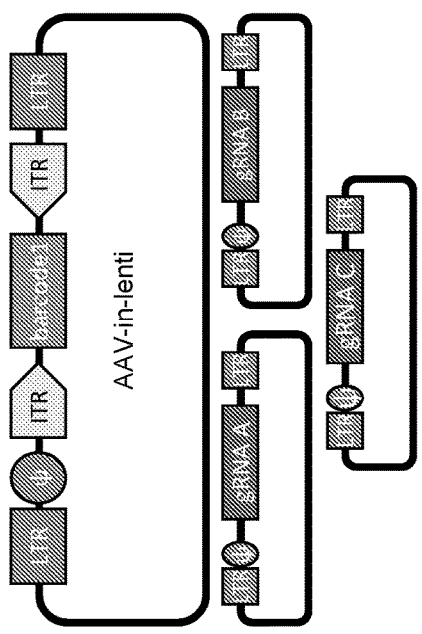

A) 1) Generate AAV-in-lenti barcode library integration lentiviral vectors, and 2) gRNA library integration lentiviral vectors

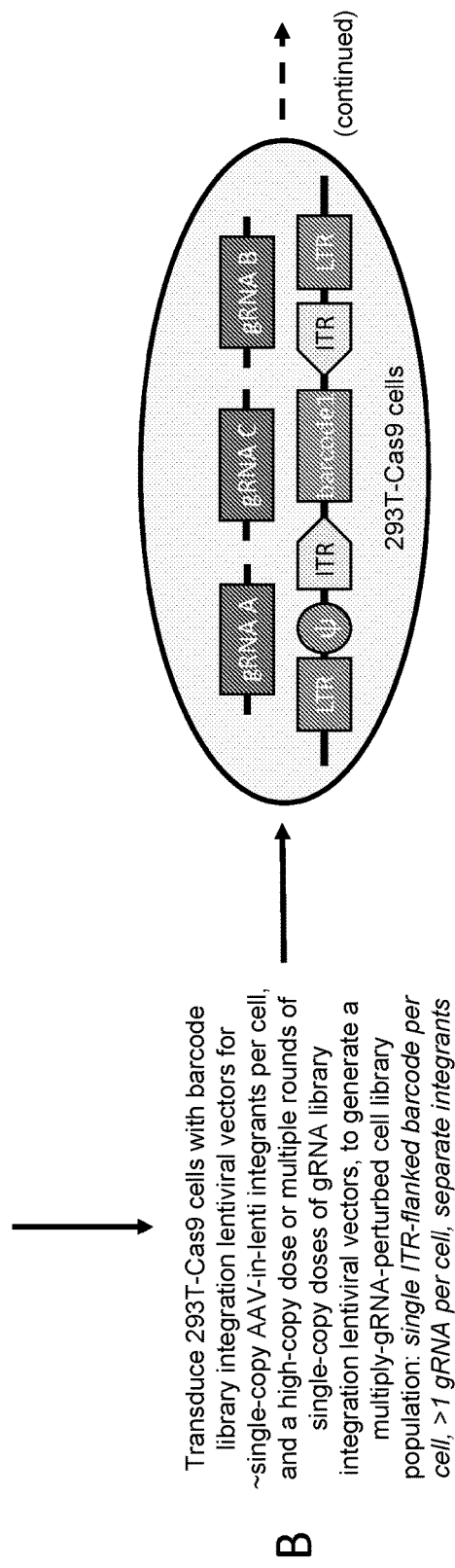

B) Transduce 293T-Cas9 cells with barcode library integration lentiviral vectors for ~single-copy AAV-in-lenti integrants per cell, and a high-copy dose or multiple rounds of single-copy doses of gRNA library integration lentiviral vectors, to generate a multiply-gRNA-perturbed cell library population: *single ITR-flanked barcode per cell, >1 gRNA per cell, separate integrants*

(continued)

MAMMALIAN CELLS AND METHODS FOR ENGINEERING THE SAME

CROSS REFERENCE TO RELATED APPLICATIONS

This application claims the benefit of U.S. Provisional Patent Application No. 63/073,365, filed Sep. 1, 2020, and U.S. Provisional Patent Application No. 63/111,238, filed Nov. 9, 2020, the contents of both of which are incorporated herein by reference in their entirety.

BACKGROUND

Markets for biologics such as, e.g., gene and cell therapies, are expanding, but are currently burdened by high manufacturing costs and difficulties associated with scaling up production. There is a continuing need for improved cell lines and methods of isolating them, for applications including but not limited to biologics production and viral vector production.

SUMMARY

The present disclosure provides, among other things, methods, systems and compositions for production and/or expression of viral vectors in mammalian cells. The present disclosure recognizes that present technologies for expression of a viral vector in mammalian cells are burdened by inefficient viral production and screens to isolate optimized mammalian cell lines. The present disclosure provides platform technologies for engineering mammalian cells and/or viral vectors for altered characteristics associated with viral vector production and other characteristics. In some embodiments, provided methods enable production and/or selection of mammalian cell lines with improved characteristics for expression and/or production of a viral vector (e.g., increased viral vector expression, increased duration of expression, increased stability, etc.). In some embodiments, methods include screening viral vectors produced by a library of mammalian cells with an identifier. Provided technologies include a surprising insight of having a viral vector take up an identifier (e.g., comprising a barcode sequence and/or a library variant) of a mammalian cell in which it is expressed, thereby enabling efficient evaluation, characterization, and/or identification of viral vector production capacity of cells in the library. For example, in some embodiments, a population of mammalian cells are each transformed with a library construct comprising an identifier with an architecture appropriate for packaging of an identifier into a viral vector (e.g., for an AAV vector an identifier may be positioned between AAV ITRs). In some embodiments, a pool of viral vectors produced by such a population of mammalian cells can be screened, selected, and/or characterized by an abundance of unique identifiers.

In some embodiments, provided are a mammalian cell(s) comprising one or more engineered sequences that together comprise: (i) at least one identifier positioned between two viral repeat sequences capable of packaging into a viral vector, and (ii) at least one polynucleotide comprising one or more nucleic acid sequences essential for production of the viral vector, wherein the mammalian cell produces viral vectors comprising the at least one identifier.

In some embodiments, a viral vector produced by the mammalian cell(s) comprises the same identifier as the identifier of the mammalian cell in which it was produced. In some embodiments, an identifier of a viral vector is derived from the identifier of the mammalian cell in which it was produced. In some embodiments, an identifier of a viral vector corresponds to the identifier of the mammalian cell from which it was produced. In some embodiments, an identifier of a viral vector is at least 50%, 55%, 60%, 65%, 70%, 75%, 80%, 85%, 90%, 91%, 92%, 93%, 94%, 95%, 96%, 97%, 98%, 99% or more identical to the identifier of the mammalian cell from which it was produced.

In some embodiments, provided are a mammalian cell(s) comprising one or more engineered sequences that together comprise: (i) at least one identifier positioned between two viral repeat sequences capable of packaging into a viral vector, (ii) at least one perturbation, and (iii) at least one polynucleotide comprising one or more nucleic acid sequences essential for production of the viral vector, where the mammalian cell produces viral vectors comprising the at least one identifier. In some embodiments, a mammalian cell further comprises a payload and/or at least one library variant. In some embodiments, a mammalian cell further comprises at least one perturbation accessory sequence.

In some embodiments, provided are a mammalian cell(s) comprising one or more engineered sequences that together comprise: (i) at least one identifier positioned between two viral repeat sequences capable of packaging into a viral vector, (ii) at least one library variant, and (iii) at least one polynucleotide comprising one or more nucleic acid sequences essential for production of the viral vector, where the mammalian cell produces viral vectors comprising the at least one identifier. In some embodiments, a mammalian cell further comprises a payload and/or at least one perturbation. In some embodiments, a mammalian cell further comprises at least one perturbation accessory sequence.

In some embodiments, provided are a mammalian cell(s) comprising one or more engineered sequences that together comprise: (i) at least one identifier positioned between two viral repeat sequences capable of packaging into a viral vector, (ii) at least one payload, and (iii) at least one polynucleotide comprising one or more nucleic acid sequences essential for production of the viral vector, where the mammalian cell produces viral vectors comprising the at least one identifier. In some embodiments, a mammalian cell further comprises at least one library variant and/or at least one perturbation. In some embodiments, a mammalian cell further comprises at least one perturbation accessory sequence.

In some embodiments, a mammalian cell further comprises at least one trans-acting integration sequence and/or at least one cis-acting integration sequence.

In some embodiments, provided are a mammalian cell(s) comprising one or more engineered sequences that together comprise: (i) at least one identifier positioned between two viral repeat sequences capable of packaging into a viral vector; (ii) at least one library variant and/or perturbation, (iii) at least one payload; (iv) at least one perturbation accessory sequence; (v) at least one trans-acting integration sequence and/or at least one cis-acting integration sequence; and (vi) at least one polynucleotide comprising one or more nucleic acid sequences essential for production of the viral vector, where the mammalian cell produces viral vectors comprising the at least one identifier.

In some embodiments, provided are a mammalian cell(s) comprising one or more engineered sequences that together comprise: (i) at least one identifier positioned between two viral repeat sequences capable of packaging into a viral vector; (ii) at least one polynucleotide comprising one or more nucleic acid sequences essential for production of the viral vector, and optionally (iii) one or more engineered sequences comprise at least one perturbation, at least one library variant, at least one payload, at least one perturbation accessory sequence, at least one trans-acting integration sequence, and/or at least one cis-acting integration sequence, and where the mammalian cell produces viral vectors comprising the at least one identifier.

In some embodiments, provided are a mammalian cell(s) comprising one or more engineered sequences that together comprise: (i) a library construct, and (ii) at least one polynucleotide comprising one or more nucleic acid sequences essential for production of the viral vector, where the library construct comprises an identifier, wherein the identifier is positioned between two viral repeat sequences capable of packaging into a viral vector, and where the mammalian cell produces viral vectors comprising the identifier. In some embodiments, mammalian cell(s) optionally further comprise one or more engineered sequences comprising: at least one perturbation, at least one library variant, at least one payload, at least one perturbation accessory sequence, at least one trans-acting integration sequence, and/or at least one cis-acting integration sequence, and where the mammalian cell produces viral vectors comprising the at least one identifier.

In some embodiments, a viral vector produced by the mammalian cell(s) comprises the same an identifier as the library construct. In some embodiments, an identifier of a viral vector is derived from the identifier of the associated library construct. In some embodiments, an identifier of a viral vector corresponds to the identifier of the library construct. In some embodiments, an identifier of a viral vector is at least 80%, 85%, 90%, 91%, 92%, 93%, 94%, 95%, 96%, 97%, 98%, 99% or more identical to the identifier of the library construct.

In some embodiments, provided are a mammalian cell(s) comprising one or more engineered sequences that together comprise: (i) a library construct, and (ii) at least one polynucleotide comprising one or more nucleic acid sequences essential for production of the viral vector, where the library construct comprises an identifier, wherein the identifier is positioned between two viral repeat sequences capable of packaging into a viral vector, and where the mammalian cell produces viral vectors comprising the identifier. In some embodiments, the library construct optionally further comprises one or more engineered sequences comprising at least one library variant and/or at least one payload. In some embodiments, a mammalian cell(s) optionally further comprise one or more engineered sequences comprising: at least one perturbation, at least one perturbation accessory sequence, at least one trans-acting integration sequence, and/or at least one cis-acting integration sequence, and where the mammalian cell produces viral vectors comprising the at least one identifier.

In some embodiments, provided are a mammalian cell population(s) comprising a plurality of mammalian cells that each individually comprise one or more engineered sequences, wherein the one or more engineered sequences together comprise: (i) at least one identifier positioned between two viral repeat sequences capable of packaging into a viral vector, (ii) at least one polynucleotide comprising one or more nucleic acid sequences essential for production of the viral vector, and where the mammalian cell population produces viral vectors that individually comprise the at least one identifier. In some embodiments, a mammalian cell population optionally further includes one or more engineered sequences comprising: at least one perturbation, at least one library variant, at least one payload, at least one perturbation accessory sequence, at least one trans-acting integration sequence, and/or at least one cis-acting integration sequence.

In some embodiments, provided are a mammalian cell population(s) comprising a plurality of mammalian cells that each individually comprise one or more engineered sequences, wherein the one or more engineered sequences together comprise: (i) at least one identifier positioned between two viral repeat sequences capable of packaging into a viral vector, (ii) at least one library variant and/or perturbation, (iii) at least one payload, and (iv) at least one polynucleotide comprising one or more nucleic acid sequences essential for production of the viral vector, where the mammalian cell population produces viral vectors that individually comprise the at least one identifier. In some embodiments, a mammalian cell population optionally further includes one or more engineered sequences comprising: at least one perturbation accessory sequence, at least one trans-acting integration sequence, and/or at least one cis-acting integration sequence.

In some embodiments, provided are a mammalian cell population(s) comprising a plurality of mammalian cells that each individually comprise one or more engineered sequences, wherein the one or more engineered sequences together comprise: (i) a library construct and (ii) at least one polynucleotide comprising one or more nucleic acid sequences essential for production of the viral vector, where the library construct comprises an identifier positioned between two viral repeat sequences capable of packaging into a viral vector, and where the mammalian cell population produces viral vectors that individually comprise the identifier. In some embodiments, a mammalian cell population optionally further includes one or more engineered sequences comprising: at least one perturbation, at least one library variant, at least one payload, at least one perturbation accessory sequence, at least one trans-acting integration sequence, and/or at least one cis-acting integration sequence.

In some embodiments, provided are a mammalian cell population(s) comprising a plurality of mammalian cells that each individually comprise one or more engineered sequences, wherein the one or more engineered sequences together comprise: (i) a library construct and (ii) at least one polynucleotide comprising one or more nucleic acid sequences essential for production of the viral vector, where the library construct comprises an identifier positioned between two viral repeat sequences capable of packaging into a viral vector, and where the mammalian cell population produces viral vectors that individually comprise the identifier. In some embodiments, the library construct optionally further comprises one or more engineered sequences comprising at least one library variant and/or at least one payload. In some embodiments, a mammalian cell population optionally further comprises one or more engineered sequences comprising: at least one perturbation, at least one perturbation accessory sequence, at least one trans-acting integration sequence, and/or at least one cis-acting integration sequence.

In some embodiments, provided mammalian cell(s) comprise a perturbation (e.g., one or more perturbations). In some embodiments, provided mammalian cell(s) produce viral vectors that comprise a perturbation (e.g., one or more perturbations). In some embodiments, provided mammalian cell(s) comprise a perturbation (e.g., one or more perturbations) that also produce viral vectors that comprise a perturbation (e.g., one or more perturbations). In some embodiments, at least one polynucleotide comprising one or more nucleic acid sequences essential for production of the viral vector comprises a perturbation (e.g., one or more perturbations). In some embodiments, provided mammalian cell(s) comprise a perturbation (e.g., one or more perturbations) and at least one polynucleotide comprising one or more nucleic acid sequences essential for production of the viral vector comprises a perturbation (e.g., one or more perturbations). In some embodiments, provided mammalian cell(s) produce viral vectors that comprise a perturbation (e.g., one or more perturbations) and at least one polynucleotide comprising one or more nucleic acid sequences essential for production of the viral vector comprises a perturbation (e.g., one or more perturbations). In some embodiments, provided mammalian cell(s) comprise a perturbation (e.g., one or more perturbations) that also produce viral vectors that comprise a perturbation (e.g., one or more perturbations), and at least one polynucleotide comprising one or more nucleic acid sequences essential for production of the viral vector comprises a perturbation (e.g., one or more perturbations).

Mammalian cells and/or mammalian cell populations may comprise any mammalian cell in the art suitable for expression of a viral vector. In some embodiments, a mammalian cell comprises a cell of a rodent, a mouse, a rat, a rabbit, a monkey, a dog, a cat, a sheep, cattle, a primate (e.g., a human), and/or a pig. In some embodiments, mammalian cell(s) include human embryonic kidney (HEK) cells, HEK 293 cells, HEK 293T cells, Expi293 cells, Chinese hamster ovary (CHO) cells, HeLa cells, HeLa S3 cells, PER.C6 cells, HKB11 cells, CAP cells, Baby Hamster Kidney fibroblasts (BHK cells) (e.g., BHK-21 cells), mouse myeloma cells (e.g., Sp2/0 cells, NS0 cells), green African monkey kidney cells (e.g., COS cells, Vero cells), A549 cells, rhesus fetal lung cells (e.g., FRhL-2 cells), or a derivative of any thereof. In some embodiments, mammalian cells comprise HEK 293 cells, HEK 293T cells, CHO cells, or a derivative thereof. In some embodiments, mammalian cells comprise HEK 293 cells, HEK 293T cells, or a derivative thereof. In some embodiments, mammalian cells comprise HeLa cells or derivatives thereof.

In some embodiments, mammalian cells are suitable for suspension cell culture. In some embodiments, mammalian cells are suitable for adherent cell culture. In some embodiments, a mammalian cell population may comprise suspension cells and/or adherent cells.

Mammalian cells and/or methods of the present disclosure may be used to produce any viral vector. In some embodiments, a viral vector produced by mammalian cells and/or methods of the present disclosure comprises a perturbation (e.g., one or more perturbations). In some embodiments, a perturbation alters one or more characteristics associated with production of the viral vector (e.g., viral vector stability, etc.) or other characteristics (e.g., altered therapeutic activity, etc.).

In some embodiments, mammalian cell(s) of a mammalian cell library have been modified to disrupt or remove the receptor(s) for a produced viral vector. In some embodiments, mammalian cells have been treated with an agent that blocks infection of a viral vector.

In some embodiments, a viral vector is an adeno-associated viral (AAV) vector, a lentiviral vector, an adenovirus vector, an alphavirus vector, a sindbis viral vector, a retrovirus vector (e.g., a gamma retrovirus vector), a polyomavirus vector, (e.g., simian virus 40 (SV40) vector), a papilloma virus vector (e.g., a bovine papilloma virus (BPV) vector), a vaccinia virus vector, a herpes simplex virus (HSV) vector, a measles virus vector, a rhabdovirus vector, a rabies viral vector, a vesicular stomatitis virus (VSV) vector, a picornavirus vector (e.g., a poliovirus vector), a reovirus vector, a senecavirus vector, an echovirus vector (e.g., RIGVIR), a semliki forest virus (SFV) vector, a flavivirus vector, an anelloviral vector, a newcastle disease virus (NDV) vector, a paramyxoviral vector, a sendai viral vector, an orthomyxoviral vector, an influenzavirus vector, a coronaviral vector, and/or a hybrid viral vector, and/or a derivative, hybrid, and/or engineered derivative thereof.

In some embodiments, mammalian cells, mammalian cell populations and/or methods provided herein are useful for expression of an adeno-associated viral (AAV) vector. In some embodiments, mammalian cell(s) comprise (i) at least one identifier positioned between two viral repeat sequences capable of packaging into an AAV vector and (ii) at least one polynucleotide comprising one or more nucleic acid sequences essential for production of the AAV vector. In some embodiments, the two viral repeat sequences are each AAV ITR sequences capable packaging into an AAV vector. In some embodiments, the two viral repeat sequences are each mammalian AAV ITR sequences. In some embodiments, the two viral repeat sequences are each human AAV ITR sequences.

In some embodiments, provided are mammalian cell populations comprising a plurality of mammalian cells, where each mammalian cell of the plurality includes: (i) a nucleic acid sequence comprising a barcode positioned between two functional AAV ITR sequences, wherein the nucleic acid sequence is integrated into the mammalian genome positioned between a pair of cis-acting integration sequences, (ii) one or more library variants that result in one or more perturbations, and (iii) one or more nucleic acid sequences essential for production of AAV vectors, where the mammalian cell population produces a plurality of AAV vectors, wherein each AAV vector comprises a barcode that corresponds to the barcode of the mammalian cell from which it was produced. In some embodiments, at least one library variant comprises a gRNA, and said mammalian cell(s) further comprise an RNA-guided nuclease. In some embodiments, AAV vectors produced by the mammalian cells further comprise a payload.

In some embodiments, cis-acting integration sequences of the mammalian cell(s) are viral repeat sequences derived from lentivirus. In some embodiments, cis-acting integration sequences of the mammalian cell(s) are recombinase recognition sites.

In some embodiments, the one or more perturbations of the mammalian cell(s) is associated with an increase in AAV production and/or AAV secretion relative to a reference mammalian cell population that lacks the one or more perturbations. In some embodiments, mammalian cell(s) comprising the one or more perturbations have at least a 10% increase in AAV production and/or AAV secretion relative to a reference mammalian cell that lacks the one or more perturbations.

In some embodiments, two viral repeat sequences of a mammalian cell and/or library construct described herein comprise a pair of inverted terminal repeats (ITRs) that are or comprise a human AAV1 ITR(s); human AAV2 ITR(s); human AAV3b ITR(s); human AAV4 ITR(s); human AAV5 ITR(s); human AAV6 ITR(s); human AAV7 ITR(s); human AAV8 ITR(s); human AAV9 ITR(s); human AAV10 ITR(s); human AAV11 ITR(s); human AAV12 ITR(s); human AAV13 ITR(s), or a combination of any thereof.

In some embodiments, two viral repeat sequences of a mammalian cell and/or library construct described herein comprise a pair of inverted terminal repeats (ITRs) that are or comprise a bovine AAV (b-AAV) ITR(s); canine AAV (CAAV) ITR(s); mouse AAV1 ITR(s); caprine AAV ITR(s); rat AAV ITR(s); or avian AAV (AAAV) ITR(s).

In some embodiments, a mammalian cell comprises one or more polynucleotides encoding one or more proteins essential for production of the AAV vector, such as an AAV capsid protein. In some embodiments, the AAV vector comprises human AAV1 capsid proteins; human AAV2 capsid proteins; human AAV3b capsid proteins; human AAV4 capsid proteins; human AAV5 capsid proteins; human AAV6 capsid proteins; human AAV7 capsid proteins; human AAV8 capsid proteins; human AAV9 capsid proteins; human AAV10 capsid proteins; human AAV11 capsid proteins; human AAV12 capsid proteins; or human AAV13 capsid proteins. In some embodiments, the AAV vector comprises human ancestral AAV capsid proteins. In some embodiments, the AAV vector comprises bovine AAV (b-AAV) capsid proteins; canine AAV (CAAV) capsid proteins; mouse AAV1 capsid proteins; caprine AAV capsid proteins; rat AAV capsid proteins; or avian AAV (AAAV) capsid proteins.

In some embodiments, mammalian cells, mammalian cell populations and/or methods provided herein are useful for expression of an AAV vector, where the mammalian cell(s) comprise (i) a library construct comprising at least one identifier positioned between two AAV ITR sequences capable of packaging into an AAV vector and (ii) at least one polynucleotide comprising one or more nucleic acid sequences essential for production of the AAV vector selected from a Rep gene, a Cap gene, a helper gene, or a combination thereof. In some embodiments, at least one polynucleotide comprising one or more nucleic acid sequences essential for formation of an AAV vector comprises: an AAV Rep gene, an AAV Cap gene, one or more AAV helper genes, or a combination thereof. In some embodiments, an AAV vector is replication competent. In some embodiments, an AAV vector is replication conditional, replication deficient, replication incompetent, and/or replication-defective.

In some embodiments, mammalian cells have been previously or concurrently genetically modified to disrupt or remove a receptor for AAV. In some embodiments, mammalian cells have been treated with an agent that blocks infection of an AAV vector In some embodiments, mammalian cells, mammalian cell populations and/or methods provided herein are useful for expression of a lentiviral vector. In some embodiments, mammalian cell(s) comprise (i) at least one identifier positioned between two viral repeat sequences capable of packaging into a lentiviral vector and (ii) at least one polynucleotide comprising one or more nucleic acid sequences essential for production of the lentiviral vector. In some embodiments, the two viral repeat sequences are each lentiviral LTR sequences capable packaging into a lentiviral vector.

In some embodiments, two viral repeat sequences of a mammalian cell and/or library construct described herein comprise a pair of LTRs that comprise HIV LTRs, SIV LTRs, equine infectious anemia viral LTRs, FIV LTRs, visna viral LTRs, or a derivative or combination thereof. In some certain embodiments, a lentiviral vector is an HIV vector and the LTRs are HIV LTRs or a derivative thereof. In some embodiments, a lentiviral vector comprises a lentiviral Psi sequence.

In some embodiments, provided are mammalian cell populations comprising a plurality of mammalian cells, where each mammalian cell of the plurality includes: (i) a nucleic acid sequence comprising a barcode positioned between two functional lentiviral LTR sequences, wherein the nucleic acid sequence is integrated into the mammalian genome positioned between a pair of cis-acting integration sequences, (ii) one or more library variants that result in one or more perturbations, and (iii) one or more nucleic acid sequences essential for production of lentiviral vectors, where the mammalian cell population produces a plurality of lentiviral vectors, wherein each lentiviral vector comprises a barcode that corresponds to the barcode of the mammalian cell from which it was produced. In some embodiments, at least one library variant comprises a gRNA, and said mammalian cell(s) further comprise an RNA-guided nuclease. In some embodiments, lentiviral vectors produced by the mammalian cells further comprise a payload In some embodiments, cis-acting integration sequences of the mammalian cell(s) are viral repeat sequences derived from lentivirus. In some embodiments, cis-acting integration sequences of the mammalian cell(s) are recombinase recognition sites.

In some embodiments, the lentiviral LTRs comprise HIV LTRs, SIV LTRs, equine infectious anemia viral LTRs, FIV LTRs, visna viral LTRs, or a derivative or combination thereof. In some certain embodiments, a lentiviral vector is an HIV vector and the LTRs are HIV LTRs or a derivative thereof. In some embodiments, a lentiviral vector comprises a lentiviral Psi sequence In some embodiments, the one or more perturbations of the mammalian cell(s) is associated with an increase in lentiviral vector production and/or lentiviral vector secretion relative to a reference mammalian cell population that lacks the one or more perturbations. In some embodiments, mammalian cell(s) comprising the one or more perturbations have at least a 10% increase in lentiviral vector production and/or lentiviral vector secretion relative to a reference mammalian cell that lacks the one or more perturbations.

In some embodiments, a lentiviral vector expressed by mammalian cells and methods of the present disclosure is a human immunodeficiency virus (HIV) vector, a simian immunodeficiency virus (SIV) vector, an equine infectious anemia virus vector, a feline immunodeficiency virus (FIV) vector, a visna virus vector, or a derivative thereof.

In some embodiments, a mammalian cell comprises one or more polynucleotides encoding one or more proteins essential for production of a lentiviral vector, such as a lentiviral gag protein or fragment thereof. In some embodiments, a gag protein comprises one or more domains selected from a matrix (MA), capsid (CA), and nucleocapsid (NC) domain. In some embodiments, a mammalian cell comprises one or more polynucleotides encoding one or more proteins essential for production of a lentiviral vector, such as a lentiviral envelope protein or a fragment thereof.

In some embodiments, a lentiviral vector is a pseudotyped lentiviral vector comprising gag protein and envelope protein that are derived from different viruses. In some embodiments, a mammalian cell comprises one or more polynucleotides encoding one or more proteins essential for production of a pseudotyped lentiviral vector comprising a gag protein and/or an env protein derived from a human immunodeficiency virus (HIV) vector, a simian immunodeficiency virus (SIV) vector, an equine infectious anemia virus vector, a feline immunodeficiency virus vector, a visna virus vector or a derivative thereof.

In some embodiments, mammalian cells, mammalian cell populations and/or methods provided herein are useful for expression of lentiviral vector, where the mammalian cell(s) comprise (i) a library construct comprising at least one identifier positioned between two lentiviral LTR and/or Psi sequences, said sequences capable of packaging into a lentiviral vector and (ii) at least one polynucleotide comprising one or more nucleic acid sequences essential for production of the lentiviral vector selected from a gag gene, a env gene, a pol gene, or a combination thereof. In some embodiments, at least one polynucleotide comprising one or more nucleic acid sequences essential for formation of a lentiviral vector comprises: a lentiviral gag gene, a lentiviral env gene, a lentiviral pol gene, or a combination thereof. In some embodiments, a lentiviral vector is replication competent. In some embodiments, a lentiviral vector is replication conditional, replication deficient, replication incompetent, and/or replication-defective.

In some embodiments, the at least one polynucleotide comprising one or more nucleic acid sequences essential for formation of a lentiviral vector comprises: a HIV gag gene, a HIV env gene, a HIV pol gene, or a combination thereof. In some embodiments, a lentiviral vector is a HIV vector that is replication competent. In some embodiments, a lentiviral vector is a HIV vector that is replication conditional, replication deficient, replication incompetent, and/or replication-defective.

In some embodiments, mammalian cells have been previously or concurrently genetically modified to disrupt or remove a receptor for lentivirus. In some embodiments, mammalian cells have been treated with an agent that blocks infection of a lentiviral vector In such embodiments, the integration vector and/or cis-acting integration sequences are not derived from lentivirus.

In some embodiments, mammalian cells, mammalian cell populations and/or methods provided herein are useful for expression of a herpes simplex virus (HSV) vector. In some embodiments, provided a mammalian cell(s) comprise (i) at least one identifier positioned between two viral repeat sequences capable of packaging into a HSV vector and (ii) at least one polynucleotide comprising one or more nucleic acid sequences essential for production of the HSV vector. In some embodiments, a HSV vector is or is derived from herpes simplex virus-1 (HSV-1), herpes simplex virus-2 (HSV-2), human cytomegalovirus (HCMV), varicella-zoster virus (VZV), epstein-barr virus (EBV), Kaposi's sarcoma-associated herpesvirus (KSHV), human herpesvirus 6 and/or human herpesvirus 7, and/or a derivative thereof.

In some embodiments, two viral repeat sequences of a mammalian cell and/or library construct described herein comprise a terminal a sequence.

In some embodiments, a mammalian cell comprises one or more polynucleotides encoding one or more proteins essential for production of a HSV vector, such as a HSV capsid protein or fragment thereof. In some embodiments, an HSV capsid comprises VP5, VP19C, VP23, pre-VP22a and/or the maturational protease (UL26 gene product).

In some embodiments, mammalian cells, mammalian cell populations and/or methods provided herein are useful for expression of a HSV vector, where the mammalian cell(s) comprise (i) a library construct comprising at least one identifier positioned between HSV terminal a sequences, said sequences capable of packaging into a HSV vector and (ii) at least one polynucleotide comprising one or more nucleic acid sequences essential for production of the HSV vector including an HSV capsid protein.

In some embodiments, mammalian cells, mammalian cell populations and/or methods provided herein are useful for expression of an HSV-AAV hybrid vector. In some embodiments, a HSV-AAV hybrid vector is replication competent. In some embodiments, a HSV-AAV hybrid vector is replication conditional, replication deficient, replication incompetent, and/or replication-defective.

In some embodiments, provided mammalian cells and/or mammalian cell populations comprise one or more polynucleotides comprising one or more nucleic acid sequences essential for production of a viral vector. In some embodiments, polynucleotides comprising one or more nucleic acid sequences essential for production of a viral vector is present episomally a mammalian cell. In some embodiments, polynucleotides comprising one or more nucleic acid sequences essential for production of a viral vector is present in a mammalian cell genome. In some embodiments, one or more nucleic acid sequences essential for production of a viral vector comprise a heterologous regulatory element (e.g., a heterologous promoter and/or heterologous enhancer). In some embodiments, one or more nucleic acid sequences essential for production of a viral vector comprise a heterologous promoter sequence that is or comprises an SV40 promoter, an elongation factor (EF)-1 promotor, a cytomegalovirus (CMV) promoter, a phosphoglycerate kinase (PGK)1 promoter, a ubiquitin (Ubc) promoter, a human beta actin promoter, a tetracycline response element (TRE) promoter, a spleen focus-forming virus (SFFV) promoter, a murine stem cell virus (MSCV) promoter, a super-core promoter (SCP), a CAG promoter, or a derivative thereof. In some embodiments, one or more nucleic acid sequences essential for production of a viral vector comprise a heterologous enhancer sequence that is or comprises a CMV early enhancer, a cAMP response-element (CRE) enhancer, or a derivative thereof. In some embodiments, one or more nucleic acid sequences essential for production of a viral vector is under the control of an inducible transcriptional control element. In some embodiments, one or more nucleic acid sequences essential for production of a viral vector can be integrated into a mammalian cell genome and under the control of an inducible transcriptional control element (e.g., inducible promoter and/or inducible enhancer). In some embodiments, one or more nucleic acid sequences essential for production of a viral vector can be present episomally in a mammalian cell and under the control of an inducible transcriptional control element (e.g., inducible promoter and/or inducible enhancer).

Any of the engineered sequences of mammalian cells and/or mammalian cell populations of the present disclosure may be present episomally and/or integrated into a mammalian cell genome. In some embodiments, one or more engineered sequences may be present episomally in a mammalian cell, including but not limited to: an identifier, a perturbation, a library variant, a payload, a perturbation accessory sequence, a trans-acting integration sequence, and/or a cis-acting integration sequence. In some embodiments, one or more engineered sequences may be integrated into in a mammalian cell genome, including but not limited to: an identifier, a perturbation, a library variant, a payload, a perturbation accessory sequence, a trans-acting integration sequence, and/or a cis-acting integration sequence.

In some embodiments, one or more engineered sequences are present in a viral vector (e.g., an identifier, a perturbation, a payload, etc.). In some embodiments, mammalian cells and/or mammalian cell populations express viral vectors that each comprise an identifier and a perturbation. In some embodiments, a viral vector comprises a perturbation that alters one or more characteristics associated with viral vector production and/or other characteristics (e.g., stability, etc.). In some embodiments, a viral vector further comprises a payload. In some embodiments, a viral vector further comprises a reporter and/or a selectable marker In some embodiments, a mammalian cell comprises a library construct, where one or more polynucleotides that make up the library construct may be present episomally in a mammalian cell, including but not limited to: an identifier, a library variant, a payload, a perturbation accessory sequence, a trans-acting integration sequence, and/or a cis-acting integration sequence. In some embodiments, a mammalian cell comprises a library construct, where one or more polynucleotides that make up the library construct may be integrated into a mammalian cell, including but not limited to: an identifier, a library variant, a payload, a perturbation accessory sequence, a trans-acting integration sequence, and/or a cis-acting integration sequence. In some embodiments, one or more polynucleotides that make up a library construct may be integrated into a mammalian cell at a low copy number, e.g., four copies or less, three copies or less, two copies or less, or a single copy.

In some embodiments, one or more engineered sequences comprise a heterologous coding sequence. In some embodiments, one or more engineered sequences comprise a heterologous gene and/or a heterologous gene segment. In some embodiments, one or more engineered sequences comprise a heterologous regulatory element (e.g., a heterologous promoter and/or heterologous enhancer). In some embodiments, one or more engineered sequences comprise a heterologous promoter sequence that is or comprises an SV40 promoter, an elongation factor (EF)-1 promoter, a cytomegalovirus (CMV) promoter, a phosphoglycerate kinase (PGK)1 promoter, a ubiquitin (Ubc) promoter, a human beta actin promoter, a tetracycline response element (TRE) promoter, a spleen focus-forming virus (SFFV) promoter, a murine stem cell virus (MSCV) promoter, a supercore promoter (SCP), a CAG promoter, or a derivative thereof. In some embodiments, one or more engineered sequences comprise a heterologous enhancer sequence is or comprises a CMV early enhancer, a cAMP response-element (CRE) enhancer, or a derivative thereof. In some embodiments, one or more engineered sequences comprise inducible transcriptional control element.

In some embodiments, provided mammalian cells and/or mammalian cell populations comprise more than one engineered sequence (e.g., an identifier, a perturbation, a library variant, a payload, a perturbation accessory sequence, a trans-acting integration sequence, and/or a cis-acting integration sequence). In some embodiments, provided mammalian cells and/or mammalian cell populations comprise two or more, three or more, four or more, five or more, six or more, seven or more, eight or more, nine or more, or ten or more engineered sequences. In some embodiments, a mammalian cell comprises up to 100 engineered sequences.

In some embodiments, provided mammalian cells and/or mammalian cell populations comprise a library construct that comprises one or more engineered sequences that may include, for example: an identifier, a library variant, a payload, a perturbation accessory sequence, a trans-acting integration sequence, and/or a cis-acting integration sequence. In some embodiments, a mammalian cell of the present disclosure comprises at least one library construct, where the at least one library construct comprises at least one engineered sequence. In some embodiments, a library construct comprises two or more, three or more, four or more, five or more, six or more, seven or more, eight or more, nine or more, or ten or more engineered sequences. In some embodiments, a library construct comprises up to 100 engineered sequences.

In some embodiments, provided mammalian cells and/or mammalian cell populations produce viral vectors that comprise one or more engineered sequences, that may include, for example, an identifier, a perturbation, a payload, and/or a cis-acting integration sequence.

In some embodiments, a mammalian cell of the present disclosure comprises at least one library construct that comprises at least one engineered sequence selected from: at least one barcode, at least one identifier, at least one library variant, at least one payload, at least one cis-acting integration sequence, or a combination thereof and/or a plurality thereof.

In some embodiments, a mammalian cell comprises at least one engineered sequence that comprises a barcode. In some embodiments, a barcode comprises a sequence that is about 5 to about 25 nucleotides. In some embodiments, provided mammalian cells comprise a plurality of unique barcodes, and wherein the plurality of unique barcodes comprise unique sequences that are about 5 to about 25 nucleotides.

In some embodiments, a library construct comprises at least one barcode. In some embodiments, a library construct comprises an identifier that comprises at least one barcode. In some embodiments, a library construct comprises an identifier that comprises at least one barcode, wherein the barcode is positioned between two viral repeat sequences. In some embodiments, a barcode is positioned between two viral repeat sequences and is not an identifier. In some embodiments, a barcode is not positioned between two viral repeat sequences.

In some embodiments, a mammalian cell comprises at least one engineered sequence that comprises a library variant. A library variant may comprise, but is not limited to, an engineered sequence that comprises a gene, an ORF, a gRNA sequence, a non-coding nucleic acid, or a combination thereof. In some embodiments, a mammalian cell comprises one, two, three, four, five, six, seven, eight, nine, or ten library variants. In some embodiments, a mammalian cell comprises up to 100 library variants.

In some embodiments, a mammalian cell comprises a plurality of library variants, where the plurality of library variants comprise at least one engineered sequence comprising: at least one unique gene, at least one unique ORF, at least one unique gRNA sequence, and/or at least one unique non-coding nucleic acid, or a combination and/or plurality thereof. In some embodiments, a mammalian cell comprises a plurality of library constructs, where the plurality of library constructs comprise: at least one unique gene, at least one unique ORF, at least one unique gRNA sequence, at least one unique non-coding nucleic acid sequence, or a combination and/or plurality thereof. In some embodiments, a mammalian cell population comprises a plurality of library constructs, where the plurality of library constructs comprise a plurality of unique genes, a plurality of unique ORFs, a plurality of unique gRNA sequences, a plurality of unique non-coding nucleic acid sequences, or a combination thereof.

In some embodiments, a library construct comprises a gRNA sequence. In some embodiments, a mammalian cell population comprises a plurality of library constructs, where the plurality of library constructs comprise at least one unique gRNA sequence. In some embodiments, a mammalian cell population comprises a plurality of library constructs, where the plurality of library constructs comprise at least 100 unique gRNA sequences.

In some embodiments, a library construct comprises an ORF. In some embodiments, a mammalian cell population comprises a plurality of library constructs, where the plurality of library constructs comprise at least one unique ORF.

In some embodiments, a mammalian cell population comprises a plurality of library constructs, where the plurality of library constructs comprise at least 100 unique ORFs.

In some embodiments, a library construct comprises a gene. In some embodiments, a mammalian cell population comprises a plurality of library constructs, where the plurality of library constructs comprise at least one unique gene. In some embodiments, a mammalian cell population comprises a plurality of library constructs, where the plurality of library constructs comprise at least 100 unique genes.

In some embodiments, a library construct comprises a noncoding nucleic acid sequence. In some embodiments, a mammalian cell population comprises a plurality of library constructs, where the plurality of library constructs each comprise at least one unique noncoding nucleic acid sequence. In some embodiments, a mammalian cell population comprises a plurality of library constructs, where the plurality of library constructs comprise at least 100 unique noncoding nucleic acid sequence.

In some embodiments, a library construct comprises at least one reporter and/or selectable marker. In some embodiments, one or more polynucleotides that comprise a library construct include a reporter and/or selectable marker.

In some embodiments, a library construct comprises an identifier. In some embodiments, a mammalian cell population comprises a plurality of library constructs, where the plurality of library constructs comprise a plurality of identifiers. In some embodiments, an identifier comprises at least one barcode and/or at least one library variant. In some embodiments, a mammalian cell comprises a library construct that comprises an identifier that comprises at least one barcode and/or at least one library variant. In some embodiments, a mammalian cell population comprises a plurality of library constructs comprising a plurality of identifiers, where the identifiers comprise a plurality of barcodes and/or a plurality of library variants.

In some embodiments, a library construct comprises a plurality of engineered sequences, where: a first subset of the plurality of engineered sequences are positioned between the two viral repeat sequences, and a second subset of the plurality of engineered sequences are positioned outside the two viral repeat sequences.

In some embodiments, provided mammalian cells and/or mammalian cell populations comprise a plurality of engineered sequences comprising at least one library variant and at least one identifier, where both the at least one library variant and the at least one identifier are positioned between the two viral repeat sequences. In some embodiments, provided mammalian cells and/or mammalian cell populations comprise a plurality of engineered sequences comprising: at least one library variant, at least one identifier, and at least one payload, where the at least one library variant, the at least one identifier, and the at least one payload are positioned between the two viral repeat sequences.

In some embodiments, provided mammalian cells and/or mammalian cell populations comprise a plurality of engineered sequences comprising at least one library variant and at least one identifier, and where at least one identifier is positioned between the two viral repeat sequences, and where at least one library variant is positioned outside the two viral repeat sequences. In some embodiments, provided mammalian cells and/or mammalian cell populations comprise a plurality of engineered sequences comprising at least one library variant, at least one identifier, and at least one payload, where the at least one identifier and the at least one payload are positioned between the two viral repeat sequences, and where the at least one library variant is positioned outside the two viral repeat sequences.

In some embodiments, provided mammalian cells and/or mammalian cell populations comprise a plurality of engineered sequences comprising at least two library variants and at least one identifier, where the at least one identifier and at least one library variant of the at least two library variants are positioned between the two viral repeat sequences, and where at least one library variant of the at least two library variants is positioned outside the two viral repeat sequences. In some embodiments, provided mammalian cells further comprise a payload positioned between the two viral repeat sequences.

In some embodiments, provided library constructs comprise at least one library variant and at least one identifier, where both the at least one library variant and the at least one identifier are positioned between the two viral repeat sequences. In some embodiments, provided library constructs comprise: at least one library variant, at least one identifier, and at least one payload, where the at least one library variant, the at least one identifier, and the at least one payload are positioned between the two viral repeat sequences.

In some embodiments, provided library constructs comprise at least one library variant and at least one identifier, and where at least one identifier is positioned between the two viral repeat sequences, and where at least one library variant is positioned outside the two viral repeat sequences. In some embodiments, provided library constructs comprise at least one library variant, at least one identifier, and at least one payload, where the at least one identifier and the at least one payload are positioned between the two viral repeat sequences, and where the at least one library variant is positioned outside the two viral repeat sequences.

In some embodiments, provided library constructs comprise at least two library variants and at least one identifier, where the at least one identifier and at least one library variant of the at least two library variants are positioned between the two viral repeat sequences, and where at least one library variant of the at least two library variants is positioned outside the two viral repeat sequences. In some embodiments, provided library constructs further comprise a payload positioned between the two viral repeat sequences.

In some embodiments, at least one identifier comprises a barcode. In some embodiments, provided mammalian cells and/or library constructs comprise at least one engineered sequence comprising at least one barcode, and wherein the at least one barcode is positioned between the two viral repeat sequences. In some embodiments, a barcode positioned between two viral repeat sequences is an identifier. In some embodiments, provided mammalian cells and/or library constructs comprise at least one engineered sequence comprising at least one barcode, and wherein the at least one barcode is positioned outside the two viral repeat sequences.

In some embodiments, provided mammalian cells and/or library constructs comprise a plurality of barcodes. In some embodiments, provided mammalian cells and/or library constructs comprise a plurality of barcodes, where at least one barcode is positioned between the two viral repeat sequences. In some embodiments, provided mammalian cells and/or library constructs comprise a plurality of barcodes, where a plurality of barcodes are positioned between the two viral repeat sequences. In some embodiments, at least one barcode positioned between two viral repeat sequences is an identifier. In some embodiments, provided mammalian cells and/or library constructs comprise a plurality of barcodes, where a first subset of the plurality of barcodes is positioned between the two viral repeat sequences, and a second subset of the plurality of barcodes is positioned outside the two viral repeat sequences.

In some embodiments, provided mammalian cells comprise more than one cop of the library construct or a portion thereof. In some embodiments, provided mammalian cells comprise 1, 2, 3, 4, 5, 6, 7, 8, 9, 10, or more copies of the library construct or a portion thereof. In some embodiments, provided mammalian cells comprise a plurality of copies of the library construct or a portion thereof. In some embodiments, provided mammalian cells comprise between one and four copies of the library construct or a portion thereof. In some embodiments, provided mammalian cells comprise exactly two copies of the library construct or a portion thereof. In some embodiments, provided mammalian cells comprise exactly one copy of a library construct or a portion thereof.

In some embodiments, provided mammalian cells comprise at least one library construct comprised of a single contiguous nucleic acid sequence. In some embodiments, provided mammalian cell populations comprise a plurality of library constructs, wherein each individual library construct is comprised of a single contiguous nucleic acid sequence, and wherein the plurality of library constructs comprise a plurality of unique nucleic acid sequences. In some embodiments, a library construct comprises more than one discontiguous nucleic acid sequence. In some embodiments, a library construct comprises at least two, three, four, five, six, seven, eight, nine, or ten discontiguous nucleic acid sequences. In some embodiments, a library construct comprises up to 100 discontiguous nucleic acid sequences.

In some embodiments, provided mammalian cell populations comprise a plurality of library constructs, where each individual library construct is comprised of discontiguous nucleic acid sequences, and wherein the library constructs comprise a plurality of unique nucleic acid sequences. In some embodiments, the nucleic acids or derivatives thereof derived from each individual mammalian cell comprise at least one unique cell identity sequence during a single cell sequencing method. In some embodiments, more than one nucleic acid sequence or derivative thereof derived from each individual mammalian cell comprises a cell identity sequence during a single cell sequencing method. In some embodiments, the nucleic acids or derivatives thereof derived from each individual library construct comprise at least one unique cell identity sequence during a single cell sequencing method. In some embodiments, more than one nucleic acid sequence or derivative thereof derived from each individual library construct comprises a cell identity sequence during a single cell sequencing method.

In some embodiments, provided mammalian cell populations comprise a plurality of library constructs, where each mammalian cell comprises a single library construct comprised of a plurality of discontiguous nucleic acid sequences, and where the library constructs comprise a plurality of unique nucleic acid sequences, and where more than one nucleic acid sequence (or derivative thereof) from the library construct comprises a cell identity sequence during a single cell sequencing method. In some embodiments, all nucleic acid sequences (or derivatives thereof) from a library construct comprise a cell identity sequence during a single cell sequencing method.

In some embodiments, provided mammalian cells and/or viral vectors comprise at least one engineered sequence comprising at least one perturbation. In some embodiments, provided mammalian cells comprise at least one perturbation that is present episomally in the mammalian cells. In some provided mammalian cells comprise at least one perturbation that is present in the genome of the mammalian cells. In some embodiments, provided mammalian cells comprise at least two perturbations, where at least one perturbation is present episomally and at least one perturbation is present in the genome of the mammalian cells.

In some embodiments, viral vectors expressed by mammalian cells provided herein comprise a perturbation (e.g., one or more perturbations). In some embodiments, a viral vector comprises an engineered sequence comprising a perturbation that is present in the viral nucleic acid. In some embodiments, a viral vector comprises an engineered sequence comprising a perturbation that is present in the ITRs. In some embodiments, a viral vector comprises an engineered sequence comprising a perturbation that is present between the ITRs.

In some embodiments, the one or more polynucleotides essential for formation of a viral vector comprise an engineered sequence comprising a perturbation (e.g., one or more perturbations). In some embodiments, the one or more polynucleotides essential for formation of a viral vector is present episomally and comprises an engineered sequence comprising a perturbation (e.g., one or more perturbations). In some embodiments, the one or more polynucleotides essential for formation of a viral vector is present in the genome of the mammalian cells and comprises an engineered sequence comprising a perturbation (e.g., one or more perturbations).

In some embodiments, provided mammalian cells and/or viral vectors comprise a plurality of unique perturbations. In some embodiments, provided mammalian cells and/or library constructs comprise at least two, three, four, five, six, seven, eight or nine unique perturbations.

In some embodiments, provided mammalian cells and/or viral vectors comprise at least one perturbation that comprises an insertion, deletion, substitution, replacement, epigenetic modification, and/or rearrangement of an endogenous genomic coding sequence. In some embodiments, an endogenous coding sequence is or comprises an endogenous gene or gene segment.

In some embodiments, provided mammalian cells and/or viral vectors comprise at least one perturbation comprises an insertion, deletion, substitution, replacement, epigenetic modification, and/or rearrangement of an endogenous genomic regulatory element. In some embodiments, an endogenous regulatory element is or comprises an endogenous promoter sequence and/or endogenous enhancer sequence.

In some embodiments, provided mammalian cells comprise at least one perturbation accessory sequence. In some embodiments, a perturbation accessory sequence comprises a RNA-guided nuclease or derivative thereof. In some embodiments, a RNA-guided nuclease comprises Cas9, Cpf1, and/or CasZ, or a derivative thereof, including fusion proteins comprising transcriptional regulators (e.g., Cas9-VPR or Cas9-KRAB-MeCP2 fusions), CRISPR protein fusions to nuclease domains (e.g. Fok1), enzymatic base-editors (e.g. versions of BE and ABE fusions), reverse transcriptase fusions (e.g. Prime Editors), CRISPR recombinases including (e.g. RecCas9), and CRISPR transposases (e.g., Tn7-like transposase systems Cas12k and Cascade complexes with TniQ). In some embodiments, a RNA-guided nuclease comprises Cas9 or derivative thereof.

Provided library constructs can be introduced into mammalian cells using any appropriate method known in the art. In some embodiments, a library construct is introduced into a mammalian cell by transfection and/or transduction. In some embodiments, a library construct is introduced into a mammalian cell by lentiviral-mediated transduction.

In some embodiments, provided mammalian cells comprise a library construct, where at least one engineered sequence of the library construct is present episomally. In some embodiments, provided mammalian cells comprise a library construct, wherein the library construct comprises at least one engineered sequence comprising at least one library variant, and wherein each individual cell comprises at least one perturbation accessory sequence, and where at least one engineered sequence is present episomally.

In some embodiments, provided mammalian cells comprise a library construct, where at least one engineered sequence of the library construct comprises at least one library variant, and where at least one library variant is present episomally. In some embodiments, at least one library variant is an effector. In some embodiments, at least one library variant becomes the at least one perturbation. In some embodiments, at least one library variant comprises at least one ORF, at least one gene, at least one non-coding nucleic acid sequence, and/or at least one gRNA, or plurality thereof.

In some embodiments, provided mammalian cells comprise a library construct, wherein the library construct comprises at least one engineered sequence comprising at least one library variant comprising at least one gRNA, and wherein each individual cell comprises at least one perturbation accessory sequence comprising an RNA-guided nuclease or a non-RNA-guided nuclease or derivative thereof, and where at least one engineered sequence is present episomally.

In some embodiments, provided mammalian cells comprise a library construct, wherein the library construct comprises at least one engineered sequence comprising at least one library variant comprising at least one gRNA, wherein each individual cell comprises at least one perturbation accessory sequence comprising an RNA-guided nuclease or a non-RNA-guided nuclease or derivative thereof, and where at least one engineered sequence is present episomally.

In some embodiments, provided mammalian cells and/or mammalian cell populations comprise at least one perturbation. In some embodiments, provided mammalian cells and/or mammalian cell populations comprise at least one perturbation that comprises a genomic sequence change, an episomal sequence change, and/or an epigenetic modification. In some embodiments, provided mammalian cells and/or mammalian cell populations comprise at least one perturbation that comprises an insertion, deletion, substitution, and/or rearrangement of an endogenous genomic coding sequence.

In some embodiments, provided mammalian cells and/or mammalian cell populations produce viral vectors that individually comprise at least one perturbation.

In some embodiments, provided mammalian cells comprise a library construct, where at least one engineered sequence of the library construct is present in the genome of the mammalian cells. In some embodiments, provided mammalian cells comprise a library construct, wherein the library construct comprises at least one engineered sequence comprising at least one library variant and wherein each individual cell comprises at least one perturbation accessory sequence, and where at least one engineered sequence is present in the genome of the mammalian cells.

In some embodiments, a library construct or portion thereof is inserted into the genome of a mammalian cell at a random insertion site. In some embodiments, a random insertion site is random within a predetermined subset of genomic locations. In some embodiments, a library construct or portion thereof is inserted into the genome of a mammalian cell at a predetermined insertion site.

In some embodiments, provided mammalian cells and/or library constructs comprise at least one trans-acting integration sequence, wherein the at least one trans-acting integration sequence comprises (i) at least one integration construct and/or integration viral vector, (ii) at least one recombinase, and/or the polypeptide, protein, nucleic acid, or polynucleotide product thereof, (iii) at least one nuclease, and/or the polypeptide, protein, nucleic acid, or polynucleotide product thereof, (iv) at least one transposase, and/or the polypeptide, protein, nucleic acid, or polynucleotide product thereof, and/or (v) at least one engineered sequence.

In some embodiments, provided mammalian cells and/or library constructs comprise at least one trans-acting integration sequence that comprises an integration construct and/or integration viral vector. In some embodiments, provided mammalian cells and/or library constructs comprise at least one pair of cis-acting integration sequences that flank the first set of viral repeat sequences, where the cis-acting integration sequences comprise a second set of viral repeat sequences. In some embodiments, an integration construct and/or integration viral vector is a lentiviral vector, a gammaretroviral vector, a spumaretroviral vector, an adeno-associated viral vector, or a derivative thereof. In some embodiments, an integration construct or integration viral vector is a lentiviral vector.

In some embodiments, provided mammalian cells and/or library constructs comprise a first set of viral repeat sequences (e.g., for packaging a sequence into a viral vector target) and cis-acting integration sequences comprising a second set of viral repeat sequences. In some embodiments, cis-acting integration sequences comprising a second set of viral repeat sequences are or comprise LTRs.

In some embodiments, provided mammalian cells and/or library constructs comprise at least one trans-acting integration sequence that comprises a nuclease, and/or the polypeptide, protein, nucleic acid, or polynucleotide product thereof.

In some embodiments, at least one trans-acting integration sequence comprises at least one nuclease, and wherein the at least one nuclease comprises an RNA-guided nuclease or fusion or derivative thereof. In some embodiments, at least one trans-acting integration sequence comprises at least one nuclease, and wherein the at least one nuclease comprises a non-RNA-guided nuclease or fusion or derivative thereof. In some embodiments, at least one nuclease comprises Cas9, CasZ, Cpf1, an engineered Fok1 nuclease domain fusion to a programmable DNA-binding domain such as a TALE protein (TALEN) or a Zinc Finger protein (ZFN), and/or a meganuclease, or a derivative thereof. In some embodiments, at least one nuclease comprises Cas9.

In some embodiments, at least one trans-acting integration sequence further comprises at least one engineered sequence. In some embodiments, at least one trans-acting integration sequence comprises an RNA-guided nuclease or fusion or derivative thereof and also comprises at least one gRNA.

In some embodiments, provided mammalian cells and/or library constructs comprise at least one pair of cis-acting integration sequences that flank the first set of viral repeat sequences, and where the cis-acting integration sequences comprise homology arm sequences.

In some embodiments, at least one trans-acting integration sequence comprises a recombinase, and/or the polypeptide, protein, nucleic acid, or polynucleotide product thereof. In some embodiments, provided mammalian cells and/or library constructs comprise at least one pair of cis-acting integration sequences that flank the first set of viral repeat sequences, and where the cis-acting integration sequences comprise recombinase recognition sites. In some embodiments, a recombinase comprises Cre, Flp, Dre, PhiC31, and/or Bxb1, or a derivative thereof.

In some embodiments, a recombinase comprises recombinase comprises Cre. In some embodiments, the recombinase recognition sites comprise LoxP sites.

In some embodiments, a recombinase comprises recombinase comprises Bxb1. In some embodiments, the recombinase recognition sites comprise Att sites.

In some embodiments, a recombinase comprises recombinase comprises Flp. In some embodiments, the recombinase recognition sites comprise Frt sites.

In some embodiments, at least one trans-acting integration sequence comprises a transposase, and/or a polypeptide, protein, nucleic acid, or polynucleotide product thereof. In some embodiments, provided mammalian cells and/or library constructs comprise at least one pair of cis-acting integration sequences that flank the first set of viral repeat sequences, and where the cis-acting integration sequences comprise transposase recognition sites. In some embodiments, a transposase comprises Piggybac transposase, Sleepingbeauty transposase, and/or Tn5 transposase, or a derivative thereof. In some certain embodiments, a transposase comprises Piggybac transposase or a derivative thereof. In some certain embodiments, a transposase comprises Sleepingbeauty transposase or a derivative thereof. In some certain embodiments, a transposase comprises Tn5 transposase or a derivative thereof.

In some embodiments, a population of mammalian cells produces viral vectors that are altered relative to a reference population. In some embodiments, provided mammalian cells and/or mammalian cell populations produce viral vectors that are altered in the way they transfer nucleic acid to a cell, relative to a reference population. In some embodiments, provided mammalian cells and/or mammalian cell populations produce viral vectors that are altered therapeutically, relative to a reference population. In some embodiments, provided mammalian cells and/or mammalian cell populations produce viral vectors that are altered in their intended application, relative to a reference population.

In some embodiments, provided mammalian cells and/or mammalian cell populations produce viral vectors that are less functional in an application, relative to a reference population. In some embodiments, provided mammalian cells and/or mammalian cell populations produce viral vectors that are nonfunctional in an application, relative to a reference population. In some embodiments, provided mammalian cells and/or mammalian cell populations produce viral vectors that are less functional and/or nonfunctional at transferring nucleic acid to a cell, relative to a reference population. In some embodiments, provided mammalian cells and/or mammalian cell populations produce viral vectors that are less functional and/or nonfunctional therapeutically, relative to a reference population. In some embodiments, provided mammalian cells and/or mammalian cell populations produce viral vectors that are less functional and/or nonfunctional in their intended application, relative to a reference population.

In some embodiments, provided mammalian cells and/or mammalian cell populations produce viral vectors that are more functional and/or enhanced in an application, relative to a reference population. In some embodiments, provided mammalian cells and/or mammalian cell populations produce viral vectors that are more functional and/or enhanced at transferring nucleic acid to a cell, relative to a reference population. In some embodiments, provided mammalian cells and/or mammalian cell populations produce viral vectors that are more functional and/or enhanced therapeutically, relative to a reference population. In some embodiments, provided mammalian cells and/or mammalian cell populations produce viral vectors that are more functional and/or enhanced in their intended application, relative to a reference population.

In some embodiments, provided mammalian cells and/or mammalian cell populations comprise at least one engineered sequence (e.g., perturbation) that alters viral vector production under a manufacturing practice relative to a reference cell population. In some embodiments, provided mammalian cells and/or mammalian cell populations comprise at least one engineered sequence (e.g., perturbation) that provides an increase in viral vector production under a manufacturing practice relative to a reference cell population. In some embodiments, a mammalian cell with altered viral vector production comprises at least 1, at least 2, at least 3, at least 4, at least 5, at least 6, at least 7, at least 8, at least 9, at least 10, or more perturbations relative to a reference cell.

In some embodiments, provided mammalian cells and/or mammalian cell populations comprise at least one engineered sequence (e.g., perturbation) that provides an increase in viral vector production under a then-current good manufacturing practice (cGMP). In some embodiments, at least one engineered sequence (e.g., perturbation) provides an increase in viral vector production under a good manufacturing practice (GMP). In some embodiments, provided mammalian cells and/or mammalian cell populations comprise at least one engineered sequence (e.g., perturbation) that provides an increase in viral vector production under a non-good manufacturing practice (non-GMP).

In some embodiments, provided mammalian cells and/or mammalian cell populations comprise at least one engineered sequence (e.g., perturbation) that provides an increase in the viability of the mammalian cell population relative to a reference cell population. In some embodiments, provided mammalian cells and/or mammalian cell populations comprise at least one perturbation that provides an increase in the duration of viral vector production by the mammalian cell population relative to a reference cell population. In some embodiments, provided mammalian cells and/or mammalian cell populations comprise at least one engineered sequence (e.g., perturbation) that provides an increase in the genomic stability of the mammalian cell population relative to a reference cell population.

In some embodiments, provided mammalian cells and/or mammalian cell populations comprise at least one engineered sequence (e.g., perturbation) that provides a decrease in the percentage of produced viral vector under a manufacturing practice that are less functional in an application, relative to a reference cell population. In some embodiments, provided mammalian cells and/or mammalian cell populations comprise at least one perturbation that provides a decrease in the percentage of produced viral vector under a manufacturing practice that are nonfunctional in an application, as compared to a reference cell population. In some embodiments, viral vectors that decreased in percentage are less functional and/or nonfunctional at transferring nucleic acid to a cell, relative to a reference cell population. In some embodiments, viral vectors that decreased in percentage are less functional and/or nonfunctional therapeutically, relative to a reference cell population. In some embodiments, viral vectors that decreased in percentage are less functional and/or nonfunctional in their intended application, relative to a reference cell population.

In some embodiments, provided mammalian cells and/or mammalian cell populations comprise at least one engineered sequence (e.g., perturbation) that provides an increase in the percentage of produced viral vector under a manufacturing practice that are more functional and/or enhanced in an application, relative to a reference cell population. In some embodiments, viral vectors that increased in percentage are more functional and/or enhanced at transferring nucleic acid to a cell, relative to a reference cell population. In some embodiments, viral vectors that increased in percentage are more functional and/or enhanced therapeutically, relative to a reference cell population. In some embodiments, viral vectors that increased in percentage are more functional and/or enhanced in their intended application, relative to a reference cell population.

In some embodiments, at least one engineered sequence (e.g., perturbation) provides an increase in the percentage of viral vector under a manufacturing practice that contain all and/or the essential nucleic acid sequences and/or other elements for their intended application, relative to a reference cell population.

In some embodiments, at least one engineered sequence (e.g., perturbation) provides a decrease in the percentage of viral vector under a manufacturing practice that have lost and/or mutated all and/or the essential nucleic acid sequences and/or other elements for their intended application, relative to a reference cell population.

In some embodiments, provided mammalian cells and/or mammalian cell populations and/or viral vectors comprise a plurality of engineered sequences, where the plurality of engineered sequences comprise a plurality of perturbations.

In some embodiments, a reference cell population is: (a) a population of comparable mammalian cells that do not include the at least one engineered sequence; and/or (b) a population of standard cells capable of producing the viral vector.

In some embodiments, a viral vector produced by a mammalian cell described herein comprises an engineered sequence (e.g., perturbation) that alters viral vector production under a manufacturing practice relative to a reference cell population. In some embodiments, a viral vector comprises a perturbation that alters functionality (e.g., therapeutic functionality, ability to transfer nucleic acid to a cell), genomic stability, manufacturing yield by a mammalian cell, duration of production by a mammalian cell, percentage of produced viral vector containing all essential nucleic acid sequences, and/or another characteristic associated with viral vector production, viral vector activity and/or viral vector application.

In some embodiments, a mammalian cell population is produced by (a) introducing into the plurality of mammalian cells a plurality of engineered sequences comprising a plurality of library constructs, wherein the individual library constructs comprise at least one identifier positioned between the first set of two viral repeat sequences, and (b) introducing into the plurality of mammalian cells the at least one polynucleotide comprising one or more nucleic acid sequences essential for production of the viral vector.

In some embodiments, a mammalian cell population is produced by introducing into the plurality of mammalian cells a plurality of engineered sequences comprising a plurality of library constructs, wherein the individual library constructs comprise at least one identifier positioned between the first set of two viral repeat sequences, wherein the plurality of mammalian cells comprise one or more nucleic acid sequences essential for production of the viral vector.

In some embodiments, provided are methods of producing viral vectors, comprising: culturing a population of mammalian cells of the present disclosure under conditions such that the mammalian cells produce viral vectors, and wherein each produced viral vector comprises at least one identifier that is derived from the at least one identifier of the mammalian cell that produced the viral vector. In some embodiments, each produced viral vector comprises at least one identifier that is identical to the at least one identifier of the mammalian cell that produced the viral vector.

In some embodiments, provided are methods comprising: (a) producing viral vectors from a library of mammalian cells, wherein the library of mammalian cells comprise a plurality of mammalian cells, wherein each mammalian cell of the plurality individually comprises: (i) at least one engineered sequence, (ii) an identifier, and (iii) at least one polynucleotide comprising one or more nucleic acid sequences essential for production of the viral vector, and wherein each viral vector comprises an identifier that is derived from the identifier of the mammalian cells that produced the viral vector; and (b) detecting the identifiers in the viral vectors. In some embodiments, each viral vector comprises an identifier that is identical to the identifier of the mammalian cells that produced the viral vector.

In some embodiments, provided are methods comprising: (a) producing viral vectors from a library of mammalian cells, wherein the library of mammalian cells comprises a plurality of mammalian cells, wherein each mammalian cell of the plurality individually comprises: (i) at least one engineered sequence, (ii) at least one identifier, and (iii) at least one polynucleotide comprising one or more nucleic acid sequences essential for production of the viral vector, and wherein each viral vector comprises at least one identifier that is derived from the at least one identifier of the mammalian cells that produced the viral vector; and (b) detecting the one or more identifiers in the viral vectors by next generation sequencing. In some embodiments, each viral vector comprises at least one identifier that is identical to the at least one identifier of the mammalian cells that produced the viral vector.

In some embodiments, provided are methods comprising: (a) producing an AAV library, wherein the AAV library comprises a plurality of AAV vectors from a library of mammalian cells, wherein the library of mammalian cells comprises a plurality of mammalian cells, wherein each mammalian cell of the plurality individually comprises: (i) at least one engineered sequence, (ii) at least one barcode sequence, and (iii) at least one polynucleotide comprising one or more nucleic acid sequences essential for production of the viral vector, wherein each AAV viral vector comprises at least one construct, and wherein the at least one construct comprises a barcode sequence that is derived from the at least one barcode sequence of the mammalian cells that produced the AAV viral vector; and (b) detecting the one or more barcode sequences in the AAV library. In some embodiments, each AAV viral vector comprises at least one construct, and wherein the at least one construct comprises a barcode sequence that is identical to the at least one barcode sequence of the mammalian cells that produced the AAV viral vector.

In some embodiments, provided are methods comprising: (a) producing an AAV library, wherein the AAV library comprises a plurality of constructs from a library of mammalian cells, wherein the library of mammalian cells comprises a plurality of mammalian cells, wherein each mammalian cell of the plurality individually comprises: (i) at least one engineered sequence, (ii) at least one barcode sequence, and (iii) at least one polynucleotide comprising one or more nucleic acid sequences essential for production of the viral vector, wherein each AAV viral vector comprises at least one construct, and wherein the at least one construct comprises a barcode sequence that is derived from the at least one barcode sequence of the mammalian cells that produced the AAV viral vector; and (b) detecting the one or more barcode sequences in the AAV library by next generation sequencing. In some embodiments, each AAV viral vector comprises at least one construct, and wherein the at least one construct comprises a barcode sequence that is identical to the at least one barcode sequence of the mammalian cells that produced the AAV viral vector. In some embodiments, provided methods further comprise a step of single cell sequencing of at least one or all nucleic acid sequences or derivatives thereof, within each individual cell of the library of mammalian cells, where the at least one or all nucleic acid sequences, or derivatives thereof, comprise a single cell identity sequence during a single cell sequencing method, and wherein the at least one or all nucleic acid sequences, or derivatives thereof, comprise at least one library construct In some embodiments, provided methods of the present disclosure further comprise single cell sequencing of at least one or all nucleic acid sequences, or derivatives thereof, within each individual cell of the library of mammalian cells, where at least one or all nucleic acid sequences, or derivatives thereof, comprise a single cell identity sequence during a single cell sequencing method, and where at least one or all nucleic acid sequences, or derivatives thereof, comprise at least one library variant comprising at least one identifier.

In some embodiments, provided methods of the present disclosure further comprise introduction of a second library construct into a mammalian cell, where the mammalian cell comprises at least one perturbation derived from a first library construct, and wherein the second library construct comprises at least one engineered sequence comprising at least one identifier positioned between the first set of two viral repeat sequences. In some embodiments, a second plurality of library constructs is introduced into a plurality of mammalian cells, wherein the plurality of mammalian cells comprises at least one perturbation derived from a first plurality of library constructs, and wherein the second plurality of library constructs comprise a plurality of engineered sequences, wherein each individual library construct in the second plurality of library constructs comprise at least one identifier positioned between the first set of two viral repeat sequences. In some embodiments, provided methods further comprise detection of the one or more identifiers and/or the one or more engineered sequences by single cell sequencing and/or next generation sequencing. In some embodiments, provided methods include more than two rounds of library construct introduction and detection of the one or more identifiers and/or the one or more engineered sequences. In some embodiments, provided methods further include use of machine learning approaches to develop a machine learning model to identify desirable combinations of target perturbations.

In some embodiments, provided methods of the present disclosure further comprise a step of removing at least one identifier a mammalian cell. In some embodiments, where provided mammalian cells and/or library constructs include a reporter and/or selectable marker, provided methods may include a step of removing the reporter and/or selectable marker.

Throughout the description, where systems or compositions are described as having, including, or comprising specific components, or where methods are described as having, including, or comprising specific steps, it is contemplated that, additionally, there are systems or compositions of the present invention that consist essentially of, or consist of, the recited components, and that there are methods according to the present invention that consist essentially of, or consist of, the recited steps.

It should be understood that the order of steps or order for performing certain action is immaterial so long as the invention remains operable. Moreover, two or more steps or actions may be conducted simultaneously.

The following description is for illustration and exemplification of the disclosure only, and is not intended to limit the invention to the specific embodiments described.

BRIEF DESCRIPTION OF THE DRAWING

The Drawing included herein, which is composed of the following Figures, is for illustration purposes only and not for limitation.

CERTAIN DEFINITIONS

Figure 1:
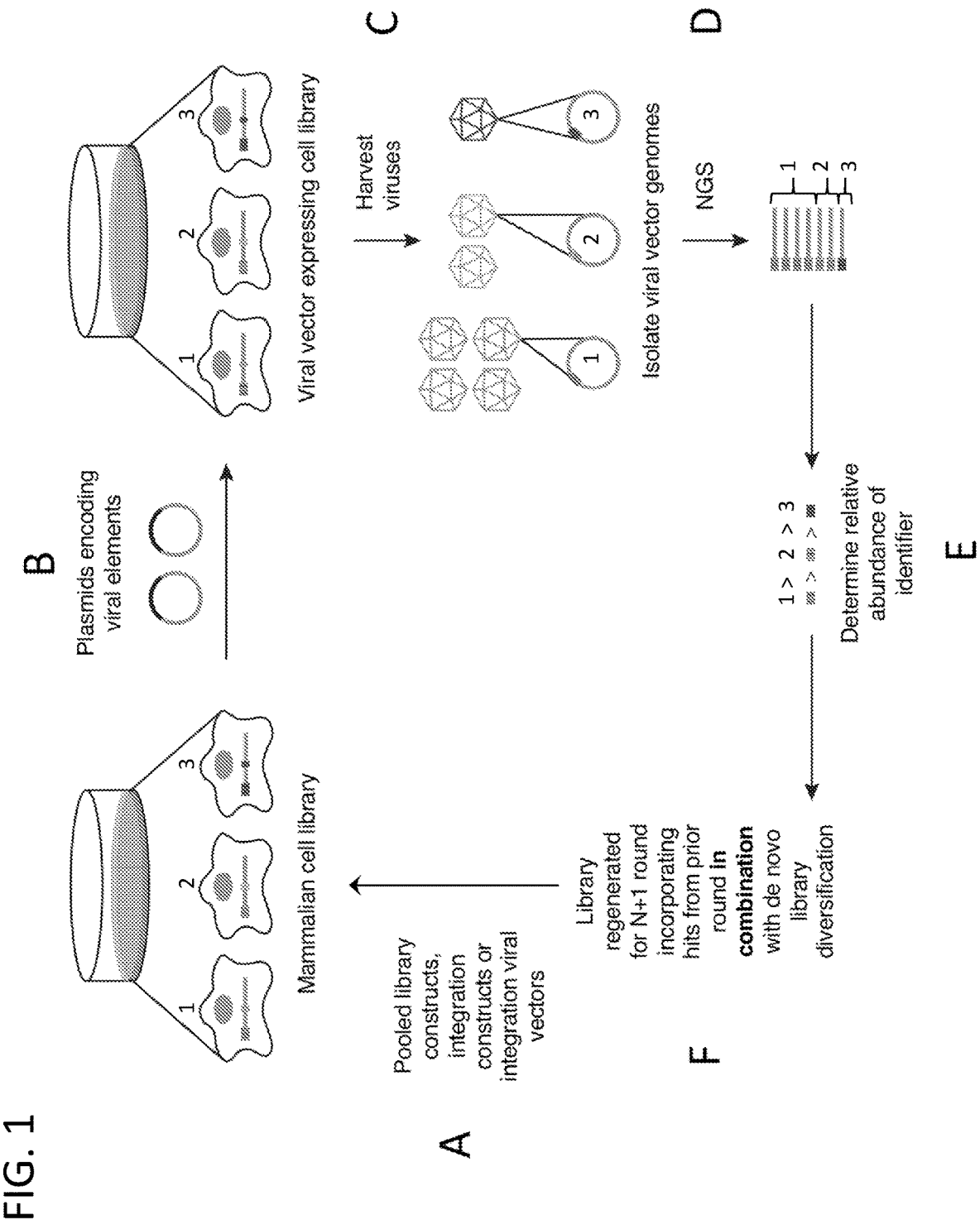
FIG. 1 depicts a schematic of a technology platform for identifying or characterizing viral vector production of mammalian cells in a library, where viral vectors take up an identifier associated with the mammalian cells from which they are expressed.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

In this application, unless otherwise clear from context, (i) the terms "a" and "an" are used herein to refer to one or to more than one (i.e., to at least one) of the grammatical object of the article; (ii) the term "or" may be understood to mean "and/or"; (iii) the terms "comprising" and "including" may be understood to encompass itemized components or steps whether presented by themselves or together with one or more additional components or steps; and (iv) where ranges are provided, endpoints are included.

Throughout the specification, whenever a polynucleotide or polypeptide is represented by a sequence of letters (e.g., A, C, G, and T, which denote adenosine, cytidine, guanosine, and thymidine, respectively in the case of a polynucleotide), such polynucleotides or polypeptides are presented in 5' to 3' or N-terminus to C-terminus order, from left to right.

About or Approximately: as used herein, the terms "about" or "approximately" may be applied to one or more values of interest, including a value that is similar to a stated reference value. In general, those skilled in the art, familiar with the context, will appreciate the relevant degree of variance encompassed by "about" or "approximately" in that context. In some embodiments, the terms "about" or "approximately" refer to a range of values that fall within ±20% (greater than or less than) of a stated reference value, unless otherwise stated or otherwise evident from context. For example, in some embodiments, the terms "about" or "approximately" may encompass a range of values that within 20%, 19%, 18%, 17%, 16%, 15%, 14%, 13%, 12%, 11%, 10%, 9%, 8%, 7%, 6%, 5%, 4%, 3%, 2%, 1%, or less of a reference value.

Amino acid: As used herein, the term "amino acid" refers to any compound and/or substance that can be incorporated into a polypeptide chain, e.g., through formation of one or more peptide bonds. In some embodiments, an amino acid has a general structure, e.g., $H_2N$—$C(H)(R)$—$COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than standard amino acids, regardless of whether it is prepared synthetically or obtained from a natural source. As will be clear from context, in some embodiments, the term "amino acid" may be used to refer to a free amino acid; in some embodiments it may be used to refer to an amino acid residue of a polypeptide.

Associated with: As used herein, the phrase "associated with" describes two events or entities, if the presence, level and/or form of one is related to, connected to, or correlated with that of the other. For example, a first entity (e.g., an identifier) is considered to be associated with a second entity (e.g., an engineered sequence), if presence and/or level of the first entity is related to or correlates with the presence and/or level of the second entity (e.g., in a mammalian cell, e.g., through cell divisions and/or genetic manipulations). In some embodiments, two or more entities are physically "associated with" one another if they are present in the same cell, genome, chromosome, or genetic region (e.g., such that they are inherited together through multiple generations of mammalian cell division). In some embodiments, a particular entity (e.g., identifier and/or engineered sequence) is considered to be associated with a particular phenotype (e.g., cellular production of viral vector) if its presence, level and/or form, e.g., correlates with an altered level or penetrance of that phenotype (e.g., cells that the entity exhibit increased viral vector production). In some embodiments, two or more entities are physically associated with one another interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Barcode: As used herein, the term "barcode" refers to any molecular feature (e.g., a nucleic acid sequence) that is capable of substantially distinguishing an entity (e.g., molecule, nucleic acid, virus, cell, etc.) or combination of entities amongst a larger heterogeneous population of entities. In some embodiments, a barcode is a type of engineered sequence. In some embodiments, a barcode is a type of engineered nucleic acid sequence. In some embodiments, a barcode is part of a library construct. In some embodiments, the library construct may comprise more than one barcode. Where a library construct comprises one or more barcodes, the one or more barcodes may be comprised (i) within the identifier, (ii) outside the identifier, or (iii) both within and outside the identifier. In some embodiments one or more barcodes, upon detection (e.g., by a next generation sequencing method), indicate the identity of one or more library variants that are not directly detected (e.g., by a next generation sequencing method). In some embodiments, a barcode may comprise a nucleic acid sequence from within a pool of known nucleic acid sequences. In some embodiments, a barcode is an exogenous nucleic acid sequence. In some embodiments, a barcode is an endogenous nucleic acid sequence. In some embodiments, a barcode may comprise both exogenous and endogenous sequences. In general, a barcode comprises a sequence having a length within a range of 3 nucleotides to 50 nucleotides. For example, in some embodiments, a barcode comprises a sequence having a length within a range bounded by a lower limit and an upper limit, the upper limit being larger than the lower limit. In some embodiments, the lower limit may be about 5 nucleotides, about 6 nucleotides, about 7 nucleotides, about 8 nucleotides, about 9 nucleotides, about 10 nucleotides, about 11 nucleotides, about 12 nucleotides, about 13 nucleotides, about 14 nucleotides, or about 15 nucleotides. In some embodiments, the upper limit may be about 10 nucleotides, about 15 nucleotides, about 20 nucleotides, about 25 nucleotides, about 30 nucleotides, about 35 nucleotides, about 40 nucleotides, about 45 nucleotides, or about 50 nucleotides. In some certain embodiments, a barcode comprises a sequence having a length within a range of 5 nucleotides to 25 nucleotides. In some certain embodiments, a barcode comprises a sequence having a length of about 5 nucleotides, about 10 nucleotides, about 15 nucleotides, about 20 nucleotides, or about 25 nucleotides.

Biologic: As used herein, the term "biologic," in its broadest sense, refers to an article made by or derived from a living organism (e.g., manufactured in a living system). Biologics, according to the present disclosure include, but are not limited to, proteins, polypeptides, nucleic acids, polynucleotides, viruses, viral vectors, therapeutic serum, toxins, antitoxins, vaccines, allergenic extracts, blood components or derivatives, gene therapy products, human tissue or cellular products. In some embodiments, a biologic is or comprises a polypeptide-based molecule that may be used to treat, cure, mitigate, prevent, or diagnose a serious or life-threatening disease or medical condition. In some embodiments, a biologic is a therapeutic biologic. Therapeutic biologics are those that may be applicable to the prevention, treatment, or cure of a disease or condition (e.g., in a mammal, e.g., in a human). In some embodiments, a biologic is a diagnostic biologic. In some embodiments, a biologic is used in manufacturing (e.g., in manufacturing of a gene therapy product or cell therapy product). In some certain embodiments, a biologic is a viral vector.

Figure 3:
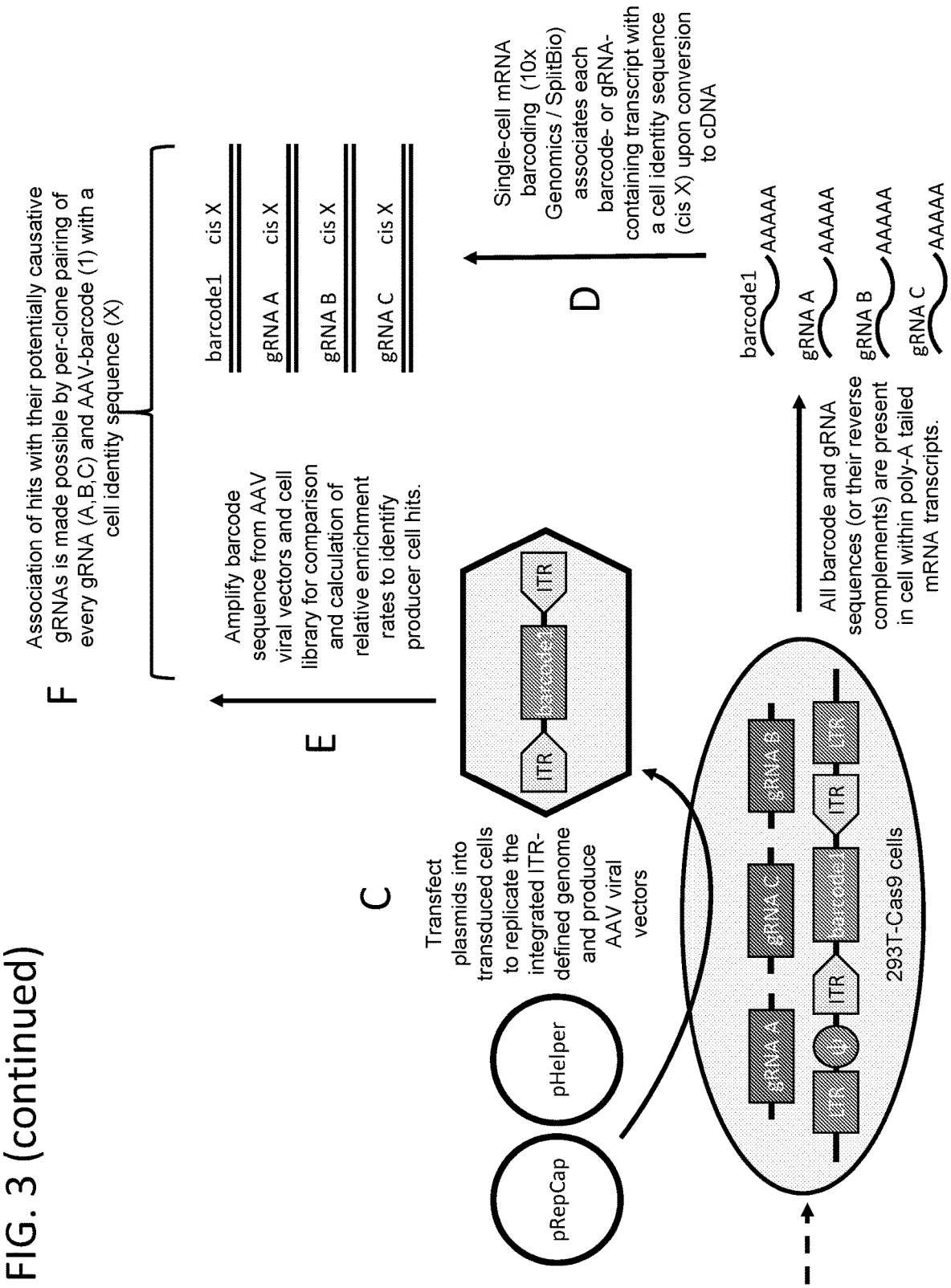
FIG. 3 depicts an exemplary scheme for identifying and/or characterizing viral vector production of mammalian cells in a library by determining relative enrichment of an identifier in a pool of viral vectors and the use of single cell sequencing methods to identify engineered sequences in the mammalian cells.

Cell identity sequence: as used herein refers to a nucleic acid sequence to label all nucleic acids to be sequenced from a particular mammalian cell as part of a single cell sequencing method. The present disclosure encompasses a recognition that single cell sequencing that uses a cell identity sequence is useful for methods where a library construct comprises multiple discontiguous nucleic acid sequences. In such methods, a given cell identity sequence can provide an association of all the identifiers and/or library variants that were present in the same cell. An exemplary schematic of a method that employs a discontiguous library construct and single cell sequencing is depicted in FIG. 3. However, the present disclosure also encompasses a recognition that single cell sequencing that uses a cell identity sequence can in some embodiments also be useful for methods where a library construct comprises a single contiguous nucleic acid sequence. The present disclosure also encompasses a recognition that a single cell identity sequence is specifically appended during reverse transcription of expressed RNAs during a single cell sequencing method. It is understood that constructs or nucleic acids intended for single cell sequencing should be contained in an expressed RNA such that all transcripts can be single cell tagged with a cell identity sequence using an appropriate primer during the reverse transcription step.

Cis-acting Integration Sequence: As used herein, the phrase "cis-acting integration sequence" with regard to a library construct refers to nucleic acid sequence(s) on the library construct itself that promotes integration into a cellular genome (e.g. of a mammalian cell) by one or more trans-acting integration sequences and/or the polypeptide, protein, nucleic acid, or polynucleotide product thereof. In some embodiments, cis-acting integration sequences are included in a library construct and flank a portion of the library construct to be integrated into a cellular genome. In some embodiments, cis-acting integration sequences comprise homology arms, recognition sites, and/or viral repeat sequences.

Comparable: As used herein, the term "comparable" refers to two or more agents, entities, situations, sets of conditions, subjects, populations, etc., that may not be identical to one another but that are sufficiently similar to permit comparison therebetween so that one skilled in the art will appreciate that conclusions may reasonably be drawn based on differences or similarities observed. In some embodiments, comparable sets of agents, entities, situations, sets of conditions, subjects, populations, etc. are characterized by a plurality of substantially identical features and one or a small number of varied features. Those of ordinary skill in the art will understand, in context, what degree of identity is required in any given circumstance for two or more such agents, entities, situations, sets of conditions, subjects, populations, etc. to be considered comparable. For example, those of ordinary skill in the art will appreciate that sets of agents, entities, situations, sets of conditions, subjects, populations, etc. are comparable to one another when characterized by a sufficient number and type of substantially identical features to warrant a reasonable conclusion that differences in results obtained or phenomena observed under or with different sets of circumstances, stimuli, agents, entities, situations, sets of conditions, subjects, populations, etc. are caused by or indicative of the variation in those features that are varied.

Complementary: As used herein, the term "complementary" refers to nucleotides or nucleotide sequences that base-pair according to the standard Watson-Crick complementary rules (adenine "A" base pairs with thymine "T", and guanine "G" base pairs with cytosine "C"). Nucleotide sequences that are "100% complementary" or which exhibit "100% complementarity" are nucleotide sequences which base-pair with one another across the entirety of at least one of the two nucleotide sequences. An oligonucleotide can be "100% complementary" to a template polynucleotide that is longer than the oligonucleotide (i.e., the oligonucleotide is "100% complementary" to the template polynucleotide if the entire sequence of the oligonucleotide base-pairs with a portion of the template polynucleotide). However, nucleic acid sequences that are "complementary" need not be 100% complementary. Generally, the term "complementary" with respect to two or more nucleic acid sequences refers to there being sufficient complementarity across the two nucleic acid sequences such that they hybridize in stringent conditions and/or at temperatures used during annealing phases of amplification methods, e.g., PCR or LCR.

Construct: As used herein, the term "construct" refers to an entity capable of carrying at least one polynucleotide. In some embodiments, a construct can be a plasmid, a transposon, a cosmid, or an artificial chromosome (e.g., a human artificial chromosome (HAC), a yeast artificial chromosome (YAC), a bacterial artificial chromosome (BAC), or a P1-derived artificial chromosome (PAC)). In some embodiments, a construct facilitates transfer of a polynucleotide to a cell. Certain constructs are capable of autonomous replication in a host cell into which they are introduced (e.g., plasmids having an origin of replication). Other constructs can be integrated into the genome of a host cell, and thereby are replicated along with the host genome. In some embodiments, provided are constructs that encode one or more elements of a viral vector. For example, in some embodiments, provided are plasmids encoding one or more elements of a viral vector for expression in a mammalian cell. In some embodiments, provided are constructs that encode one or more elements of a viral vector. In some embodiments, a construct is a viral vector.

Control: As used herein, the term "control" refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. For example, in one experiment, a "test" (i.e., a variable being tested) is applied. In a second experiment, a "control," the variable being tested is not applied. In some embodiments, a control is a historical control (e.g., of a test or assay performed previously, or an amount or result that is previously known). In some embodiments, a control is or comprises a printed or otherwise saved record. In some embodiments, a control is a positive control. In some embodiments, a control is a negative control.

Corresponding to: As used herein in the context of polypeptides and nucleic acids, the term "corresponding to", designates the position/identity of an amino acid residue or a nucleotide residue, respectively, through comparison with an appropriate reference polypeptide or nucleic acid sequence. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at position 190 in the reference polypeptide; those of ordinary skill in the art readily appreciate how to identify "corresponding" amino acids (see. e.g., Benson et al. Nucl. Acids Res. (1 Jan. 2013) 41 (D1): D36-D42; Pearson et al. PNAS Vol. 85, pp. 2444-2448, April 1988). Those skilled in the art will be aware of various sequence alignment strategies, including software programs (e.g., BLAST, FASTA, etc.) that can be utilized, for example, to identify "corresponding" residues in polypeptides and/or nucleic acids in accordance with the present disclosure.

Endogenous: As used herein, the term "endogenous" refers to anything that is present in its natural context. With reference to nucleic acids, "endogenous" can, for example, refer to nucleic acids or sequences thereof, that are derived from inside a cell. For example, an endogenous nucleic acid sequence is one that would naturally be present in the genome of a mammalian cell without manipulation by the hand of man (e.g., in its native location and under control of native expression element(s)).

Engineered: As used herein, the term "engineered" refers to an aspect of having been manipulated by the hand of man. In the context of nucleic acids, engineering can include any type of modification that can be made to a nucleic acid. In some embodiments, a polynucleotide may be considered to be "engineered" when a sequence has been manipulated by the hand of man to generate a sequence that is not found in that context in nature, for example, including a deletion, insertion, substitution, replacement, rearrangement, and/or fusion to a second sequence. For example, an engineered polynucleotide may include two or more sequences that are not linked together in that order in nature, but because they are manipulated by the hand of man to be directly linked to one another in the engineered polynucleotide. Analogously, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). In some embodiments, an engineered cell (e.g., an engineered mammalian cell) refers to a cell that has been subjected to a manipulation, so that its genetic, epigenetic, and/or phenotypic identity is altered relative to an appropriate reference cell such as otherwise identical cell that has not been so manipulated. In some embodiments, the manipulation is or comprises a genetic manipulation. In some embodiments, an engineered cell is one that has been manipulated so that it contains and/or expresses a particular agent of interest (e.g., a protein, a nucleic acid, and/or a particular form thereof) in an altered amount and/or according to altered timing relative to such an appropriate reference cell. As is common practice and is understood by those in the art, progeny of an engineered polynucleotide or cell are typically still referred to as "engineered" even though the actual manipulation was performed on a prior entity.

Engineered sequence: As used herein, the phrase "engineered sequence" refers to a sequence (e.g., of nucleotides) that has been manipulated by the hand of man. In some embodiments, an engineered sequence is an engineered nucleic acid sequence. In some embodiments, an engineered nucleic acid sequence can include a sequence as read in the 5' to 3' direction and/or 3' to 5' direction. An engineered nucleic acid sequence can include any type of modification that can be made to a nucleic acid (e.g., introduction, substitution, deletion, replacement, rearrangement, epigenetic modification, etc.). In some embodiments, an engineered sequence is or includes a genetic modification of the genomic sequence of a mammalian cell. In some embodiments, an engineered sequence is or includes an epigenetic modification of the genomic DNA of the mammalian cell. In some embodiments, an engineered sequence is or includes an episomal sequence (e.g., introduction or modification of a sequence that is present episomally within a cell). In some embodiments, an engineered sequence is or includes an episomal sequence with one or more epigenetic features. In some embodiments an engineered sequence is or includes an identifier. In some embodiments an engineered sequence is or includes a polynucleotide comprising one or more nucleic acid sequences essential for production of a viral vector. In some embodiments an engineered sequence is or includes a perturbation. In some embodiments an engineered sequence is or includes a library variant. In some embodiments an engineered sequence is or includes a payload. In some embodiments an engineered sequence is or includes a perturbation accessory sequence. In some embodiments an engineered sequence is or includes a trans-acting integration sequence. In some embodiments an engineered sequence is or includes a cis-acting integration sequence. In some embodiments an engineered sequence is or includes a library construct. In some embodiments an engineered sequence is or includes a barcode.

Episomal: As used herein, the term "episomal" refers to extrachromosomal genetic material that may autonomously replicate. In some embodiments, genetic material (e.g., DNA) that is episomal may be in the context of a plasmid, a cosmid, a fosmid, an artificial chromosome (e.g., a human artificial chromosome (HAC), a yeast artificial chromosome (YAC), a bacterial artificial chromosome (BAC), or a P1-derived artificial chromosome (PAC)), or a viral vector.

Exogenous: As used herein, the term "exogenous" refers to any entity that is or has been introduced into an organism or a cell. For example, an "exogenous nucleic acid" is a nucleic acid that is derived from outside an organism or cell. In some embodiments, an exogenous nucleic acid in a mammalian cell has been introduced through a cell membrane (e.g., by the hand of man). In some embodiments, an exogenous nucleic acid may be or comprise a nucleotide sequence that exists in the native genome in a non-native context (e.g., at a different location and/or under the control of non-natural expression element(s)). In some embodiments, an exogenous nucleic acid may be or comprise a nucleotide sequence that did not previously exist in the genome of the organism or cell (e.g., from a different organism). Exogenous nucleic acids include exogenous genes. An "exogenous gene" is a nucleic acid or sequence thereof that has been introduced into an organism or a cell (e.g., by transformation/transfection) that codes for the expression of an RNA and/or protein, and is also referred to herein as a "transgene."

Extrachromosomal: As used herein the term "extrachromosomal" refers to genetic material that is not included in a chromosome. In the context of mammalian cells, chromosomes include nuclear chromosomes and mitochondrial chromosomes. Extrachromosomal genetic material includes episomal genetic material.

Gene: As used herein, the term "gene" refers to a DNA sequence in a chromosome that codes for a gene product (e.g., an RNA product, e.g., a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). As used herein, the term "gene" generally refers to a portion of a nucleic acid that encodes a polypeptide or fragment thereof, the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid. In some embodiments, a gene may encode a polypeptide, but that polypeptide may not be functional, e.g., a gene variant may encode a polypeptide that does not function in the same way, or at all, relative to the wild-type gene.

Genome: As used herein, the term "genome" refers to the total genetic information carried by an individual organism or cell, represented by the complete nucleic acid sequences of its chromosomes.

Guide Sequence: As used here, the term "guide sequence" refers to a nucleic acid sequence corresponding to that of a guide RNA for nuclease-mediated editing (e.g., with an RNA-guided nuclease). The terms "guide RNA" and "gRNA" refer to any nucleic acid that promotes the specific association (or "targeting") of an RNA-guided nuclease such as Cas9 or Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). Guide RNAs, whether unimolecular or modular, include a "guide sequence" that is fully or partially complementary to a sequence within a target, such as a DNA sequence in the genome of a cell where editing is desired. Guide sequences are referred to by various names in the literature, including without limitation "targeting domain", "complementarity regions" (e.g., WO 2016/073990 by Cotta-Ramusino et al.), "spacers" (e.g., Briner et al., Molecular Cell 56(2), 333-339, Oct. 23, 2014) and generically as "crRNAs" (e.g., Jiang et al. Nat Biotechnol. 2013 March; 31(3): 233-239). Irrespective of the names they are given, guide sequences are typically about 10 to 30 nucleotides in length. In some embodiments, a guide sequence is 15 to 25 nucleotides in length. In certain embodiments, a guide sequence is 16 to 24 nucleotides in length (for instance, 16, 17, 18, 19, 20, 21, 22, 23 or 24 nucleotides in length). In some embodiments, a guide sequence is at or near the 5' terminus of a gRNA (e.g., with Cas9 or a nuclease derived or obtained therefrom). In some embodiments, a guide sequence is at or near the 3' terminus of a gRNA (e.g., with Cpf1 or a nuclease derived or obtained therefrom).

Heterologous: As used herein, the term "heterologous" refers to any entity that does not naturally occur in the specific context (e.g., cell or organism) in which it is present. In the context of nucleic acids, heterologous refers to sequences that do not naturally occur together (e.g., in the same polynucleotide or in the same cell). In some embodiments, a heterologous sequence can be a rearrangement, replacement, insertion, substitution of a sequence into a non-endogenous context (e.g., from a different genomic position or from a different organism). For example, a heterologous promoter sequence or heterologous enhancer sequence may be one that is naturally associated with a different gene or from a different organism. In some embodiments, a heterologous sequence is present the genome of a mammalian cell. In some embodiments, a heterologous sequence is present episomally in a mammalian cell.

Homology: As used herein, the term "homology" or "homolog" refers to the overall relatedness between oligonucleotide molecules (e.g., DNA molecules and/or RNA molecules) and/or between polypeptide molecules. In some embodiments, oligonucleotide molecules (e.g., DNA molecules and/or RNA molecules) and/or polypeptide molecules are considered to be "homologous" to one another if their sequences are at least 15%, 20%, 25%, 30%, 35%, 40%, 45%, 50%, 55%, 60%, 65%, 70%, 75%, 80%, 85%, 90%, 95%, or 99% identical. In some embodiments, oligonucleotide molecules (e.g., DNA molecules and/or RNA molecules) and/or polypeptide molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

Identifier: As used herein refers to an element that (i) can be detected (e.g., by next generation sequencing) and (ii) enables identification of a mammalian cell or clonal cell line from which a viral vector is produced and/or derived. The present disclosure provides identifiers that are shared and/or transferred between a mammalian cell and a viral vector. In some embodiments, an identifier comprises a nucleic acid sequence. In some embodiments, an identifier comprises one or more barcodes, one or more library variants, or a combination thereof. In some embodiments, an identifier comprises a sequence that can be detected, e.g., by PCR (e.g., quantitative PCR), hybridization (e.g., using probes), and/or sequencing (e.g., next generation sequencing and/or Sanger sequencing). In some embodiments, an identifier is or comprises a nucleic acid sequence that is shared and/or transferred between a mammalian cell and a viral vector. In some embodiments, an identifier is included in a library construct (e.g. for introduction into mammalian cells). In some embodiments, an identifier is included in a library construct between genetic architecture appropriate for packaging of the identifier into a viral vector (e.g., viral repeat sequences, e.g., AAV ITR sequences). In some embodiments, an identifier is present in the genome (e.g., between viral repeat sequences) of a viral vector. In some embodiments, detection of an identifier in the genome (e.g., between viral repeat sequences) of a viral vector is associated with a mammalian cell or clonal cell line from which the viral vector was produced or derived. In some embodiments, detection of an identifier in the genome (e.g., between viral repeat sequences) of a viral vector is associated with the presence of one or more library constructs and/or one or more library variants associated with a mammalian cell or clonal cell line from which the viral vector was produced or derived. In some embodiments, provided methods can include a step of sequencing an identifier (e.g., using next generation sequencing methods) to determine a relative abundance of a particular viral vector in a pool or sample of viral vector.

Identity: As used herein, the term "identity" refers to overall relatedness between polymeric molecules, e.g., between nucleic acid molecules (e.g., DNA molecules and/or RNA molecules) and/or between polypeptide molecules. Calculation of percent identity of two nucleic acid or polypeptide sequences, for example, can be performed by aligning two sequences for optimal comparison purposes (e.g., gaps can be introduced in one or both of a first and a second sequences for optimal alignment and non-identical sequences can be disregarded for comparison purposes). In some embodiments, a length of a sequence aligned for comparison purposes is at least 30%, at least 40%, at least 50%, at least 60%, at least 70%, at least 80%, at least 90%, at least 95%, or substantially 100% of length of a reference sequence; nucleotides at corresponding positions are then compared. When a position in the first sequence is occupied by the same residue (e.g., nucleotide or amino acid) as a corresponding position in the second sequence, then the two molecules (i.e., first and second) are identical at that position. Percent identity between two sequences is a function of the number of identical positions shared by the two sequences being compared, taking into account the number of gaps, and the length of each gap, which needs to be introduced for optimal alignment of the two sequences. Comparison of sequences and determination of percent identity between two sequences can be accomplished using a mathematical algorithm. For example, percent identity between two nucleotide sequences can be determined using the algorithm of Meyers and Miller (CABIOS, 1989, 4: 11-17, which is herein incorporated by reference in its entirety), which has been incorporated into the ALIGN program (version 2.0).

Integration construct or Integration viral vector: As used herein, refers to a construct that promotes genomic integration of a construct, such as a library construct. In some embodiments, an integration construct is an integration viral vector that comprises an enveloped viral vector (e.g., a lentiviral vector). For example, in some embodiments, a library construct is introduced into mammalian cells in the context of an integration viral vector (e.g., a lentiviral vector) to generate mammalian cells with a library construct integrated into the mammalian cell genome; such mammalian cells will produce a viral vector that includes an identifier.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Library construct: as used herein refers to one or more nucleic acid constructs for generating a mammalian cell library. As used herein, a library construct comprises (i) at least one identifier, (ii) genetic architecture appropriate for packaging of the identifier into a viral vector (e.g., viral repeat sequences, e.g., AAV ITR sequences), and (iii) any library variants if not already contained within the identifier. A library construct may also comprise other engineered sequences, such as but not limited to any cis-acting integration sequences (if genomic integration of the library construct) is relevant, and/or any barcodes. In some embodiments, all elements of a library construct are included on a single (i.e., one) contiguous piece of nucleic acid (e.g., DNA). In some embodiments, a library construct refers to multiple, separate and discontiguous pieces of nucleic acid (e.g., DNA). Where a library construct comprises multiple nucleic acids (i.e., a discontiguous library construct), it will comprise at least one construct comprising an identifier positioned between sequences for packaging the identifier into a viral vector (e.g., viral repeat sequences, e.g., AAV ITR sequences). In some embodiments where a library construct is discontiguous, a library construct further comprises one or more constructs, where each individual construct comprises one or more library variants. Provided methods that employ a discontiguous library construct will also include a step of identifying one or more library variants of the library construct (e.g., single cell sequencing of the mammalian cell). For example, FIG. 3 depicts a method with a library construct comprising separate pieces of DNA that shows a cell comprising a construct comprising an identifier (e.g., a barcode flanked by ITRs) and three additional constructs that comprise library variants (e.g., three separate and unique gRNAs), where the identifier (e.g., barcode) is packaged into a viral vector, and the association with the library variants is determined through single cell sequencing. It is envisioned that for many methods where a single, contiguous library construct is employed, single cell sequencing would not always be required, but may be still useful in some contexts.

Library variant: as used herein refers to an element of a library construct that gives rise to a perturbation that varies between cells. For example, in a population of cells, each cell would get a different library construct that comprises a unique library variant or combination of library variants. For example, a library variant may comprise a gene, ORF, gRNA sequence, non-coding nucleic acid, or a plurality and/or combination thereof. In the context of the present disclosure, a library variant is distinct from a barcode, but one or more library variants can be associated with one or more barcodes. In some embodiments, one or more library variants and/or barcodes may be contained within or outside the identifier within the library construct. In some embodiments, one or more barcodes themselves can be directly detected (e.g., in a next generation sequencing method) rather than the library variants themselves. In some embodiments a library variant may be referred to herein as an effector, whereby the library variant effects or brings about the perturbation that varies between cells. In some embodiments, a library variant may itself become the perturbation that varies between cells. For example, in some embodiments, a library variant that is a gRNA is an effector, that along with an RNA-guided nuclease (e.g., perturbation accessory sequence), brings about a deletion within the cell's genomic DNA. In other embodiments, a library variant that is an ORF or a gene sequence, upon its transfection into the cell and in some cases integration into the genomic DNA (e.g., as carried out by trans-acting and cis-acting integration sequences), itself becomes the perturbation or modification of the cell's genetic material.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs.

Payload: As used herein, the term "payload" refers to any entity of interest for delivery by a viral vector produced by methods of the present disclosure. For example, such a payload may be desired to be introduced into a cell, organ, organism, and/or biological system (e.g., comprising cells). In some embodiments, a payload sequence is or comprises a heterologous nucleic acid sequence for delivery by a viral vector of the present disclosure. In some embodiments, a payload sequence comprises one or more of an encoding region, a gene regulatory element, and a transcription terminator. Non-limiting examples of gene regulatory elements include promoters, transcriptional activators, enhancers, and polyadenylation signals. In some embodiments, a payload sequence comprises an encoding region, a gene regulatory element, and a transcription terminator, positioned relative to each other such that the encoding region is between the gene regulatory element and the transcription terminator. In some embodiments, an encoding region encodes a gene product. In some embodiments, the gene product is an RNA. In some embodiments, an encoding region encodes a polypeptide (such as a protein, such as a glycoprotein). In some embodiments, an encoding region encodes a fusion polypeptide and/or a chimeric polypeptide. In some embodiments, the encoding region encodes one gene product. In some embodiments, the encoding region encodes more than one gene product (e.g., 2, 3, 4, 5, 6, 7 or more gene products). In some embodiments, an encoding region encodes a regulatory RNA (e.g., a siRNA, microRNA, etc.). In some particular embodiments, a payload encodes one or more entities for gene editing (e.g., a gRNA-mediated editing system). In some embodiments, a payload encodes a protein product.

Perturbation: As used herein refers to a genetic modification in a mammalian cell a produced viral vector, polynucleotides essential for production of viral vectors, and/or other constructs, that results and/or is identified from a method as described herein. In some embodiments, mammalian cells, produced viral vectors, polynucleotides essential for production of viral vectors, and/or other constructs, include one or more perturbations. These are generated, produced, identified, and/or selected from mammalian cell libraries of the present disclosure for expression and/or production of viral vectors. In some embodiments, a perturbation is a result of one or more library variants. In some embodiments a perturbation is a genetic modification that is not a result of a library variant but a genetic modification that results and/or is identified from the method as described herein. In some embodiments, a perturbation comprises a genetic modification in at least one polynucleotide comprising one or more nucleic acid sequences essential for production of the viral vector. In some embodiments, a perturbation is associated with one or more desired characteristics of a mammalian cell (e.g., for expression of a viral vector (e.g., independently and/or synthetically)) or viral vector. In some embodiments, a perturbation comprises a genomic sequence change (e.g., genomic insertion, deletion, substitution, rearrangement, etc.), an episomal sequence change, and/or an epigenetic modification.

Perturbation accessory sequence: As used herein includes any sequence that aids in creating a perturbation in combination with the library construct. For example, in some embodiments, a library construct comprises a library variant that comprises a gRNA, and a perturbation accessory sequence comprises a sequence encoding an RNA-guided nuclease or other elements for nuclease-mediated perturbing.

Polypeptide: As used herein, the term "polypeptide" refers to any polymeric chain of residues (e.g., amino acids) that are typically linked by peptide bonds. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may include one or more pendant groups or other modifications, e.g., modifying or attached to one or more amino acid side chains, at a polypeptide's N-terminus, at a polypeptide's C-terminus, or any combination thereof. In some embodiments, such pendant groups or modifications may be acetylation, amidation, lipidation, methylation, pegylation, etc., including combinations thereof. In some embodiments, polypeptides may contain L-amino acids, D-amino acids, or both and may contain any of a variety of amino acid modifications or analogs known in the art. In some embodiments, useful modifications may be or include, e.g., terminal acetylation, amidation, methylation, etc. In some embodiments, a protein may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, a protein is antibodies, antibody fragments, biologically active portions thereof, and/or characteristic portions thereof.

Polynucleotide: As used herein, the term "polynucleotide" refers to any polymeric chain of nucleic acids. In some embodiments, a polynucleotide is or comprises RNA; in some embodiments, a polynucleotide is or comprises DNA. In some embodiments, a polynucleotide is, comprises, or consists of one or more natural nucleic acid residues. In some embodiments, a polynucleotide is, comprises, or consists of one or more nucleic acid analogs. In some embodiments, a polynucleotide analog differs from a nucleic acid in that it does not utilize a phosphodiester backbone. Alternatively or additionally, in some embodiments, a polynucleotide has one or more phosphorothioate and/or 5'-N-phosphoramidite linkages rather than phosphodiester bonds. In some embodiments, a polynucleotide is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a polynucleotide is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a polynucleotide comprises one or more modified sugars (e.g., 2'-fluororibose, ribose, 2'-deoxyribose, arabinose, and hexose) as compared with those in natural nucleic acids. In some embodiments, a polynucleotide has a nucleotide sequence that encodes a functional gene product such as an RNA or protein. In some embodiments, a polynucleotide includes one or more introns. In some embodiments, a polynucleotide is prepared by one or more of isolation from a natural source, enzymatic synthesis by polymerization based on a complementary template (in vivo or in vitro), reproduction in a recombinant cell or system, and chemical synthesis. In some embodiments, a polynucleotide is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a polynucleotide is partly or wholly single stranded; in some embodiments, a polynucleotide is partly or wholly double stranded. In some embodiments, a polynucleotide has a nucleotide sequence comprising at least one element that encodes, or is the complement of a sequence that encodes, a polypeptide. In some embodiments, a polynucleotide has enzymatic activity.

Predetermined: As used herein, the term "predetermined" refers to prior to the start of an experiment and/or analysis. For example, in some embodiments, a location or characteristic of an engineered sequence can be considered predetermined when a set of possible outcomes (e.g., an insertion site) is known prior to the physical act of introducing the engineered sequence (e.g., an engineered sequence can be inserted into one of several different genomic locations).

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means.

Reference: As used herein, the term "reference" describes a standard or control relative to which a comparison is performed. For example, in some embodiments, an agent, animal, individual, population, sample, sequence or value of interest is compared with a reference or control agent, animal, individual, population, sample, sequence or value, respectively. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control. In some embodiments, a reference is a negative control reference; in some embodiments, a reference is a positive control reference. In some embodiments, a comparison is performed to a reference cell or reference cell population, which has comparable genetic features and has been cultured under comparable conditions (except with respect to the variable that is being analyzed). In some certain embodiments, a reference cell differs with respect to the presence of at least one engineered sequence and/or at least one barcode sequence but is otherwise comparable.

RNA-guided nuclease: As used herein, the term "RNA-guided nuclease" refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a single- or double-stranded break. RNA-guided nucleases only capable of cleaving a single strand of a double-stranded nucleic acid molecule are referred to herein as nickases. In some embodiments, an RNA-guided nuclease is or is derived from Cas9, Cas Z, CpfI, and/or Fok1.

Trans-acting integration sequence: As used herein, the phrase "trans-acting integration sequence" with regard to a library construct refers to nucleic acid sequences not necessarily included as part of a library construct itself, that are necessary for integration of the library construct into a mammalian cell genome. The trans-acting integration sequence and/or the polypeptide, protein, nucleic acid, or polynucleotide product thereof (e.g., recombinase) carries out integration of a library construct or a portion thereof, into a cellular genome (e.g., a mammalian cell) in coordination with the cis-acting integration sequences (e.g., recombinase sites). In some embodiments, more than one trans-acting integration sequence is necessary for integration of a library construct.

Transformation or Transfection: As used herein, the terms "transformation" or "transfection" refer to any process by which exogenous DNA is introduced into a host cell (e.g., a mammalian host cell). Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection or transduction, electroporation, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Viral Vector: As used herein, the term "viral vector" refers to an entity that is (i) capable of carrying at least one polynucleotide, and that (ii) includes viral proteins (e.g., capsid proteins, e.g., viral capsid proteins and/or variants or derivatives thereof). In some embodiments, a viral vector comprises one or more nucleic acid molecules. In some embodiments, a viral vector may facilitate transfer of nucleic acid to a cell. In some embodiments, a viral vector comprises one or more nucleic acid sequences and one or more viral capsid proteins. In some embodiments, a viral vector comprises capsid proteins and/or nucleic acid sequences derived from an adeno-associated virus (AAV) vector, an adenovirus vector, a lentivirus vector, and/or a retrovirus vector. In some embodiments, a viral vector comprises an envelope.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

DETAILED DESCRIPTION

Biologics, including cell and gene therapies, vaccines, and biologic reagents, are a rapidly growing market. Biologics may be manufactured within cells or themselves be cells (e.g., cell therapy, e.g., CAR-T). For example, mammalian cells may be used to synthesize a virus, which may then be used as a therapeutic (e.g., vaccine, gene therapy), or the mammalian cells may be used as a therapeutic. However, supply chains for producing biologics, and particularly those that employ viral vectors, are highly inefficient. Even subtle changes in a viral vector or mammalian host cell can impact manufacturing yield. For example, viral vector payload and serotype may impact mammalian cell metabolism, viability, viral vector assembly, viral vector production and/or viral vector expression. Biological production of viral vectors, such as in mammalian cell culture, is important in order to reduce costs and also to comply with good manufacturing practices. The present disclosure recognizes a problem with production of viral vectors in that mammalian cell lines are typically not optimized and/or screening platforms to isolate optimized cell lines are also inefficient. Current manufacturing of viral vectors is insufficient because of both the high costs and long production times for biological production and the increasing market demand for larger quantities of viral vectors.

The present disclosure provides, among other things, platform technologies for expressing viral vectors in mammalian cells. The present disclosure provides methods that use a library-based approach to screen, assess, and/or characterize mammalian cells or cell lines based on their capacity to express viral vectors. Provided technologies encompass an insight of having a viral vector take up an identifier (e.g., comprising a barcode sequence and/or a library variant) of a mammalian cell in which it is expressed, thereby enabling sequencing of viral vector genomes (e.g., between viral repeat sequences) to provide an efficient and robust method for identification of mammalian cells with higher viral vector expression and/or other features of viral vector production. Provided methods, systems, and compositions offer a rapid, robust platform for engineering mammalian cells with beneficial viral vector characteristics (e.g., increased viral vector expression, increased duration of expression, increased stability, etc.).

Mammalian Cell Platforms for Viral Vector Expression

The present disclosure provides platform technologies for producing, screening, selecting, engineering, and/or identifying mammalian cell(s) or cell line(s) for expression of a viral vector. The present disclosure provides methods that use a library-based approach with an identifier to indicate the mammalian cell origin within the library. The present disclosure provides a novel platform technology, where viral vectors expressed by the mammalian cells take up an identifier (e.g., comprising a barcode and/or library variant). Viral vectors produced from a mammalian cell library can be pooled and analyzed (e.g., by sequencing, e.g., by next generation sequencing) for desired characteristics. The uptake of an identifier by the viral vectors enables rapid identification of the mammalian cells that produce viral vectors, with desired characteristics such as but not limited to enhanced or improved viral vector production. The present disclosure encompasses a recognition that mammalian cell libraries can be screened for cell lines with desired characteristics of viral vector production (e.g., improved viral vector production) by sequencing identifiers of viral vectors (e.g., comprising a barcode and/or library variant). For example, a relative abundance of a particular identifier amongst a pool of identifiers from viral vectors expressed by a mammalian cell library can correlate with the relative viral vector productivity of a particular mammalian cell line in a library (e.g., a particular identifier in high abundance may correlate with a mammalian cell line with higher viral vector productivity).

FIG. 1 provides a schematic of an exemplary technology for screening mammalian cells for viral vector expression or other viral vector characteristics. Provided technologies employ a mammalian cell library that has been engineered to include an identifier (e.g., comprising a barcode and/or a library variant) with appropriate genetic elements for packaging of the identifier into a viral vector (e.g., viral repeat sequences, e.g., AAV ITRs for expression of an AAV vector) (depicted FIG. 1, step A). In some embodiments, an identifier is in the context of a library construct, which can be a single contiguous polynucleotide or two or more discontiguous polynucleotides. In some embodiments, a library construct further comprises, e.g., at least one library variant. In some embodiments, a library variant may affect viral vector production or other characteristics. In some embodiments, a library variant may give rise to a perturbation, e.g., one or more genetic modifications that may affect viral vector production or other characteristics. In some embodiments, mammalian cells are genetically engineered to include one or more engineered sequences that include an identifier positioned between viral packaging sequences and optionally any of a perturbation, a library variant, a payload, a perturbation accessory sequence, a trans-acting integration sequence and/or a cis-acting integration sequence.

Mammalian cells of the mammalian cell library can also comprise (e.g., is already present episomally and/or integrated within the mammalian cell genome) or be engineered to include (e.g., transfected with) genetic material sufficient to express a viral vector (depicted in FIG. 1, step B). Transfection or transduction of a mammalian cell library with genetic material (e.g., one or more engineered sequences) may be used to generate a viral vector-producing mammalian cell library.

The genetic material can comprise, e.g., viral genes for replication and viral genes that encode necessary viral proteins, e.g., capsid proteins. For AAV vectors, genetic material sufficient to express a viral vector can include (i) genes encoding AAV Rep proteins and AAV Cap proteins; and (ii) adenoviral genes required to support AAV replication (e.g., E2, E4 and VARNA). In some embodiments, a viral vector further comprises a payload (e.g., a nucleic acid encoding a payload). In some embodiments, a payload comprises an expression cassette with promoter, ORF, and polyA signal. In some embodiments, mammalian cells of the mammalian cell library are transfected with genetic material sufficient to express a viral vector including a payload and an identifier.

In some embodiments, provided technologies include a unique approach whereby a viral vector takes up an identifier (e.g., in the viral vector genome, e.g., between viral repeat sequences). Accordingly, each clonal population of mammalian cells of the library will express viral vectors with a unique identifier. This enables direct characterization of the viral vectors and identification of the mammalian cell from which it was produced. Generally, a viral vector-producing mammalian cell library of the present disclosure will include at least an engineered sequence comprising an identifier positioned between sequences for packaging of the identifier into a viral vector (e.g., viral repeat sequences, e.g., AAV ITRs for expression of an AAV vector), and genetic material sufficient for expression of a viral vector of interest. Mammalian cells of a viral vector-producing mammalian cell library may also comprise one or more (e.g., up to 100 unique) library variants and/or perturbations. One or more perturbations may be present in a mammalian cell and/or a viral vector expressed by a mammalian cell.

Any of the engineered sequences (e.g., encoding a viral vector, an identifier, and/or other engineered sequence) can be present episomally (e.g., on one or more plasmids) and/or be integrated into the genome of mammalian cells. For example, in some embodiments, one or more nucleic acid sequences essential for production of the viral vector can be integrated into a mammalian cell. In some embodiments, one or more nucleic acid sequences essential for production of the viral vector can be present episomally in a mammalian cell. In some embodiments, one or more nucleic acid sequences essential for production of the viral vector can be inducibly expressed (e.g., under the control of an inducible promoter).

In some embodiments, viral vector producing mammalian cell libraries are cultured, and viral vectors are harvested using any appropriate method(s) known in the art (depicted in FIG. 1, step C). In some embodiments, total viral vectors produced by the mammalian cells of the library are harvested. In some embodiments, viral vectors produced by the mammalian cells of the library are harvested corresponding to an interval of time. For example, viral vectors can be harvested daily, every two days, every 3 days, or longer interval, to assess viral vector production over a period of time. In some embodiments, mammalian cells can be washed and viral vectors harvested after prolonged periods (e.g., to assess sustained production of viral vectors). In some embodiments, genetic material of viral vectors (e.g., that includes an identifier) is isolated.

The viral vectors can be pooled and genetic material sequenced (e.g., using next generation sequencing) (depicted in FIG. 1, step D). The presence of an identifier in a pool of viral vectors indicates that a mammalian cell or mammalian clonal cell line in the mammalian cell library (that also has an identifier) can produce viral vectors. In some embodiments, a relative abundance of one or more identifiers is determined. In some embodiments, a relative abundance of an identifier determined from a pool of viral vectors correlates with relative viral vector production by the corresponding cell line. In some embodiments, a relative abundance of identifiers can be used to determine a quantity (e.g., relative quantity) of particular viral vectors produced by different mammalian cells in the library. In some embodiments, abundance of identifier in a viral vector pool can be used to determine impact of various engineered sequences (e.g., library variants and/or perturbations) on the viral vector production capacity of mammalian cells in the library.

The present disclosure recognizes that the amount or abundance of viral vectors may be a reflection of a bias (e.g., increased cell division or cell numbers for a particular mammalian cell or mammalian clonal cell line), and not necessarily a level of viral vector production associated with a mammalian cell or clonal cell line. Accordingly, in some embodiments, the amount or abundance of a viral vector may be normalized. In some embodiments, amount or abundance of viral vector detected may be normalized, for example, against an amount of cells and/or quantity of cellular DNA. In some embodiments, a cell library includes approximately the same number of cells within each sample of cells in the library.

Mammalian cells associated with desired viral vector characteristics (e.g., high expression) can be identified and their engineered sequences determined (e.g., by genomic sequencing). For example, mammalian cells can be selected that exhibit increased viral vector production under a manufacturing practice (e.g., under a current good manufacturing practice (cGMP)) as compared to a reference cell. Increased viral vector production can be an increase in the number of viral vectors over a fixed period of time or production for an extended amount of time, as compared to a reference cell. In some embodiments, mammalian cells can be selected that produce viral vectors for a longer amount of time relative to a reference cell (e.g., due to increased viability, increased genomic stability, and/or increased duration of viral vector production). A reference cell can include a comparable mammalian cell that does not include an engineered sequence and/or a standard cell (e.g., that is capable of producing a viral vector).

The selected mammalian cell candidates can generally be used for production of viral vector(s) and/or the corresponding library variants and/or perturbations identified can be used to inform construction of a new mammalian cell library (depicted in FIG. 1, panel F). The library-based platform approach can be repeated until engineered mammalian cells are identified that express viral vectors with desired characteristics and/or in desired quantity. Engineered sequences associated with desired characteristics can be analyzed, for example, using machine learning (ML) approaches to develop a machine learning model. A trained machine learning model is useful for informing future designs and reducing the number of mammalian cell libraries to be screened and/or the size of each mammalian cell library, thereby reducing time and cost. In some embodiments, mammalian cell libraries can be designed and/or the method performed to identify engineered sequences that synergistically interact (e.g., two or more engineered sequences combined) in mammalian cells to have the desired characteristics (e.g., a certain level of viral vector production). In some embodiments, a resulting mammalian cell obtained from the platform technology described herein will have one, two, three, four, five, six, seven, eight, nine, ten, or more engineered sequences (e.g., one, two, three, four, five, six, seven, eight, nine, ten, or more perturbations). In some embodiments, provided methods are useful for producing, screening, selecting, engineering, and/or identifying a mammalian cell with desired properties of viral vector production (e.g., production as a certain level, production for a desired duration, etc.). In some embodiments, provided methods are useful for producing, screening, selecting, engineering, and/or identifying one or more perturbations or combinations of perturbations that affect viral vector production. In some embodiments, selected mammalian cell candidates can be used for production of viral vector(s) after additional modification (e.g., removal of an identifier). In some embodiments, the corresponding library variants and/or perturbations identified can be used to inform construction of an analogous mammalian cell line or cell lines (e.g., perturbations can be introduced into the same ancestral cell line, a similar ancestral cell line wherein one or more polynucleotides comprising one or more nucleic acid sequences essential for production of the viral vector are integrated within the mammalian cell genome, and/or a very different ancestral cell line).

In some embodiments, mammalian cells are engineered to include one or more components of a viral vector that are under the control of an inducible transcriptional control element (e.g., promoter). In some embodiments, a mammalian cell that includes genetic elements of a viral vector are manipulated to further include a library construct. In some embodiments, a mammalian cell comprises a polynucleotide with one or more elements essential for production of a viral vector under the control of an inducible transcriptional control element (e.g., episomally and/or integrated into the mammalian genome) and is further engineered to include a library construct.

One of skill in the art will recognize that while the schematic of FIG. 1 depicts engineering a mammalian cell library to include one or more engineered sequences and one or more identifiers and then introducing genetic elements of a viral vector, these steps for engineering a viral vector-expressing mammalian cell library can be performed in any order and using any methods known in the art. For example, engineering a viral vector expressing mammalian cell library can be performed in any order and using any methods known in the art. For example, in some embodiments, introduction of an engineered sequence(s), identifier(s), and elements of a viral vector are introduced simultaneously or substantially simultaneously. In some embodiments, mammalian cell libraries are generated that comprise unique engineered sequences and polynucleotides essential for formation of a viral vector and subsequently an identifier is introduced. In some embodiments, mammalian cell libraries are generated that comprise unique engineered sequences including identifiers and subsequently polynucleotides essential for formation of a viral vector are introduced.

Provided methods can be used for generating, identifying and/or selecting mammalian cells with desired characteristics for a production of any desired viral vector. Generally, such a viral vector will be functional for its desired purpose. For example, in some embodiments, a viral vector for gene therapy will be functional to deliver a payload (e.g., a nucleic acid, e.g., to target cells). In some embodiments, a viral vector is an oncolytic viral vector that is capable of killing cancer cells. In some embodiments, a viral vector is therapeutically active. However, in some embodiments, provided methods may yield non-functional viral vectors that lack one or more functional characteristics, but retain other characteristics of interest. In some embodiments, a viral vector is non-functional or has reduced function for a particular characteristic. For example, in some embodiments, a viral vector may have a reduced ability to transfer a payload or may not be able to transfer a payload. In some embodiments, a viral vector may have reduced ability to kill cancer cells. In some embodiments, a viral vector may be therapeutically inactive.

Viral Vectors

In some embodiments, mammalian cell lines of the present disclosure are useful for production of viral vectors. In some embodiments, produced viral vectors are used as biologics and/or therapies themselves. In some embodiments, produced viral vectors are used in the research, production, and/or manufacturing processes that generate many biologics and/or therapies. For example, viral vectors can be used in many ways that include but are not limited to vaccines, cancer therapies (e.g., oncolytic therapies), and/or gene therapies (e.g., in vivo gene and/or genomic editing). As another example, viral vectors can be used in many ways that include but are not limited to the research, production, and/or manufacturing of vaccines, cancer therapies (e.g., oncolytic therapies), gene therapies (e.g., ex vivo gene and/or genomic editing), and/or cell therapies (e.g., ex vivo gene and/or genomic editing). Accordingly, there are a large spectrum of viral vectors for these various applications.

Methods of the present disclosure can be used to select and/or identify mammalian cells with beneficial characteristics for expression of a viral vector, e.g., any viral vector known in the art or described herein; the disclosure is not limited to any particular viral vector.

Viral vectors can be of different size, carrying capacity, have different genomic structure (e.g., DNA and/or RNA, and single-stranded and/or double stranded). In some embodiments, a viral vector can be used to deliver nucleic acids to cells for transient expression or long term expression. In some embodiments, a viral vector has a broad range of host cells. In some embodiments, a viral vector can have a limited and/or specific type of host cells.

Provided mammalian cells and/or mammalian cell populations comprise one or more polynucleotides comprising one or more nucleic acid sequences essential for production of a viral vector. In some embodiments, a polynucleotides comprising one or more nucleic acid sequences essential for production of a viral vector is present episomally a mammalian cell. In some embodiments, a polynucleotides comprising one or more nucleic acid sequences essential for production of a viral vector is present in a mammalian cell genome. In some embodiments, one or more nucleic acid sequences essential for production of a viral vector is under the control of an inducible transcriptional control element. For example, in some certain embodiments, one or more nucleic acid sequences essential for production of a viral vector can be integrated into a mammalian cell genome under the control of an inducible transcriptional control element (e.g., inducible promoter and/or inducible enhancer). Viruses from which viral vectors can be derived include, but are not limited to, adeno-associated virus (AAV), adenovirus, lentivirus, alphavirus (e.g., sindbis virus), retrovirus (e.g., gamma retrovirus), polyomavirus (e.g., simian virus 40 (SV40)), papilloma virus (e.g., bovine papilloma virus (BPV)), poxvirus (e.g., vaccinia virus), herpes simplex virus (HSV), measles virus, rhabdovirus (e.g., rabies virus), vesicular stomatitis virus (VSV), picornavirus (e.g., poliovirus), reovirus, senecavirus, echovirus (e.g., RIGVIR), semliki forest virus (SFV), flavivirus, anellovirus (https://www.ringtx.com), newcastle disease virus (NDV), paramyxovirus (e.g., sendai virus), sendai viral vector, orthomyxovirus (e.g., influenzavirus), coronavirus, and hybrid and/or engineered viruses and/or viral vectors.

In some certain embodiments, a viral vector in the context of the present disclosure is derived from an adeno-associated virus, adenovirus, lentivirus, retrovirus, and/or herpes simplex virus.

In some embodiments, mammalian cell lines of the present disclosure are useful for production of viral vectors, such as adeno-associated virus vectors, adenovirus vectors, lentivirus vectors, retrovirus vectors, and/or herpes simplex virus vectors.

In some embodiments, a produced viral vector of the present disclosure is suitable for production and/or manufacturing processes that generate many biologics and/or therapies, using current good manufacturing practices (cGMP). In some embodiments, a viral vector is suitable for use in the industrial-scale manufacturing of a biologic product. In some embodiments, a viral vector is suitable for use in a method of manufacture that conforms with local regulatory standards (e.g., FDA and/or EMA regulatory standards).

Viral vectors may be live and attenuated. In some embodiments, a viral vector may be replication conditional. In some embodiments a viral vector may be replication deficient. In some embodiments a viral vector may be replication incompetent. In some embodiments, a viral vector is replication-defective. In some embodiments, a viral vector is replication competent. In some embodiments, a viral vector is non-pathogenic.

In some embodiments, the present disclosure provides a unique approach whereby a viral vector takes up an identifier from a mammalian cell in which it is expressed and incorporates it into its viral nucleic acid (e.g., viral genome or construct, e.g., between viral repeat sequences). Accordingly, viral vectors produced by mammalian cells and/or technologies of the present disclosure will have an identifier in their viral nucleic acid (e.g., viral genome or construct, e.g., between viral repeat sequences). In some embodiments, a viral vector produced by mammalian cells and/or methods of the present disclosure will comprise a capsid and an engineered sequence such as a nucleic acid, wherein the nucleic acid comprises (i) a payload, (ii) an identifier, and (iii) one or more sequences of a viral genome (e.g., for AAV may be between AAV ITR sequence(s)). In some embodiments, the identifier and/or the payload or a portion of thereof is later removed from the viral vector. In some embodiments, the identifier and/or the payload or a portion thereof is later removed from the viral vector, wherein the payload or a portion thereof is replaced with another payload or a portion thereof.

Adeno-Associated Virus (AAV) Vectors

In some embodiments, viral vectors produced by methods and mammalian cells of the present disclosure are adeno-associated virus (AAV) vectors. AAVs are commonly used viral vectors for gene delivery. In some embodiments, an AAV vector has low immunogenicity (e.g., in humans). In some embodiments, an AAV vector is compatible with a broad range of host cells. In some embodiments, an AAV vector can transduce both dividing and quiescent cells. In some embodiments, a mammalian cell of the present disclosure produces an AAV vector as described herein.

In some embodiments, the present disclosure provides nucleic acid sequences encoding one or more elements essential for production of an AAV vector. Essential elements for an AAV vector can include Rep proteins and/or capsid (Cap) proteins (e.g., VP1, VP2 and VP3, which form an AAV capsid). In some embodiments, essential elements for an AAV vector can be encoded on one or more constructs (e.g., that may be integrated or present episomally within a mammalian cell. In some embodiments, nucleic acids encoding one or more elements essential for production of an AAV vector are integrated into the genome of a mammalian cell. In some embodiments, nucleic acids encoding one or more elements essential for production of an AAV vector are present episomally in a mammalian cell.

In some embodiments, the present disclosure provides AAV vectors that include a capsid and a nucleic acid comprising a payload. In some embodiments, an AAV vector has an icosahedral protein capsid that encompasses a linear, single stranded DNA nucleic acid.

In some embodiments, a viral vector produced by mammalian cells and/or methods of the present disclosure will comprise an AAV capsid and a nucleic acid, wherein the nucleic acid comprises (i) a payload, (ii) an identifier (e.g., comprising a barcode and/or library variant), and (iii) two ITR sequences (e.g., derived from AAV).

In some embodiments, an AAV vector is derived from a human AAV1; AAV2; AAV3b; AAV4; AAV5; AAV6; AAV7; AAV8; AAV9; AAV10; AAV11; AAV 12; AAV13, or any derivative therefrom. In some embodiments, an AAV vector is a synthetic and/or hybrid human AAV vector. In some embodiments, an AAV vector is derived from a bovine AAV (b-AAV); canine AAV (CAAV); mouse AAV1; caprine AAV; rat AAV; or avian AAV (AAAV).

In some embodiments, AAV vectors can be described as having a serotype, which is a description of the capsid strain and the strain of certain sequences of the nucleic acid (e.g., ITRs). For example, in some embodiments an AAV vector may be described as AAV2, wherein the vector has an AAV2 capsid and a nucleic acid that comprises characteristic AAV2 Inverted Terminal Repeats (ITRs). In some embodiments, an AAV vector may be described as a pseudotype, wherein the capsid and ITRs are derived from different AAV strains, for example, AAV2/9 would refer to an AAV vector that comprises a construct utilizing the AAV2 ITRs and an AAV9 capsid.

In some embodiments, an AAV vector does not have a serotype and/or pseudotype. In some embodiments, an AAV vector comprises engineered AAV capsid and/or ITRs (e.g., that do not have significant homology to that of a known AAV serotype).

In some embodiments, AAV vectors of the present disclosure comprise an AAV capsid. In some embodiments, an AAV capsid is from or derived from an AAV capsid of an AAV2, 3, 4, 5, 6, 7, 8, 9, 10, rh8, rh10, rh39, rh43 or Anc80 serotype, or one or more hybrids thereof. In some embodiments, an AAV capsid is from an AAV ancestral serotype. In some embodiments, an AAV capsid is an ancestral (Anc) AAV capsid. An Anc capsid is created from a construct sequence that is constructed using evolutionary probabilities and evolutionary modeling to determine a probable ancestral sequence. Thus, an Anc capsid/construct sequence is not known to have existed in nature. In some embodiments, an AAV capsid is an artificially engineered sequence (e.g., that does not have significant homology to a known AAV serotype capsid).

As provided herein, AAV vectors of the present disclosure may include any combination of AAV capsids and AAV nucleic acids (e.g., comprising a payload and/or AAV ITRs). For example, wild type or variant AAV capsid that encapsidates an AAV nucleic acid comprising an identifier and/or a payload flanked by AAV-derived ITRs.

Generally, an AAV nucleic acid is comprised of single-stranded deoxyribonucleic acid (ssDNA). In some embodiments, an AAV nucleic acid comprises one or more components derived from or modified from a naturally occurring AAV genome. In some embodiments, an AAV nucleic acid comprises inverted terminal repeats (ITRs) sequences that have been derived from or modified from an AAV. In some embodiments, an AAV nucleic acid comprises a payload sequence and two ITRs. In some embodiments, an AAV vector comprises a capsid and a ssDNA comprising a payload sequence and two viral repeat sequences, e.g., ITR sequences, one at each end of the DNA strand (5' and 3').

In some embodiments, provided AAV nucleic acids comprise a payload that includes a coding sequence and one or more regulatory and/or control sequences, and optionally 5' and 3' AAV derived inverted terminal repeats (ITRs). In some embodiments, provided AAV nucleic acids are packaged into an AAV capsid to form an AAV vector.

In certain some embodiments, a viral vector comprises a nucleic acid comprising an identifier and/or a payload sequence and associated regulatory elements that are flanked by 5' or "left" and 3' or "right" AAV ITR sequences. 5' and left designations refer to a position of an ITR sequence relative to an entire construct, read left to right, in a sense direction. One of ordinary skill in the art would understand how to modify a given ITR sequence for use as either a 5'/left or 3'/right ITR, or an antisense version thereof.

In some embodiments, AAV nucleic acids of AAV vectors described herein typically include the cis-acting 5' and 3' ITR sequences (see, e.g., B. J. Carter, in "Handbook of Parvoviruses," ed., P. Tijsser, CRC Press, pp. 155-168, 1990, which is incorporated herein by reference in its entirety). In some embodiments, at least 80% of a typical ITR sequence (e.g., at least 85%, at least 90%, or at least 95%) is incorporated into a construct provided herein. The ability to modify these ITR sequences is within the skill of the art. (See, e.g., texts such as Sambrook et al., "Molecular Cloning. A Laboratory Manual", 2d ed., Cold Spring Harbor Laboratory, New York, 1989; and K. Fisher et al., J Virol. 70:520-532, 1996, each of which is incorporated in its entirety by reference). In some embodiments, an identifier and/or a payload sequence is flanked by 5' and 3' AAV ITR sequences. In some embodiments, an AAV nucleic acid comprises an identifier and a payload flanked by 5' and 3' AAV ITR sequences. The AAV ITR sequences may be obtained from any known AAV, including presently identified AAV types.

In some embodiments, an AAV vector nucleic acid comprises a payload, an identifier, and two AAV ITRs. In some embodiments, an AAV vector comprises a capsid and a dsDNA comprising (i) a payload and/or an identifier, and (ii) two AAV ITR sequences, one at each end of the DNA strand (5' and 3').

Generally, ITRs are able to form a hairpin. The ability to form a hairpin can contribute to an ITR's ability to self-prime, allowing primase-independent synthesis of a second DNA strand. ITRs can also aid in efficient encapsulation of an AAV construct in an AAV vector. An AAV ITR sequence may be obtained from any known AAV, including mammalian AAV types.

In some embodiments, an ITR includes one or more modifications, e.g., truncations, deletions, substitutions or insertions, of a naturally occurring ITR sequence. The ability to modify these ITR sequences is within the skill of the art. (See, e.g., texts such as Sambrook et al. "Molecular Cloning. A Laboratory Manual", 2d ed., Cold Spring Harbor Laboratory, New York (1989); and K. Fisher et al., J Virol., 70:520-532 (1996), each of which is incorporated in its entirety herein by reference). For example, AAV2-derived ITR sequences are about 145 nucleotides in length. In some embodiments, an ITR comprises fewer than 145 nucleotides, e.g., 127, 130, 134 or 141 nucleotides. For example, in some embodiments, an ITR comprises 110, 111, 112, 113, 114, 115, 116, 117, 118, 119, 120, 121, 122, 123,124, 125, 126, 127, 128, 129, 130, 131, 132, 133, 134, 135, 136, 137, 138, 139, 140, 141, 142, 143 144, or 145 nucleotides.

In some embodiments, an AAV vector payload also comprises conventional control elements that are operably linked to the coding sequence in a manner that permits its transcription, translation and/or expression in a cell transfected with a construct or infected with the viral vector produced by the disclosure. In some embodiments, an AAV vector payload optionally comprises a promoter, an enhancer, an untranslated region (e.g., a 5' UTR, 3' UTR), a Kozak sequence, an internal ribosomal entry site (IRES), splicing sites (e.g., an acceptor site, a donor site), a polyadenylation site, and/or any combination thereof.

In some embodiments, an AAV vector payload is less than 4 kb. In some embodiments, an AAV vector payload can include a sequence that is at least 500 bp, at least 1 kb, at least 1.5 kb, at least 2 kb, at least 2.5 kb, at least 3 kb, at least 3.5 kb, at least 4 kb, or at least 4.5 kb. In some embodiments, an AAV vector payload can include a sequence that is at most 7.5 kb, at most 7 kb, at most 6.5 kb, at most 6 kb, at most 5.5 kb, at most 5 kb, at most 4.5 kb, at most 4 kb, at most 3.5 kb, at most 3 kb, or at most 2.5 kb. In some embodiments, an AAV vector payload can include a sequence that is about 1 kb to about 2 kb, about 1 kb to about 3 kb, about 1 kb to about 4 kb, about 1 kb to about 5 kb, about 2 kb to about 3 kb, about 2 kb to about 4 kb, about 2 kb to about 5kb, about 3 kb to about 4 kb, about 3 kb to about 5 kb, or about 4 kb to about 5 kb.

In some embodiments, an AAV vector can direct long-term expression of a payload. In some embodiments, an AAV vector can direct transient expression of a payload.

In some embodiments, an AAV vector produced by mammalian cells and/or methods of the present disclosure will comprise an AAV capsid and a nucleic acid, wherein the nucleic acid comprises (i) a payload, (ii) an identifier (e.g., a barcode and/or a library variant), and (iii) two viral repeat sequences (e.g., ITRs derived from AAV).

In some embodiments, mammalian cells of a mammalian cell library are genetically modified to comprise one or more nucleic acid sequences essential for production of an AAV vector. In some embodiments, mammalian cells of a mammalian cell library may have one or more AAV vector components provided such as, e.g., rep sequences, cap sequences, and helper functions required for producing an AAV vector. In some embodiments, one or more components of an AAV vector (e.g., an AAV Rep gene, an AAV Cap gene, one or more helper genes, or a combination thereof) are under the control of an inducible transcriptional control element (e.g., promoter and/or enhancer). In some embodiments, a mammalian cell (e.g., of a population of mammalian cells) comprises: (i) an identifier positioned between two viral repeat sequences, and (ii) one or more polynucleotides comprising an AAV Rep gene, an AAV Cap gene, one or more helper genes, and/or a combination thereof, wherein the mammalian cell(s) produce an AAV vector comprising the identifier. In some embodiments, the AAV vector comprises a payload. In some embodiments, an identifier and/or payload or a portion of thereof is later removed from the AAV vector. In some embodiments where an identifier and/or payload or a portion thereof was removed from the AAV vector, the payload or a portion thereof is replaced with a different payload or a portion thereof.

Adenovirus Vectors

In some embodiments, viral vectors produced by methods and mammalian cells of the present disclosure are adenovirus vectors. Adenoviruses are non-enveloped viruses that are commonly used as vaccines because of the strong immunogenic response they induce. Some adenoviruses are utilized for cancer therapy because of their ability to preferentially infect and kill cancer cells.

In some embodiments, an adenovirus vector is derived from a human adenovirus. Human adenoviruses encompass a family of at least 51 serotypes that are classified into several subgroups. For example, subgroup A includes adenovirus serotypes 12, 18, and 31. Subgroup B includes adenovirus serotypes 3, 7, 11a, 11p, 14, 16, 21, 34, 35 and 50. Subgroup C includes adenovirus serotypes 1, 2, 5, and 6. Subgroup D includes adenovirus serotypes 8, 9, 10, 13, 15, 17, 19, 19p, 20, 22-30, 32, 33, 36-39, 42-49 and 51. Subgroup E includes adenovirus serotype 4. Subgroup F includes adenovirus serotypes 40 and 41. An adenovirus vector of the present disclosure can be of any adenovirus group, subgroup, and/or serotype.

In some embodiments, an adenovirus vector is derived from any serotype, such as a serotype 1 to a serotype 51 (e.g. 1, 2, 4, 5 . . . 51). For example, in some embodiments, an adenovirus is an adenovirus type 2 or adenovirus type 5. In some certain embodiments, an adenovirus vector is derived, at least in part, from adenovirus type 5.

In some embodiments, an adenovirus vector is replication-defective (e.g., certain essential viral genes are deleted and/or replaced with a payload sequence). Any of the adenovirus vectors used in methods described herein can include a deletion in any one or more of the E1, E2a, E2b, E3, or E4 coding regions. In some embodiments, an adenovirus vector is replication-defective and lacks the E4 locus (e.g., E4 coding region is deleted). In some embodiments, a replication-defective adenovirus vector is useful as a vaccine, for cancer therapy and/or for gene therapy.

Generally, adenoviruses are characterized by high transduction efficiency and direct high transgene expression. In some embodiments, an adenovirus vector can direct transient expression of a payload. In some embodiments, an adenovirus vector directs transient expression of a payload in a target cell.

In some embodiments, an adenovirus vector is replication-competent. For example, replication-competent adenovirus vectors (e.g., oncolytic vectors) can be engineered to replicate preferentially in cancer cells and to destroy cancer cells through the natural process of lytic viral replication.

In some embodiments, the present disclosure provides adenovirus vectors that include a capsid and a nucleic acid comprising a payload. In some embodiments, an adenovirus vector has an icosahedral protein capsid that encompasses a linear duplex nucleic acid. In some embodiments, an adenovirus vector is about 90-100 nm in diameter. In some embodiments, an adenovirus vector has an icosahedral protein capsid that encompasses a linear, double stranded DNA.

Generally, an adenovirus vector nucleic acid is comprised of double-stranded DNA (dsDNA) and has one or more components derived from or modified from a naturally occurring adenovirus genome. In some embodiments, an adenovirus vector nucleic acid comprises inverted terminal repeats (ITRs) sequences that have been derived from or modified from an adenovirus of any serotype (e.g., adenovirus type 5). In some embodiments, an adenovirus vector nucleic acid comprises a payload and two viral repeat sequences, such as ITRs. In some embodiments, an adenovirus vector nucleic acid comprises an identifier and two viral repeat sequences, such as ITRs. In some embodiments, an adenovirus vector nucleic acid comprises a payload, an identifier, and two viral repeat sequences, such as ITRs. In some embodiments, an adenovirus vector comprises a capsid and a dsDNA comprising (i) a payload and/or an identifier, and (ii) two ITR sequences, one at each end of the DNA strand (5' and 3').

In some embodiments, adenovirus ITRs have a sequence that has a length about 40 bp to about 200 bp. For example, ITRs of human adenovirus type 5 are 103 bp. In some embodiments, an adenovirus ITR comprises a length of about 30 bp, about 40 bp, about 50 bp, about 60 bp, about 70 bp, about 80 bp, about 90 bp, about 100 bp, about 110 bp, about 120 bp, about 130 bp, about 140 bp, about 150 bp, about 160 bp, about 170 bp, about 180 bp, about 190 bp, about 200 bp, about 220 bp, about 240 bp, about 260 bp, about 280 bp, about 300 bp, about 325 bp, about 350 bp, about 375 bp, or about 400 bp. In some certain embodiments, an adenovirus ITR sequence is about 50 to about 250 bp.

In some embodiments, provided adenovirus vectors comprise an adenoviral-derived capsid and a nucleic acid that comprises a payload and one or more adenovirus-derived sequences (e.g., such as ITRs). In some embodiments, provided adenovirus vectors comprise an adenoviral-derived capsid and a nucleic acid that comprises an identifier, a payload, and at least two viral repeat sequences. In some embodiments, an adenoviral vector comprises an identifier that comprises a barcode and/or a library variant. In some embodiments, an adenoviral vector payload includes a coding sequence and one or more regulatory and/or control sequences. In some embodiments, an adenoviral vector comprises 5' and 3' adenovirus-derived inverted terminal repeats (ITRs). In some certain embodiments, an adenovirus vector comprises a capsid and an engineered adenovirus genome, wherein the engineered genome comprises a deletion of certain sequences (e.g., an E1 deletion and/or E3 deletion) and an insertion of a payload and/or an identifier.

In some embodiments, an adenovirus vector payload is less than 7.5 kb. In some embodiments, an adenovirus vector payload can include a sequence that is at least 500 bp, at least 1 kb, at least 1.5 kb, at least 2 kb, at least 2.5 kb, at least 3 kb, at least 3.5 kb, at least 4 kb, at least 4.5 kb, at least 5 kb, at least 5.5 kb, at least 6 kb, at least 6.5 kb, at least 7 kb, at least 7.5 kb. In some embodiments, an adenovirus vector payload can include a sequence that is at most 10 kb, at most 9.5 kb, at most 9 kb, at most 8.5 kb, at most 8 kb, at most 7.5 kb, at most 7 kb, at most 6.5 kb, at most 6 kb, at most 5.5 kb, at most 5 kb, at most 4.5 kb, or at most 4 kb. In some embodiments, an adenovirus vector payload can include a sequence that is about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 4 kb, about 2 kb to about 6 kb, about 2 kb to about 8 kb, about 2 kb to about 10kb, about 4 kb to about 6 kb, about 4 kb to about 8 kb, or about 5 kb to about 8 kb.

In some embodiments, an adenovirus vector produced by mammalian cells and/or methods of the present disclosure will comprise an adenovirus capsid and a nucleic acid, wherein the nucleic acid comprises (i) a payload, (ii) an identifier (e.g., a barcode and/or a library variant), and (iii) two viral repeat sequences (e.g., ITRs derived from adenovirus).

In some embodiments, mammalian cells of a mammalian cell library are genetically modified to comprise one or more nucleic acid sequences essential for production of an adenovirus vector. In some embodiments, mammalian cells of a mammalian cell library may have one or more adenovirus vector components provided such as, e.g., rep sequences, cap sequences, and helper functions required for producing an adenovirus vector. In some embodiments, one or more components of an adenovirus vector (e.g., an adenovirus Rep gene, an adenovirus Cap gene, one or more helper genes, or a combination thereof) are under the control of an inducible transcriptional control element (e.g., promoter and/or enhancer). In some embodiments, a mammalian cell (e.g., of a population of mammalian cells) comprises: (i) an identifier positioned between two viral repeat sequences, and (ii) one or more polynucleotides comprising an adenovirus Rep gene, an adenovirus Cap gene, one or more helper genes, and/or a combination thereof, wherein the mammalian cell(s) produce adenovirus vector comprising the identifier. In some embodiments, the adenovirus vector comprises a payload. In some embodiments, an identifier and/or payload or a portion of thereof is later removed from the adenovirus vector. In some embodiments where an identifier and/or payload or a portion thereof was removed from the adenovirus vector, the payload or a portion thereof is replaced with a different payload or a portion thereof.

Retroviral and Lentivirus Vectors

In some embodiments, viral vectors produced by methods and mammalian cells of the present disclosure are retroviral vectors. Retroviruses are enveloped viruses that replicate in a host cell by using a viral reverse transcriptase enzyme to transcribe its RNA into DNA. The retroviral DNA replicates as part of the host genome and is referred to as a provirus. Retroviral vectors may include, but are not limited to, those based upon or derived from murine leukemia virus (MuLV), gibbon ape leukemia virus (GaLV), ecotropic retroviruses, simian immunodeficiency virus (SIV), human immunodeficiency virus (HIV), and combinations thereof.

In some embodiments, viral vectors produced by methods and mammalian cells of the present disclosure are lentivirus vectors. Lentiviral vectors are versatile tools because of their ability to transduce non-dividing cells. In some embodiments, a lentivirus vector is capable of infecting infect both dividing and non-dividing cells. Generally, lentiviral vectors enable long-term and/or stable gene expression and are integrated into a host cell genome.

Lentiviruses are enveloped particles that are about 80 to about 120 nm in diameter. In some embodiments, the present disclosure provides lentiviral vectors have a diameter within a range of about 50 nm to about 200 nm in diameter. In some embodiments, the present disclosure provides lentiviral vectors have a diameter within a range of about 80 nm to about 120 nm in diameter.

Lentiviruses may contain several structural proteins, including matrix, capsid, nucleocapsid, envelope, and reverse transcriptase proteins. In some embodiments, the present disclosure provides lentiviral vectors that include a capsid, an envelope. In some embodiments, the present disclosure provides lentiviral vectors that include a capsid, an envelope, and a nucleic acid. In some embodiments, the present disclosure provides lentiviral vectors that include a capsid, an envelope, and a nucleic acid that comprises a payload and/or an identifier.

In some embodiments, a lentivirus vector produced by mammalian cells and/or methods of the present disclosure will comprise a lentivirus capsid (or a derivative thereof), an envelope, and a nucleic acid, where the nucleic acid comprises (i) a payload, (ii) an identifier, and (iii) two long terminal repeat (LTR) sequences (e.g., derived from lentivirus). In some embodiments, the two LTR sequences are capable packaging a nucleic acid into a lentiviral vector. In some embodiments, a lentivirus vector comprises a lentiviral Psi sequence (or a derivative or engineered variant thereof).

In some embodiments, lentiviral vectors include those based on Human Immunodeficiency Virus (HIV-1), HIV-2, feline immunodeficiency virus (FIV), equine infectious anemia virus, Simian Immunodeficiency Virus (SIV), and maedi-visna virus (MVV). In some embodiments, a lentiviral nucleic acid (i.e., engineered genome) and envelope glycoproteins will be based on different viruses, such that the resulting viral vector is pseudotyped.

In some embodiments, a lentiviral vector is derived from HIV-1. In some embodiments, a lentiviral vector is derived from HIV-1 and comprises capsid protein and nucleic acid comprising (i) a payload, (ii) an identifier, and (iii) two long terminal repeat (LTR) sequences (e.g., derived from lentivirus). In some embodiments, a lentiviral vector is a HIV vector and wherein the mammalian cell comprises two viral repeat sequences comprising HIV LTR sequences. In some embodiments, a lentiviral vector is a SIV vector and wherein the mammalian cell comprises two viral repeat sequences comprising SIV LTR sequences. In some embodiments, a lentiviral vector is an equine infectious anemia viral vector and wherein the mammalian cell comprises two viral repeat sequences comprising equine infectious anemia viral LTR sequences. In some embodiments, a lentiviral vector is a FIV vector and wherein the mammalian cell comprises two viral repeat sequences comprising FIV LTR sequences. In some embodiments, a lentiviral vector is a visna viral vector and wherein the mammalian cell comprises two viral repeat sequences comprising visna viral LTR sequences.

In some embodiments, a lentiviral vector comprises a gag protein or a fragment thereof. In some embodiments, a lentiviral vector comprises a gag protein that comprises one or more domains selected from a matrix (MA), capsid (CA), and nucleocapsid (NC) domain. In some embodiments, a lentiviral vector comprises an envelope protein or a fragment thereof. In some embodiments, a lentiviral vector is a pseudotyped lentiviral vector, wherein the gag protein and the envelope protein are derived from different viruses. In some embodiments, a lentiviral vector comprises a gag protein and/or an env protein derived from a human immunodeficiency virus (HIV) vector, a simian immunodeficiency virus (SIV) vector, an equine infectious anemia virus vector, a feline immunodeficiency virus vector, a visna virus vector or a derivative thereof.

In some embodiments, a lentiviral vector comprises (i) a lentiviral gag gene, (ii) a lentiviral env gene, (iii) a lentiviral pol gene, or (iv) a combination thereof. In some embodiments, mammalian cells that express a lentiviral vector comprise one or more of (i) a lentiviral gag gene, (ii) a lentiviral env gene, and (iii) a lentiviral pol gene.

In some embodiments, safety features are incorporated into a lentivirus vector, which can include, e.g., self-inactivating long terminal repeat (LTR) and integration deficiency. In certain embodiments, integration deficiency may be conferred by elements of the vector genome but may also derive from elements of the packaging system (e.g., a non-functional integrase protein that may not be part of the vector genome but supplied in trans).

Lentiviruses have a single stranded RNA (ssRNA) genome. In some embodiments, a lentivirus vector comprises a nucleic acid that is ssRNA, and comprises a payload and sequences derived from a lentivirus, such as HIV-1 and/or SIV. In some embodiments, a payload is flanked by long terminal repeat (LTR) sequences, which facilitate integration of the transfer plasmid sequences into the host genome. In some embodiments, a lentivirus vector comprises a nucleic acid that is ssRNA, and comprises an identifier and viral repeat sequences (e.g. HIV-1 and/or SIV LTRs). In some embodiments, a lentivirus vector comprises a nucleic acid that is ssRNA, and comprises a payload, an identifier, and viral repeat sequences (e.g. HIV-1 and/or SIV LTRs).

In some embodiments, a lentiviral vector nucleic acid may comprise sequences from the 5' and 3' LTRs of a lentivirus, and in particular may comprise the R and U5 sequences from the 5' LTR of a lentivirus and an inactivated or self-inactivating 3' LTR from a lentivirus. LTR sequences may be LTR sequences from any lentivirus from any species.

For example, they may be LTR sequences from HIV, SIV, FIV or BIV. In some embodiments, LTR sequences are HIV LTR sequences.

In some embodiments, a lentivirus vector payload is less than 8 kb. In some embodiments, a lentivirus vector payload can include a sequence that is at least 500 bp, at least 1 kb, at least 1.5 kb, at least 2 kb, at least 2.5 kb, at least 3 kb, at least 3.5 kb, at least 4 kb, at least 4.5 kb, at least 5 kb, at least 5.5 kb, at least 6 kb, at least 6.5 kb, at least 7 kb, at least 7.5 kb, or at least 8 kb. In some embodiments, a lentivirus vector payload can include a sequence that is at most 10 kb, at most 9.5 kb, at most 9 kb, at most 8.5 kb, at most 8 kb, at most 7.5 kb, at most 7 kb, at most 6.5 kb, at most 6 kb, at most 5.5 kb, at most 5 kb, at most 4.5 kb, or at most 4 kb. In some embodiments, a lentivirus vector payload can include a sequence that is about 1 kb to about 2 kb, about 1 kb to about 3 kb, about 1 kb to about 4 kb, about 1 kb to about 5 kb, about 1 kb to about 6 kb, about 1 kb to about 7 kb, about 1 kb to about 8 kb, about 1 kb to about 9 kb, about 1 kb to about 10 kb, about 2 kb to about 4 kb, about 2 kb to about 6 kb, about 2 kb to about 8 kb, about 2 kb to about 10kb, about 4 kb to about 6 kb, about 4 kb to about 8 kb, or about 5 kb to about 8 kb.

In some embodiments, mammalian cells of a mammalian cell library are genetically modified to comprise one or more nucleic acid sequences essential for production of a lentivirus vector. In some embodiments, mammalian cells of a mammalian cell library may have one or more lentivirus vector components provided. In some embodiments, one or more components of a lentivirus vector are under the control of an inducible transcriptional control element (e.g., promoter and/or enhancer). In some embodiments, a mammalian cell (e.g., of a population of mammalian cells) comprises: (i) an identifier positioned between two viral repeat sequences, and (ii) one or more polynucleotides essential for production of the lentivirus vector, wherein the mammalian cell(s) produce a lentivirus vector comprising the identifier. In some embodiments, the lentivirus vector comprises a payload. In some embodiments, an identifier and/or payload or a portion thereof is later removed from the lentivirus vector. In some certain embodiments where an identifier and/or payload or a portion thereof was removed from the lentivirus vector, the payload or a portion thereof is replaced with a different payload or a portion thereof.

HSV Vectors

In some embodiments, viral vectors produced by methods and mammalian cells of the present disclosure are herpes simplex viruses (HSV) vectors. HSV is a large enveloped virus with an icosadeltahedral capsid containing a toroidal dsDNA genome. HSV is characterized in vivo by life-long latent infection of neurons. This characteristic makes HSV vectors useful for long-term transgene expression. In some embodiments, an HSV vector is a replication-competent attenuated vector, a replication-incompetent recombinant vector, or a replication-defective helper-dependent vector.

In some embodiments, an HSV vector has a diameter that is within a range that is between about 120 nm to about 200 nm. In some embodiments, an HSV vector is an enveloped particle that is about 120 to about 200 nm in diameter. In some embodiments, an HSV vector has a diameter that is within a range that is between about 100 nm to about 200 nm.

In some embodiments, an HSV vector is from or derived from herpes simplex virus-1 (HSV-1), herpes simplex virus-2 (HSV-2), human cytomegalovirus (HCMV), varicella-zoster virus (VZV), epstein-barr virus (EBV), Kaposi's sarcoma-associated herpesvirus (KSHV), human herpesvirus 6 and/or human herpesvirus 7, and/or a derivative thereof. In some embodiments, an HSV vector is from or derived from HSV-1, HSV-2, or a combination thereof (e.g., include capsid from HSV-1 and include nucleic acid sequences derived from HSV-2).

In some embodiments, a viral vector is an HSV-AAV hybrid vector.

A native HSV-1 genome consists of two stretches of genomic coding regions, referred to as long and short unique segments ($U_L$ and $U_S$), which are each flanked by inverted repeated sequences ($TR_L/IR_L$ and $IR_S/TR_S$, respectively). In some embodiments, an HSV vector is engineered to defect or delete ICP0, ICP4, ICP22, ICP27 and/or ICP47 to reduce toxicity. Methods and considerations for designing HSV vectors are known in the art, for example, Manservigi, et al., *Open Virol J.* 2010; 4: 123-156.

In some embodiments, the present disclosure provides HSV vectors that include capsid protein and a nucleic acid comprising a payload. In some embodiments, an HSV vector comprises a capsid comprising VP5, VP19C, VP23, pre-VP22a and/or the maturational protease (UL26 gene product).

In some embodiments, an HSV nucleic acid further comprises a sequence obtained or derived from an HSV virus (e.g., $TR_L/IR_L$ and/or $IR_S/TR_S$ sequences). In some embodiments, the present disclosure provides HSV vectors that include capsid protein and a nucleic acid comprising HSV viral repeat sequences (e.g., $TR_L/IR_L$ and/or $IR_S/TR_S$ sequences). In some embodiments, the present disclosure provides HSV vectors that include a capsid, an envelope, and a nucleic acid comprising a payload. In some embodiments, the present disclosure provides HSV vectors that include a capsid, an envelope, and a nucleic acid comprising a payload and HSV viral repeat sequences (e.g., $TR_L/IR_L$ and/or $IR_S/TR_S$ sequences).

In some embodiments, a HSV vector payload is less than 100 kb. In some embodiments, a HSV vector payload can include a sequence that is at least 1 kb, at least 2 kb, at least 3 kb, at least 4 kb, at least 5 kb, at least 6 kb, at least 7 kb, at least 8 kb, at least 9 kb, at least 10 kb, at least 15 kb, at least 20 kb, at least 25 kb, at least 30 kb, at least 40 kb, or at least 50 kb. In some embodiments, a HSV vector payload can include a sequence that is at most 150 kb, at most 140 kb, at most 130 kb, at most 120 kb, at most 110 kb, at most 100 kb, at most 90 kb, at most 80 kb, at most 70 kb, at most 60 kb, at most 50 kb, at most 40 kb, at most 30 kb, at most 25 kb, at most 20 kb, at most 15 kb, or at most 10 kb. In some embodiments, a lentivirus vector payload can include a sequence that is about 1 kb to about 150 kb, about 1 kb to about 100 kb, about 1 kb to about 50 kb, about 1 kb to about 25 kb, about 5 kb to about 100 kb, about 5 kb to about 90 kb, about 5 kb to about 80 kb, about 5 kb to about 70 kb, about 5 kb to about 60 kb, about 5 kb to about 50 kb, about 5 kb to about 40 kb, about 5 kb to about 30 kb, about 5 kb to about 25 kb, about 5 kb to about 20 kb, about 5 kb to about 15 kb, about 5 kb to about 10 kb, about 10 kb to about 100 kb, about 10 kb to about 50 kb, or about 10 kb to about 25 kb.

In some embodiments, the present disclosure provides HSV vectors that include capsid protein and a nucleic acid comprising an identifier. In some embodiments, the present disclosure provides HSV vectors that include capsid protein and a nucleic acid comprising an identifier and HSV viral repeat sequences (e.g., $TR_L/IR_L$ and/or $IR_S/TR_S$ sequences). In some embodiments, the present disclosure provides HSV vectors that include a capsid, an envelope, and a nucleic acid comprising an identifier. In some embodiments, the present disclosure provides HSV vectors that include a capsid, an envelope, and a nucleic acid comprising an identifier and HSV viral repeat sequences (e.g., $TR_L/IR_L$ and/or $IR_S/TR_S$ sequences). In some embodiments, a HSV vector comprises the two viral repeat sequences comprising a terminal a sequence.

In some embodiments, an HSV nucleic acid comprises a payload, an identifier, and one or more sequences obtained or derived from an HSV virus. In some embodiments, HSV vectors produced by methods and/or mammalian cells of the present disclosure include an HSV capsid, an envelope, and a nucleic acid comprising a payload, an identifier, and one or more sequences obtained or derived from an HSV virus (e.g., $TR_L/IR_L$ and/or $IR_S/TR_S$ sequences). In some embodiments, an HSV vector comprises an HSV capsid, an envelope, and a nucleic acid comprising a payload and/or an identifier, flanked by HSV viral repeat sequences (e.g., $TR_L/IR_L$ and/or $IR_S/TR_S$ sequences).

In some embodiments, mammalian cells of a mammalian cell library are genetically modified to comprise one or more nucleic acid sequences essential for production of an HSV vector. In some embodiments, mammalian cells of a mammalian cell library may have one or more HSV vector components provided. In some embodiments, one or more components of an HSV vector are under the control of an inducible transcriptional control element (e.g., promoter and/or enhancer). In some embodiments, a mammalian cell (e.g., of a population of mammalian cells) comprises: (i) an identifier positioned between two viral repeat sequences, and (ii) one or more polynucleotides essential for production of the HSV vector, wherein the mammalian cell(s) produce an HSV vector comprising the identifier. In some embodiments, the HSV vector comprises a payload. In some embodiments, an identifier and/or payload or a portion thereof is later removed from the HSV vector. In some certain embodiments where an identifier and/or payload or a portion thereof was removed from the HSV vector, the payload or a portion thereof is replaced with a different payload or a portion thereof.

Library Constructs

The present disclosure provides library constructs for engineering mammalian cells in the context of the present disclosure. In some embodiments, a library construct may comprise two or more, three or more, four or more, five or more, six or more, seven or more, eight or more, nine or more, or ten or more engineered sequences. In some embodiments, a library construct may comprise up to 100 engineered sequences.

A library construct includes at least an identifier and genetic architecture appropriate for packaging of the identifier into a viral vector. A library construct as used herein will also include any library variants. In some embodiments, a library construct further includes a payload for packaging into a viral vector (e.g., between viral repeat sequences). For example, in some embodiments, a library construct comprises (i) an identifier and a payload, which are positioned between viral repeat sequences, and (ii) at least one engineered sequence comprising at least one library variant.

In some embodiments, a library construct further includes one or more constructs that include cis-acting integration sequences (e.g., homology arms, recognition sites, and/or viral repeat sequences). For example, in some embodiments, a library construct comprises (i) an identifier and a payload, which are positioned between viral repeat sequences, (ii) at least one engineered sequence comprising at least one library variant, and (iii) cis-acting integration sequences for integration of the library construct or a portion thereof, into a mammalian cell genome.

In some embodiments, a library construct further includes at least one barcode. For example, in some embodiments, a library construct comprises (i) an identifier and a payload, which are positioned between viral repeat sequences, (ii) at least one engineered sequence comprising at least one library variant, and (iii) at least one barcode. As another example, in some embodiments, a library construct comprises (i) an identifier and a payload, which are positioned between viral repeat sequences, (ii) at least one engineered sequence comprising at least one library variant, (iii) at least one barcode, and (iv) cis-acting integration sequences for integration of the library construct or a portion thereof, into a mammalian genome.

In some embodiments, a library construct further comprises at least one engineered sequence comprising at least one reporter and/or selectable marker. In some embodiments, one or more polynucleotides that comprise a library construct include a reporter and/or selectable marker. Any suitable reporter (e.g., GFP, RFP, YFP, lacZ, etc.) or selectable marker (e.g., that confers a trait that can be artificially selected, e.g., a resistance cassette, etc.) can be used in the context of the present disclosure.

Library Construct Contiguity

A library construct may be a single contiguous construct or multiple discontiguous constructs. In some embodiments, a library construct is a single (i.e., one) contiguous construct. In such embodiments that have a single contiguous library construct, characterization of the resulting viral vectors will provide information directly about any library variants (e.g., determination of an identifier for a viral vector can be correlated directly to any library variants). In some embodiments, a library construct comprises multiple discontiguous constructs. In such embodiments where a library construct is a discontiguous library construct, provided methods will also include a step of identifying library variants in the mammalian cell (e.g., by single cell sequencing).

In some embodiments, a population of mammalian cells comprise a plurality of library constructs, wherein each individual library construct is comprised of a single contiguous nucleic acid sequence, and wherein the plurality of library constructs comprise a plurality of unique nucleic acid sequences. In some embodiments, a population of mammalian cells comprise a plurality of library constructs, wherein each individual library construct is comprised of discontiguous nucleic acid sequences, and wherein the plurality of library constructs comprise a plurality of unique nucleic acid sequences.

In some embodiments, provided mammalian cells comprise a library construct comprising a plurality of polynucleotides, where each individual mammalian cell comprises exactly one unique polynucleotide of a first subset of the plurality of polynucleotides that make up the library construct and two or more unique polynucleotides of a second subset of the plurality of polynucleotides that make up the library construct. For example, in some embodiments, each individual mammalian cell comprises exactly one unique identifier and two or more unique library variants. In some embodiments, provided mammalian cells comprise a library construct comprising a plurality of polynucleotides, where each individual mammalian cell comprises exactly two unique polynucleotide of a first subset of the plurality of polynucleotides that make up the library construct and multiple unique polynucleotides of a second subset of the plurality of polynucleotides that make up the library construct. For example, in some embodiments, each individual mammalian cell comprises exactly two unique identifiers and multiple unique library variants.

Contiguous Library Constructs

In some embodiments, a library construct is a single contiguous construct comprising at least one identifier flanked by genetic architecture appropriate for packaging of the identifier into a viral vector (e.g., viral repeat sequences, e.g., AAV ITR sequences), and any library variants. In some embodiments, a single contiguous library construct comprises an identifier and one or more library variants where both the identifier and the library variants are positioned between viral repeat sequences. In some embodiments, a single contiguous library construct comprises an identifier positioned between viral repeat sequences and one or more library variants positioned outside the viral repeat sequences. In some embodiments, a single contiguous library construct comprises an identifier and one or more library variants positioned between viral repeat sequences and one or more additional library variants positioned outside the viral repeat sequences. In some embodiments, a library construct is a contiguous library construct and comprises a reporter and/or selectable marker. Some exemplary configurations of single contiguous library constructs are provided in Table 1 below.

TABLE 1

Exemplary Library Constructs as a Single Contiguous Construct

| Identifier | Library Variant(s) (e.g., gRNA, ORF, gene (mammalian and/or viral), non-coding nucleic acid, or portion, plurality or combination thereof) | Perturbation | Payload |
| --- | --- | --- | --- |
| Barcode | Library variant(s) located between viral repeat sequences | KO, SNP, activation, repression, insertion | If any, between viral repeat sequences |
| Barcode | Library variant(s) located outside viral repeat sequences | KO, SNP, activation, repression, insertion | If any, between viral repeat sequences |
| Barcode | Library variants located both between viral repeat sequences and outside viral repeat sequences | KO, SNP, activation, repression, insertion | If any, between viral repeat sequences |
| Library Variant - gRNA | Library variant(s) located between viral repeat sequences | KO, SNP, activation, repression, insertion | If any, between viral repeat sequences |
| Library Variant - gRNA | Library variants located both between viral repeat sequences and outside viral repeat sequences | KO, SNP, activation, repression, insertion | If any, between viral repeat sequences |
| Library Variant - ORF | Library variant(s) located between viral repeat sequences | KO, SNP, activation, repression, insertion | If any, between viral repeat sequences |
| Library Variant - ORF | Library variants located both between viral repeat sequences and outside viral repeat sequences | KO, SNP, activation, repression, insertion | If any, between viral repeat sequences |
| Library Variant - gene or portion thereof | Library variant(s) located between viral repeat sequences | KO, SNP, activation, repression, insertion | If any, between viral repeat sequences |
| Library Variant - gene or portion thereof | Library variants located both between viral repeat sequences and outside viral repeat sequences | KO, SNP, activation, repression, insertion | If any, between viral repeat sequences |
| Library Variant - non-coding nucleic acid | Library variant(s) located between viral repeat sequences | KO, SNP, activation, repression, insertion | If any, between viral repeat sequences |
| Library Variant - non-coding nucleic acid | Library variants located both between viral repeat sequences and outside viral repeat sequences | KO, SNP, activation, repression, insertion | If any, between viral repeat sequences |
| Barcode and Library Variant | Library variant(s) located between viral repeat sequences | KO, SNP, activation, repression, insertion | If any, between viral repeat sequences |
| Barcode and Library Variant | Library variants located both between viral repeat sequences and outside viral repeat sequences | KO, SNP, activation, repression, insertion | If any, between viral repeat sequences |

Location in Cell and Copy Number

In some embodiments, a library construct is episomal and/or integrated into the mammalian cell genome. In some embodiments, a library construct is a single contiguous construct that is episomal. In some embodiments, a library construct is a single contiguous construct that is integrated into the mammalian cell genome.

In some embodiments, a library construct further comprises cis-acting integration sequences for integration into a mammalian cell genome. For example, any of the exemplary embodiments of Table 1 may further include cis-acting integration sequences (e.g., homology arms, recognition sites, and/or viral repeat sequences).

In some embodiments, a single contiguous library construct is integrated into a mammalian cell genome. In some embodiments, a single contiguous library construct comprises cis-acting integration sequences. In some embodiments, a single contiguous library construct comprises cis-acting integration sequences located at the 3' and 5' ends of the library construct. In some embodiments, a single contiguous library construct is integrated into a mammalian cell genome at low copy number (e.g., 10 or fewer copies of the library construct). In some embodiments, four or fewer copies of a single contiguous library construct are integrated into a mammalian cell genome. In some embodiments, three or fewer copies of a single contiguous library construct are integrated into a mammalian cell genome. In some embodiments, two or fewer copies of a single contiguous library construct are integrated into a mammalian cell genome. In some embodiments, a single copy of a single contiguous library construct is integrated into a mammalian cell genome.

In some embodiments, a single contiguous library construct is present episomally in a mammalian cell. In some embodiments, a single contiguous library construct is present episomally in a mammalian cell at a low copy number (e.g., 10 or fewer copies of the library construct, e.g., 4 or fewer copies of the library construct, e.g., 3 or fewer copies of the library construct, 2 or fewer copies of the library construct, e.g., single (one) copy of the library construct).

Discontiguous Library Constructs

In some embodiments, provided methods and cells include a discontiguous library construct that enable, e.g., simultaneous screening of multiple library variants. In some embodiments, a library construct comprises multiple discontiguous constructs, where at least one construct comprises an identifier and genetic architecture appropriate for packaging of the identifier into a viral vector. In some embodiments, a discontiguous library construct comprises a first construct comprising an identifier positioned between viral repeat sequences and one or more additional constructs. In some embodiments, a discontiguous library construct comprises a first construct comprising an identifier and a payload positioned between viral repeat sequences and one or more additional constructs comprising one or more library variants. In some embodiments, a discontiguous library construct comprises a first construct comprising, for example, any of the single contiguous library constructs described in Table 1 and one or more additional constructs (e.g., comprising additional library variants).

In some embodiments, an additional, discontiguous library construct comprises a component of a viral vector, e.g., a viral Cap gene, and a barcode. In some embodiments, a library includes library constructs with viral vector components (e.g., Cap genes) that are engineered or of different serotypes. For example a library of viral Cap genes may simultaneously be screened, with Cap genes of different serotypes (e.g., to select mammalian cells with improved characteristics for viral vectors of multiple different serotypes).

In some certain embodiments, one or more additional constructs comprise a library variant that is a variant viral vector component (e.g., engineered or of a varying serotype). In some embodiments, a library construct comprises a library constructs described in Table 1 and one or more additional constructs, where at least one additional construct comprises a viral Cap gene and a barcode.

In some embodiments, multiple distinct libraries of library variants are screened, each of which is associated with a distinct identifier. For example, a library of gRNA library variants and a library of Cap gene variants can simultaneously be screened; this would enable selection of gRNA variants that enrich with different Cap gene library variants (e.g., to select for those gRNA-mediated perturbations that have beneficial effects with different viral vector serotypes).

In some embodiments, a library construct further comprises one, two, three, four, five, or more constructs each comprising one or more library variants. In some embodiments, the one or more additional constructs comprising one or more library variants and/or the construct comprising an identifier, further comprise one or more barcodes.

In some embodiments, a library construct is a discontiguous library construct comprising two, three, four, five, six, seven, eight, nine or ten discontiguous nucleic acid sequences (e.g., individual constructs). In some embodiments, a library construct is a discontiguous library construct comprising up to 20 discontiguous nucleic acid sequences, up to 30 discontiguous nucleic acid sequences, up to 40 discontiguous nucleic acid sequences, up to 50 discontiguous nucleic acid sequences, up to 60 discontiguous nucleic acid sequences, up to 70 discontiguous nucleic acid sequences, up to 80 discontiguous nucleic acid sequences, up to 90 discontiguous nucleic acid sequences, or up to 100 discontiguous nucleic acid sequences.

In some embodiments, a library construct is discontiguous and one or more individual polynucleotides of the library construct include a reporter and/or selectable marker. In some embodiments, a library construct is discontiguous and a plurality of individual polynucleotides of the library construct include a reporter and/or selectable marker. In some embodiments, a library construct is discontiguous and each of the individual polynucleotides of the library construct include a reporter and/or selectable marker.

TABLE 2

Exemplary Discontiguous Library Constructs

| First Construct | Additional Construct(s) |
| --- | --- |
| Barcode positioned between viral repeat sequences (for packaging into a viral vector) | One or more additional constructs each comprising at least one library variant, and optionally each library variant is associated with a barcode. |
| Barcode positioned between viral repeat sequences (for packaging into a viral vector) | One or more additional constructs each comprising two or more library variants, and optionally each library variant is associated with a barcode. |
| Barcode and Payload positioned between viral repeat sequences (for packaging into a viral vector) | One or more additional constructs each comprising at least one library variant, and optionally each library variant is associated with a barcode. |

TABLE 2-continued

Exemplary Discontiguous Library Constructs

| First Construct | Additional Construct(s) |
| --- | --- |
| Barcode and Payload positioned between viral repeat sequences (for packaging into a viral vector) | One or more additional constructs each comprising two or more library variants, and optionally each library variant is associated with a barcode. |
| Library Variant (as identifier) and Payload positioned between viral repeat sequences (for packaging into a viral vector) | One or more additional constructs each comprising at least one library variant, and optionally each library variant is associated with a barcode. |
| Library Variant (as identifier) and Payload positioned between viral repeat sequences (for packaging into a viral vector) | One or more additional constructs each comprising two or more library variants, and optionally each library variant is associated with a barcode. |
| Barcode, Payload, and Library Variant positioned between viral repeat sequences (for packaging into a viral vector) | One or more additional constructs each comprising at least one library variant, and optionally each library variant is associated with a barcode. |
| Barcode, Payload, and Library Variant positioned between viral repeat sequences (for packaging into a viral vector) | One or more additional constructs each comprising two or more library variants, and optionally each library variant is associated with a barcode. |

Location in Cell and Copy Number

In some embodiments, a library construct is discontiguous and one or more individual constructs are episomal. In some embodiments, a library construct is discontiguous and one or more individual constructs are integrated into the mammalian cell genome. In some embodiments, a library construct is discontiguous and at least one construct is episomal and at least one construct is integrated into the mammalian cell genome.

In some embodiments, one or more individual constructs of a discontiguous library construct are integrated into a mammalian cell genome. In some embodiments, one or more individual constructs of a discontiguous library construct comprise cis-acting integration sequences. In some embodiments, one or more individual constructs of a discontiguous library construct comprise comprises cis-acting integration sequences located at the 3' and 5' ends of each construct. In some embodiments, cis-acting integration sequences comprise viral repeat sequences (e.g., positioned outside any viral repeat sequences for packaging into a viral vector).

In some embodiments where a library construct comprises multiple discontiguous constructs, one or more individual constructs are present episomally in a mammalian cell. In some embodiments, one or more individual constructs are present episomally in a mammalian cell at a low copy number (e.g., 10 or fewer copies of the library construct, e.g., 4 or fewer copies of the library construct, e.g., 3 or fewer copies of the library construct, 2 or fewer copies of the library construct, e.g., single (one) copy of the library construct).

Identifiers

The present disclosure provides identifiers that can be detected and that enable identification of a mammalian cell or clonal cell line from which a viral vector is produced and/or derived. In some embodiments, a relative abundance of a particular identifier can be characterized, detected, and/or quantified among a pooled sample of viral vectors (e.g., each comprising an identifier). In some embodiments, at least a portion of an identifier is detected. In some embodiments, an identifier is detected by sequencing (e.g., by next generation sequencing). For example, in some embodiments, at least a portion of an identifier is detected by next generation sequencing and/or single cell sequencing and/or Sanger sequencing.

In some embodiments, an identifier is present in a mammalian cell and also in a viral vector expressed by the mammalian cell. In some embodiments, the present disclosure provides an identifier that is present in the context of a library construct. In some embodiments, an identifier is positioned between sequences for packaging into a viral vector (e.g., viral repeat sequences, e.g., AAV ITRs for expression of an AAV vector). In some embodiments, a viral vector expressed by a mammalian cell as described herein comprises an identifier, for example, in the nucleic acid of the viral vector. In some embodiments, a viral vector expressed by a mammalian cell as described herein comprises a nucleic acid comprising an identifier positioned between two viral repeat sequences (e.g., ITRs for an AAV vector). In some embodiments, at least a portion of an identifier within a viral vector nucleic acid is detected by next generation sequencing and/or single cell sequencing and/or Sanger sequencing.

In some embodiments, a mammalian cell that expresses a viral vector and the viral vector expressed both comprise the same identifier. In some embodiments, an identifier of a viral vector corresponds to the identifier of the mammalian cell from which it was produced. In some embodiments, an identifier of a viral vector is derived from the identifier of the mammalian cell in which it was produced. In some embodiments, an identifier of a viral vector and an identifier of the mammalian cell in which the viral vector was produced are at least 50%, 55%, 60%, 65%, 70%, 75%, 80%, 85%, 90%, 91%, 92%, 93%, 94%, 95%, 96%, 97%, 98%, 99% or more identical.

In some embodiments, an identifier comprises a barcode. In some embodiments, an identifier is or comprises a barcode and is present in a library construct positioned between sequences for packaging into a viral vector (e.g., viral repeat sequences, e.g., AAV ITRs for expression of an AAV vector). In some embodiments, an identifier is or comprises a barcode that is present in the viral vector nucleic acid. In some embodiments, provided methods include detecting an identifier comprising a barcode from a sample of viral vector.

In some embodiments, an identifier comprises a library variant. In some embodiments, an identifier comprises a library variant and is present in a library construct positioned between sequences for packaging into a viral vector (e.g., viral repeat sequences, e.g., AAV ITRs for expression of an AAV vector). In some embodiments, an identifier comprises a library variant that is present in the viral vector nucleic acid. In some embodiments, provided methods include detecting an identifier comprising a library variant from a sample of viral vector.

In some embodiments, an identifier comprises a barcode and a library variant. In some embodiments, an identifier comprises a barcode and a library variant and is present in a library construct positioned between sequences for packaging into a viral vector (e.g., viral repeat sequences, e.g., AAV ITRs for expression of an AAV vector). In some embodiments, an identifier comprises a barcode and a library variant that are present in the viral vector nucleic acid. In some embodiments, provided methods include detecting at least a portion of an identifier comprising a barcode and a library variant from a sample of viral vector.

Barcodes

The present disclosure encompasses a recognition that barcodes may be useful for tracking association between different components. In some embodiments, a barcode is a type of engineered sequence. In some embodiments, a barcode is a type of engineered nucleic acid sequence. In some embodiments a barcode is part of a library construct.

In some embodiments, a library construct comprises one or more barcodes that upon detection (e.g., by a next generation sequencing method) indicate the identity of one or more library variants and/or other engineered sequences that are not directly detected. In some embodiments, one barcode is associated with one or more engineered sequences. For example, in some embodiments, one barcode is associated with one or more library variants. In some embodiments, one barcode is associated with one engineered sequence. For example, in some embodiments, one barcode is associated with one library variant.

In some embodiments, a barcode does not comprise an identifier. In some embodiments, a barcode comprises an identifier. In some embodiments, a barcode comprises an identifier that comprises a nucleic acid sequence. In some embodiments, a barcode comprises an identifier that comprises an engineered sequence. In some embodiments, an identifier does not comprise a barcode. In some embodiments, an identifier comprises a barcode. In some embodiments, an identifier comprises a barcode that comprises a nucleic acid sequence. In some embodiments, an identifier comprises a barcode that comprises an engineered sequence. In some embodiments, a mammalian cell comprises a plurality of barcodes, wherein at least one barcode is an identifier and at least one barcode is not an identifier.

In some embodiments, a library construct comprises a barcode. In some embodiments, a barcode is used as an identifier. In some embodiments, a barcode is used as an identifier and is positioned between two viral repeat sequences. In some embodiments, a barcode is not used as an identifier. In some embodiments, a barcode is not used as an identifier and is positioned between two viral repeat sequences, but is not detected (e.g., by next sequencing). In some embodiments, a library construct comprises a barcode sequence that is positioned outside of two viral repeat sequences and is therefore not packaged into a viral vector.

In some embodiments, a barcode is used as an identifier, wherein the barcode is present in a library construct positioned between sequences for packaging into a viral vector (e.g., viral repeat sequences, e.g., AAV ITRs for expression of an AAV vector). In some embodiments, a barcode is used as an identifier that enables identification of a mammalian cell or clonal cell line from which a viral vector is produced and/or derived). In some embodiments, the relative abundance of the barcode indicates the relative productivity of the mammalian cell from which it was derived. In some embodiments, a barcode is used as an identifier and upon detection (e.g., by a next generation sequencing method), also indicates the identity of one or more library variants and/or engineered sequences that are not directly detected.

In some embodiments, a barcode is not used as an identifier but upon detection (e.g., by a next generation sequencing method and/or a single cell sequencing method) indicates the identity of one or more library variants and/or engineered sequences that are not directly detected. For example, in some embodiments where a library construct is discontiguous, a barcode may be used to track one or more library variants. In some embodiments, a discontiguous library construct comprises a first construct comprising an identifier positioned between viral repeat sequences and one or more additional constructs that each comprise a barcode. In some embodiments, a library construct further comprises one, two, three, four, five, or more constructs each comprising one or more library variants, wherein each individual construct further comprises a barcode. In some embodiments, each library variant is each associated with a unique barcode. As another example, in some embodiments where a library construct is contiguous, a barcode may also be used to track one or more library variants. In some embodiments, a contiguous library construct comprises an identifier positioned between viral repeat sequences. In some embodiments, a library construct further comprises one or more library variants and one or more barcodes. In some embodiments, each library variant is each associated with a unique barcode.

In some embodiments, a barcode comprises a nucleic acid sequence having a length within a range of 3 nucleotides to 50 nucleotides. In some embodiments, a barcode comprises a nucleic acid sequence having a length within a range bounded by a lower limit and an upper limit, the upper limit being larger than the lower limit. In some embodiments, the lower limit may be about 5 nucleotides, about 6 nucleotides, about 7 nucleotides, about 8 nucleotides, about 9 nucleotides, about 10 nucleotides, about 11 nucleotides, about 12 nucleotides, about 13 nucleotides, about 14 nucleotides, or about 15 nucleotides. In some embodiments, the upper limit may be about 10 nucleotides, about 15 nucleotides, about 20 nucleotides, about 25 nucleotides, about 30 nucleotides, about 35 nucleotides, about 40 nucleotides, about 45 nucleotides, or about 50 nucleotides. In some certain embodiments, a barcode comprises a sequence having a length within a range of 5 nucleotides to 25 nucleotides. In some certain embodiments, a barcode comprises about 5 nucleotides, about 10 nucleotides, about 15 nucleotides, about 20 nucleotides, or about 25 nucleotides. In some embodiments, a barcode comprises DNA and/or RNA. In some embodiments, a barcode comprises a DNA sequence having a length within a range of 3 nucleotides to 50 nucleotides, or about 5 nucleotides to about 25 nucleotides. In some embodiments, a barcode comprises a RNA sequence having a length within a range of 3 nucleotides to 50 nucleotides, or about 5 nucleotides to about 25 nucleotides.

In some embodiments, provided methods include detecting a barcode (e.g., by sequencing, e.g., by next-generation sequencing and/or single cell sequencing and/or Sanger sequencing).

Library Variants

The present disclosure provides mammalian cells comprising one or more library variants that gives rise to a perturbation that varies between mammalian cells of a library. In some embodiments, a library variant gives rise to a perturbation that may impact certain characteristics of viral vector production. In some embodiments, a library variant comprises an engineered sequence that gives rise to a perturbation. In some embodiments, a library variant is a sequence change. In some embodiments, a library variant is an epigenetic change. In some embodiments a library variant in an effector, whereby the library variant effects or brings about the perturbation that varies between cells. In some embodiments, a library variant may itself become the perturbation that varies between cells. For example, in some embodiments, a library variant that is a gRNA is an effector, that along with an RNA-guided nuclease (e.g., perturbation accessory sequence), brings about a deletion within the cell's genomic DNA. In other embodiments, a library variant is an ORF or a gene sequence, that upon its transfection into the cell and in some cases integration into the genomic DNA (e.g., as carried out by trans-acting and cis-acting integration sequences), itself becomes the perturbation or modification of the cell's genetic material.

In some embodiments, a library variant comprises a guide RNA sequence. In some embodiments, a library variant comprising a guide RNA sequence can also be an identifier (e.g., a unique gRNA sequence that associates the viral vector with the mammalian cell in which it was produced). In some embodiments, a mammalian cell comprises a library variant comprising a guide sequence, which can be taken up by a viral vector. In some embodiments, a guide sequence is about 10 to 30 nucleotides in length. In some embodiments, a guide sequence is 15 to 25 nucleotides in length. In certain embodiments, a guide sequence is 16 to 24 nucleotides in length (for instance, 16, 17, 18, 19, 20, 21, 22, 23 or 24 nucleotides in length). In some embodiments, a guide sequence is at or near the 5' terminus of a gRNA (e.g., with Cas9 or a nuclease derived or obtained therefrom). In some embodiments, a guide sequence is at or near the 3' terminus of a gRNA (e.g., with Cpf1 or a nuclease derived or obtained therefrom).

In some embodiments, a library variant encodes a guide RNA sequence that is associated with introducing a genomic deletion. In some embodiments, a library variant encodes a guide RNA sequence that is associated with introducing a genomic mutation (e.g., SNP). In some embodiments, a library variant encodes a guide RNA sequence that is associated with introducing a genomic rearrangement. In some embodiments, a library variant encodes a guide RNA sequence that is associated with altering expression of a gene (e.g., activation and/or repression).

In some embodiments, a library variant comprises one or more ORFs. In some embodiments, a library variant comprises an ORF. In some embodiments, a library variant comprises an ORF that encodes an RNA sequence. In some embodiments, an ORF encodes a polypeptide (such as a protein, such as a glycoprotein). In some embodiments, an ORF encodes a fusion polypeptide and/or a chimeric polypeptide.

In some embodiments, a library variant comprises one or more genes. In some embodiments, a library variant comprises a gene. In some embodiments, a library variant comprises a gene that encodes an RNA sequence. In some embodiments, a gene encodes a polypeptide (such as a protein, such as a glycoprotein). In some embodiments, a gene encodes a fusion polypeptide and/or a chimeric polypeptide. In some embodiments, a library variant comprises a mammalian gene. In some embodiments, a library variant comprises a viral gene (e.g., a Cap gene).

In some embodiments, a library variant encodes a non-coding nucleic acid sequence. In some embodiments, an library variant encodes a regulatory RNA sequence (e.g., a siRNA, microRNA, etc.)

In some embodiments, a library variant or a portion thereof is also an identifier, but a library construct may include one or more additional library variants that are not identifiers. In some embodiments, a library variant or a portion thereof is an identifier, where the library variant is positioned between sequences for packaging into a viral vector (e.g., viral repeat sequences, e.g., AAV ITRs for expression of an AAV vector). In some embodiments, a library variant is not an identifier (e.g., is not packaged into a viral vector). In some embodiments where a library variant or a portion thereof is an identifier, the library variant or portion thereof will be unique to that particular mammalian cell or cell line (and viral vectors expressed therefrom).

In some embodiments, a library variant comprises a component of a viral vector. For example an engineered component of a viral vector and/or a component of a varying serotype. In this way different engineered or serotypes of viral vectors may be screened. In some embodiments, a library variant comprises a Cap gene (e.g., of varying serotype).

In some embodiments, provided mammalian cells individually comprise at least one library variant wherein the at least one library variant comprises at least one engineered sequence that comprises at least one gene, at least one ORF, at least one gRNA sequence, at least one unique non-coding nucleic acid, or a combination and/or a plurality thereof. In some embodiments, a mammalian cell or mammalian cell population comprises a plurality of library variants, wherein the plurality of library variants comprise at least one engineered sequence comprising: at least one unique gene, at least one unique ORF, at least one unique gRNA sequence, and/or at least one unique non-coding nucleic acid, or a combination and/or plurality thereof.

In some embodiments, provided mammalian cells comprise one or more library variants. In some embodiments, provided mammalian cells comprise two, three, four, five, six, seven, eight, nine, ten, or more library variants. In some embodiments, provided mammalian cells comprise at least 100 library variants. In some embodiments, provided mammalian cells comprise about 2 to about 100 library variants, about 2 to about 20 library variants, about 3 to about 30 library variants, about 4 to about 40 library variants, about 5 to about 50 library variants. In some embodiments, provided mammalian cells comprise no more than 10 library variants, no more than 20 library variants, no more than 30 library variants, no more than 40 library variants, no more than 50 library variants, no more than 60 library variants, no more than 70 library variants, no more than 80 library variants, no more than 90 library variants, or no more than 100 library variants.

In some embodiments, a library construct comprises at least one library variant and at least one identifier, where both the at least one library variant and the at least one identifier are positioned between two viral repeat sequences. In some embodiments, a library construct comprises at least one library variant and at least one identifier, where the at least one identifier are positioned between two viral repeat sequences and the at least one library variant is positioned outside the two viral repeat sequences. In some embodiments, a library construct comprises at least two library variants and an identifier, where the identifier and at least one library variant are positioned between two viral repeat sequences and at least one library variant is positioned outside the two viral repeat sequences. In some embodiments, a library construct further comprises one or more additional engineered sequences that are positioned between and/or outside the two viral repeat sequences. For example, in some embodiments, a library construct further comprises a payload that is positioned between the two viral repeat sequences. As another example, in some embodiments, a library construct further comprises one or more additional barcodes that are positioned between and/or outside the two viral repeat sequences.

In some embodiments, a library construct comprises an identifier that is a library variant and one or more additional library variants. In some embodiments, a library construct is a single contiguous library construct, comprising an identifier that is a library variant positioned between sequences for packaging into a viral vector (e.g., viral repeat sequences, e.g., AAV ITRs for expression of an AAV vector) and one or more additional library variants positioned outside the sequences for packaging into a viral vector. In some embodiments, a library construct is a discontiguous library construct, comprising an identifier that is a library variant positioned between sequences for packaging into a viral vector (e.g., viral repeat sequences, e.g., AAV ITRs for expression of an AAV vector) and one or more additional constructs comprising one or more additional library variants. In some certain embodiments, one or more additional library variants comprises a component of a viral vector (e.g., a Cap gene).

In some embodiments, a library construct comprises an identifier that is a barcode and one or more library variants. In some embodiments, a library construct is a single contiguous library construct, comprising an identifier that is a barcode positioned between sequences for packaging into a viral vector (e.g., viral repeat sequences, e.g., AAV ITRs for expression of an AAV vector) and one or more library variants positioned outside the sequences for packaging into a viral vector. In some embodiments, a library construct is a discontiguous library construct, comprising an identifier that is a barcode positioned between sequences for packaging into a viral vector (e.g., viral repeat sequences, e.g., AAV ITRs for expression of an AAV vector) and one or more additional constructs comprising one or more library variants.

Some exemplary configurations of library variants in library constructs are provided in Table 3 below.

TABLE 3

Exemplary Library Variants in Library Constructs

| Format | Identifier | Library Variant | Perturbation |
| --- | --- | --- | --- |
| Single Contiguous Library Construct | Library variant between viral repeat sequences | gRNA, integrated into the cell genome | Genomic KO |
| Single Contiguous Library Construct | Barcode between viral repeat sequences | gRNA, integrated into the cell genome | Genomic SNP |
| Single Contiguous Library Construct | Library variant between viral repeat sequences | gRNA, integrated into the cell genome | Genomic activation |
| Single Contiguous Library Construct | Barcode between viral repeat sequences | gRNA, integrated into the cell genome | Genomic repression |
| Single Contiguous Library Construct | Library variant between viral repeat sequences | ORF, integrated into the cell genome | Genomic insertion |
| Single Contiguous Library Construct | Library variant between viral repeat sequences | gRNA, episomal | Genomic KO |
| Single Contiguous Library Construct | Barcode between viral repeat sequences | gRNA, episomal | Genomic SNP |
| Single Contiguous Library Construct | Library variant between viral repeat sequences | gRNA, episomal | Genomic activation |
| Single Contiguous Library Construct | Barcode between viral repeat sequences | gRNA, episomal | Genomic repression |
| Single Contiguous Library Construct | Library variant between viral repeat sequences | ORF, episomal | Episomal new gene or increased copy number |
| Discontiguous Library Construct | Library variant between viral repeat sequences | gRNA, integrated into the cell genome | Genomic KO |
| Discontiguous Library Construct | Barcode between viral repeat sequences | gRNA, integrated into the cell genome | Genomic SNP |
| Discontiguous Library Construct | Library variant between viral repeat sequences | gRNA, integrated into the cell genome | Genomic activation |
| Discontiguous Library Construct | Barcode between viral repeat sequences | gRNA, integrated into the cell genome | Genomic repression |
| Discontiguous Library Construct | Library variant between viral repeat sequences | ORF, integrated into the cell genome | Genomic insertion |
| Discontiguous Library Construct | Barcode between viral repeat sequences | gRNA, episomal | Genomic KO |
| Discontiguous Library Construct | Library variant between viral repeat sequences | gRNA, episomal | Genomic SNP |
| Discontiguous Library Construct | Barcode between viral repeat sequences | gRNA, episomal | Genomic activation |
| Discontiguous Library Construct | Library variant between viral repeat sequences | gRNA, episomal | Genomic repression |
| Discontiguous Library Construct | Barcode between viral repeat sequences | ORF, episomal | Episomal new gene or increased copy number |

In some embodiments, provided methods include detecting one or more library variants (e.g., by sequencing, e.g., by next-generation sequencing).

Viral Repeat Sequences

The present disclosure provides architecture appropriate for packaging of an identifier into a viral vector, such as, e.g., viral repeat sequences. In some embodiments, a viral repeat sequence is a DNA and/or RNA sequence. In some embodiments, a viral repeat sequence is a DNA sequence. In some embodiments, a viral repeat sequence is a RNA sequence. In some embodiments, any nucleic acid sequence positioned in between two viral repeat sequences will be packaged into a viral vector.

In some embodiments, a viral repeat sequence is derived from the same type of virus as a target viral vector. For example, in some embodiments, a target viral vector is an AAV vector and a viral repeat sequence is derived from AAV. In some embodiments, a viral repeat sequence is derived from the same strain of virus as a target viral vector. For example, in some embodiments, a target viral vector is an AAV5 vector and viral repeat sequences are ITRs derived from AAV5. In some embodiments, a viral repeat sequence is derived from the different strain of virus as a target viral vector, but are still capable of packaging into a target viral vector. In some embodiments, a viral repeat sequence is an engineered viral repeat sequence (e.g., includes sequences derived from two or more viruses). In some embodiments, a viral repeat sequence is a synthetic viral repeat sequence (e.g., designed based on a consensus viral repeat sequence).

In some embodiments, a target viral vector is an AAV vector and the viral repeat sequences comprise a sequence of AAV ITRs or derivatives thereof. In some embodiments, viral repeat sequence is derived from the different strain of AAV than an AAV vector, but is still capable of being taken up by the target viral vector. In some embodiments, viral repeat sequences are engineered AAV ITR sequences. In some embodiments, viral repeat sequences are synthetic AAV ITR sequences.

In some embodiments, a target viral vector is an adenovirus vector and the viral repeat sequences comprise a sequence of adenovirus ITRs or derivatives thereof. In some embodiments, a viral repeat sequence is derived from a different strain of adenovirus than an adenovirus vector, but is still capable of being taken up by the target viral vector. In some embodiments, viral repeat sequences are engineered adenovirus ITR sequences. In some embodiments, viral repeat sequences are synthetic adenovirus ITR sequences.

In some embodiments, a target viral vector is a lentiviral vector and the viral repeat sequences comprise a sequence of lentiviral LTRs or derivatives thereof. In some embodiments, a target viral vector is an HIV-1 vector and the viral repeat sequences comprise a sequence of HIV-1 LTRs or derivatives thereof. In some embodiments, a viral repeat sequence is derived from a different strain of lentivirus than a target lentiviral vector, but is still capable of being taken up by the target lentiviral vector. In some embodiments, viral repeat sequences are engineered adenovirus ITR sequences. In some embodiments, viral repeat sequences are synthetic adenovirus ITR sequences.

In some embodiments, a target viral vector is an HSV vector and the viral repeat sequences comprise a sequence of HSV $TR_L/IR_L$ and/or HSV $IR_S/TR_S$ and/or derivatives thereof. In some embodiments, a target viral vector is an HSV-1 vector and/or an HSV-2 vector and the viral repeat sequences comprise a sequence of HSV $TR_L/IR_L$ and/or HSV $IR_S/TR_S$ and/or derivatives thereof. In some embodiments, a viral repeat sequence is derived from a different strain of HSV than a target HSV vector, but is still capable of being taken up by the target HSV vector. In some embodiments, viral repeat sequences are engineered HSV $TR_L/IR_L$ and/or HSV $IR_S/TR_S$ sequences. In some embodiments, viral repeat sequences are synthetic HSV $TR_L/IR_L$ and/or HSV $IR_S/TR_S$ sequences.

Payloads

Among other things, the present disclosure provides viral vectors that include a payload. Payloads are generally any sequence of interest that are desired to be introduced into a cell, organ, organism, and/or biological system (e.g., comprising cells). For example, in some embodiments, a viral vector can comprise a payload that can be used to edit cells (e.g., encoding genomic editing tools, e.g., for use in gene therapy and/or cell therapy). In some embodiments, a payload is included in a library construct. In some embodiments, a payload is included in a library construct and positioned between sequences for packaging into a viral vector (e.g., viral repeat sequences, e.g., AAV ITRs for expression of an AAV vector).

In some embodiments, a payload sequence comprises one or more of an encoding region, a gene regulatory element, and a transcription terminator. Non-limiting examples of gene regulatory elements include promoters, transcriptional activators, enhancers, and polyadenylation signals. In some embodiments, the payload sequence comprises an encoding region, a gene regulatory element, and a transcription terminator, positioned relative to each other such that the encoding region is between the gene regulatory element and the transcription terminator.

In some embodiments, an encoding region encodes a gene product. In some embodiments, the gene product is an RNA. In some embodiments, an encoding region encodes a polypeptide (such as a protein, such as a glycoprotein). In some embodiments, an encoding region encodes a fusion polypeptide and/or a chimeric polypeptide. In some embodiments, the encoding region encodes one gene product. In some embodiments, the encoding region encodes more than one gene product (e.g., 2, 3, 4, 5, 6, 7 or more gene products). In some embodiments, an encoding region encodes a regulatory RNA (e.g., a siRNA, microRNA, etc.).

In some embodiments, a payload of a viral vector described herein may be a gene therapy payload and may encode any protein or portion thereof beneficial to a subject, such as one with a disease or disorder. The protein may be an extracellular, intracellular or membrane-bound protein. The protein can be a therapeutic protein. In some embodiments, the subject to whom the gene therapy is administered has a disease or disorder whereby the subject's endogenous version of the protein is defective or produced in limited amounts or not at all. In some such embodiments, the payload encodes a non-defective version of the protein. In some embodiments, the subject to whom the gene therapy is administered has a disease or disorder mediated by a target gene (e.g., by a level of expression of the target gene and/or level of activity of a target polypeptide), and the payload encodes an inhibitor of the target gene or target polypeptide. Examples of therapeutic proteins include, but are not limited to, infusible or injectable therapeutic proteins, enzymes, enzyme cofactors, hormones, blood or blood coagulation factors, cytokines and interferons, growth factors, adipokines, etc.

In some embodiments, a payload may include gene editing components. In some embodiments, a payload may comprise an excising nucleic acid (e.g., where a viral vector delivers an RNA-guided nuclease to a target cell). In some embodiments, a payload comprising gene editing components may encode any suitable endonucleases known in the art. For example, a payload may encode or comprise one or more components of a CRISPR (clustered regularly interspaced short palindromic repeats)/Cas system.

A payload sequence can be of any length that is compatible with the associated viral vector. In some embodiments, a payload sequence is flanked by one or more sequences obtained or derived from a virus (e.g., ITR sequences for AAV). In some embodiments, a payload sequence is positioned between sequences for packaging into a viral vector. In some embodiments, a payload sequence is positioned between viral repeat sequences (e.g., ITR sequences for AAV).

Promoters

In some embodiments, a payload comprises a promoter. The term "promoter" refers to a DNA sequence recognized by enzymes/proteins that can promote and/or initiate transcription of an operably linked coding sequence (e.g., gene). For example, a promoter typically refers to, e.g., a nucleotide sequence to which an RNA polymerase and/or any associated factor binds and from which it can initiate transcription. Thus, in some embodiments, a payload comprises a coding sequence operably linked to one of the non-limiting example promoters described herein.

In some embodiments, a promoter is an inducible promoter, a constitutive promoter, a mammalian cell promoter, a viral promoter, a chimeric promoter, an engineered promoter, a tissue-specific promoter, or any other type of promoter known in the art.

A variety of promoters are known in the art, which can be used herein. Non-limiting examples of promoters that can be used herein include: human EF1α, human cytomegalovirus (CMV) (U.S. Pat. No. 5,168,062, which is incorporated in its entirety herein by reference), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g., human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene $H-2_K b$, HSP70, proliferin, tumor necrosis factor, thyroid stimulating hormone a gene, immunoglobulin light chain, T-cell receptor, HLA DQa and DQ, interleukin-2 receptor, MHC class II, MHC class II HLA-DRa, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, spleen focus-forming virus (SFFV) promoter, murine stem cell virus (MSCV) promoter, supercore promoter (SCP), and Gibbon Ape Leukemia Virus (GALV) promoters. Additional examples of promoters are known in the art. See, e.g., Lodish, Molecular Cell Biology, Freeman and Company, New York 2007, each of which is incorporated in its entirety herein by reference. In some embodiments, a promoter is the CMV immediate early promoter. In some embodiments, the promoter is a CAG promoter or a CAG/CBA promoter.

The term "constitutive" promoter refers to a nucleotide sequence that, when operably linked with a coding sequence (e.g., a protein coding sequence), causes RNA to be transcribed from the nucleic acid in a cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, Cell 41:521-530, 1985, which is incorporated in its entirety herein by reference), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Additional examples of inducible promoters are known in the art.

Examples of inducible promoters regulated by exogenously supplied compounds include the zinc-inducible sheep metallothionein (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system, and the rapamycin-inducible system.

The term "tissue-specific" promoter refers to a promoter that is active only in certain specific cell types and/or tissues (e.g., transcription of a specific gene occurs only within cells expressing transcription regulatory and/or control proteins that bind to the tissue-specific promoter).

In some embodiments, regulatory and/or control sequences impart tissue-specific gene expression capabilities. In some cases, tissue-specific regulatory and/or control sequences bind tissue-specific transcription factors that induce transcription in a tissue-specific manner.

Enhancers

In some instances, a payload can include an enhancer sequence. The term "enhancer" refers to a nucleotide sequence that can increase the level of transcription of a nucleic acid coding sequence (e.g., a protein). Enhancer sequences (generally 50-1500 bp in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include an RSV enhancer, a CMV enhancer, a CMV early enhancer, a cAMP response-element (CRE) enhancer, and/or a SV40 enhancer.

Additional Sequences

In some embodiments, any of the payloads described herein can include an untranslated region (UTR), such as a 5' UTR or a 3' UTR. UTRs of a gene are transcribed but not translated. A 5' UTR starts at the transcription start site and continues to the start codon but does not include the start codon. A 3' UTR starts immediately following the stop codon and continues until the transcriptional termination signal.

In some embodiments, a payload encoding a protein provided herein can include a polyadenylation (poly(A)) signal sequence. Most nascent eukaryotic mRNAs possess a poly(A) tail at their 3' end, which is added during a complex process that includes cleavage of the primary transcript and a coupled polyadenylation reaction driven by the poly(A) signal sequence (see, e.g., Proudfoot et al., Cell 108:501-

512, 2002, which is incorporated herein by reference in its entirety). A poly(A) tail confers mRNA stability and transferability (Molecular Biology of the Cell, Third Edition by B. Alberts et al., Garland Publishing, 1994, which is incorporated herein by reference in its entirety). In some embodiments, a poly(A) signal sequence is positioned 3' to the coding sequence.

In some embodiments, a payload encoding a protein can include an internal ribosome entry site (IRES). An IRES forms a complex secondary structure that allows translation initiation to occur from any position with an mRNA immediately downstream from where the IRES is located (see, e.g., Pelletier and Sonenberg, Mal. Cell. Biol. 8(3):1103-1112, 1988). There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV).

In some embodiments, any of the constructs provided herein can include splice donor and/or splice acceptor sequences, which are functional during RNA processing occurring during transcription. In some embodiments, splice sites are involved in trans-splicing.

In some embodiments, payloads provided herein can optionally include a sequence encoding a reporter polypeptide and/or protein ("a reporter sequence") and/or a sequence encoding a selectable marker (e.g., that confers a trait that can be artificially selected, e.g., a resistance cassette, etc.). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with control elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry). Similarly, when associated with control elements which drive their expression, the selectable marker sequence can confer traits that can also be artificially selected by conventional means.

Locations of Library Construct Elements Relative to Viral Repeat Sequences

A library construct can comprise one or more engineered sequences. In some embodiments, a library construct comprises a plurality of engineered sequences. In some embodiments, the library construct comprises viral repeat sequences for packaging of a viral vector.

The one or more and/or plurality of engineered sequences on the library construct can be in many locations and/or combination of locations with respect to one another and with respect to the viral repeat sequences on the library construct. For example, in some embodiments, a mammalian cell or mammalian cell population comprises at least one library construct comprising a plurality of engineered sequences, wherein a first subset of the plurality of engineered sequences are positioned between the viral repeat sequences, and a second subset of the plurality of engineered sequences are positioned outside the viral repeat sequences.

In some embodiments, a plurality of engineered sequences on the library construct comprise at least one library variant and at least one identifier. In some embodiments, all library variants and identifiers are positioned between the viral repeat sequences. In some embodiments, the identifier is positioned between the viral repeat sequences and all library variants are positioned outside the viral repeat sequences. In some embodiments, the plurality of engineered sequences comprise at least two library variants and at least one identifier. In some embodiments, the identifier and at least one library variant are positioned between the viral repeat sequences and at least one library is positioned outside the viral repeat sequences.

In some embodiments, the plurality of engineered sequences comprise at least one library variant, at least one identifier, and at least one payload. In some embodiments, all library variants, identifiers, and payloads are positioned between the viral repeat sequences. In some embodiments, all identifiers and payloads are positioned between the viral repeat sequences and all library variants are positioned outside the viral repeat sequences. In some embodiments, the plurality of engineered sequences comprise at least two library variants, at least one payload, and at least one identifier. In some embodiments, all identifiers, payloads, and at least one library variant are positioned between the viral repeat sequences and at least one library is positioned outside the viral repeat sequences.

In some embodiments, the library construct further comprises at least one engineered sequence comprising at least one reporter and/or selectable marker. In some embodiments, all reporters and/or selectable markers are positioned between the viral repeat sequences. In some embodiments, all reporters and/or selectable markers are positioned outside the viral repeat sequences. In some embodiments, the library construct comprises both at least one reporter and at least one selectable marker. In some embodiments, both the at least one reporter and the at least one selectable marker are positioned between the viral repeat sequences. In some embodiments, both the at least one reporter and the at least one selectable marker are positioned outside the viral repeat sequences. In some embodiments, at least one reporter is positioned between the viral repeat sequences and at least one selectable marker is positioned outside the viral repeat sequences. In some embodiments, at least one selectable marker is positioned between the viral repeat sequences and at least one reporter is positioned outside the viral repeat sequences.

In some embodiments, the library construct further comprises at least one engineered sequence comprising at least one barcode. In some embodiments all barcodes are positioned between the viral repeat sequences. In some embodiments, all barcodes are positioned outside the viral repeat sequences. In some embodiments, the library construct comprises a plurality of barcodes, wherein a first subset is positioned between the viral repeat sequences and a second subset is positioned outside the viral repeat sequences.

In some embodiments, the library construct comprises at least one identifier and at least one barcode. In some embodiments, the at least one barcode is used as an identifier and in some embodiments, the at least one barcode is not used as an identifier. In some embodiments, at least one barcode is positioned between the viral repeat sequences and the at least one barcode or a portion thereof is used as an identifier. In some embodiments, at least one barcode is positioned between the viral repeat sequences and the at least one barcode is not used as an identifier. In some embodiments, the library construct comprises at least one identifier and at least two barcodes. In some embodiments, all identifiers and at least one barcode are positioned between the viral repeat sequences, and at least one barcode is positioned outside the viral repeat sequences, wherein the at least one barcode positioned between the viral repeat sequences (or a portion thereof) is used as an identifier. In some embodiments, all identifiers and at least one barcode are positioned between the viral repeat sequences, and at least one barcode is positioned outside the viral repeat sequences, wherein neither of the at least two barcodes is used as an identifier.

In some embodiments, a library construct comprises at least two barcodes and further comprises at least one additional engineered sequence, where no barcodes are used as identifiers and all barcodes are used to track additional engineered sequences. For example, in some embodiments, a library construct comprises at least two barcodes and further comprises at least one library variant, where no barcodes are used as identifiers and all barcodes are used to track library variants. In some embodiments, one barcode is used as an identifier and additional barcodes are used to track library variants.

In some embodiments, one barcode indicates a single engineered sequence (e.g., a single library variant). In some embodiments, one barcode indicates more than one engineered sequence (e.g., more than one library variant). In some embodiments, more than one barcode indicates one engineered sequence (e.g., one library variant). In some embodiments, more than one barcode indicates more than one engineered sequence (e.g., more than one library variant). In some embodiments, no barcodes are used as identifiers and all barcodes are used to track other engineered sequences comprising barcodes. In some embodiments, one barcodes is used as an identifier and additional barcodes are used to track other engineered sequences comprising barcodes.

Use of Constructs in Mammalian Cells
Other Features of Constructs and Engineered Sequences
Promoters In some embodiments, a construct comprises a promoter. The term "promoter" refers to a DNA sequence recognized by enzymes/proteins that can promote and/or initiate transcription of an operably linked coding sequence (e.g., gene). For example, a promoter typically refers to, e.g., a nucleotide sequence to which an RNA polymerase and/or any associated factor binds and from which it can initiate transcription. Thus, in some embodiments, an engineered sequence comprises a coding sequence operably linked to one of the non-limiting example promoters described herein.

In some embodiments, a promoter is an inducible promoter, a constitutive promoter, a mammalian cell promoter, a viral promoter, a chimeric promoter, an engineered promoter, a tissue-specific promoter, or any other type of promoter known in the art.

A variety of promoters are known in the art, which can be used herein. Non-limiting examples of promoters that can be used herein include: human EF1α, human cytomegalovirus (CMV) (U.S. Pat. No. 5,168,062, which is incorporated in its entirety herein by reference), human ubiquitin C (UBC), mouse phosphoglycerate kinase 1, polyoma adenovirus, simian virus 40 (SV40), β-globin, β-actin, α-fetoprotein, γ-globin, β-interferon, γ-glutamyl transferase, mouse mammary tumor virus (MMTV), Rous sarcoma virus, rat insulin, glyceraldehyde-3-phosphate dehydrogenase, metallothionein II (MT II), amylase, cathepsin, MI muscarinic receptor, retroviral LTR (e.g., human T-cell leukemia virus HTLV), AAV ITR, interleukin-2, collagenase, platelet-derived growth factor, adenovirus 5 E2, stromelysin, murine MX gene, glucose regulated proteins (GRP78 and GRP94), α-2-macroglobulin, vimentin, MHC class I gene H-$2_K$b, HSP70, proliferin, tumor necrosis factor, thyroid stimulating hormone a gene, immunoglobulin light chain, T-cell receptor, HLA DQa and DQ, interleukin-2 receptor, MHC class II, MHC class II HLA-DRa, muscle creatine kinase, prealbumin (transthyretin), elastase I, albumin gene, c-fos, c-HA-ras, neural cell adhesion molecule (NCAM), H2B (TH2B) histone, rat growth hormone, human serum amyloid (SAA), troponin I (TN I), duchenne muscular dystrophy, human immunodeficiency virus, spleen focus-forming virus (SFFV) promoter, murine stem cell virus (MSCV) promoter, supercore promoter (SCP), and Gibbon Ape Leukemia Virus (GALV) promoters. Additional examples of promoters are known in the art. See, e.g., Lodish, Molecular Cell Biology, Freeman and Company, New York 2007, each of which is incorporated in its entirety herein by reference. In some embodiments, a promoter is the CMV immediate early promoter. In some embodiments, the promoter is a CAG promoter or a CAG/CBA promoter.

The term "constitutive" promoter refers to a nucleotide sequence that, when operably linked with a coding sequence (e.g., a protein coding sequence), causes RNA to be transcribed from the nucleic acid in a cell under most or all physiological conditions.

Examples of constitutive promoters include, without limitation, the retroviral Rous sarcoma virus (RSV) LTR promoter, the cytomegalovirus (CMV) promoter (see, e.g., Boshart et al, Cell 41:521-530, 1985, which is incorporated in its entirety herein by reference), the SV40 promoter, the dihydrofolate reductase promoter, the beta-actin promoter, the phosphoglycerol kinase (PGK) promoter, and the EF1-alpha promoter (Invitrogen).

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech, and Ariad. Additional examples of inducible promoters are known in the art.

Examples of inducible promoters regulated by exogenously supplied compounds include the zinc-inducible sheep metallothionein (MT) promoter, the dexamethasone (Dex)-inducible mouse mammary tumor virus (MMTV) promoter, the T7 polymerase promoter system, the ecdysone insect promoter, the tetracycline-repressible system, the tetracycline-inducible system, the RU486-inducible system, and the rapamycin-inducible system.

The term "tissue-specific" promoter refers to a promoter that is active only in certain specific cell types and/or tissues (e.g., transcription of a specific gene occurs only within cells expressing transcription regulatory and/or control proteins that bind to the tissue-specific promoter).

In some embodiments, regulatory and/or control sequences impart tissue-specific gene expression capabilities. In some cases, tissue-specific regulatory and/or control sequences bind tissue-specific transcription factors that induce transcription in a tissue-specific manner.

Enhancers

In some instances, a construct can include an enhancer sequence. The term "enhancer" refers to a nucleotide sequence that can increase the level of transcription of a nucleic acid coding sequence (e.g., a protein). Enhancer sequences (generally 50-1500 bp in length) generally increase the level of transcription by providing additional binding sites for transcription-associated proteins (e.g., transcription factors). In some embodiments, an enhancer sequence is found within an intronic sequence. Unlike promoter sequences, enhancer sequences can act at much larger distance away from the transcription start site (e.g., as compared to a promoter). Non-limiting examples of enhancers include an RSV enhancer, a CMV enhancer, a CMV early enhancer, a cAMP response-element (CRE) enhancer, and/or a SV40 enhancer.

Additional Sequences

In some embodiments, any of the constructs described herein can include an untranslated region (UTR), such as a 5' UTR or a 3' UTR. UTRs of a gene are transcribed but not translated. A 5' UTR starts at the transcription start site and continues to the start codon but does not include the start codon. A 3' UTR starts immediately following the stop codon and continues until the transcriptional termination signal.

In some embodiments, a construct comprising an engineered sequence encoding a protein provided herein can include a polyadenylation (poly(A)) signal sequence. Most nascent eukaryotic mRNAs possess a poly(A) tail at their 3' end, which is added during a complex process that includes cleavage of the primary transcript and a coupled polyadenylation reaction driven by the poly(A) signal sequence (see, e.g., Proudfoot et al., Cell 108:501-512, 2002, which is incorporated herein by reference in its entirety). A poly(A) tail confers mRNA stability and transferability (Molecular Biology of the Cell, Third Edition by B. Alberts et al., Garland Publishing, 1994, which is incorporated herein by reference in its entirety). In some embodiments, a poly(A) signal sequence is positioned 3' to the coding sequence.

In some embodiments, a construct comprising an engineered sequence encoding a protein can include an internal ribosome entry site (IRES). An IRES forms a complex secondary structure that allows translation initiation to occur from any position with an mRNA immediately downstream from where the IRES is located (see, e.g., Pelletier and Sonenberg, Mal. Cell. Biol. 8(3):1103-1112, 1988). There are several IRES sequences known to those in skilled in the art, including those from, e.g., foot and mouth disease virus (FMDV), encephalomyocarditis virus (EMCV), human rhinovirus (HRV), cricket paralysis virus, human immunodeficiency virus (HIV), hepatitis A virus (HAV), hepatitis C virus (HCV), and poliovirus (PV).

In some embodiments, any of the constructs provided herein can include splice donor and/or splice acceptor sequences, which are functional during RNA processing occurring during transcription. In some embodiments, splice sites are involved in trans-splicing.

In some embodiments, any of the constructs provided herein can optionally include a sequence encoding a reporter polypeptide and/or protein ("a reporter sequence") and/or a sequence encoding a selectable marker (e.g., that confers a trait that can be artificially selected, e.g., a resistance cassette, etc.). Non-limiting examples of reporter sequences include DNA sequences encoding: a beta-lactamase, a beta-galactosidase (LacZ), an alkaline phosphatase, a thymidine kinase, a green fluorescent protein (GFP), a red fluorescent protein, an mCherry fluorescent protein, a yellow fluorescent protein, a chloramphenicol acetyltransferase (CAT), and a luciferase. Additional examples of reporter sequences are known in the art. When associated with control elements which drive their expression, the reporter sequence can provide signals detectable by conventional means, including enzymatic, radiographic, colorimetric, fluorescence, or other spectrographic assays; fluorescent activating cell sorting (FACS) assays; immunological assays (e.g., enzyme linked immunosorbent assay (ELISA), radioimmunoassay (RIA), and immunohistochemistry). Similarly, when associated with control elements which drive their expression, the selectable marker sequence can confer traits that can also be artificially selected by conventional means.

Mammalian Cell Engineering and Cellular Construct Entry

In some embodiments, the present disclosure provides methods that include preparing or obtaining a mammalian cell library. Any methods for suitable for genetic modification can be used to manipulate mammalian cells in the context of the present disclosure, e.g., to introduce a library construct, introduce another construct, and/or to introduce a perturbation. For example, numerous methods are known in the art for introducing exogenous nucleic acid (e.g., DNA) into eukaryotic cells, including transfection, infection (e.g., viral transduction), or electroporation.

Methods for delivering constructs to mammalian cells can vary depending on the need. In certain embodiments, certain constructs may be delivered as nucleic acid (e.g., DNA) constructs in one or more plasmids. Delivery methods include but are not limited to, electroporation, microinjection, gene gun, impalefection, hydrostatic pressure, continuous infusion, sonication, magnetofection, chemical vehicles (e.g., oligonucleotides, lipoplexes, polymersomes, polyplexes, dendrimers, inorganic nanoparticles, and cell-penetrating peptides), viral vectors (e.g., integration constructs and/or integration viral vectors, e.g., replication-competent viral vectors, replication incompetent viral vectors, replication deficient viral vectors, replication-defective viral vectors, replication competent viral vectors, and/or replication conditional viral vectors).

In some embodiments, a mammalian cell library is genetically modified to comprise a library construct and/or other construct. A library construct and/or other construct may be delivered by any suitable method known in the art, e.g., to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y., which is incorporated in its entirety herein by reference). In some embodiments, provided methods comprise transfecting one or more nucleic acids comprising a library construct into mammalian cells of the library.

In some embodiments, a mammalian cell library is genetically modified to comprise one or more nucleic acid sequences essential for production of a viral vector. In some embodiments, mammalian cell libraries that express and/or produce viral vectors may have one or more viral vector components provided to the mammalian cell in trans. For example, recombinant AAV constructs and/or engineered sequences, rep sequences, cap sequences, and helper functions required for producing an AAV vector of the disclosure may be delivered to a packaging host cell using any appropriate construct.

A construct encoding viral elements may be delivered by any suitable method known in the art, e.g., to those with skill in nucleic acid manipulation and include genetic engineering, recombinant engineering, and synthetic techniques (see, e.g., Sambrook et al, Molecular Cloning: A Laboratory Manual, Cold Spring Harbor Press, Cold Spring Harbor, N.Y., which is incorporated in its entirety herein by reference). In some embodiments, provided methods comprise transfecting one or more nucleic acids comprising viral constructs or encoding viral vector components into mammalian cells of the library. In some embodiments, provided methods comprise transfecting one or more plasmid(s) containing or consisting essentially of nucleic acid molecule(s)

coding for a viral vector. In some embodiments, viral vector components are included on one or more plasmids that are transfected into the cells. In some embodiments, viral vector components are included on one, two, three, or more plasmids that are each transfected into the cells.

In some embodiments a viral vector is an adeno-associated virus (AAV), and viral transfection comprises transfecting plasmid(s) containing or consisting essentially of nucleic acid molecule(s) coding for the AAV vector into mammalian cells, and supplying AAV vector rep and/or cap obligatory for replication and packaging of the AAV vector. In some embodiments, one, two, three, or more plasmids that each include components of the AAV vector are transfected into the cells. In some certain embodiments, plasmids (e.g., 1 to 5 plasmids, e.g., 3 plasmids) which combined provide various AAV components, including helper virus, payload (e.g., therapeutic gene), rep and/or cap are transfected into cells.

In some certain embodiments, viral transfection of an AAV construct may be done using a triple transfection method (e.g., as described in U.S. Pat. No. 6,001,650, which is incorporated in its entirety herein by reference). In some embodiments, AAV vectors are produced by transfecting a host cell with one or more constructs comprising one or more nucleic acid sequences essential for production of an AAV vector, including but not limited to, rep sequences and/or cap sequences, and/or a construct comprising helper functions. In some embodiments, the rep and cap sequences function in trans for productive AAV vector replication and encapsidation. In some embodiments, the construct comprising rep and/or cap sequences support efficient AAV construct production without generating any detectable wild type AAV vectors (i.e., AAV vectors containing functional rep and cap genes). A helper function construct encodes nucleotide sequences for non-AAV derived viral and/or cellular functions upon which AAV vectors are dependent for replication, which may include those functions required for AAV construct replication, including, without limitation, those moieties involved in activation of AAV vector gene transcription, stage specific AAV vector mRNA splicing, AAV DNA replication, synthesis of cap expression products, and/or AAV vector capsid assembly. These viral-based functions can be derived from any known helper viruses such as, for example, adenovirus, herpesvirus (other than herpes simplex virus type-1), and vaccinia virus.

In some embodiments, it may be beneficial to prevent produce viral vectors from reinfecting mammalian cells of a mammalian cell library. In some embodiments, mammalian cell(s) of a mammalian cell library have been modified to disrupt or remove the receptor(s) for the produced viral vector. In some embodiments, mammalian cells have been treated with an infection/blocking agent.

For example, in some embodiments, produced viral vectors are or comprise AAV vectors and the mammalian cell library has been previously or concurrently genetically modified to disrupt or remove a receptor for AAV. In some embodiments, produced viral vectors are or comprise lentiviral vectors and the mammalian cell library has been previously or concurrently genetically modified to disrupt or remove a receptor for lentivirus. In some embodiments, mammalian cells have been treated with an agent that blocks infection of a lentiviral vector In such embodiments, the integration vector and/or cis-acting integration sequences are not derived from lentivirus.

Location of Constructs and Engineered Sequences in a Mammalian Cell

Any of the constructs described herein may be present in a mammalian cell extrachromosomally and/or integrated into the mammalian cell genome.

In some embodiments, a library construct is episomal and/or integrated into the mammalian cell genome. In some embodiments, a library construct is a single contiguous construct that is episomal. In some embodiments, a library construct is a single contiguous construct that is integrated into the mammalian cell genome. In some embodiments, a library construct is discontiguous and one or more individual constructs are episomal. In some embodiments, a library construct is discontiguous and one or more individual constructs are integrated into the mammalian cell genome. In some embodiments, a library construct is discontiguous and at least one construct is episomal and at least one construct is integrated into the mammalian cell genome.

In some embodiments, one or more sequences essential for production of a viral vector are present extrachromosomally (e.g., episomally) within a mammalian cell. In some embodiments, one or more sequences essential for production of a viral vector are integrated into the genome of a mammalian cell.

In some embodiments, one or more sequences essential for production of a viral vector are integrated into the genome of a mammalian cell where one or more sequences is inducibly expressed. In some embodiments, all sequences essential for production of a viral vector are integrated into the genome of a mammalian cell where one or more sequences is inducibly expressed. In some embodiments, all sequences essential for production of a viral vector are integrated into the genome of a mammalian cell where two or more sequences are inducibly expressed. In some embodiments, all sequences essential for production of a viral vector are integrated into the genome of a mammalian cell where all sequences are inducibly expressed.

Any methods known in the art for integrating sequences can be used. In some embodiments, integration is targeted integration (e.g., at a predetermined site). In some embodiments, integration is random integration (e.g., at a random site). In some embodiments integration is random within a predetermined subset of genomic locations.

In some embodiments, one or more engineered sequences (e.g., a library construct and/or other construct) are pre-integrated into the cells of the mammalian library using methods known in the art. In some embodiments, mammalian cells with one or more integrated sequences are transfected with sequences encoding a viral vector. In some embodiments, one or more viral vector sequences are also integrated into the genome.

In some embodiments, mammalian cell libraries for culturing viral vectors may be stably engineered to contain one or more such viral components (e.g., recombinant AAV construct, rep sequences, cap sequences, and/or helper functions) using methods known to those of skill in the art. In some embodiments, such a stable mammalian cell contains such viral vector component(s) under the control of an inducible promoter. In some embodiments, such viral vector component(s) may be under the control of a constitutive promoter. In some embodiments, a selected stable mammalian cell may contain selected component(s) under the control of a constitutive promoter and other selected component(s) under the control of one or more inducible promoters. For example, a stable mammalian cell that, e.g., contains E1 helper functions under the control of a constitutive promoter, and rep and/or cap genes under the control of inducible promoters. Other stable mammalian cells may be generated by one of skill in the art using routine methods as a base for producing a mammalian cell library. Such stably expressing mammalian cell lines may then be manipulated to include a variety of different engineered sequences, including identifier sequences, thereby generating a viral vector-producing mammalian cell library.

In some embodiments, exogenous DNA (e.g. a library construct) is integrated into the genomic DNA, such that the exogenous DNA is contiguous with the genomic DNA of the mammalian cell. In some embodiments, integration is mediated by natural DNA repair mechanisms that are endogenous to the cell. For example, integration can occur simply by introducing the exogenous DNA into a cell, allowing the site-specific nuclease to create an integration site, and allowing the donor DNA to be integrated. Cells may be kept in culture for sufficient time for the DNA to be integrated. This will usually result in a mixed population of cells, including (i) recombinant cells into which the exogenous DNA has integrated at the integration site created by the site-specific nuclease, and optionally (ii) cells in which exogenous DNA has integrated at sites other than the desired integration site and/or optionally (iii) cells that into which exogenous DNA has not integrated. Selection methods known in the art may be used to enrich for cells with genetic compositions in the library.

Episomal Library Constructs

In some embodiments, the present disclosure provides mammalian cells where one or more constructs (e.g., a library construct and/or construct encoding sequences essential for production of a viral vector) is not integrated into the mammalian cell genome but exists episomally. Any methods known in the art for introducing episomal constructs into mammalian cells can be used.

In some embodiments, a single contiguous library construct is exists episomally in a mammalian cell. In some embodiments, one or more individual constructs of a discontiguous library construct exist episomally in a mammalian cell (e.g., a construct comprising an identifier and viral packaging sequences). In some embodiments, all individual constructs of a discontiguous library construct exist episomally in a mammalian cell.

In some embodiments, exogenous nucleic acid (e.g., DNA) can be introduced into mammalian cells by standard transfection or electroporation methods. In some embodiments, exogenous nucleic acid introduced into mammalian cells can be present in the cell episomally in single, low or high copy number. In some embodiments, exogenous nucleic acid introduced into mammalian cells may be present genomically and/or episomally with variable copy number. Selection and/or screening methods known in the art may be used to enrich for cells with an episomal construct (e.g., library construct).

In some embodiments, a pool of viral vectors generated by a first mammalian cell library is used to transfect mammal cells to generate a second mammalian cell library. In some embodiments, the second mammalian cell library episomally expresses the library variants. In some embodiments, a pool of viral vectors generated by a first mammalian cell library is a pool of AAV vectors. In some embodiments, a pool of AAV vectors generated by a first mammalian cell library is used to transduce mammalian cells to generate a second mammalian cell library that episomally comprises an identifier.

Integrated Library Constructs

In some embodiments, the present disclosure provides mammalian cells where one or more constructs (e.g., a library construct and/or construct encoding sequences essential for production of a viral vector) is integrated into the mammalian cell genome. Any methods known in the art for integrating sequences can be used.

In some embodiments, integration of a construct (e.g., a library construct) within a mammalian cell genome is mediated by at least one trans-acting integration sequence. In some embodiments, at least one trans-acting integration sequence comprises (i) an integration construct and/or integration viral vector, (ii) a recombinase, (iii) a nuclease, (iv) a transposase, and/or a derivative and/or fusion thereof. In some embodiments, integration of a construct (e.g., a library construct) within a mammalian cell genome is mediated by at least one trans-acting integration sequence in coordination with cis-acting integration sequences. In some embodiments, cis-acting integration sequences comprise (i) viral repeat sequences, (ii) recombinase recognition sites, (iii) homology arms, and/or (iv) transposase recognition sites and/or a derivative thereof.

In some embodiments, a construct to be integrated into a mammalian genome (e.g., a library construct) comprises at least one pair of cis-acting integration sequences that flank the sequence to be integrated. For example, provided is a library construct comprising a first set of viral repeat sequences that flank an identifier and/or a payload, wherein the first set of viral repeat sequences are flanked by cis-acting integration sequences.

In some embodiments, integration of a construct into a mammalian cell genome is targeted integration. In some embodiments, integration of a construct into a mammalian cell genome is random integration. In some embodiments, a construct is integrated into a mammalian cell genome at a random insertion site. In some embodiments, the random insertion site is random within a predetermined subset of genomic locations. In some embodiments, the insertion of the library construct within the mammalian cell genome comprises a predetermined insertion site.

In some embodiments, a library construct (e.g., one or more individual nucleic acids associated with a library construct) is integrated into a mammalian genome. In some embodiments, a single contiguous library construct is integrated into a mammalian genome. In some embodiments, one or more individual constructs of a discontiguous library construct are integrated into a mammalian genome (e.g., a construct comprising an identifier and viral packaging sequences). In some embodiments, all individual constructs of a discontiguous library construct are integrated into a mammalian genome.

In some embodiments, exogenous nucleic acid (e.g., DNA) can be introduced into mammalian cells by standard transfection or electroporation methods. In some embodiments, exogenous nucleic acid introduced into mammalian cells can integrate into the genome in single, low or high copy number and/or be present in the cell episomally in single, low or high copy number. In some embodiments, exogenous nucleic acid introduced into mammalian cells may be present genomically and/or episomally with variable copy number. Selection and/or screening methods known in the art may be used to enrich for cells with an integrated construct (e.g., library construct).

Viral Transduction-Mediated Integration

In some embodiments, a library construct is integrated into a mammalian genome by viral transduction-mediated integration. In some embodiments, for example, provided is a library construct comprising a first set of viral repeat sequences that flank an identifier and/or a payload, wherein the first set of viral repeat sequences are flanked by cis-acting integration sequences comprising a second set of viral repeat sequences. In some embodiments, at least one trans-acting integration sequence comprises an integration viral vector and/or integration construct, where the integration viral vector is a lentiviral vector, a gammaretroviral vector, a spumaretroviral vector, an adeno-associated viral vector, or a derivative thereof.

In some embodiments, an integration viral vector is a lentiviral vector. In some embodiments, a lentiviral integration vector mediates integration of a library construct or a portion thereof into a mammalian cell genome. In some embodiments, a library construct comprises a first set of viral repeat sequences (e.g., AAV ITRs for packaging of an AAV vector) that flank an identifier and/or a payload, wherein the first set of viral repeat sequences are flanked by cis-acting integration sequences comprising a second set of viral repeat sequences (e.g., lentivirus LTRs for integration of the library construct or a portion thereof into a mammalian genome).

Some exemplary scenarios for lentiviral transduction-mediated integration of a library construct are provided in Table 4 below. Each of the embodiments of Table 4 can be in the context of a single contiguous library construct or a discontiguous library construct. In some embodiments, a library construct is a discontiguous library construct and an individual construct comprising an identifier is integrated into the genome. In some embodiments, a library construct is a discontiguous library construct and two or more individual constructs of the library construct are integrated into the mammalian genome by lentiviral transduction-mediated integration. In some embodiments, all of the individual constructs of a discontiguous library construct are integrated into the mammalian genome by lentiviral transduction-mediated integration.

the first set of viral repeat sequences are flanked by cis-acting integration sequences comprising homology arms.

In some embodiments, at least one trans-acting integration sequence comprises a nuclease and/or fusion and/or derivative thereof, comprising Cas9, CasZ, Cpf1, an engineered Fok1 nuclease domain fusion to a programmable DNA-binding domain such as a TALE protein (TALEN) or a Zinc Finger protein (ZFN), and/or a meganuclease, and/or a derivative thereof. In some embodiments, a nuclease is or comprises Cas9.

In some embodiments, at least one trans-acting integration sequence comprises a zinc-finger nuclease. A zinc-finger nuclease (ZFN) is an artificial restriction enzyme, which is generated by combining a zinc finger DNA-binding domain with a DNA-cleavage domain. The most common cleavage domain in ZFNs is the non-specific cleavage domain from the type IIs restriction endonuclease FokI, which can be targeted using a guide sequence. Methods of using ZFNs are described, for example, in WO 2009146179 A1, WO 2008060510 A2 and CN 102174576 A, which are incorporated by reference in their entireties.

In some embodiments, at least one trans-acting integration sequence comprises a transcription activator-like effector nuclease (TALEN). TALENs are restriction enzymes that can be engineered to cut specific sequences of DNA. Methods of using TALENs are described, for example, in WO 2014134412 A1, WO 2013163628 A2 and WO 2014040370 A1, which are incorporated by reference in their entireties.

In some embodiments, at least one trans-acting integration sequence comprises a non-RNA-guided nuclease and/or fusion and/or derivative thereof. In some embodiments, insertion of a library construct within the mammalian cell genome is mediated by at least two trans-acting integration sequences, where at least one trans-acting integration sequence comprises an RNA-guided nuclease and/or fusion and/or derivative thereof, and least one trans-acting integration sequence comprises a gRNA sequence.

In some embodiments, insertion of a library construct within the mammalian cell genome is mediated by at least one trans-acting integration sequence, and wherein the at least one trans-acting integration sequence comprises a

TABLE 4

Exemplary scenarios with lentiviral transduction-mediated integration

| Scenario | Library Variant | Location | Cis-acting Integration Sequences | Trans-acting Integration Sequences |
| --- | --- | --- | --- | --- |
| AAV-in-lenti-mediated integration of gRNA KO library | gRNA, introduced by lentiviral transduction | Randomly integrated | LTRs flanking viral packaging sequences (e.g., AAV ITRs) | Integration viral vector (e.g., lentiviral vector) |
| AAV-in-lenti-mediated integration of gRNA SNP library | gRNA, introduced by lentiviral transduction | Randomly integrated | LTRs flanking viral packaging sequences (e.g., AAV ITRs) | Integration viral vector (e.g., lentiviral vector) |
| AAV-in-lenti integration-mediated of gRNA activation library | gRNA, introduced by lentiviral transduction | Randomly integrated | LTRs flanking viral packaging sequences (e.g., AAV ITRs) | Integration viral vector (e.g., lentiviral vector) |
| AAV-in-lenti-mediated integration of gRNA repression library | gRNA, introduced by lentiviral transduction | Randomly integrated | LTRs flanking viral packaging sequences (e.g., AAV ITRs) | Integration viral vector (e.g., lentiviral vector) |
| AAV-in-lenti-mediated integration of insertion library | ORF, introduced by lentiviral transduction | Randomly integrated | LTRs flanking viral packaging sequences (e.g., AAV ITRs) | Integration viral vector (e.g., lentiviral vector) |

Nuclease-Mediated Integration

In some embodiments, a library construct is integrated into a mammalian genome by nuclease-mediated integration. In some embodiments, for example, provided is a library construct comprising a first set of viral repeat sequences that flank an identifier and/or a payload, wherein nuclease (e.g., RNA-guided nuclease or non-RNA-guided nuclease) and/or fusion and/or derivative thereof, and where the library construct comprises at least one pair of cis-acting integration sequences that are homology arms. In some embodiments, a library construct comprises an identifier the library construct are integrated into the mammalian genome by nuclease-mediated integration. In some embodiments, all of the individual constructs of a discontiguous library construct are integrated into the mammalian genome by nuclease-mediated integration.

TABLE 5

Exemplary scenarios with nuclease-mediated integration

| Scenario | Library Variant | Location | Cis-acting Integration Sequences | Trans-acting Integration Sequences |
|---|---|---|---|---|
| CRISPR-mediated integration of gRNA KO library | gRNA, introduced by transfection | Targeted | Homology arms | Nuclease (e.g., Cas) and gRNA |
| CRISPR-mediated integration of gRNA SNP library | gRNA, introduced by transfection | Targeted | Homology arms | Nuclease (e.g., Cas) and gRNA |
| CRISPR-mediated integration of gRNA activation library | gRNA, introduced by transfection | Targeted | Homology arms | Nuclease (e.g., Cas) and gRNA |
| CRISPR-mediated integration of gRNA repression library | gRNA, introduced by transfection | Targeted | Homology arms | Nuclease (e.g., Cas) and gRNA |
| CRISPR-mediated integration of insertion library | ORF, introduced by transfection | Targeted | Homology arms | Nuclease (e.g., Cas) and gRNA | and/or a payload between two viral packaging sequences (e.g., viral repeat sequences), all of which are located in between cis-acting integration sequences comprising homology arm sequences.

In some embodiments, insertion of a library construct within the mammalian cell genome is mediated by at least two trans-acting integration sequences, where at least one trans-acting integration sequence comprises a nuclease (e.g., RNA-guided nuclease) and/or fusion and/or derivative thereof and at least one trans-acting integration sequence comprises a gRNA sequence. In some embodiments, a library construct comprises an identifier and/or a payload between two viral packaging sequences (e.g., viral repeat sequences), all of which are located in between cis-acting integration sequences comprising homology arm sequences.

In some embodiments, a library construct is integrated into the genome of a mammalian cell by nuclease-mediated integration (e.g., using CRISPR/Cas9). In some embodiments, integration of a library construct is mediated by natural DNA repair mechanisms that are endogenous to the cell. For example, integration can occur simply by introducing the exogenous DNA into a cell, allowing the site-specific nuclease to create an integration site, and allowing the donor DNA to be integrated.

In some embodiments, insertion of a library construct within the mammalian cell genome is mediated by a Cas9. In some embodiments, a library construct comprises an identifier and/or a payload between AAV ITR sequences, all of which are located in between cis-acting integration sequences comprising homology arm sequences.

Some exemplary scenarios for nuclease-mediated integration of a library construct are provided in Table 5 below. Each of the embodiments of Table 5 can be in the context of a single contiguous library construct or a discontiguous library construct. In some embodiments, a library construct is a discontiguous library construct and an individual construct comprising an identifier is integrated into the genome. In some embodiments, a library construct is a discontiguous library construct and two or more individual constructs of Recombinase-Mediated Integration In some embodiments, a library construct is integrated into a mammalian genome by recombinase-mediated integration. In some embodiments, for example, provided is a library construct comprising a first set of viral repeat sequences that flank an identifier and/or a payload, wherein the first set of viral repeat sequences are flanked by cis-acting integration sequences comprising recombinase recognition sites.

In some embodiments, at least one trans-acting integration sequence comprises a recombinase. In some embodiments the recombinase comprises Cre, Flp, Dre, PhiC31, and/or Bxb1, and/or a derivative and/or fusion thereof.

In some embodiments, a trans-acting integration sequence comprises a recombinase comprising Cre. In some embodiments, Cre mediates integration of a library construct or a portion thereof into a mammalian cell genome. In some embodiments, a library construct comprises a first set of viral repeat sequences (e.g., AAV ITRs for packaging of an AAV vector) that flank an identifier and/or a payload, wherein the first set of viral repeat sequences are flanked by cis-acting integration sequences comprising LoxP sites.

In some embodiments, a trans-acting integration sequence comprises a recombinase comprising Bxb1. In some embodiments, Bxb1 mediates integration of a library construct or a portion thereof into a mammalian cell genome. In some embodiments, a library construct comprises a first set of viral repeat sequences (e.g., AAV ITRs for packaging of an AAV vector) that flank an identifier and/or a payload, wherein the first set of viral repeat sequences are flanked by cis-acting integration sequences comprising Att sites.

In some embodiments, a trans-acting integration sequence comprises a recombinase comprising Flp. In some embodiments, Flp mediates integration of a library construct or a portion thereof into a mammalian cell genome. In some embodiments, a library construct comprises a first set of viral repeat sequences (e.g., AAV ITRs for packaging of an AAV vector) that flank an identifier and/or a payload, wherein the first set of viral repeat sequences are flanked by cis-acting integration sequences comprising Frt sites.

Some exemplary scenarios for recombinase-mediated integration of a library construct are provided in Table 6 below. Each of the embodiments of Table 6 can be in the context of a single contiguous library construct or a discontiguous library construct. In some embodiments, a library construct is a discontiguous library construct and an individual construct comprising an identifier is integrated into the genome. In some embodiments, a library construct is a discontiguous library construct and two or more individual constructs of the library construct are integrated into the mammalian genome by recombinase-mediated integration. In some embodiments, all of the individual constructs of a discontiguous library construct are integrated into the mammalian genome by recombinase-mediated integration.

mediates integration of a library construct or a portion thereof into a mammalian cell genome. In some embodiments, a library construct comprises a first set of viral repeat sequences (e.g., AAV ITRs for packaging of an AAV vector) that flank an identifier and/or a payload, wherein the first set of viral repeat sequences are flanked by cis-acting integration sequences comprising transposase recognition sites.

In some embodiments, a trans-acting integration sequence comprises a transposase comprising Piggybac transposase. In some embodiments, Piggybac transposase mediates integration oaf library construct or a portion thereof into a mammalian cell genome. In some embodiments, a library construct comprises a first set of viral repeat sequences (e.g., AAV ITRs for packaging of an AAV vector) that flank an

TABLE 6

Exemplary scenarios with recombinase-mediated integration

| Scenario | Library Variant | Location | Cis-acting Integration Sequences | Trans-acting Integration Sequences |
|---|---|---|---|---|
| Recombinase-mediated integration of gRNA KO library | gRNA, introduced by transfection | Targeted | Recognition sites such as LoxP, Att, Frt | Recombinase such as Cre, Bxb1, Flp |
| Recombinase-mediated integration of gRNA SNP library | gRNA, introduced by transfection | Targeted | Recognition sites such as LoxP, Att, Frt | Recombinase such as Cre, Bxb1, Flp |
| Recombinase-mediated integration of gRNA activation library | gRNA, introduced by transfection | Targeted | Recognition sites such as LoxP, Att, Frt | Recombinase such as Cre, Bxb1, Flp |
| Recombinase-mediated integration of gRNA repression library | gRNA, introduced by transfection | Targeted | Recognition sites such as LoxP, Att, Frt | Recombinase such as Cre, Bxb1, Flp |
| Recombinase-mediated integration of insertion library | ORF, introduced by transfection | Targeted | Recognition sites such as LoxP, Att, Frt | Recombinase such as Cre, Bxb1, Flp |

Transposase-Mediated Integration

In some embodiments, a library construct is integrated into a mammalian genome by transposase-mediated integration. In some embodiments, for example, provided is a library construct comprising a first set of viral repeat sequences that flank an identifier and/or a payload, wherein the first set of viral repeat sequences are flanked by cis-acting integration sequences comprising transposase recognition sites.

In some embodiments, at least one trans-acting integration sequence comprises a transposase. In some embodiments the transposase comprises Sleepingbeauty transposase and/or Piggybac transposase and/or a derivative and/or fusion thereof.

In some embodiments, a trans-acting integration sequence comprises a transposase comprising Sleepingbeauty transposase. In some embodiments, Sleepingbeauty transposase identifier and/or a payload, wherein the first set of viral repeat sequences are flanked by cis-acting integration sequences comprising transposase recognition sites.

Some exemplary scenarios for transposase-mediated integration of a library construct are provided in Table 7 below. Each of the embodiments of Table 7 can be in the context of a single contiguous library construct or a discontiguous library construct. In some embodiments, a library construct is a discontiguous library construct and an individual construct comprising an identifier is integrated into the genome. In some embodiments, a library construct is a discontiguous library construct and two or more individual constructs of the library construct are integrated into the mammalian genome by transposase-mediated integration. In some embodiments, all of the individual constructs of a discontiguous library construct are integrated into the mammalian genome by transposase-mediated integration.

TABLE 7

Exemplary scenarios with transposase-mediated integration

| Scenario | Library Variant | Location | Cis-acting Integration Sequences | Trans-acting Integration Sequences |
|---|---|---|---|---|
| Transposase-mediated integration of gRNA KO library | gRNA, introduced by transfection | Random | Recognition sites | Transposase such as Piggybac or Sleepingbeauty |
| Transposase- | gRNA, | Random | Recognition sites | Transposase such |

TABLE 7-continued

Exemplary scenarios with transposase-mediated integration

| Scenario | Library Variant | Location | Cis-acting Integration Sequences | Trans-acting Integration Sequences |
|---|---|---|---|---|
| mediated integration of gRNA SNP library | introduced by transfection | | | as Piggybac or Sleepingbeauty |
| Transposase-mediated integration of gRNA activation library | gRNA, introduced by transfection | Random | Recognition sites | Transposase such as Piggybac or Sleepingbeauty |
| Transposase-mediated integration of gRNA repression library | gRNA, introduced by transfection | Random | Recognition sites | Transposase such as Piggybac or Sleepingbeauty |
| Transposase-mediated integration of insertion library | ORF, introduced by transfection | Random | Recognition sites | Transposase such as Piggybac or Sleepingbeauty |

Mammalian Cells

The present disclosure provides mammalian cells identified and/or produced using methods described herein. In some embodiments, provided mammalian cells express a viral vector. In some embodiments, provided mammalian cells contain one or more polynucleotides essential for production of a viral vector.

The present disclosure also provides a mammalian cell that includes any of the viral vectors, constructs, and/or compositions described herein. In some embodiments, the present disclosure provides mammalian cells comprising: (i) an identifier, (ii) an engineered sequence, and (iii) one or more elements essential for production of a viral vector.

In some embodiments, provided mammalian cells comprise: (i) an identifier positioned between viral packaging sequences (e.g., viral repeat sequences, e.g., AAV ITRs), (ii) an engineered sequence comprising a perturbation and/or perturbation accessory sequence, and (iii) one or more elements essential for production of a viral vector. In some embodiments, provided mammalian cells comprise: (i) library construct, and (ii) one or more elements essential for production of a viral vector, where the library construct comprises an identifier positioned between viral packaging sequences (e.g., viral repeat sequences, e.g., AAV ITRs), and optionally a library variant and/or a cis-acting integration sequence.

In some embodiments, provided technologies include a unique approach whereby a viral vector takes up an identifier (e.g., in the viral vector genome, e.g., between viral repeat sequences). Accordingly, viral vectors expressed by mammalian cells of the library will each include an identifier. This enables direct characterization of the viral vectors and identification of the mammalian cell from which it was produced.

In some embodiments, a mammalian cell produces a viral vector that comprises a payload and an identifier (e.g., in a viral vector nucleic acid). In some embodiments, sequencing of the viral vector nucleic acid can identify the abundance of the identifier (e.g., barcode and/or library variant) in the viral vector pool. Without wishing to be bound by theory, abundance of an identifier can link an engineered sequence with a phenotypic change, such as changes in viral vector expression. For example, an abundant identifier in a viral vector pool can identify that cells that comprise library variants (and resulting perturbations) that (e.g., corresponding with that identifier) that may have improved viral vector production.

In some embodiments, a mammalian cell comprises (i) an identifier positioned between two viral repeat sequences capable of packaging into a viral vector, (ii) at least one polynucleotide comprising one or more nucleic acid sequences essential for production of the viral vector, where the mammalian cell produces viral vectors comprising the at least one identifier. In some embodiments, an identifier comprises a unique library variant (e.g., a guide sequence, an ORF, etc.). In some embodiments, an identifier comprises a barcode and the mammalian cell further comprises one or more library variants. In some embodiments, a mammalian cell comprises a library construct and one or more nucleic acid sequences essential for production of a viral vector.

In some embodiments, provided mammalian cells are produced by introducing into the mammalian cells (i) a library construct and (ii) one or more nucleic acid sequences essential for production of the viral vector.

In some embodiments, the present disclosure provides mammalian cells that have been engineered to include perturbations identified using methods described herein. In some embodiments, a mammalian cell comprises one, two, three, four, five, six, seven, eight, nine, ten or more perturbations identified using methods of the present disclosure. In some embodiments, a mammalian cell comprises one or more perturbations (e.g., that impact viral vector production) and nucleic acid sequences essential for production of a viral vector. In some embodiments, a mammalian cell (i) comprises one or more perturbations and (ii) produces a viral vector that delivers a payload. In some embodiments, a mammalian cell does not comprise an identifier (e.g., it has been removed and/or a mammalian cell with the identified perturbations has been engineered).

In some embodiments, provided are a mammalian cell(s) comprising one or more engineered sequences that together comprise: (i) a library construct comprising an identifier positioned between a first set of two viral repeat sequences capable of packaging into a viral vector, and (ii) at least one polynucleotide comprising one or more nucleic acid sequences essential for production of the viral vector, where the library construct comprises an identifier. In some embodiments, a library construct further comprises at least one perturbation and/or at least one library variant. In some embodiments, a library construct further comprises at least one payload. In some embodiments, a library construct further comprises at least one perturbation accessory sequence. In some embodiments, a library construct further comprises at least one trans-acting integration sequence, and/or at least one cis-acting integration sequence.

Any suitable mammalian cell line known in the art can be engineered or screened in the context of the present disclosure. Mammalian cells for expression of viral vectors can include any mammalian cell type known in the art. Representative mammalian cells include, but are not limited to, human embryonic kidney (HEK) cells (e.g., HEK 293 cells, HEK 293T cells, Expi293 cells), Chinese hamster ovary (CHO) cells, HeLa cells (e.g., HeLa S3 cells), PER.C6 cells, HKB11 cells, CAP cells, Baby Hamster Kidney fibroblasts (BHK cells) (e.g., BHK-21 cells), mouse myeloma cells (e.g., Sp2/0 cells and NS0 cells), green African monkey kidney cells (e.g., COS cells and Vero cells), A549 cells, rhesus fetal lung cells (e.g., FRhL-2 cells), and any derivatives thereof. In some embodiments, the mammalian cells can support the viral life cycle. In some embodiments, mammalian cells of the present disclosure are highly transfectable.

Mammalian cells for viral production are known in the art. Representative examples of such cells include, but are not limited to human embryonic kidney (HEK) 293 cells and derivatives thereof (e.g., the 293T strain, 293SF-3F6 strain), HeLa cells, A549 cells, KB cells, CKT1 cells, NIH/sT3 cells, Vero cells, Chinese hamster ovary (CHO) cells, or any eukaryotic cell that supports the viral life cycle.

In some certain embodiments, mammalian cells for the expression of viral vectors are CHO cells. CHO cells have different lineages, including CHO-K1, CHO—S, CHO-DG44, and CHO-DXB11. In some certain embodiments, mammalian cells for the expression of viral vectors are HEK 293 cells. In some certain embodiments, mammalian cells for the expression of viral vectors are HEK 293T cells. In some certain embodiments, mammalian cells for the expression of viral vectors are HeLa cells.

In some embodiments, mammalian cells of the present disclosure are suitable for adherent cell culture. In some embodiments, mammalian cells are cultured in an adherent cell culture medium. In some embodiments, mammalian cells can be grown under serum-free conditions.

In some embodiments, mammalian cells of the present disclosure are suitable for suspension cell culture. In some embodiments, mammalian cells suitable for suspension cell culture are CHO cells (e.g., CHO—K1, CHO—S, CHO-DG44, and/or CHO-DXB11 cells), HEK 293 cells (e.g., 293SF, 3F6, 293T), HeLa cells, and derivatives thereof. In some certain embodiments, mammalian cells can be cultured in suspension under serum-free conditions. In some embodiments, HEK293 cells have the ability to grow in suspension under serum-free conditions.

In some embodiments, mammalian cells are cultured in suspension cell culture. In some embodiments, mammalian cells for suspension cell culture as suitable for culturing in large quantities (e.g., ≥1 L capacity, ≥2 L capacity, ≥3 L capacity, ≥4 L capacity, ≥5 L capacity, ≥10 L capacity, ≥20 L capacity, ≥30 L capacity, ≥40 L capacity, ≥50 L capacity, ≥60 L capacity, ≥70 L capacity, ≥80 L capacity, ≥90 L capacity, ≥100 L capacity, ≥200 L capacity, ≥300 L capacity, ≥400 L capacity, or ≥500 L capacity).

In some embodiments, a mammalian cell line of the present disclosure is suitable for manufacturing of biologics (e.g., viral vectors). In some embodiments, a mammalian cell line is suitable for use in industrial-scale manufacturing of a biologic product. In some embodiments, a mammalian cell line is suitable for use in a method of manufacture that conforms with local regulatory standards (e.g., FDA and/or EMA regulatory standards). In some embodiments, a mammalian cell line is suitable for manufacturing of biologics (e.g., viral vectors) using current good manufacturing practices (cGMP). In some embodiments, a mammalian cell line is suitable for manufacturing of biologics (e.g., viral vectors) using good manufacturing practices (GMP). In some embodiments, a mammalian cell line is suitable for manufacturing of biologics (e.g., viral vectors) using non-good manufacturing practices (non-GMP).

Perturbations

The present disclosure provides mammalian cells, produced viral vectors, polynucleotides essential for production of viral vectors, and/or other constructs, that include one or more perturbations. These are generated, produced, identified, and/or selected from mammalian cell libraries of the present disclosure for expression and/or production of viral vectors. As used herein, a perturbation comprises a genetic modification in a mammalian cell, a produced viral vector, polynucleotides essential for production of viral vectors, and/or other constructs, that results and/or is identified from a method as described herein.

In some embodiments, a perturbation is a result of one or more library variants. In some embodiments, a perturbation is a genetic modification that is not a result of a library variant but a genetic modification that results and/or is identified from the method as described herein. In some embodiments, a perturbation comprises a genetic modification in at least one polynucleotide comprising one or more nucleic acid sequences essential for production of the viral vector.

In some embodiments, within a population of mammalian cells and/or viral vectors, the mammalian cells and/or viral vectors each individually comprise at least one engineered sequence comprising a plurality of unique perturbations. In some embodiments, within a population of mammalian cells and/or viral vectors, the mammalian cells and/or viral vectors each individually comprise at least one engineered sequence comprising at least two, three, four, five, six, seven, eight or nine unique perturbations.

In some embodiments, a perturbation comprises an engineered sequence in the mammalian cell, produced viral vectors, polynucleotides essential for production of viral vectors, and/or other constructs that can includes a genomic sequence change (e.g., genomic insertion, deletion or knock out, substitution (e.g., SNP), replacement, rearrangement, etc.), an episomal sequence change (e.g., insertion, deletion or knock out, SNP (substitution), replacement, rearrangement, etc.), and/or an epigenetic modification (e.g., activation, repression, etc.). In some embodiments, a perturbation comprises an engineered sequence in the viral vector. In some embodiments, a perturbation comprises an engineered sequence in the at least one polynucleotide comprising one or more nucleic acid sequences essential for production of the viral vector. In some embodiments, a viral vector produced by a mammalian cell and/or method described herein comprises a perturbation.

In some embodiments, a perturbation comprises a modification to an endogenous coding sequence. In some embodiments, the endogenous coding sequence comprises an endogenous gene or gene segment. In some embodiments, a perturbation comprises a modification to an endogenous regulatory element, wherein the regulatory element comprises at least one promoter sequence and/or at least one enhancer sequence.

Types of Perturbations

In some embodiments, a perturbation comprises one or more genomic and/or episomal modifications. In some embodiments, a perturbation comprises one or more deletions or knock outs, SNPs (substitutions), replacements, insertions, rearrangements, and/or epigenetic modifications (e.g., activations (e.g., activation of one or more genes) and/or repressions (e.g., repression of one or more genes)).

In some embodiments, a perturbation comprises a genomic or episomal deletion or knock out. In some embodiments, a perturbation comprising a genomic or episomal deletion or knock out results from expression of one or more library variants that are part of a gRNA deletion or knockout library. In some embodiments, a perturbation comprising a genomic or episomal deletion or knock out does not result from expression of one or more library variants. In some embodiments, a library variant is introduced into a mammalian cell by any suitable means. In some embodiments, a library variant is included in a library construct that is part of a gRNA deletion or KO library.

In some embodiments, a perturbation comprises a genomic or episomal SNP. In some embodiments, a perturbation comprising a genomic or episomal SNP results from expression of one or more library variants that are part of a gRNA SNP library. In some embodiments, a perturbation comprising a genomic or episomal SNP does not result from expression of one or more library variants. In some embodiments, a library variant is introduced into a mammalian cell by any suitable means. In some embodiments, a library variant is included in a library construct that is part of a gRNA SNP library.

In some embodiments, a perturbation comprises a genomic or episomal activation (e.g., of one or more genes). In some embodiments, a perturbation comprising a genomic or episomal activation results from expression of one or more library variants that are part of a gRNA activation library. In some embodiments, a perturbation comprising a genomic or episomal activation does not result from expression of one or more library variants. In some embodiments, a library variant is introduced into a mammalian cell by any suitable means. In some embodiments, a library variant is included in a library construct that is part of a gRNA activation library.

In some embodiments, a perturbation comprises a genomic or episomal repression (e.g., of one or more genes). In some embodiments, a perturbation comprising a genomic or episomal repression results from expression of one or more library variants that are part of a gRNA repression library. In some embodiments, a perturbation comprising a genomic or episomal repression does not result from expression of one or more library variants. In some embodiments, a library variant is introduced into a mammalian cell by any suitable means. In some embodiments, a library variant is included in a library construct that is part of a gRNA repression library.

In some embodiments, a perturbation comprises a genomic or episomal insertion (e.g., of one or more genes). In some embodiments, a perturbation comprising a genomic or episomal insertion results from expression of one or more library variants that are part of a gRNA insertion library. In some embodiments, a perturbation comprising a genomic or episomal insertion does not result from expression of one or more library variants. In some embodiments, a library variant is introduced into a mammalian cell by any suitable means. In some embodiments, a library variant is included in a library construct that is part of an insertion library.

In some embodiments, one or more perturbations comprising one or more engineered sequences can be introduced into mammalian cells of a mammalian cell library using genomic editing. Some exemplary classes of perturbations and associated library scenarios and perturbation accessories provided in Table 8 below.

TABLE 8

Exemplary Perturbations in Mammalian Cells

| Perturbation | Scenario(s) | Perturbation Accessory Sequence |
| --- | --- | --- |
| Genomic KO | AAV-in-lenti-mediated integration of gRNA KO library<br>CRISPR-mediated integration of gRNA KO library<br>Recombinase-mediated integration of gRNA KO library<br>Transposon-mediated integration of gRNA KO library<br>Episomal gRNA KO library | Cas |
| Genomic SNP | AAV-in-lenti-mediated integration of gRNA SNP library<br>CRISPR-mediated integration of gRNA SNP library<br>Recombinase-mediated integration of gRNA SNP library<br>Transposon-mediated integration of gRNA SNP library<br>Episomal gRNA SNP library | Cas |
| Genomic activation | AAV-in-lenti-mediated integration of gRNA activation library<br>CRISPR-mediated integration of gRNA activation library<br>Recombinase-mediated integration of gRNA activation library<br>Transposon-mediated integration of gRNA activation library<br>Episomal gRNA activation library | Cas |
| Genomic repression | AAV-in-lenti-mediated integration of gRNA repression library<br>CRISPR-mediated integration of gRNA repression library<br>Recombinase-mediated integration of gRNA repression library<br>Transposon-mediated integration of gRNA repression library<br>Episomal gRNA repression library | Cas |
| Genomic insertion | AAV-in-lenti-mediated integration of insertion library<br>CRISPR-mediated integration of insertion library<br>Recombinase-mediated integration of insertion library<br>Transposon-mediated integration of insertion library | N/A |
| Episomal insertion | Episomal insertion library (viral repeat-flanked sequence is contained on a closed circular plasmid) | N/A |

Perturbation Accessory Sequences

In some embodiments, provided mammalian cells comprise a perturbation accessory sequence that aids in creating a perturbation in combination with a library construct. For example, in some embodiments, mammalian cells comprise (i) a library construct comprising one or more library variants that comprise a gRNA, (ii) a perturbation accessory sequence comprising a sequence encoding an RNA-guided nuclease and/or a derivative and/or fusions thereof, and/or (iii) other elements for nuclease-mediated perturbing. In some embodiments, a perturbation accessory sequence comprises an RNA-guided nuclease that is derived from Cas9, CasZ, Cpf1, and/or Fok1.

In some embodiments, a perturbation accessory sequence includes an RNA-guided nuclease comprises Cas9, Cpf1, and/or CasZ, or a derivative thereof, including fusion proteins comprising transcriptional regulators (e.g., Cas9-VPR or Cas9-KRAB-MeCP2 fusions), CRISPR protein fusions to nuclease domains (e.g. Fok1), enzymatic base-editors (e.g. versions of BE and ABE fusions), reverse transcriptase fusions (e.g. Prime Editors), CRISPR recombinases including (e.g. RecCas9), and CRISPR transposases (e.g., Tn7-like transposase systems Cas12k and Cascade complexes with TniQ).

In some embodiments, a perturbation accessory element includes a Cpf1 endonuclease. In some embodiments, a Cpf1 includes Cpf1 homologs and orthologs of the Cpf1 polypeptides disclosed in Zetsche et al. (2015) Cell 163: 759-771 as well as the Cpf1 polypeptides disclosed in U.S. 2016/0208243. Other engineered Cpf1 variants are known to those of ordinary skill in the art and included within the scope of the current disclosure (see, e.g., WO/2017/184768).

In some embodiments, provided mammalian cells are produced by introducing into the mammalian cells (i) a library construct, (ii) a perturbation accessory sequence, and (iii) one or more nucleic acid sequences essential for production of the viral vector. In some embodiments, a viral vector expressing cell library of the present disclosure is generated by introducing into each cell (e.g., mammalian cell): (i) a library construct, (ii) a perturbation accessory sequence, and (iii) one or more nucleic acid sequences essential for production of the viral vector.

In some embodiments, provided methods include expressing a perturbation accessory sequence in mammalian cells. In some embodiments, provided methods comprise screening viral vectors produced by a mammalian cell library, where each cell of the library comprises: (i) a library construct, (ii) a perturbation accessory sequence, and (iii) one or more nucleic acid sequences essential for production of the viral vector.

For example, mammalian cells may use genomic editing to introduce one or more engineered sequences (e.g., library variants).

In some embodiments, a library variant and a perturbation accessory sequence correspond to components adapted from naturally occurring CRISPR systems: a guide RNA (as a library variant) and an RNA-guided nuclease (as a perturbation accessory element). In a CRISPR/Cas system, a guide RNA (gRNA) forms a complex with an endonuclease, such as a Cas9 endonuclease. The complex is then guided by the gRNA to a DNA target sequence, typically located in the genome of a target cell. Cas9 or Cas9 endonuclease refers to an RNA-guided endonuclease comprising a Cas9 protein, or a fragment thereof (e.g., a protein comprising an active or inactive DNA cleavage domain of Cas9 or a partially inactive DNA cleavage domain (e.g., a Cas9 nickase), and/or the gRNA binding domain of Cas9). Cas9 recognizes a short motif in the CRISPR repeat sequences (the PAM or proto-spacer adjacent motif) to help distinguish self from non-self Cas9 endonuclease and guide RNA (e.g., single guide RNA) sequences and structures are well known to those of skill in the art (see, e.g., Ferretti et al., Proc. Natl. Acad. Sci. U.S.A. 98:4658-4663(2001); Deltcheva et al., Nature 471:602-607 (2011); and Jinek et al., Science 337:816-821(2012)).

Potential Features of Screened Mammalian Cells and Viral Vectors

In some embodiments, a perturbation is associated with one or more characteristics (e.g., desired characteristics) of the viral vector and/or for expression and/or production of a viral vector (e.g., independently and/or synthetically). In some embodiments, a single (one) perturbation is associated with one or more characteristics (e.g., desired characteristics) of the viral vector and/or for expression and/or production of a viral vector. In some embodiments, two or more perturbations together are associated with one or more characteristics (e.g., desired characteristics) of the viral vector and/or for expression and/or production of a viral vector.

In some embodiments, a mammalian cell and/or viral vector comprises at least one perturbation, and is associated with, for example, production of viral vectors that are altered in some way in an application and/or an intended application. In some embodiments, a mammalian cell and/or viral vector comprises at least one perturbation, and is associated with, for example, production of viral vectors that are altered in the way they transfer nucleic acid to a cell. In some embodiments, a mammalian cell and/or viral vector comprises at least one perturbation, and is associated with, for example, production of viral vectors that are altered therapeutically.

In some embodiments, a mammalian cell and/or viral vector comprises at least one perturbation, and is associated with, for example, production of viral vectors that are nonfunctional and/or less functional in some way. In some embodiments, a mammalian cell and/or viral vector comprises at least one perturbation, and is associated with, for example, production of viral vectors that more functional and/or enhanced in some way.

In some embodiments, at least one perturbation is associated with altered (e.g., increased) viral vector potency or ability to infect cells. In some embodiments, at least one perturbation is associated with altered (e.g., increased) ability to transduce host cells.

In some embodiments, a mammalian cell and/or viral vector comprises at least one perturbation, and is associated with, for example, production of viral vectors that are nonfunctional and/or less functional at transferring nucleic acid to a cell. In some embodiments, a mammalian cell and/or viral vector comprises at least one perturbation, and is associated with, for example, production of viral vectors that are more functional and/or enhanced at transferring nucleic acid to a cell. In some embodiments, a mammalian cell and/or viral vector comprises at least one perturbation, and is associated with, for example, production of viral vectors that are nonfunctional and/or less functional therapeutically. In some embodiments, a mammalian cell and/or viral vector comprises at least one perturbation, and is associated with, for example, production of viral vectors that are more functional and/or enhanced therapeutically.

In some embodiments, a mammalian cell and/or viral vector comprises at least one perturbation, and is associated with, for example, altered expression and/or production of a viral vector. In some embodiments, a mammalian cell and/or viral vector comprises at least one perturbation, and is associated with increased expression and/or production of a viral vector. In some embodiments, a mammalian cell and/or viral vector comprises at least one perturbation, and is associated with increased secretion of a viral vector. In some embodiments, a mammalian cell and/or viral vector comprises at least one perturbation, and is associated with, for example, altered (e.g., increased) expression and/or production of a viral vector under a then-current good manufacturing practice (cGMP). In some embodiments, a mammalian cell and/or viral vector comprises at least one perturbation, and is associated with, for example, altered (e.g., increased) expression, production and/or secretion of a viral vector under a good manufacturing practice (GMP). In some embodiments, a mammalian cell and/or viral vector comprises at least one perturbation, and is associated with, for example, altered (e.g., increased) expression, production and/or secretion of a viral vector under a non-good manufacturing practice (non-GMP).

In some embodiments, a mammalian cell or mammalian cell population comprises at least one perturbation that is associated with increased production of viral vector. In some embodiments, a mammalian cell comprising the at least one perturbation has an at least 2 fold, at least 3 fold, at least 4 fold, at least 5 fold, at least 6 fold, at least 7 fold, at least 8 fold, at least 9 fold, at least 10 fold, at least 12 fold, at least 15 fold, at least 20 fold, at least 25 fold, or at least 50 fold increase in viral vector production compared to comparable mammalian cell that lacks the at least one perturbation.

In some embodiments, a mammalian cell comprising the at least one perturbation has an at least 2 fold, at least 3 fold, at least 4 fold, at least 5 fold, at least 6 fold, at least 7 fold, at least 8 fold, at least 9 fold, at least 10 fold, at least 12 fold, at least 15 fold, at least 20 fold, at least 25 fold, or at least 50 fold increase in viral vector expression compared to comparable mammalian cell that lacks the at least one perturbation.

In some embodiments, a viral vector comprises at least one perturbation that is associated with increased viral vector production and/or expression. In some embodiments, a mammalian cell(s) expresses viral vector comprising the at least one perturbation at a higher level than a comparable mammalian cell that expresses viral vector that lacks the perturbation. In some embodiments, a viral vector comprising the at least one perturbation is produced and/or expressed at a level that is at least 2 fold, at least 3 fold, at least 4 fold, at least 5 fold, at least 6 fold, at least 7 fold, at least 8 fold, at least 9 fold, at least 10 fold, at least 12 fold, at least 15 fold, at least 20 fold, at least 25 fold, or at least 50 fold higher than expression of a comparable viral vector that lacks the perturbation.

In some embodiments, a mammalian cell and/or viral vector comprises at least one perturbation, and is associated with, for example altered (e.g., increased) duration of expression and/or production of a viral vector. In some embodiments, a mammalian cell and/or viral vector comprises at least one perturbation, and is associated with, for example altered (e.g., increased) viability of the mammalian cell. In some embodiments, a mammalian cell and/or viral vector comprises at least one perturbation, and is associated with, for example altered (e.g., increased) stability (e.g., genomic stability) of the mammalian cell.

In some embodiments, a mammalian cell and/or viral vector comprises at least one perturbation, and is associated with, for example altered (e.g., increased) stability (e.g., genomic stability) of the viral vector. In some embodiments, a mammalian cell and/or viral vector comprises at least one perturbation, and is associated with, for example an altered (e.g., decreased) percentage of empty viral vector produced.

In some embodiments, a mammalian cell and/or viral vector requires one or more or two or more perturbations to yield any of the above associations, effects or phenotypes. For example, in some embodiments, a mammalian cell and/or viral vector with one or more or two or more perturbations has an altered level of viral vector production (e.g., increased or decreased). In some embodiments, a mammalian cell and/or viral vector requires two or more perturbations that interact synthetically in a mammalian cell and/or viral vector to yield any of the above associations, effects or phenotypes. For example, in some embodiments, two or more perturbations interact synthetically in a mammalian cell and/or viral vector to result in an altered level of viral vector production (e.g., increased or decreased).

In some embodiments, any of the above associations, effects or phenotypes is compared relative to a reference population, wherein the reference population is a population of comparable or standard mammalian cells and/or viral vectors that do not include the at least one perturbation.

Cell Engineering Platform Methods

The present disclosure provides methods of engineering and/or screening of a mammalian cell library for characteristics of viral vector expression and/or production, and/or other characteristics.

In some embodiments, the present disclosure provides methods of producing and/or manufacturing viral vectors from a mammalian cell library, wherein each mammalian cell of the library individually comprises one or more engineered sequence comprising (i) an identifier and (ii) at least one nucleic acid sequence that expresses one or more elements essential for formation of a viral vector, and where each viral vector expressed comprises the identifier.

In some embodiments, the present disclosure provides methods of screening a mammalian cell library, wherein each mammalian cell of the library individually comprises one or more engineered sequence comprising (i) an identifier and (ii) at least one nucleic acid sequence that expresses one or more elements essential for formation of a viral vector, and where each viral vector expressed comprises the identifier. In some embodiments, the method comprises a step of detecting the identifiers in the viral vectors (e.g., by next generation sequencing and/or single cell sequencing).

In some embodiments, the present disclosure provides methods of producing AAV vectors from a mammalian cell library, wherein each mammalian cell of the library individually comprises one or more engineered sequence comprising (i) an identifier and (ii) at least one nucleic acid sequence that expresses one or more elements essential for formation of an AAV vector, and where each AAV vector expressed comprises the identifier. In some embodiments, at least one engineered sequence comprises a library variant. In some embodiments, at least one engineered sequence comprises a library variant and a barcode. In some embodiments, the identifier comprises a barcode. In some embodiments, a library variant produces at least one perturbation in the mammalian cell and/or viral vector (e.g., a perturbation that alters an aspect of AAV vector production).

In some embodiments, the present disclosure provides methods of screening a mammalian cell library for characteristics related to AAV vector production, wherein each mammalian cell of the library individually comprises one or more engineered sequences comprising (i) an identifier and (ii) at least one nucleic acid sequence that expresses one or more elements essential for formation of an AAV vector, and where each AAV vector expressed comprises the identifier.

In some embodiments, the method comprises a step of detecting the identifiers in the AAV vectors (e.g., by next generation sequencing). In some embodiments, a relative abundance of particular identifiers is determined relative to all identifiers in a pool of AAV vectors.

In some embodiments, at least one engineered sequence further comprises a payload, reporter, selectable marker, perturbation accessory sequence, trans-acting integration sequence, and/or cis-acting integration sequence.

In some embodiments, the present disclosure provides methods that include (i) a viral vector-expressing and/or -producing mammalian cell library, where each mammalian cell of the library includes (a) a library construct comprising an identifier positioned between viral packaging sequences and (b) one or more polynucleotides essential for production of a viral vector; (ii) culturing mammalian cells of the library to produce viral vectors comprising the identifier, and (iii) detecting the identifiers in a pool of viral vectors.

In some embodiments, the present disclosure provides methods that include (i) an AAV vector-expressing and/or -producing mammalian cell library, where each mammalian cell of the library includes (a) a library construct comprising an identifier positioned between AAV ITR sequences and (b) one or more polynucleotides essential for production of an AAV vector; (ii) culturing mammalian cells of the library to produce AAV vectors comprising the identifier, and (iii) detecting the identifiers in a pool of AAV vectors.

Figure 2:
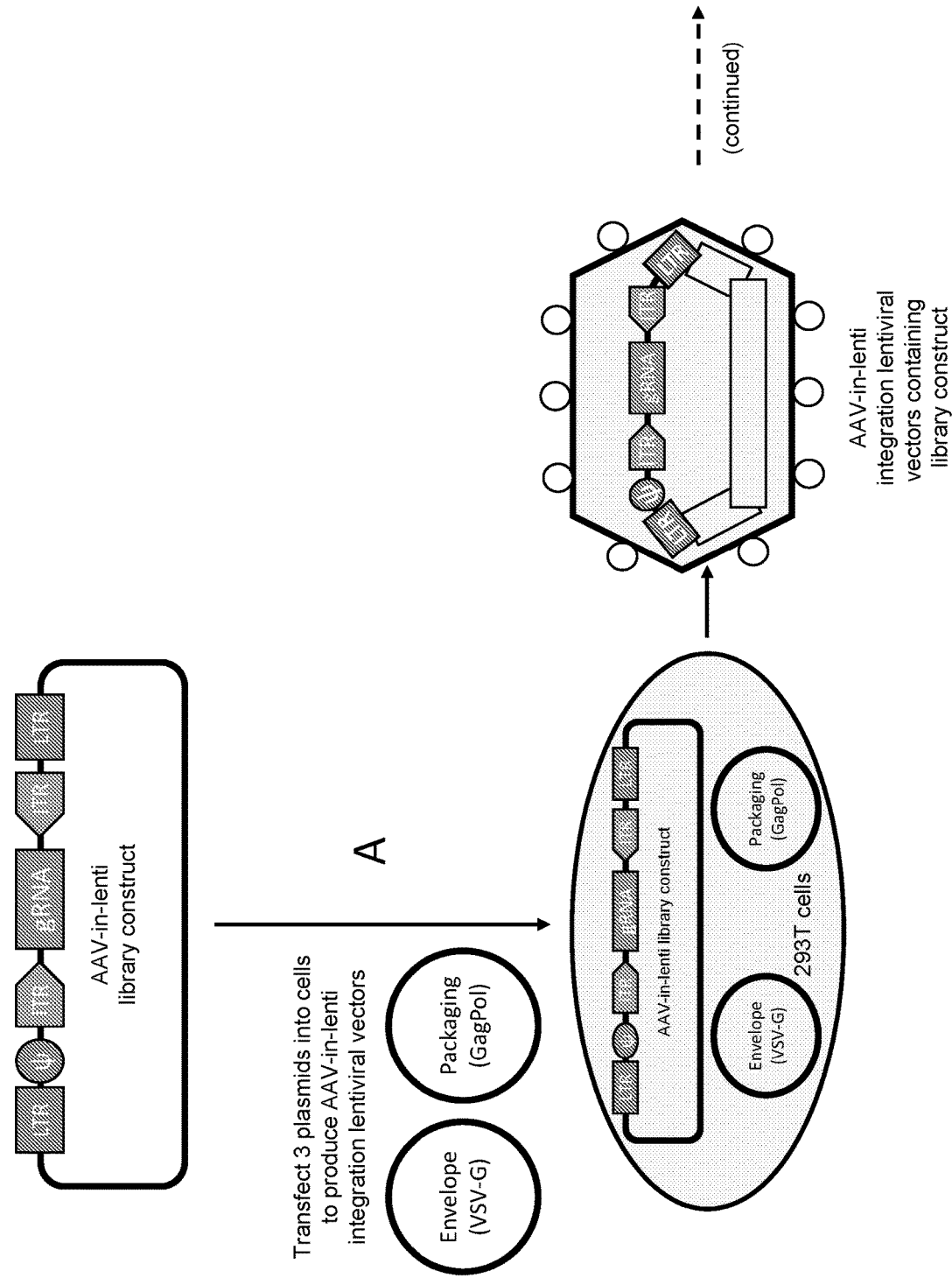
FIG. 2 depicts an exemplary scheme for generation of a mammalian cell library that expresses AAV viral vectors that include an identifier, wherein lentivirus is used for single or low copy integration of a library construct into the mammalian cell genome.
Figure 2:
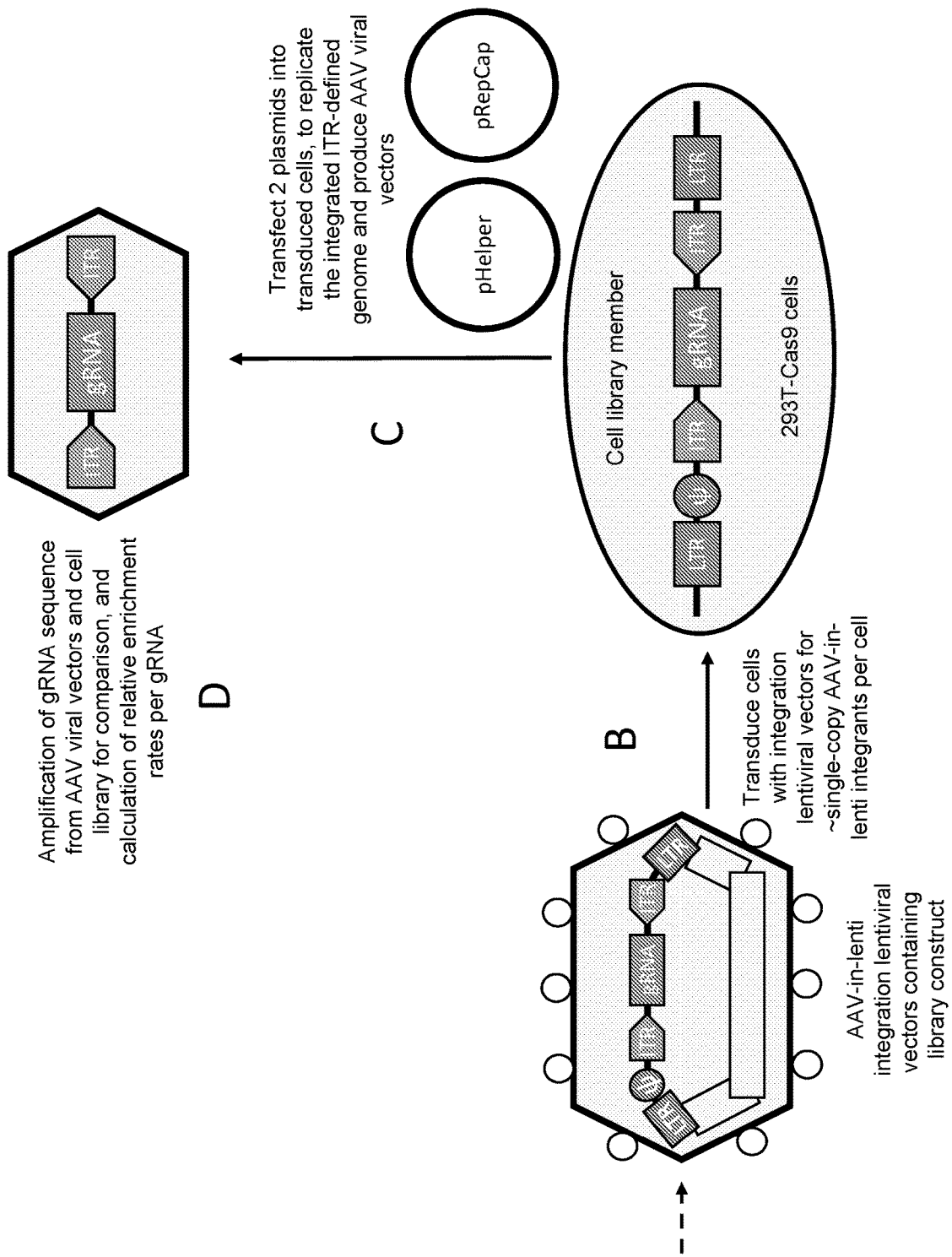

FIG. 2 provides a schematic of an exemplary platform method for engineering a viral vector-expressing and/or -producing mammalian cell library using an exemplary single contiguous library construct for expression of an AAV viral vector with an identifier. Mammalian cells are engineered to include (i) a single contiguous library construct and (ii) AAV constructs with sequences essential for AAV expression (e.g., helper and rep/cap), depicted FIG. 2, step C. The exemplary schematic employs an integration viral vector (e.g., AAV-in-*lenti* integration lentiviral vector) for integration of the single library construct into mammalian cells of the library.

In some embodiments, a lentiviral vector is generated that comprises a library construct. To generate lentiviral vectors comprising a library construct, a first subset of mammalian cells are engineered to include sequences essential for lentivirus expression (e.g., envelope and gag) and a library construct that comprises an identifier (e.g., a unique library variant (e.g., gRNA) and/or a barcode) that is flanked by viral packaging sequences (e.g., AAV ITRs), all of which is flanked by cis-acting integration sequences (e.g., lentivirus LTRs). In some embodiments, a library construct may further comprise a payload.

In some embodiments, the AAV-in-*lenti* integration lentiviral vector library can be used to generate a mammalian cell library, where using a second subset of mammalian cells, the library constructs are integrated into the mammalian cell genomes at low copy number (e.g., at approximately single copy, e.g., one copy, or no more than two copies, or no more than three copies, or no more than four copies). In some embodiments, a library construct (e.g., for an AAV-producing mammalian cell library) can be integrated by other means (e.g., nuclease-mediated integration, recombinase-mediated integration, transposase-mediated integration, etc.) or expressed episomally in mammalian cells. In various embodiments, mammalian cells of a mammalian cell library should include consistent and low copy number of a library construct (e.g., single copy). FIG. 2, step D depicts expression of AAV vectors from the resulting mammalian cell library, which can be screened in accordance with methods provided herein.

FIG. 3 provides a schematic of an exemplary platform method for engineering a viral vector-expressing and/or -producing mammalian cell library using an exemplary discontiguous library construct for expression and/or production of an AAV viral vector with an identifier. In some embodiments, a discontiguous library construct is provided as a series of constructs that together make up a library construct. In some embodiments, a discontiguous library construct comprises an AAV-in-lenti construct comprising an identifier (e.g., a barcode) and one or more additional constructs that each comprise one or more library variants, as depicted in FIG. 3, step A. In some embodiments each of these additional constructs contains one or more barcodes as well. In some embodiments, library constructs include cis-acting integration sequences for genomic integration by other means (e.g., homology arms for nuclease-mediated integration, recombination sites for recombinase-mediated integration, transposase sites for transposase-mediated integration, etc.) or may be for episomal expression in mammalian cells.

A first subset of mammalian cells are transduced with the various AAV-in-lenti integration lentiviral vector library that make up the library construct, as depicted in FIG. 3, step B. For example, cells may be transduced with an AAV-in-lenti construct comprising an identifier (e.g., barcode), where the identifier is flanked by ITR sequences, which are flanked by LTR sequences. In some embodiments, the AAV-in-lenti integration lentiviral vectors comprising an identifier (e.g., barcode) are transduced into a second subset of mammalian cells under conditions to obtain mammalian cells with approximately a single-copy (one) of a library construct per cell. In some embodiments, individual library constructs comprising library variants are introduced and/or integrated into mammalian cells at a high-copy dose or multiple rounds of single-copy doses (e.g., using integration lentiviral vectors), to generate a multiply-library variant (e.g., gRNA)-perturbed mammalian cell library population. In some embodiments, each cell of the mammalian cell library comprises a single ITR-flanked barcode per cell, and greater than one 1 library variant (e.g., gRNA) per cell.

Mammalian cells are engineered to include sequences essential for AAV expression (e.g., helper and rep/cap), depicted FIG. 3, step C. In methods employing a discontiguous library construct, at least a portion of mammalian cells of the library and/or at least a portion of AAV vectors are sequenced. FIG. 3, step D depicts single cell sequencing of mammalian cells and FIG. 3, step E depicts sequencing of identifiers in AAV vectors. Notably, these sequencing steps may be conducted in any order. For example, in some embodiments, sequencing of AAV vectors may be first conducted to determine identifiers associated with desired characteristics of mammalian cells and/or viral vectors (e.g., for viral vector production), and then cells can be sequenced by single cell sequencing to associate particular identifiers (e.g., identifiers identified previously) with their potentially causative library variants. In some embodiments, only those mammalian cells associated with selected identifiers may be sequenced by single cell sequencing. In some embodiments, sequencing of AAV vectors and single cell sequencing mammalian cells is conducted substantially simultaneously.

One of skill in the art will recognize that while the schematic in FIG. 2 and FIG. 3 depict screening a mammalian cell library for characteristics of viral vector expression and/or production, the order of steps may be adjusted as appropriate.

In some embodiments, a pool of viral vectors generated by a first mammalian cell library is used to transduce mammal cells to generate a second mammalian cell library that comprises the library variants. In some embodiments, the first mammalian cell library comprises an integrated library construct. In some embodiments, the first mammalian cell library comprises an episomal library construct. In some embodiments, the second mammalian cell library comprises an integrated library construct. In some embodiments, the second mammalian cell library comprises an episomal library construct.

In some embodiments, viral vector is harvested and/or pooled from a first mammalian cell library. In some embodiments, viral vector is an AAV viral vector and a first mammalian cell library is generated using an AAV-in-Lenti library, an AAV-in-Transposase library, or an episomal AAV library. In some embodiments, viral vector harvested and/or pooled from a first mammalian cell library is used to transfect mammalian cells and generate a second mammalian cell library. In some embodiments, the second mammalian cell library episomally expresses the library variants. In some embodiments, a pool of AAV vectors generated by a first mammalian cell library is used to transduce mammalian cells to generate a second mammalian cell library that episomally comprises the identifier.

Harvest and Pooling of Viral Vectors

Virus vector expressing mammalian cell libraries are cultured, and viral vectors produced are harvested, using any appropriate methods known in the art.

The viral vector-expressing mammalian cells may be cultured by batch culturing, fed-batch culturing, or continuous culturing. The viral vector-expressing mammalian cells may be cultured in suspension or attached to solid carriers in shaker flasks, fermenters, or bioreactors. After culturing, the mammalian cells and/or supernatant can be harvested and the nucleic acid can be isolated and purified from the proper fraction using methods known in the art.

In some embodiments, the viral vectors are harvested from the mammalian cell library. In some embodiments, viral vector is harvested after sufficient time for expression by the mammalian cells, which can vary based on the mammalian cell type and culture conditions.

In some embodiments, total viral vectors produced by the mammalian cells of the viral vector-expressing mammalian cell library are harvested. In some embodiments, viral vectors produced by the mammalian cells of the viral vector-expressing cell library are harvested corresponding to an interval of time. For example, viral vectors can be harvested daily, every two days, every 3 days, or longer interval, to assess viral vector production over time.

In some embodiments, viral vector is harvested when mammalian cells reach a cell density within a particular range. In some embodiments, viral vector is harvested after a particular amount of time. In some embodiments, viral vector is harvested between 12 hours and 2 weeks after viral transfection. In some embodiments, viral vector is harvested between 24 and 144 hours after viral transfection. In some embodiments, viral vector is harvested from the cell media. In some embodiments, mammalian cells are lysed in the process of harvesting viral vectors. In some embodiments, viral vector is harvested when mammalian cells produce at least a threshold level of viral vector (e.g., and average of at least about $1 \times 10^3$ viral vectors per mammalian cell prior to purification).

In some embodiments, mammalian cells can be washed and viral vectors harvested after prolonged periods (e.g., to assess sustained production of viral vectors). In some embodiments, viral vector nucleic acid from the viral vectors (e.g., that includes an identifier) are isolated.

In some embodiments, mammalian cells are pooled prior to harvesting. In some embodiments, viral vectors are pooled prior to sequencing of viral vector nucleic acid (e.g., DNA and/or RNA).

Viral Vector Sequencing

In some embodiments, provided methods and technologies include sequencing of viral vector nucleic acids. In some embodiments, the viral vector nucleic acid is quantified prior to sequencing. In some embodiments, viral vector nucleic acid is not quantified prior to sequencing. Any suitable sequencing method in the art can be used.

In some embodiments, viral vector titers post-purification are determined. In some embodiments, titers are determined using quantitative PCR. In certain embodiments, a TaqMan probe specific to a construct is utilized to determine construct levels. Provided methods and technologies, in various embodiments, include an amplification step wherein viral vector nucleic acid material (or portion thereof, for example, an identifier) is amplified. While any application-appropriate amplification reaction is contemplated as compatible with some embodiments, by way of specific example, in some embodiments, an amplification step may be or comprise a polymerase chain reaction (PCR), rolling circle amplification (RCA), multiple displacement amplification (MDA), isothermal amplification, and any combination thereof.

In some embodiments, sequencing to be used in the context of the present methods is includes next generation sequencing. There are a number of different NGS platforms using different sequencing technologies. In general, NGS platforms perform sequencing of millions of small fragments of DNA in parallel. In some embodiments, NGS is or includes Solexa sequencing, which simultaneously identifies DNA bases, as each base emits a unique fluorescent signal, and adding them to a nucleic acid chain. In some embodiments, NGS is or includes 454 sequencing, which detects pyrophosphate release, again using fluorescence, after nucleotides are incorporated by polymerase to a new strand of DNA. In some embodiments, NGS is or includes ion torrent: Proton/PGM sequencing, which measures the direct release of H+(protons) from the incorporation of individual bases by DNA polymerase.

Abundance of identifiers in a pool of viral vector nucleic acid can be analyzed. The identifier sequence can be used to select mammalian cells that promote the desired viral vector characteristic (e.g., high production). Increased viral vector production can be an increase in the number of viral vectors over a fixed period of time or production for an extended amount of time, e.g., as compared to a reference cell. In some embodiments, samples of viral vector pools at different points in tie can be analyzed (e.g., to assess mammalian cell lines that produce viral vectors at later time points). Using the identifier in the viral vectors, the corresponding mammalian cells can be identified and the engineered sequences (e.g., library variants) in that cell determined. For example, this can be done by direct and pre-determined association of the library variant with the identifier (e.g., in cases with a contiguous library construct), or by an additional step of single cell sequencing followed by association of identifiers with potentially causative library variants (e.g., in cases with a discontiguous library construct).

Single Cell Sequencing

In some embodiments, methods of the present disclosure include a step of single cell sequencing. In some embodiments, where mammalian cells include a library construct (e.g., a discontiguous library construct), provided methods include a step of single cell sequencing (e.g., to identify one or more engineered sequences in a mammalian cell that are not packaged into a viral vector. In some embodiments, it is understood that a step of single cell sequencing can also be useful for cases where a contiguous library construct is used.

In some embodiments, where a library construct comprises multiple discontiguous constructs, provided methods include a step of single cell sequencing. In some embodiments, a nucleic acid (e.g., of a construct) to be sequenced by single cell sequencing is expressed as RNA in a mammalian cell. In some embodiments, provided methods that include single cell sequencing comprise a step of labeling one or more expressed sequences (e.g., RNA, e.g., mRNA) with a cell identity sequence. In some embodiments, all expressed sequences (e.g., RNA, e.g., mRNA) are labeled with a cell identity sequence. In some embodiments, mammalian cells of libraries will express poly-A tailed mRNAs that comprise any identifiers and/or library variants present in the cell.

In some embodiments, one or more library variants are labeled with a cell identity sequence. In some embodiments, all library variants are labeled with a cell identity sequence. In some embodiments, all library variants and all identifiers are labeled with a cell identity sequence. In some embodiments, each mammalian cell or cell line of a mammalian cell library comprises a unique cell identity sequence. Accordingly, a cell identity sequence associates nucleic acid from constructs comprised on contiguous or discontiguous library construct (which the sequenced nucleic acid will comprise), with the individual mammalian cell or cell line from which it was derived.

The present disclosure also encompasses a recognition that a single cell identity sequence is specifically appended during reverse transcription of expressed RNAs upon conversion to cDNA, during a single cell sequencing method. It is understood that constructs or nucleic acids intended for single cell sequencing should be contained in an expressed RNA such that all transcripts can be single cell tagged with a cell identity sequence using an appropriate primer during the reverse transcription step.

In some embodiments, provided methods include both a step of single cell sequencing of mammalian cells of a mammalian cell library and a step of viral vector sequencing (e.g., using next generation sequencing). The present disclosure encompasses a recognition that through sequencing both viral vectors and mammalian cells an association can be determined between viral vector abundance and any library variant(s) in a mammalian cell.

In some embodiments, provided methods include a step of viral vector sequencing (e.g., using next generation sequencing) followed by a step of single cell sequencing. In some embodiments, single cell sequencing of mammalian cells of a mammalian cell library is performed on those mammalian cell lines selected based on viral vector sequencing.

In some embodiments, single cell sequencing of mammalian cells of a mammalian cell library is performed simultaneously with viral vector sequencing (e.g., using next generation sequencing). In some embodiments, single cell sequencing of mammalian cells of a mammalian cell library is performed prior to viral vector sequencing.

Analysis

In some embodiments, the present disclosure encompasses a recognition that abundance of a particular identifier in a viral pool can be used to identify mammalian cells (among cells in the library) with improved characteristics, e.g., viral vector characteristics or viral vector production characteristics (e.g., high expression and/or production). Corresponding engineered sequences (e.g., library variants) in the mammalian cells can be determined. For example, this can be done by direct and pre-determined association of the library variant with the sequenced identifier (e.g., in cases with a contiguous library construct), or by an additional step of single cell sequencing followed by association of identifiers with potentially causative library variants (e.g., in cases with a discontiguous library construct).

In some embodiments, provided methods and technologies include a step of selection or screening prior to viral vector sequencing. For example, viral vector produced by a library of mammalian cells may be selected or screened for functional characteristics of a viral vector, such as, for example, viral vector stability, viral vector potency, ability of viral vector to infect cells, viral vector binding (e.g., to a receptor), ability of viral vector to transfer nucleic acid, etc. In some embodiments, such selected viral vectors are pooled and sequenced. Using such methods, mammalian cells and/or perturbations may be identified that have multiple beneficial characteristics. For example, a cell line that produces a high level of viral vector that is also stable.

In some embodiments, provided methods and technologies include a selection or screening step after viral vector sequencing. For example, selected or screened candidate viral vectors or the perturbations (e.g., genetic changes) identified can be used to inform construction of a viral vector library that can be analyzed for various characteristics. For example, such a viral vector library can be selected or screened for their ability to transduce mammalian cells.

The selected mammalian cell candidates can be used for production of viral vector, or the perturbations (e.g., genetic changes) identified used to inform construction of a new mammalian cell library. The library-based platform approach (depicted in FIG. 1, panels A to F) can be repeated until engineered mammalian cells are identified that express viral vectors with desired characteristics and/or in desired quantity. Engineered sequences associated with desired characteristics can be analyzed, for example, using machine learning (ML) approaches to develop a machine learning model. A trained machine learning model is useful for informing future designs and reducing the number of mammalian cell libraries to be screened, thereby reducing time and cost. In some embodiments, mammalian cell libraries can be designed and/or the method performed to identify engineered sequences that synergistically interact (e.g., two or more engineered sequences combined) in mammalian cells to have the desired characteristics (e.g., a certain level of viral vector production). In some embodiments, a resulting mammalian cell obtained from the platform technology described herein will have one, two, three, four, five, or more engineered sequences (e.g., library variants and/or perturbations), such that the mammalian cell with desired properties of viral vector production is generated (e.g., production at a certain level, production for a desired duration, etc.).

In some embodiments, a machine learning model is trained to generate a prediction indicating whether an engineered sequence (e.g., perturbation), with one or more additional perturbations in the mammalian cell and/or viral vector, is likely to have synergistic and/or further improved viral vector characteristics.

In various embodiments, a machine learning model is any one of a regression model (e.g., linear regression, logistic regression, or polynomial regression), decision tree, random forest, support vector machine, Naïve Bayes model, k-means cluster, or neural network (e.g., feed-forward networks, convolutional neural networks (CNN), or deep neural networks (DNN)). A machine learning model can be trained using a machine learning implemented method, such as any one of a linear regression algorithm, logistic regression algorithm, decision tree algorithm, support vector machine classification, Naïve Bayes classification, K-Nearest Neighbor classification, random forest algorithm, deep learning algorithm, gradient boosting algorithm, and dimensionality reduction techniques. In various embodiments, a machine learning model is trained using supervised learning algorithms, unsupervised learning algorithms, semi-supervised learning algorithms (e.g., partial supervision), weak supervision, transfer, multi-task learning, or any combination thereof. In various embodiments, the machine learning model comprises parameters that are tuned during training of the machine learning model. For example, the parameters are adjusted to minimize a loss function, thereby improving the predictive capacity of the machine learning model.

Generally, a machine learning model is trained to differentiate between one or more edits that result in a change in viral vector expression. For example, a machine learning model is trained to recognize patterns across the training examples that contribute towards an increase or decrease in viral vector expression. As a specific example, a machine learning model is trained to identify particular genomic locations that, if edited, likely cause a mammalian cell to increase and/or extend viral vector production. As another specific example, a machine learning model can be trained to identify particular genomic locations that, if edited, result in a mammalian cell with increased and/or extended viral vector production.

In various embodiments, the identified edits are categorized using predicted score outputted by a machine learning model. As one example, identified edits that are assigned a score above a threshold value are categorized as candidate edits for further testing. In various embodiments, the threshold score is 0.5, 0.6, 0.7, 0.75, 0.8, 0.85, 0.90, 0.91, 0.92, 0.93, 0.94, 0.95, 0.96, 0.97, 0.98, or 0.99. Identified edits that do not satisfy the threshold score criterion are categorized as non-candidate edits.

Altogether, the implementation of the machine learning model enables in silico prediction and categorization of edits that can be rapidly screened out. Thus, only candidate edits are used in genomic designs for further testing whereas non-candidate edits are removed from further consideration. This eliminates the need to test all combinations of edits in vitro which is significantly time-consuming and costly.

Applications

The present disclosure provides, among other things, mammalian cells for expressing viral vectors, constructs for generating mammalian cells, and viral vectors generated using the methods described herein. Viral vectors and associated mammalian cells may be useful in a number of applications, including but not limited to, vaccines, cancer therapy (e.g., oncolytic therapies), gene therapy, and/or cell therapy (e.g., CAR-T). Viral vectors and mammalian cells may be used in the research and manufacturing processes that generate biologics and/or therapies, or as biologics themselves.

For example, in some embodiments, viral vectors can be used in many ways that include but are not limited to vaccines, cancer therapies (e.g., oncolytic therapies), and/or gene therapies (e.g., in vivo gene and/or genomic editing). As another example, in some embodiments, viral vectors can be used in many ways that include but are not limited to the research, production, and/or manufacturing of vaccines, cancer therapies (e.g., oncolytic therapies), gene therapies (e.g., ex vivo gene and/or genomic editing), and/or cell therapies (e.g., ex vivo gene and/or genomic editing). Accordingly, there are a large spectrum of viral vectors for these various applications.

In some embodiments, provided are compositions comprising library constructs, viral vectors, and/or mammalian cells as described herein. In some embodiments, provided are uses of methods described herein to produce a mammalian cell. In some embodiments, provided are uses of methods described herein to produce a viral vector (e.g., an AAV vector). In some embodiments, provided are uses of methods described herein to produce a library construct.

In some embodiments, provided are uses of a library construct, viral vector and/or method described herein to produce an engineered mammalian cell. In some embodiments, provided is a method of manufacturing a mammalian cell that expresses a viral vector, said method comprising introducing one or more perturbations identified using a screening method described herein.

The present disclosure also provides methods of treating a subject with a composition (e.g., a pharmaceutical composition) using a viral vector and/or mammalian cell described herein.

Exemplary Applications of Mammalian Cells and Viral Vectors

Mammalian cells of the present disclosure can be used in a number of applications including, but not limited to, vaccines, cancer therapy (e.g., oncolytic therapies), gene therapy, and/or cell therapies (e.g., CAR-T). Mammalian cells may be used in the research and manufacturing processes that generate biologics and/or therapies, or as biologics. For example, in some embodiments, mammalian cells can be used to produce viral vectors that can be used directly as biologics and/or therapies, including but not limited to: vaccines, cancer therapies (e.g., oncolytic therapies), and/or gene therapies (e.g., in vivo gene and/or genomic editing). As another example, in some embodiments, mammalian cells can be used to produce viral vectors that can be used for the research, production, and/or manufacturing of biologics and/or therapies, including but not limited to: vaccines, cancer therapies (e.g., oncolytic therapies), gene therapies (e.g., ex vivo gene and/or genomic editing), and/or cell therapies (e.g., ex vivo gene and/or genomic editing).

In some embodiments, a mammalian cell of the present disclosure produces viral vector at a desired level. In some embodiments, a mammalian cell of the present disclosure comprises one or more perturbations that impact viral vector production.

In some embodiments, provided is a method of manufacturing a viral vector, comprising, culturing a mammalian cell described herein. In some embodiments, provided is a method of manufacturing a target level of viral vector, comprising culturing a mammalian cell described herein. In some embodiments, provided is a use of mammalian cells for producing a viral vector (e.g., an AAV vector) at a level above a threshold level. In some embodiments, a mammalian cell for producing a viral vector comprises one or more perturbations and produces viral vector at a higher level than a corresponding mammalian cell that lacks the one or more perturbations.

In some embodiments, provided are methods for producing viral vectors in mammalian cells that can then be used to generate cell therapies. In some embodiments, a produced viral vector has a payload encoding a chimeric antigen receptor for generating a CAR-T cell, wherein the generated CAR-T cell can be administered to a subject.

In some embodiments, the present disclosure provides a method of manufacturing and/or producing a vaccine comprising culturing a mammalian cell of the present disclosure, wherein the viral vector comprises a payload comprising a vaccine component. In some embodiments, provided is a method of manufacturing and/or producing an AAV-based vaccine.

In some embodiments, the present disclosure provides a method of manufacturing and/or producing an oncolytic viral vector comprising culturing a mammalian cell of the present disclosure, wherein the viral vector is an oncolytic viral vector.

In some embodiments, provided are methods for producing viral vectors in mammalian cells that can be as gene therapies. In some embodiments, a produced viral vector has a payload that permits in vivo gene therapy, wherein the generated viral vector can be administered to a subject.

In some embodiments, provided are methods for producing viral vectors in mammalian cells that can then be used for ex vivo gene therapy. In some embodiments, a produced viral vector has a payload that permits ex vivo gene therapy, wherein the generated viral vector can be used to generate a therapeutic cell that can then be administered to a subject.

CERTAIN EXEMPLARY EMBODIMENTS

Exemplary Methods of Guide RNA-Based Screening for Viral Vector Production

In some embodiments, provided technologies employ a mammalian cell library that has been genetically engineered using guide RNA directed nuclease-mediated editing (e.g., to induce a perturbation). In some embodiments, each mammalian cell has at least one targeted genome modification (i.e., an engineered sequence that is a library variant) by expression of an RNA-guided endonuclease and a guide RNA molecule specific for a target sequence. In some embodiments, a targeted genomic modification is or comprises inactivation of a gene, deletion of a gene, modification of a gene, insertion into a gene, and/or substitution of all or part of a gene. In some embodiments, the identifier is a guide sequence (e.g., a guide RNA sequence or a guide DNA sequence encoding a guide sequence). Thus, guide RNA directed nuclease-mediated editing can be used in mammalian cells to simultaneously engineer a nucleic acid sequence and provide an identifier (e.g., the guide sequence). In some embodiments, mammalian cells are transformed with a library construct comprising at least one construct that comprises an identifier that is a guide sequence, where the identifier is positioned between sequences for packaging of the identifier into a viral vector (e.g., viral repeat sequences, e.g., AAV ITRs for expression of an AAV vector).

In some embodiments, a mammalian cell includes at least one sequence that has been edited by guide RNA directed nuclease-mediated editing (e.g., a perturbation). In some embodiments, a mammalian cell comprises at least one sequence that has been edited by guide RNA directed nuclease-mediated editing and one or more additional engineered sequences (e.g., by nuclease-mediated editing and/or other methods). In some embodiments, a mammalian cell in a library comprises at least two or more engineered sequences (e.g., two or more perturbations).

In some embodiments, a method includes transfection of the mammalian cells of the library with constructs that include sequences for expression of a viral vector (e.g., AAV vector, depicted as including genetic elements of helper, Tx gene, Rep Cap), thereby generating a viral vector-producing mammalian cell library. In some embodiments, guide RNA directed nuclease-mediated editing is performed prior to construct transfection. In some embodiments, guide RNA directed nuclease-mediated editing is performed approximately simultaneously with construct transfection, meaning that the guide RNA mediated editing components and the viral vector components are transfected into the mammalian library at the same time.

In some embodiments, guide RNA directed nuclease-mediated editing is performed substantially simultaneously with construct transfection. In some embodiments, guide RNA directed nuclease-mediated editing is performed on mammalian cells that already have genetic elements for expression of a viral vector (e.g., after transfection of the mammalian cells with sequences to express a viral vector). In some embodiments, guide RNA directed nuclease-mediated editing is performed on mammalian cells that have already been engineered to express a viral vector (e.g., an AAV vector). In some embodiments, one or more elements for expression of a viral vector are integrated into a mammalian cell genome. In some embodiments, one or more elements for expression of a viral vector are present extrachromosomally in a mammalian cell.

Regardless of the order of steps, one of skill in the art can generate a mammalian cell library where each cell or cell line comprises one or more engineered sequences and at least one identifier (e.g., a library variant comprising a guide sequence), and genetic elements sufficient for expression of a viral vector. Accordingly, provided are viral vector-producing mammalian cell libraries, wherein each cell comprises (i) at least one library variant (e.g., an engineered sequence), (i) at least one identifier (e.g., comprising a guide sequence), and (iii) viral elements sufficient for expression of a viral vector of interest.

In some embodiments, provided technologies include a unique approach whereby a viral vector takes up the guide sequence into the viral vector genome (e.g., between viral repeat sequences). This enables direct characterization of the viral vectors and identification of an associated engineered sequence (e.g., a library variant). In some embodiments, a library variant can serve as an identifier of the mammalian cell (which may contain additionally mutations, that can be identified, e.g., by sequencing).

In some certain embodiments, provided mammalian cells are transfected with one or more constructs encoding a viral vector, for example one, two, three, or more plasmids (e.g., rep/cap, helper, tx plasmid) are transfected into the cells. In some embodiments, 1 or more of the viral vector sequences are integrated into the genome. In some embodiments, 1 or more of the viral vector sequences are episomal. In some embodiments, a viral vector includes a payload (e.g., that comprises guide and nuclease sequences) (in such a case genomic engineering (e.g., introducing an engineered sequence), introducing an identification sequence, and construct transfection steps may all take place simultaneously).

In some embodiments, a mammalian cell in the library is transfected with a tx plasmid that comprises a payload sequence. In some embodiments, a viral expressing mammalian cell produces an AAV that carries at least a payload and a guide RNA.

In some embodiments, a mammalian cell in the library is transfected with a tx plasmid that comprises at least two guide RNA s and Cas9 encoded, where a first gRNA binds a patient's genome and a second guide RNA binds the mammalian cell population (and serves as an identifier). In some embodiments, a viral expressing mammalian cell produces an AAV that carries at least a nuclease, a first guide RNA, a second guide RNA.

Viral vector expressing cell libraries are cultured and viral vectors are harvested, using any appropriate methods known in the art. In some embodiments, the viral genomic DNA (e.g., that includes a guide sequence) is isolated and the viral nucleic acid (e.g., DNA) is sequenced (e.g., using next generation sequencing). The relative abundance of an identifier (e.g., a guide sequence) may be determined (e.g., relative to other guide sequences), and this correlates with the abundance of those particular viral vectors. In some certain embodiments, a mammalian cell in a library described herein.

Exemplary Methods of Barcode-based Screening for Viral Production

In some embodiments, provided technologies employ a mammalian cell library that has been genetically engineered to include a barcode sequence and one or more engineered sequences (including mutations, insertions, deletions, replacements, substitutions, rearrangements, etc.). In some embodiments, provided methods include generating and/or obtaining a mammalian cell library where each cell has a barcode sequence and one or more engineered sequences (e.g., including one or more mutations of interest).

In some embodiments, a barcode sequence is introduced into a mammalian cell before introducing an engineered sequence (e.g., by targeted or by random mutagenesis and/or editing). In some embodiments a barcode sequence is introduced into a mammalian cell substantially simultaneously with an engineered sequence. In some embodiments, a barcode sequence is introduced into a mammalian cell after introducing an engineered sequence.

The mammalian cells of the mammalian cell library are then transfected to express a viral vector (e.g., AAV vector, depicted as including genetic elements of helper, Tx gene, Rep Cap), thereby generating a viral infected mammalian cell library (depicted in upper-right portion of FIG. 1). Generally, a viral infected mammalian cell library of the present disclosure will include an engineered sequence, a barcode sequence, and viral elements sufficient for expression of a viral vector of interest.

In some certain embodiments, provided mammalian cells are transfected with a viral vector, for example one, two, three, or more plasmids (e.g., rep/cap, helper, tx plasmid) are transfected into the cells. In some embodiments, 1 or more of the viral vector sequences are integrated into the genome. In some embodiments, 1 or more of the viral vector sequences are episomal.

In some embodiments, two or more of (i) a barcode sequence, (ii) an engineered sequence, and (iii) genetic elements for expression of a viral vector, are introduced into mammalian cells substantially simultaneously. In some embodiments, all three are introduced substantially simultaneously. In some embodiments, introduction of a barcode sequence and/or engineered sequence is performed on mammalian cells after transfection of the mammalian cells with sequences to express a viral vector. In some embodiments, introduction of a barcode sequence and/or engineered sequence is performed on mammalian cells that have already been engineered to express a viral vector (e.g., an AAV vector). In some embodiments, one or more elements for expression of a viral vector are integrated into a mammalian cell genome. In some embodiments, one or more elements for expression of a viral vector are present extrachromosomally in a mammalian cell.

In some embodiments, provided technologies include a unique approach whereby a viral vector takes up the barcode sequence into the viral vector genome (e.g., between viral repeat sequences). This enables direct characterization of the viral vectors and identification of the mammalian cell from which the viral vector was produced.

In some embodiments, a viral vector expressed by a mammalian cell comprises a payload and a barcode. In some certain embodiments, a viral vector includes barcode and payload (e.g., payload may include a gRNA and nuclease (e.g., Cas9)). In some certain embodiments, a viral vector (e.g., AAV) produced by a mammalian cell library using such methods can include a payload (e.g., Cas9/gRNA), and a barcode. The barcode sequence can be used to determine which mammalian cells within the library are high viral vector producers and to identify engineered sequences of interest.

Viral vector expressing cell libraries are cultured and viral vectors are harvested, using any appropriate methods known in the art. In some embodiments, the viral nucleic acid (e.g., genomic DNA, e.g., that includes a barcode sequence) is isolated and the viral nucleic acid (e.g., genomic DNA) is sequenced (e.g., using next generation sequencing). The relative abundance of a barcode may be determined (e.g., relative to other viral vector barcodes), and this correlates with the abundance of a particular viral vector. In some certain embodiments, a mammalian cell in a library described herein.

Certain Numbered Exemplary Embodiments

Embodiment 1. A mammalian cell comprising one or more engineered sequences that together comprise (a) at least one identifier positioned between a first set of two viral repeat sequences capable of packaging into a viral vector, and (b) at least one polynucleotide comprising one or more nucleic acid sequences essential for production of the viral vector, and wherein the mammalian cell produces viral vectors comprising the at least one identifier.

Embodiment 2. A mammalian cell comprising one or more engineered sequences that together comprise: (a) at least one identifier positioned between a first set of two viral repeat sequences capable of packaging into a viral vector, and (b) at least one polynucleotide comprising one or more nucleic acid sequences essential for production of the viral vector, and (c) at least one perturbation, and wherein the mammalian cell produces viral vectors comprising the at least one identifier.

Embodiment 3. A mammalian cell comprising one or more engineered sequences that together comprise: (a) at least one identifier positioned between a first set of two viral repeat sequences capable of packaging into a viral vector, and (b) at least one polynucleotide comprising one or more nucleic acid sequences essential for production of the viral vector, and (c) at least one perturbation, and (d) at least one library variant, and wherein the mammalian cell produces viral vectors comprising the at least one identifier.

Embodiment 4. A mammalian cell comprising one or more engineered sequences that together comprise: (a) at least one identifier positioned between a first set of two viral repeat sequences capable of packaging into a viral vector, and (b) at least one polynucleotide comprising one or more nucleic acid sequences essential for production of the viral vector, and (c) at least one perturbation, and (d) at least one library variant, and (e) at least one payload, and wherein the mammalian cell produces viral vectors comprising the at least one identifier.

Embodiment 5. A mammalian cell comprising one or more engineered sequences that together comprise: (a) at least one identifier positioned between a first set of two viral repeat sequences capable of packaging into a viral vector, and (b) at least one polynucleotide comprising one or more nucleic acid sequences essential for production of the viral vector, and (c) at least one perturbation, and (d) at least one library variant, and (e) at least one payload, and (f) at least one perturbation accessory sequence, and wherein the mammalian cell produces viral vectors comprising the at least one identifier.

Embodiment 6. A mammalian cell comprising one or more engineered sequences that together comprise: (a) at least one identifier positioned between a first set of two viral repeat sequences capable of packaging into a viral vector, and (b) at least one polynucleotide comprising one or more nucleic acid sequences essential for production of the viral vector, and (c) at least one perturbation, and (d) at least one library variant, and (e) at least one payload, and (f) at least one perturbation accessory sequence, and (g) at least one trans-acting integration sequence, and wherein the mammalian cell produces viral vectors comprising the at least one identifier.

Embodiment 7. A mammalian cell comprising one or more engineered sequences that together comprise: a) at least one identifier positioned between a first set of two viral repeat sequences capable of packaging into a viral vector, and (b) at least one polynucleotide comprising one or more nucleic acid sequences essential for production of the viral vector, and (c) at least one perturbation, and (d) at least one library variant, and (e) at least one payload, and (f) at least one perturbation accessory sequence, and (g) at least one trans-acting integration sequence, and (h) at least one cis-acting integration sequence, and wherein the mammalian cell produces viral vectors comprising the at least one identifier.

Embodiment 8. A mammalian cell population comprising a plurality of mammalian cells that each individually comprise one or more engineered sequences, wherein the one or more engineered sequences together comprise: (a) at least one identifier positioned between a first set of two viral repeat sequences capable of packaging into a viral vector, and (b) at least one polynucleotide comprising one or more nucleic acid sequences essential for production of the viral vector, and wherein the mammalian cell population produces viral vectors that individually comprise the at least one identifier.

Embodiment 9. A mammalian cell comprising one or more engineered sequence that together comprise: (a) at least one identifier positioned between a first set of two viral repeat sequences capable of packaging into a viral vector, and (b) at least one polynucleotide comprising one or more nucleic acid sequences essential for production of the viral vector, and optionally wherein one or more engineered sequences comprise at least one perturbation, at least one library variant, at least one payload, at least one perturbation accessory sequence, at least one trans-acting integration sequence, and/or at least one cis-acting integration sequence, and wherein the mammalian cell produces viral vectors that individually comprise the at least one identifier.

Embodiment 10. A mammalian cell population comprising a plurality of mammalian cells that each individually comprise one or more engineered sequences, wherein the one or more engineered sequences together comprise: (a) at least one identifier positioned between a first set of two viral repeat sequences capable of packaging into a viral vector, and (b) at least one polynucleotide comprising one or more nucleic acid sequences essential for production of the viral vector, and optionally wherein one or more engineered sequences comprise at least one perturbation, at least one library variant, at least one payload, at least one perturbation accessory sequence, at least one trans-acting integration sequence, and/or at least one cis-acting integration sequence, and wherein the mammalian cell population produces viral vectors that individually comprise the at least one identifier.

Embodiment 11. A mammalian cell comprising one or more engineered sequences that together comprise: (a) at least one library construct, and (b) at least one polynucleotide comprising one or more nucleic acid sequences essential for production of the viral vector, and wherein the at least one library construct comprises at least one identifier, wherein the identifier is positioned between a first set of two viral repeat sequences capable of packaging into a viral vector, and wherein the mammalian cell produces viral vectors comprising the at least one identifier.

Embodiment 12. A mammalian cell population comprising a plurality of mammalian cells that each individually comprise one or more engineered sequences, wherein the one or more engineered sequences together comprise: (a) at least one library construct, and (b) at least one polynucleotide comprising one or more nucleic acid sequences essential for production of the viral vector, and wherein the at least one library construct comprises at least one identifier, wherein the identifier is positioned between a first set of two viral repeat sequences capable of packaging into a viral vector, and wherein the mammalian cell population produces viral vectors that individually comprise the at least one identifier.

Embodiment 13. A mammalian cell comprising one or more engineered sequences that together comprise: (a) at least one library construct, wherein the at least one library construct comprises at least one identifier, wherein the identifier is positioned between a first set of two viral repeat sequences capable of packaging into a viral vector, and (b) at least one polynucleotide comprising one or more nucleic acid sequences essential for production of the viral vector, and optionally wherein one or more engineered sequences comprise at least one perturbation, at least one library variant, at least one payload, at least one perturbation accessory sequence, at least one trans-acting integration sequence, and/or at least one cis-acting integration sequence, and wherein the mammalian cell population produces viral vectors that individually comprise the at least one identifier.

Embodiment 14. A mammalian cell population comprising a plurality of mammalian cells that each individually comprise one or more engineered sequences, wherein the one or more engineered sequences together comprise: (a) at least one library construct, wherein the at least one library construct comprises at least one identifier, wherein the identifier is positioned between a first set of two viral repeat sequences capable of packaging into a viral vector, and (b) at least one polynucleotide comprising one or more nucleic acid sequences essential for production of the viral vector, and optionally wherein one or more engineered sequences comprise at least one perturbation, at least one library variant, at least one payload, at least one perturbation accessory sequence, at least one trans-acting integration sequence, and/or at least one cis-acting integration sequence, and wherein the mammalian cell population produces viral vectors that individually comprise the at least one identifier.

Embodiment 15. The mammalian cell or mammalian cell population of any one of embodiments 1 to 14, wherein the mammalian cells each individually comprise human embryonic kidney (HEK) cells, HEK 293 cells, HEK 293T cells, Expi293 cells, Chinese hamster ovary (CHO) cells, HeLa cells, HeLa S3 cells, PER.C6 cells, HKB11 cells, CAP cells, Baby Hamster Kidney fibroblasts (BHK cells) (e.g., BHK-21 cells), mouse myeloma cells (e.g., Sp2/0 cells, NS0 cells), green African monkey kidney cells (e.g., COS cells and Vero cells), A549 cells, rhesus fetal lung cells (e.g., FRhL-2 cells), or a derivative of any thereof.

Embodiment 16. The mammalian cell or mammalian cell population of embodiment 15, or derivatives thereof, wherein the mammalian cells each individually comprise suspension cells and/or adherent cells.

Embodiment 17. The mammalian cell or mammalian cell population of any one of embodiments 1 to 16, wherein the mammalian cells each individually comprise HEK 293 cells, HEK 293T cells, CHO cells, or a derivative thereof.

Embodiment 18. The mammalian cell or mammalian cell population of any one of embodiments 1 to 17, wherein the mammalian cells each individually comprise HEK 293 cells, HEK 293T cells, or a derivative thereof.

Embodiment 19. The mammalian cell or mammalian cell population of any one of embodiments 1 to 16, wherein the mammalian cells each individually comprise HeLa cells.

Embodiment 20. The mammalian cell or mammalian cell population of any one of embodiments 1 to 19, wherein the viral vector is an adeno-associated viral (AAV) vector, a lentiviral vector, an adenovirus vector, an alphavirus vector, a sindbis viral vector, a retrovirus vector (e.g., a gamma retrovirus vector), a polyomavirus vector, (e.g., simian virus 40 (SV40) vector), a papilloma virus vector (e.g., a bovine papilloma virus (BPV) vector), a vaccinia virus vector, a herpes simplex virus (HSV) vector, a measles virus vector, a rhabdovirus vector, a rabies viral vector, a vesicular stomatitis virus (VSV) vector, a picornavirus vector (e.g., a poliovirus vector), a reovirus vector, a senecavirus vector, an echovirus vector (e.g., RIGVIR), a semliki forest virus (SFV) vector, a flavivirus vector, an anelloviral vector (https://www.ringtx.com), a newcastle disease virus (NDV) vector, a paramyxoviral vector, a sendai viral vector, an orthomyxoviral vector, an influenzavirus vector, a coronaviral vector, and/or a hybrid viral vector, and/or a derivative, hybrid, and/or engineered derivative thereof.

Embodiment 21. The mammalian cell or mammalian cell population of any one of embodiments 1 to 20, wherein the viral vector is an adeno-associated viral (AAV) vector.

Embodiment 22. The mammalian cell or mammalian cell population of any one of embodiments 1 to 21, wherein the first set of two viral repeat sequences are each AAV ITR sequences capable packaging into an AAV vector.

Embodiment 23. The mammalian cell or mammalian cell population of any one of embodiments 1 to 22, wherein the AAV vector comprises human AAV1 capsid proteins; human AAV2 capsid proteins; human AAV3b capsid proteins; human AAV4 capsid proteins; human AAV5 capsid proteins; human AAV6 capsid proteins; human AAV7 capsid proteins; human AAV8 capsid proteins; human AAV9 capsid proteins; human AAV10 capsid proteins; human AAV11 capsid proteins; human AAV12 capsid proteins; or human AAV13 capsid proteins.

Embodiment 24. The mammalian cell or mammalian cell population of any one of embodiments 1 to 23, wherein the AAV vector comprises human ancestral AAV capsid proteins.

Embodiment 25. The mammalian cell or mammalian cell population of any one of embodiments 1 to 24, wherein the viral vector comprises an AAV vector, wherein the AAV vector comprises a first set of two viral repeat sequences that comprise a pair of inverted terminal repeats (ITRs) that are or comprise a human AAV1 ITR(s); human AAV2 ITR(s); human AAV3b ITR(s); human AAV4 ITR(s); human AAV5 ITR(s); human AAV6 ITR(s); human AAV7 ITR(s); human AAV8 ITR(s); human AAV9 ITR(s); human AAV10 ITR(s); human AAV11 ITR(s); human AAV12 ITR(s); or human AAV13 ITR(s).

Embodiment 26. The mammalian cell or mammalian cell population of any one of embodiments 1 to 25, wherein the AAV vector comprises bovine AAV (b-AAV) capsid proteins; canine AAV (CAAV) capsid proteins; mouse AAV1 capsid proteins; caprine AAV capsid proteins; rat AAV capsid proteins; or avian AAV (AAAV) capsid proteins.

Embodiment 27. The mammalian cell or mammalian cell population of any one of embodiments 1 to 26, wherein the viral vector comprises an AAV vector, wherein the AAV vector comprises a pair of ITRs that are or comprise a bovine AAV (b-AAV) ITR(s); canine AAV (CAAV) ITR(s); mouse AAV1 ITR(s); caprine AAV ITR(s); rat AAV ITR(s); or avian AAV (AAAV) ITR(s).

Embodiment 28. The mammalian cell or mammalian cell population of any one of embodiments 1 to 27, wherein the at least one polynucleotide comprising one or more nucleic acid sequences essential for formation of a viral vector comprises: (a) an AAV Rep gene; (b) an AAV Cap gene; (c) one or more AAV helper genes; or (d) a combination thereof.

Embodiment 29. The mammalian cell or mammalian cell population of any one of embodiments 1-20, wherein the viral vector is a lentiviral vector.

Embodiment 30. The mammalian cell or mammalian cell population of embodiment 29, wherein the lentiviral vector is a human immunodeficiency virus (HIV) vector, a simian immunodeficiency virus (SIV) vector, an equine infectious anemia virus vector, a feline immunodeficiency virus vector, a visna virus vector, or a derivative thereof.

Embodiment 31. The mammalian cell or mammalian cell population of embodiments 29 or 30, wherein the first set of two viral repeat sequences are each lentiviral LTR sequences capable of packaging into a lentiviral vector.

Embodiment 32. The mammalian cell or mammalian cell population of any one of embodiments 29 to 31, wherein the lentiviral vector comprises a lentiviral Psi sequence.

Embodiment 33. The mammalian cell or mammalian cell population of any one of embodiments 29 to 32, wherein the lentiviral vector comprises a gag protein or a fragment thereof.

Embodiment 34. The mammalian cell or mammalian cell population of any one of embodiments 29 to 33, wherein the gag protein comprises one or more domains selected from a matrix (MA), capsid (CA), and nucleocapsid (NC) domain.

Embodiment 35. The mammalian cell or mammalian cell population of any one of embodiments 29 to 34, wherein the lentiviral vector comprises an envelope protein or a fragment thereof.

Embodiment 36. The mammalian cell or mammalian cell population of any one of embodiments 29 to 35, wherein the lentiviral vector is a pseudotyped lentiviral vector comprising a gag protein and envelope protein that are derived from different viruses.

Embodiment 37. The mammalian cell or mammalian cell population of any one of embodiments 29 to 36, wherein the lentiviral vector comprises a gag protein and/or an env protein derived from a human immunodeficiency virus (HIV) vector, a simian immunodeficiency virus (SIV) vector, an equine infectious anemia virus vector, a feline immunodeficiency virus vector, a visna virus vector or a derivative thereof.

Embodiment 38. The mammalian cell or mammalian cell population of any one of embodiments 29 to 37, wherein the viral vector comprises a lentiviral vector, wherein the first set of two viral repeat sequences comprise lentiviral LTR and/or Psi sequences derived from a human immunodeficiency virus (HIV) vector, a simian immunodeficiency virus (SIV) vector, an equine infectious anemia virus vector, a feline immunodeficiency virus vector, a visna virus vector, or a derivative thereof.

Embodiment 39. The mammalian cell or mammalian cell population of any one of embodiments 29 to 38, wherein the at least one polynucleotide comprising one or more nucleic acid sequences essential for formation of a viral vector comprises (a) a lentiviral gag gene; (b) a lentiviral env gene; (c) a lentiviral pol gene; or (d) a combination thereof.

Embodiment 40. The mammalian cell or mammalian cell population of any one of embodiments 1 to 20, wherein the viral vector is a herpes simplex virus (HSV) vector.

Embodiment 41. The mammalian cell or mammalian cell population of embodiment 40, wherein the HSV vector is derived from herpes simplex virus-1 (HSV-1), herpes simplex virus-2 (HSV-2), human cytomegalovirus (HCMV), varicella-zoster virus (VZV), epstein-barr virus (EBV), Kaposi's sarcoma-associated herpesvirus (KSHV), human herpesvirus 6 and/or human herpesvirus 7, and/or a derivative thereof.

Embodiment 42. The mammalian cell or mammalian cell population of embodiment 40 or 41, wherein the viral vector is an HSV vector and the first set of two viral repeat sequences comprises a terminal a sequence.

Embodiment 43. The mammalian cell or mammalian cell population of any one of embodiments 40 to 42, wherein the capsid comprises VP5, VP19C, VP23, pre-VP22a and/or the maturational protease (UL26 gene product).

Embodiment 44. The mammalian cell or mammalian cell population of any one of embodiments 1 to 28 or 40 to 43, wherein the viral vector is an HSV-AAV hybrid vector.

Embodiment 45. The mammalian cell or mammalian cell population of any one of embodiments 1 to 44, wherein the viral vector is a replication competent viral vector.

Embodiment 46. The mammalian cell or mammalian cell population of any one of embodiments 1 to 45, wherein the viral vector is a replication conditional, replication deficient, replication incompetent, and/or replication-defective viral vector.

Embodiment 47. The mammalian cell or mammalian cell population of any one of embodiments 1 to 46, wherein at least one engineered sequence is present episomally in each individual mammalian cell.

Embodiment 48. The mammalian cell or mammalian cell population of any one of embodiments 1 to 47, wherein at least one engineered sequence is present in the genome of each individual mammalian cell.

Embodiment 49. The mammalian cell or mammalian cell population of any one of embodiments 1 to 48, wherein at least one engineered sequence is present in the genome of each individual mammalian cell, and wherein the at least one engineered sequence is inducibly expressed.

Embodiment 50. The mammalian cell or mammalian cell population of any one of embodiments 1 to 49, wherein at least one engineered sequence comprises a heterologous coding sequence.

Embodiment 51. The mammalian cell or mammalian cell population of embodiment 50, wherein the heterologous coding sequence comprises a heterologous gene and/or a heterologous gene segment.

Embodiment 52. The mammalian cell or mammalian cell population of any one of embodiments 1 to 51, wherein at least one engineered sequence comprises a heterologous regulatory element.

Embodiment 53. The mammalian cell or mammalian cell population of embodiment 52, wherein the heterologous regulatory element is or comprises a heterologous promoter sequence and/or a heterologous enhancer sequence.

Embodiment 54. The mammalian cell or mammalian cell population of embodiment 53, wherein the heterologous promoter sequence is or comprises an SV40 promoter, an elongation factor (EF)-1 promoter, a cytomegalovirus (CMV) promoter, a phosphoglycerate kinase (PGK)1 promoter, a ubiquitin (Ubc) promoter, a human beta actin promoter, a tetracycline response element (TRE) promoter, a spleen focus-forming virus (SFFV) promoter, a murine stem cell virus (MSCV) promoter, a supercore promoter (SCP), a CAG promoter, or a derivative thereof.

Embodiment 55. The mammalian cell or mammalian cell population of embodiment 53 or 54, wherein the heterologous enhancer sequence is or comprises a CMV early enhancer, a cAMP response-element (CRE) enhancer, or a derivative thereof.

Embodiment 56. The mammalian cell or mammalian cell population of any one of embodiments 1 to 55, wherein the mammalian cells each individually comprise two or more, three or more, four or more, five or more, six or more, seven or more, eight or more, nine or more, or ten or more engineered sequences.

Embodiment 57. The mammalian cell or mammalian cell population of any one of embodiments 1 to 56, wherein the mammalian cells each individually comprise up to 100 engineered sequences.

Embodiment 58. The mammalian cell or mammalian cell population of any one of embodiments 1 to 57, wherein each individual mammalian cell comprises at least one library construct, and wherein the at least one library construct comprises at least one engineered sequence.

Embodiment 59. The mammalian cell or mammalian cell population of any one of embodiments 1 to 58, wherein each individual mammalian cell comprises at least one library construct, wherein the at least one library construct comprises at least one engineered sequence comprising at least one barcode, at least one identifier, at least one library variant, at least one payload, at least one cis-acting integration sequence, or a combination and/or plurality thereof.

Embodiment 60. The mammalian cell or mammalian cell population of embodiment 59, wherein the at least one barcode comprises a sequence that is about 5 to about 25 nucleotides.

Embodiment 61. The mammalian cell or mammalian cell population of embodiments 59 or 60, wherein the population of mammalian cells comprise a plurality of unique barcodes, and wherein the plurality of unique barcodes comprise unique sequences that are about 5 to about 25 nucleotides.

Embodiment 62. The mammalian cell or mammalian cell population of any one of embodiments 59 to 61, wherein the mammalian cells each individually comprise one, two, three, four, five, six, seven, eight, nine, or ten library variants.

Embodiment 63. The mammalian cell or mammalian cell population of any one of embodiments 59 to 61, wherein the mammalian cells each individually comprise up to 100 library variants.

Embodiment 64. The mammalian cell or mammalian cell population of any one of embodiments 59 to 61, wherein the at least one library variant comprises at least one engineered sequence that comprises at least one gene, at least one ORF, at least one gRNA sequence, at least one non-coding nucleic acid, or a combination and/or a plurality thereof.

Embodiment 65. The mammalian cell population of any one of embodiments 1 to 64, wherein the population of mammalian cells comprise a plurality of library variants, and wherein the plurality of library variants comprise at least one engineered sequence comprising: at least one unique gene, at least one unique ORF, at least one unique gRNA sequence, and/or at least one unique non-coding nucleic acid, or a combination and/or plurality thereof.

Embodiment 66. The mammalian cell population of any one of embodiments 1 to 65, wherein the population of mammalian cells comprise a plurality of library constructs, and wherein the plurality of library constructs comprise: at least one unique gene, at least one unique ORF, at least one unique gRNA sequence, at least one unique non-coding nucleic acid, or a combination and/or plurality thereof.

Embodiment 67. The mammalian cell or mammalian cell population of any one of embodiments 64 to 66, wherein the at least one library construct comprises at least one gRNA sequence.

Embodiment 68. The mammalian cell population of any one of embodiments 64 to 66, wherein the population of mammalian cells comprise a plurality of library constructs, wherein the plurality of library constructs comprise at least one unique gRNA sequence.

Embodiment 69. The mammalian cell population of any one of embodiments 64 to 66, wherein the population of mammalian cells comprise a plurality of library constructs, wherein the plurality of library constructs comprise at least 100 unique gRNA sequences.

Embodiment 70. The mammalian cell or mammalian cell population of any one of embodiments 64 to 66, wherein the at least one library construct comprises at least one ORF.

Embodiment 71. The mammalian cell population of any one of embodiments 64 to 66, wherein the population of mammalian cells comprise a plurality of library constructs, wherein the plurality of library constructs comprise at least one unique ORF.

Embodiment 72. The mammalian cell population of any one of embodiments 64 to 66, wherein the population of mammalian cells comprise a plurality of library constructs, wherein the plurality of library constructs comprise at least 100 unique ORFs.

Embodiment 73. The mammalian cell or mammalian cell population of any one of embodiments 64 to 66, wherein the at least one library construct comprises at least one gene.

Embodiment 74. The mammalian cell population of any one of embodiments 64 to 66, wherein the population of mammalian cells comprise a plurality of library constructs, wherein the plurality of library constructs comprise at least one unique gene.

Embodiment 75. The mammalian cell population of any one of embodiments 64 to 66, wherein the population of mammalian cells comprise a plurality of library constructs, wherein the plurality of library constructs comprise at least 100 unique genes.

Embodiment 76. The mammalian cell or mammalian cell population of any one of embodiments 64 to 66, wherein the at least one library construct comprises at least one noncoding nucleic acid sequence.

Embodiment 77. The mammalian cell population of any one of embodiments 64 to 66, wherein the population of mammalian cells comprise a plurality of library constructs, wherein the plurality of library constructs comprise at least one unique noncoding nucleic acid sequence.

Embodiment 78. The mammalian cell population of any one of embodiments 64 to 66, wherein the population of mammalian cells comprise a plurality of library constructs, wherein the plurality of library constructs comprise at least 100 unique noncoding nucleic acid sequences.

Embodiment 79. The mammalian cell or mammalian cell population of any one of embodiments 58 to 78, wherein the at least one library construct comprises at least one reporter and/or selectable marker, or a combination and/or plurality thereof.

Embodiment 80. The mammalian cell or mammalian cell population of any one of embodiments 58 to 79, wherein the at least one library construct comprises at least one identifier.

Embodiment 81. The mammalian cell population of any one of embodiments 58 to 79, wherein the population of mammalian cells comprise a plurality of library constructs comprising a plurality of identifiers.

Embodiment 82. The mammalian cell or mammalian cell population of any one of embodiments 80 to 81, wherein each individual mammalian cell comprises an identifier comprising a single barcode.

Embodiment 83. The mammalian cell or mammalian cell population of any one of embodiments 80 to 81, wherein the at least one identifier comprises (a) at least one barcode and/or (b) at least one library variant.

Embodiment 84. The mammalian cell population of any one of embodiments 80 to 81, wherein the population of mammalian cells comprise a plurality of identifiers comprising (a) a plurality of barcodes and/or (b) a plurality of library variants.

Embodiment 85. The mammalian cell or mammalian cell population of any one of embodiments 58 to 84, (i) wherein the at least one library construct comprises a plurality of engineered sequences, wherein (a) a first subset of the plurality of engineered sequences are positioned between the first set of two viral repeat sequences, and (b) a second subset of the plurality of engineered sequences are positioned outside the first set of two viral repeat sequences.

Embodiment 86. The mammalian cell or mammalian cell population of embodiment 85, wherein the plurality of engineered sequences comprise (i) at least one library variant and (ii) at least one identifier, (ii) wherein both the at least one library variant and the at least one identifier are positioned between the first set of two viral repeat sequences.

Embodiment 87. The mammalian cell or mammalian cell population of embodiment 85, wherein the plurality of engineered sequences comprise (i) at least one library variant, at least one identifier, and at least one payload, (ii) wherein the at least one library variant, the at least one identifier, and the at least one payload are positioned between the first set of two viral repeat sequences.

Embodiment 88. The mammalian cell or mammalian cell population of embodiment 85, wherein the plurality of engineered sequences comprise at least one library variant and at least one identifier, and wherein (a) the at least one identifier is positioned between the first set of two viral repeat sequences, and (b) the at least one library variant is positioned outside the first set of two viral repeat sequences.

Embodiment 89. The mammalian cell or mammalian cell population of embodiment 85, wherein the plurality of engineered sequences comprise at least one library variant, at least one identifier, and at least one payload, wherein (a) the at least one identifier and the at least one payload are positioned between the first set of two viral repeat sequences, and (b) the at least one library variant is positioned outside the first set of two viral repeat sequences.

Embodiment 90. The mammalian cell or mammalian cell population of embodiment 85, wherein the plurality of engineered sequences comprise at least two library variants and at least one identifier, wherein (a) the at least one identifier and at least one library variant of the at least two library variants are positioned between the first set of two viral repeat sequences, and (b) at least one library variant of the at least two library variants is positioned outside the first set of two viral repeat sequences.

Embodiment 91. The mammalian cell or mammalian cell population of embodiment 85, wherein the plurality of engineered sequences comprise at least two library variants, at least one payload, and at least one identifier, wherein (a) the at least one identifier, the at least one payload, and at least one library variant of the at least two library variants are positioned between the first set of two viral repeat sequences, and (b) at least one library variant of the at least two library variants is positioned outside the first set of two viral repeat sequences.

Embodiment 92. The mammalian cell or mammalian cell population of any one of embodiments 85 to 91, wherein the at least one identifier comprises at least one barcode.

Embodiment 93. The mammalian cell or mammalian cell population of any one of embodiments 85 to 91, wherein the at least one library construct comprises at least one engineered sequence comprising at least one barcode, and wherein the at least one barcode is positioned between the first set of two viral repeat sequences.

Embodiment 94. The mammalian cell or mammalian cell population of any one of embodiments 85 to 91, wherein the at least one library construct comprises at least one engineered sequence comprising at least one barcode, and wherein the at least one barcode is positioned outside the first set of two viral repeat sequences.

Embodiment 95. The mammalian cell or mammalian cell population of any one of embodiments 85 to 91, wherein the at least one library construct comprises at least one engineered sequence comprising a plurality of barcodes, and wherein (a) a first subset of the plurality of barcodes is positioned between the first set of two viral repeat sequences, and (b) a second subset of the plurality of barcodes is positioned outside the first set of two viral repeat sequences.

Embodiment 96. The mammalian cell or mammalian cell population of any one of embodiments 58 to 95, wherein the mammalian cells each individually comprise more than one copy of the library construct or portion thereof.

Embodiment 97. The mammalian cell population of any one of embodiments 58 to 95, wherein the population of mammalian cells comprise a plurality of copies of the library construct or portion thereof.

Embodiment 98. The mammalian cell or mammalian cell population of any one of embodiments 58 to 95, wherein the mammalian cells each individually comprise between one and four copies of the library construct or portion thereof.

Embodiment 99. The mammalian cell or mammalian cell population of any one of embodiments 58 to 95, wherein the mammalian cells each individually comprise two copies of the library construct or portion thereof.

Embodiment 100. The mammalian cell or mammalian cell population of any one of embodiments 58 to 95, wherein the mammalian cells each individually comprise exactly one copy of the library construct.

Embodiment 101. The mammalian cell or mammalian cell population of any one of embodiments 58 to 100, wherein the at least one library construct comprises a single contiguous nucleic acid sequence.

Embodiment 102. The mammalian cell population of any one of embodiments 58 to 101, wherein the population of mammalian cells comprises a plurality of library constructs, wherein each individual library construct is comprised of a single contiguous nucleic acid sequence, and wherein the plurality of library constructs comprise a plurality of unique nucleic acid sequences.

Embodiment 103. The mammalian cell or mammalian cell population of any one of embodiments 58 to 102, wherein the at least one library construct comprises more than one discontiguous nucleic acid sequence.

Embodiment 104. The mammalian cell or mammalian cell population of any one of embodiments 58 to 103, wherein the at least one library construct comprises at least two, three, four, five, six, seven, eight, nine, or ten discontiguous nucleic acid sequences.

Embodiment 105. The mammalian cell or mammalian cell population of any one of embodiments 58 to 104, wherein the at least one library construct comprises up to 100 discontiguous nucleic acid sequences.

Embodiment 106. The mammalian cell population of any one of embodiments 58 to 105, wherein the population of mammalian cells comprises a plurality of library constructs, wherein each individual library construct is comprised of discontiguous nucleic acid sequences, and wherein the library constructs comprise a plurality of unique nucleic acid sequences.

Embodiment 107. The mammalian cell or mammalian cell population of any one of embodiments 58 to 106, wherein the nucleic acids or derivatives thereof derived from each individual mammalian cell comprise at least one unique cell identity sequence during a single cell sequencing method.

Embodiment 108. The mammalian cell or mammalian cell population of any one of embodiments 58 to 107 wherein more than one nucleic acid sequence or derivative thereof comprises a cell identity sequence during a single cell sequencing method.

Embodiment 109. The mammalian cell population of any one of embodiments 58 to 108, wherein the population of mammalian cells comprises a plurality of library constructs, wherein each individual library construct is comprised of discontiguous nucleic acid sequences, wherein the library constructs comprise a plurality of unique nucleic acid sequences, and wherein more than one nucleic acid sequence (or derivative thereof) from the library construct comprises a cell identity sequence during a single cell sequencing method.

Embodiment 110. The mammalian cell population of any one of embodiments 58 to 109, wherein the population of mammalian cells comprises a plurality of library constructs, wherein each individual library construct is comprised of discontiguous nucleic acid sequences, wherein the library constructs comprise a plurality of unique nucleic acid sequences, and wherein all nucleic acid sequences (or derivatives thereof) from the library construct comprise a cell identity sequence during a single cell sequencing method.

Embodiment 111. The mammalian cell or mammalian cell population of any one of embodiments 1 to 110, wherein the mammalian cells each individually comprise at least one engineered sequence comprising at least one perturbation and wherein the at least one perturbation is present episomally in the mammalian cells.

Embodiment 112. The mammalian cell or mammalian cell population of any one of embodiments 1 to 111, wherein the mammalian cells each individually comprise at least one engineered sequence comprising at least one perturbation and wherein the at least one perturbation is present in the genome of the mammalian cells.

Embodiment 113. The mammalian cell or mammalian cell population of any one of embodiments 1 to 112, wherein the mammalian cells each individually comprise at least two engineered sequences comprising at least two perturbations and wherein at least one perturbation is present episomally and at least one perturbation is present in the genome of the mammalian cells.

Embodiment 114. The mammalian cell or mammalian cell population of any one of embodiments 1 to 113, wherein the mammalian cells each individually comprise at least one engineered sequence comprising a plurality of unique perturbations.

Embodiment 115. The mammalian cell or mammalian cell population of any one of embodiments 1 to 114, wherein the mammalian cells each individually comprise at least one engineered sequence comprising at least two, three, four, five, six, seven, eight or nine unique perturbations.

Embodiment 116. The mammalian cell or mammalian cell population of any one of embodiments 111 to 115, wherein the at least one perturbation comprises an insertion, deletion, substitution, replacement, epigenetic modification, and/or rearrangement of an endogenous genomic coding sequence.

Embodiment 117. The mammalian cell or mammalian cell population of embodiment 116, wherein the endogenous coding sequence is or comprises an endogenous gene or gene segment.

Embodiment 118. The mammalian cell or mammalian cell population of any one of embodiments 111 to 115, wherein the at least one perturbation comprises an insertion, deletion, substitution, replacement, epigenetic modification, and/or rearrangement of an endogenous genomic regulatory element.

Embodiment 119. The mammalian cell or mammalian cell population of embodiment 118, wherein the endogenous regulatory element is or comprises an endogenous promoter sequence and/or endogenous enhancer sequence.

Embodiment 120. The mammalian cell or mammalian cell population of any one of embodiments 111 to 115, wherein the mammalian cells each individually comprise at least one engineered sequence comprising at least one perturbation accessory sequence, and wherein the at least one perturbation accessory sequence comprises at least one RNA-guided nuclease or derivative thereof.

Embodiment 121. The mammalian cell or mammalian cell population of embodiment 120, wherein the at least one RNA-guided nuclease comprises Cas9, Cpf1, and/or CasZ, or a derivative thereof, including fusion proteins comprising transcriptional regulators (e.g., Cas9-VPR or Cas9-KRAB-MeCP2 fusions), CRISPR protein fusions to nuclease domains (e.g. Fok1), enzymatic base-editors (e.g. versions of BE and ABE fusions), reverse transcriptase fusions (e.g. Prime Editors), CRISPR recombinases including (e.g. Rec-Cas9), and CRISPR transposases (e.g., Tn7-like transposase systems Cas12k and Cascade complexes with TniQ).

Embodiment 122. The mammalian cell or mammalian cell population of embodiment 120, wherein the at least one RNA-guided nuclease comprises Cas9 or derivative thereof.

Embodiment 123. The mammalian cell or mammalian cell population of any one of embodiments 1 to 122, wherein the library construct is introduced into each individual cell via transfection.

Embodiment 124. The mammalian cell or mammalian cell population of embodiment 123, wherein the engineered sequence comprises at least one library construct that is introduced into each individual cell via viral transduction.

Embodiment 125. The mammalian cell or mammalian cell population of embodiment 124, wherein the library construct is introduced into each individual cell via lentiviral-mediated transduction.

Embodiment 126. The mammalian cell or mammalian cell population of any one of embodiments 123 to 125, wherein the at least one library construct or a portion thereof, is present episomally in the mammalian cells.

Embodiment 127. The mammalian cell or mammalian cell population of embodiment 126, wherein the at least one library construct comprises at least one engineered sequence comprising at least one library variant, and wherein each individual cell comprises at least one perturbation accessory sequence.

Embodiment 128. The mammalian cell or mammalian cell population of embodiment 126, wherein the at least one library construct comprises at least one engineered sequence comprising at least one library variant.

Embodiment 129. The mammalian cell or mammalian cell population of any one of embodiments 127 to 128, wherein the at least one library variant comprises at least one effector.

Embodiment 130. The mammalian cell or mammalian cell population of any one of embodiments 127 to 128, wherein the at least one library variant becomes the at least one perturbation.

Embodiment 131. The mammalian cell or mammalian cell population of any one of embodiments 129 to 130, wherein the at least one library variant comprises at least one ORF, at least one gene, at least one non-coding nucleic acid sequence, and/or at least one gRNA, or plurality thereof.

Embodiment 132. The mammalian cell or mammalian cell population of embodiment 131, wherein the at least one library variant is a gRNA and the at least one perturbation accessory sequence is an RNA-guided nuclease or derivative thereof.

Embodiment 133. The mammalian cell or mammalian cell population of embodiment 131, wherein the at least one perturbation accessory sequence is a non-RNA-directed nuclease or derivative thereof.

Embodiment 134. The mammalian cell or mammalian cell population of any one of embodiments 126 to 133, comprising at least one perturbation.

Embodiment 135. The mammalian cell or mammalian cell population of any one of embodiments 126 to 134, comprising at least one perturbation that comprises that comprises a genomic sequence change, an episomal sequence change, and/or an epigenetic modification.

Embodiment 136. The mammalian cell or mammalian cell population of any one of embodiments 126 to 135, wherein the perturbation comprises an insertion, deletion, substitution, and/or rearrangement of an endogenous genomic coding sequence.

Embodiment 137. The mammalian cell or mammalian cell population of any one of embodiments 123 to 125, wherein the at least one library construct or a portion thereof, is present in the genome of the mammalian cells.

Embodiment 138. The mammalian cell or mammalian cell population of embodiment 137, wherein the insertion of the at least one library construct within the mammalian cell genome is at a random insertion site.

Embodiment 139. The mammalian cell or mammalian cell population of embodiment 138, wherein the random insertion site is random within a predetermined subset of genomic locations.

Embodiment 140. The mammalian cell or mammalian cell population of embodiment 137, wherein the insertion of the at least one library construct within the mammalian cell genome is at a predetermined insertion site.

Embodiment 141. The mammalian cell or mammalian cell population of any one of embodiments 137 to 140, comprising at least one trans-acting integration sequence, wherein the at least one trans-acting integration sequence comprises (a) at least one integration construct and/or integration viral vector, (b) at least one recombinase, and/or the polypeptide, protein, nucleic acid, or polynucleotide product thereof, (c) at least one nuclease, and/or the polypeptide, protein, nucleic acid, or polynucleotide product thereof, (d) at least one transposase, and/or the polypeptide, protein, nucleic acid, or polynucleotide product thereof, and/or (e) at least one engineered sequence.

Embodiment 142. The mammalian cell or mammalian cell population of embodiment 141, wherein the at least one trans-acting integration sequence comprises at least one integration construct and/or integration viral vector.

Embodiment 143. The mammalian cell or mammalian cell population of embodiment 141 (a) wherein each individual mammalian cell comprises at least one engineered sequence comprising at least one pair of cis-acting integration sequences that flank the first set of viral repeat sequences, and (b) wherein the cis-acting integration sequences comprise a second set of viral repeat sequences.

Embodiment 144. The mammalian cell or mammalian cell population of embodiment 143, wherein the integration construct and/or integration viral vector is a lentiviral vector, a gammaretroviral vector, a spumaretroviral vector, an adeno-associated viral vector, or a derivative thereof.

Embodiment 145. The mammalian cell or mammalian cell population of embodiment 144, wherein the integration construct or integration viral vector is a lentiviral vector.

Embodiment 146. The mammalian cell or mammalian cell population of embodiment 145, wherein the first set of viral repeat sequences are or comprise ITRs and the second set of viral repeat sequences are or comprise LTRs.

Embodiment 147. The mammalian cell or mammalian cell population of embodiment 141, wherein the at least one trans-acting integration sequence comprises a nuclease, and/or the polypeptide, protein, nucleic acid, or polynucleotide product thereof.

Embodiment 148. The mammalian cell or mammalian cell population of embodiment 147, wherein the at least one trans-acting integration sequence comprises at least one nuclease, and wherein the at least one nuclease comprises an RNA-guided nuclease or fusion or derivative thereof.

Embodiment 149. The mammalian cell or mammalian cell population of embodiment 147, wherein the at least one trans-acting integration sequence comprises at least one nuclease, and wherein the at least one nuclease comprises a non-RNA-guided nuclease or fusion or derivative thereof.

Embodiment 150. The mammalian cell or mammalian cell population of embodiment 148, wherein the at least one trans-acting integration sequence further comprises at least one engineered sequence.

Embodiment 151. The mammalian cell or mammalian cell population of embodiment 148, wherein the at least one trans-acting integration sequence further comprises at least one gRNA.

Embodiment 152. The mammalian cell or mammalian cell population of any one of embodiments 147 to 151, (a) wherein each individual mammalian cell comprises at least one engineered sequence comprising the at least one pair of cis-acting integration sequences that flank the first set of viral repeat sequences, and (b) wherein the cis-acting integration sequences comprise homology arm sequences.

Embodiment 153. The mammalian cell or mammalian cell population of embodiment 152, wherein the at least one nuclease comprises Cas9, CasZ, Cpf1, an engineered Fok1 nuclease domain fusion to a programmable DNA-binding domain such as a TALE protein (TALEN) or a Zinc Finger protein (ZFN), and/or a meganuclease, or a derivative thereof.

Embodiment 155. The mammalian cell or mammalian cell population of embodiment 153, wherein the at least one nuclease comprises Cas9.

Embodiment 156. The mammalian cell or mammalian cell population of embodiments 141, wherein the at least one trans-acting integration sequence comprises a recombinase, and/or the polypeptide, protein, nucleic acid, or polynucleotide product thereof.

Embodiment 157. The mammalian cell or mammalian cell population of embodiment 156 (a) wherein each individual mammalian cell comprises at least engineered sequence comprising the at least one pair of cis-acting integration sequences that flank the first set of viral repeat sequences, and (b) wherein the cis-acting integration sequences comprise recombinase recognition sites.

Embodiment 158. The mammalian cell or mammalian cell population of embodiment 157, wherein the at least one recombinase comprises Cre, Flp, Dre, PhiC31, and/or Bxb1, or a derivative thereof.

Embodiment 159. The mammalian cell or mammalian cell population of embodiment 158, wherein the at least one recombinase comprises Cre.

Embodiment 160. The mammalian cell or mammalian cell population of embodiment 159, wherein the recombinase recognition sites comprise LoxP sites.

Embodiment 161. The mammalian cell or mammalian cell population of embodiment 158, wherein the at least one recombinase comprises Bxb1.

Embodiment 162. The mammalian cell or mammalian cell population of embodiment 161, wherein the recombinase recognition sites comprise Att sites.

Embodiment 163. The mammalian cell or mammalian cell population of embodiment 158, wherein the at least one recombinase comprises Flp.

Embodiment 164. The mammalian cell or mammalian cell population of embodiment 163, wherein the recombinase recognition sites comprise Frt sites.

Embodiment 165. The mammalian cell or mammalian cell population of embodiments 141, wherein the at least one trans-acting integration sequence comprises a transposase, and/or a polypeptide, protein, nucleic acid, or polynucleotide product thereof.

Embodiment 166. The mammalian cell or mammalian cell population of embodiment 165 (a) wherein each individual mammalian cell comprises at least one engineered sequence comprising the at least one pair of cis-acting integration sequences that flank the first set of viral repeat sequences, and (b) wherein the cis-acting integration sequences comprise transposase recognition sites.

Embodiment 167. The mammalian cell or mammalian cell population of embodiment 166, wherein the at least one transposase comprises Piggybac transposase, Sleepingbeauty transposase, and/or Tn5 transposase, or a derivative thereof.

Embodiment 168. The mammalian cell or mammalian cell population of embodiment 167, wherein the at least one transposase comprises Piggybac transposase.

Embodiment 169. The mammalian cell or mammalian cell population of embodiment 167, wherein the at least one transposase comprises Sleepingbeauty transposase.

Embodiment 170. The mammalian cell or mammalian cell population of any one of embodiments 1 to 169, wherein the population of cells produces viral vectors that are altered relative to a reference population.

Embodiment 171. The mammalian cell or mammalian cell population of embodiment 170, wherein the population of cells produces viral vectors that are altered in the way they transfer nucleic acid to a cell, relative to a reference population.

Embodiment 172. The mammalian cell or mammalian cell population of embodiment 170, wherein the population of cells produces viral vectors that are altered therapeutically, relative to a reference population.

Embodiment 173. The mammalian cell or mammalian cell population of any one of embodiments 1 to 172, wherein the population of cells produces viral vectors that are altered in their intended application, relative to a reference population.

Embodiment 174. The mammalian cell or mammalian cell population of any one of embodiments 1 to 173, wherein the population of cells produces viral vectors that are less functional in an application, relative to a reference population.

Embodiment 175. The mammalian cell or mammalian cell population of any one of embodiments 1 to 174, wherein the population of cells produces viral vectors that are nonfunctional in an application, relative to a reference population.

Embodiment 176. The mammalian cell or mammalian cell population of any one of embodiments 174 or 175, wherein the population of cells produces viral vectors that are less functional and/or nonfunctional at transferring nucleic acid to a cell, relative to a reference population.

Embodiment 177. The mammalian cell or mammalian cell population of any one of embodiments 174 to 175, wherein the population of cells produces viral vectors that are less functional and/or nonfunctional therapeutically, relative to a reference population.

Embodiment 178. The mammalian cell or mammalian cell population of any one of embodiments 174 to 175, wherein the population of cells produces viral vectors that are less functional and/or nonfunctional in their intended application, relative to a reference population.

Embodiment 179. The mammalian cell or mammalian cell population of any one of embodiments 1 to 178, wherein the population of cells produces viral vectors that are more functional and/or enhanced in an application, relative to a reference population.

Embodiment 180. The mammalian cell or mammalian cell population of embodiment 179, wherein the population of cells produces viral vectors that are more functional and/or enhanced at transferring nucleic acid to a cell, relative to a reference population.

Embodiment 181. The mammalian cell or mammalian cell population of embodiment 179, wherein the population of cells produces viral vectors that are more functional and/or enhanced therapeutically, relative to a reference population.

Embodiment 182. The mammalian cell or mammalian cell population of embodiments 179, wherein the population of cells produces viral vectors that are more functional and/or enhanced in their intended application, relative to a reference population.

Embodiment 183. The mammalian cell or mammalian cell population of any one of embodiments 1 to 182, wherein at least one engineered sequence alters viral vector production under a manufacturing practice relative to a reference cell population.

Embodiment 184. The mammalian cell or mammalian cell population of any one of embodiments 1 to 183, wherein at least one engineered sequence provides an increase in viral vector production under a manufacturing practice relative to a reference cell population.

Embodiment 185. The mammalian cell or mammalian cell population of embodiment 183 or 184, wherein the at least one engineered sequence that alters viral vector production, comprises at least one perturbation.

Embodiment 186. The mammalian cell or mammalian cell population of embodiment 185, wherein the at least one perturbation provides an increase in viral vector production under a then-current good manufacturing practice (cGMP).

Embodiment 187. The mammalian cell or mammalian cell population of embodiment 185, wherein the at least one perturbation provides an increase in viral vector production under a good manufacturing practice (GMP).

Embodiment 188. The mammalian cell or mammalian cell population of embodiment 185, wherein the at least one perturbation provides an increase in viral vector production under a non-good manufacturing practice (non-GMP).

Embodiment 189. The mammalian cell or mammalian cell population of any one of embodiments 1 to 188, wherein at least one engineered sequence provides an increase in the viability of the mammalian cell population relative to a reference cell population.

Embodiment 190. The mammalian cell or mammalian cell population of any one of embodiments 1 to 189, wherein at least one engineered sequence provides an increase in the duration of viral vector production by the mammalian cell population relative to a reference cell population.

Embodiment 191. The mammalian cell or mammalian cell population of any one of embodiments 1 to 190, wherein at least one engineered sequence provides an increase in the genomic stability of the mammalian cell population relative to a reference cell population.

Embodiment 192. The mammalian cell or mammalian cell population of any one of embodiments 1 to 185, wherein at least one engineered sequence provides a decrease in the percentage of produced viral vector under a manufacturing practice that are less functional in an application, relative to a reference cell population.

Embodiment 193. The mammalian cell or mammalian cell population of any one of embodiments 1 to 185, wherein at least one engineered sequence provides a decrease in the percentage of produced viral vector under a manufacturing practice that are nonfunctional in an application, as compared to a reference cell population.

Embodiment 194. The mammalian cell or mammalian cell population of embodiment 192 or 193, wherein the viral vectors that decreased in percentage are less functional and/or nonfunctional at transferring nucleic acid to a cell, relative to a reference cell population.

Embodiment 195. The mammalian cell or mammalian cell population of embodiment 192 or 193, wherein the viral vectors that decreased in percentage are less functional and/or nonfunctional therapeutically, relative to a reference cell population.

Embodiment 196. The mammalian cell or mammalian cell population of embodiment 192 or 193, wherein the viral vectors that decreased in percentage are less functional and/or nonfunctional in their intended application, relative to a reference cell population.

Embodiment 197. The mammalian cell or mammalian cell population of any one of embodiments 1 to 191, wherein at least one engineered sequence provides an increase in the percentage of produced viral vector under a manufacturing practice that are more functional and/or enhanced in an application, relative to a reference cell population.

Embodiment 198. The mammalian cell or mammalian cell population of embodiment 197, wherein the viral vectors that increased in percentage are more functional and/or enhanced at transferring nucleic acid to a cell, relative to a reference cell population.

Embodiment 199. The mammalian cell or mammalian cell population of embodiment 197, wherein the viral vectors that increased in percentage are more functional and/or enhanced therapeutically, relative to a reference cell population.

Embodiment 200. The mammalian cell or mammalian cell population of embodiment 197, wherein the viral vectors that increased in percentage are more functional and/or enhanced in their intended application, relative to a reference cell population.

Embodiment 201. The mammalian cell or mammalian cell population of any one of embodiments 1 to 191, wherein at least one engineered sequence provides an increase in the percentage of viral vector under a manufacturing practice that contain all and/or the essential nucleic acid sequences and/or other elements for their intended application, relative to a reference cell population.

Embodiment 202. The mammalian cell or mammalian cell population of any one of embodiments 1 to 191, wherein at least one engineered sequence provides a decrease in the percentage of viral vector under a manufacturing practice that have lost and/or mutated all and/or the essential nucleic acid sequences and/or other elements for their intended application, relative to a reference cell population.

Embodiment 203. The mammalian cell or mammalian cell population of any one of embodiments 1 to 202, wherein each individual mammalian cell comprises least one engineered sequence comprising at least one perturbation.

Embodiment 204. The mammalian cell population of any one of embodiments 1 to 203, wherein the mammalian cell population comprises a plurality of engineered sequences, wherein the plurality of engineered sequences comprise a plurality of perturbations.

Embodiment 205. The mammalian cell population of any one of embodiments 1 to 204, wherein each individual mammalian cell comprises a plurality of engineered sequences that comprise a plurality of perturbations.

Embodiment 206. The mammalian cell or mammalian cell population of any one of embodiments 1 to 205, wherein the reference cell population is (a) a population of comparable mammalian cells that do not include the at least one engineered sequence; and/or (b) a population of standard cells capable of producing the viral vector.

Embodiment 207. The mammalian cell population of any one of embodiments 1 to 206, produced by the steps of (a) introducing into the plurality of mammalian cells a plurality of engineered sequences comprising a plurality of library constructs, wherein the individual library constructs comprise at least one identifier positioned between the first set of two viral repeat sequences, and (b) introducing into the plurality of mammalian cells the at least one polynucleotide comprising one or more nucleic acid sequences essential for production of the viral vector.

Embodiment 208. The mammalian cell population of any one of embodiments 1 to 206, produced by the steps of introducing into the plurality of mammalian cells a plurality of engineered sequences comprising a plurality of library constructs, wherein the individual library constructs comprise at least one identifier positioned between the first set of two viral repeat sequences, wherein the plurality of mammalian cells comprise one or more nucleic acid sequences essential for production of the viral vector.

Embodiment 209. A method of producing viral vectors, comprising: culturing a population of mammalian cells as in any one of embodiments 1 to 206 under conditions such that the mammalian cells produce viral vectors, and wherein each produced viral vector comprises at least one identifier that is derived from the at least one identifier of the mammalian cell that produced the viral vector Embodiment 210. The method of embodiment 209, wherein each produced viral vector comprises at least one identifier that is identical to the at least one identifier of the mammalian cell that produced the viral vector.

Embodiment 211. A method, comprising (a) producing viral vectors from a library of mammalian cells, wherein the library of mammalian cells comprise a plurality of mammalian cells, wherein each mammalian cell of the plurality individually comprises: (i) at least one engineered sequence, (ii) at least one identifier, and (iii) at least one polynucleotide comprising one or more nucleic acid sequences essential for production of the viral vector, and wherein each viral vector comprises at least one identifier that is derived from to the at least one identifier of the mammalian cells that produced the viral vector; and (b) detecting the one or more identifiers in the viral vectors.

Embodiment 212. The method of embodiment 211, wherein each viral vector comprises at least one identifier that is identical to the at least one identifier of the mammalian cells that produced the viral vector.

Embodiment 213. A method, comprising (a) producing viral vectors from a library of mammalian cells, wherein the library of mammalian cells comprises a plurality of mammalian cells, wherein each mammalian cell of the plurality individually comprises: (i) at least one engineered sequence, (ii) at least one identifier, and (iii) at least one polynucleotide comprising one or more nucleic acid sequences essential for production of the viral vector, and wherein each viral vector comprises at least one identifier that is derived from the at least one identifier of the mammalian cells that produced the viral vector; and (b) detecting the one or more identifiers in the viral vectors by next generation sequencing.

Embodiment 214. The method of embodiment 213, wherein each viral vector comprises at least one identifier that is identical to the at least one identifier of the mammalian cells that produced the viral vector.

Embodiment 215. A method comprising the steps of (a) producing an AAV library, wherein the AAV library comprises a plurality of AAV vectors from a library of mammalian cells, wherein the library of mammalian cells comprises a plurality of mammalian cells, wherein each mammalian cell of the plurality individually comprises: (i) at least one engineered sequence, (ii) at least one barcode sequence, and (iii) at least one polynucleotide comprising one or more nucleic acid sequences essential for production of the viral vector, wherein each AAV viral vector comprises at least one construct, and wherein the at least one construct comprises a barcode sequence that is derived from the at least one barcode sequence of the mammalian cells that produced the AAV viral vector; and (b) detecting the one or more barcode sequences in the AAV library.

Embodiment 216. The method of embodiment 215, wherein each AAV viral vector comprises at least one construct, and wherein the at least one construct comprises a barcode sequence that is identical to the at least one barcode sequence of the mammalian cells that produced the AAV viral vector.

Embodiment 217. A method comprising the steps of (a) producing an AAV library, wherein the AAV library comprises a plurality of constructs from a library of mammalian cells, wherein the library of mammalian cells comprises a plurality of mammalian cells, wherein each mammalian cell of the plurality individually comprises: (i) at least one engineered sequence, (ii) at least one barcode sequence, and (iii) at least one polynucleotide comprising one or more nucleic acid sequences essential for production of the viral vector, wherein each AAV viral vector comprises at least one construct, and wherein the at least one construct comprises a barcode sequence that is derived from the at least one barcode sequence of the mammalian cells that produced the AAV viral vector; and (b) detecting the one or more barcode sequences in the AAV library by next generation sequencing.

Embodiment 218. The method of embodiment 217, wherein each AAV viral vector comprises at least one construct, and wherein the at least one construct comprises a barcode sequence that is identical to the at least one barcode sequence of the mammalian cells that produced the AAV viral vector.

Embodiment 219. The method of any one of embodiments 209 to 218, further comprising single cell sequencing of at least one or all nucleic acid sequences or derivatives thereof, within each individual cell of the library of mammalian cells, wherein the at least one or all nucleic acid sequences, or derivatives thereof, comprise a single cell identity sequence during a single cell sequencing method, and wherein the at least one or all nucleic acid sequences, or derivatives thereof, comprise at least one library construct.

Embodiment 220. The method of any one of embodiments 209 to 218, further comprising single cell sequencing of at least one or all nucleic acid sequences or derivatives thereof, within each individual cell of the library of mammalian cells, wherein the at least one or all nucleic acid sequences, or derivatives thereof, comprise a single cell identity sequence in the context of a single cell sequencing method, and wherein the at least one or all nucleic acid sequences, or derivatives thereof, comprise at least one library variant comprising at least one identifier.

Embodiment 221. The method of any one of embodiments 209 to 220, wherein a second library construct is introduced into a mammalian cell, wherein the mammalian cell comprises at least one perturbation derived from a first library construct, and wherein the second library construct comprises at least one engineered sequence comprising at least one identifier positioned between the first set of two viral repeat sequences.

Embodiment 222. The method of any one of embodiments 209 to 221, wherein the a second plurality of library constructs is introduced into a plurality of mammalian cells, wherein the plurality of mammalian cells comprises at least one perturbation derived from a first plurality of library constructs, and wherein the second plurality of library constructs comprise a plurality of engineered sequences, wherein each individual library construct in the second plurality of library constructs comprise at least one identifier positioned between the first set of two viral repeat sequences.

Embodiment 223. The method of any one of embodiments 221 to 222, further comprising detection of the one or more identifiers and/or the one or more engineered sequences by single cell sequencing and/or next generation sequencing.

Embodiment 224. The method of any one of embodiments 221 to 223 involving more than two rounds of library construct introduction and detection of the one or more identifiers and/or the one or more engineered sequences.

Embodiment 225. The method of any one of embodiments 221 to 224, further comprising the use of machine learning approaches to develop a machine learning model to identify desirable combinations of target perturbations.

Embodiment 226. The method of any one of embodiments 207 to 225, wherein the at least one identifier is removed from the cell.

Embodiment 227. The method of any one of embodiments 209 to 226, wherein each produced viral vector comprises a reporter and/or selectable marker.

Embodiment 228. The method of embodiment 227, wherein the method further comprises a step of removing the reporter and/or selectable marker.

Embodiment 229. A mammalian cell population comprising a plurality of mammalian cells that each individually comprise: (a) at least one engineered nucleic acid sequence, (b) at least one barcode sequence, and (c) at least one polynucleotide comprising one or more nucleic acid sequences essential for production of a viral vector, wherein the plurality of mammalian cells produce a plurality of the viral vector.

Embodiment 230. The mammalian cell population of embodiment 229, wherein the at least one engineered nucleic acid sequence provides an increase in viral vector production under a manufacturing practice as compared to a reference cell population.

Embodiment 231. The mammalian cell population of embodiment 229 or 230, wherein the at least one engineered nucleic acid sequence provides an increase in the produced viral vector under a then-current good manufacturing practice (cGMP).

Embodiment 232. The mammalian cell population of any one of embodiments 229 to 231, wherein the at least one engineered nucleic acid sequence provides an increase in the viability of the mammalian cell population relative to a reference cell population.

Embodiment 233. The mammalian cell population of any one of embodiments 229 to 232, wherein the at least one engineered nucleic acid sequence provides an increase in duration of viral vector production by the mammalian cell population relative to a reference cell population.

Embodiment 234. The mammalian cell population of any one of embodiments 229 to 233, wherein the at least one engineered nucleic acid sequence provides an increase in genomic stability of the mammalian cell population relative to a reference cell population.

Embodiment 235. The mammalian cell population of any one of embodiments 230 to 234, wherein the reference cell population is: (i) a population of comparable mammalian cells that do not include the at least one engineered nucleic acid sequence; or (ii) a population of standard cells capable of producing the viral vector.

Embodiment 236. The mammalian cell population of any one of embodiments 229 to 235, wherein at least one of (a) to (c) is present episomally in the mammalian cells.

Embodiment 237. The mammalian cell population of any one of embodiments 229 to 236, wherein at least one of (a) to (c) is present in the genome of the mammalian cells.

Embodiment 238. The mammalian cell population of any one of embodiments 229 to 237, wherein the at least one barcode sequence consists of a single barcode sequence and the at least one engineered nucleic acid sequence consists of a single engineered nucleic acid sequence.

Embodiment 239. The mammalian cell population of embodiment 238, wherein the at least one barcode sequence is associated with the at least one engineered nucleic acid sequence.

Embodiment 240. The mammalian cell population of any one of embodiments 229 to 237, wherein the at least one barcode sequence consists of a first barcode sequence and a second barcode sequence, and wherein the at least one engineered nucleic acid sequence consists of a first engineered nucleic acid sequence and a second engineered nucleic acid sequence.

Embodiment 241. The mammalian cell population of embodiment 240, wherein the first barcode sequence is associated with the first engineered nucleic acid sequence and the second barcode sequence is associated with the second engineered nucleic acid sequence.

Embodiment 242. The mammalian cell population of embodiment 240 or 241, wherein the second engineered nucleic acid sequence had been selected and/or introduced into the mammalian cell population after the first engineered nucleic acid sequence.

Embodiment 243. The mammalian cell population of any one of embodiments 240 to 242, further comprising a third engineered sequence that is associated with a third barcode sequence.

Embodiment 244. The mammalian cell population of any one of embodiments 229 to 237, wherein the at least one barcode sequence consists of a single barcode sequence and the at least one engineered nucleic acid sequence consists of at least two engineered nucleic acid sequences.

Embodiment 245. The mammalian cell population of any one of embodiments 229 to 237, wherein the at least one barcode sequence consists of a single barcode sequence and the at least one engineered nucleic acid sequence consists of two, three, four, or five engineered nucleic acid sequences.

Embodiment 246. The mammalian cell population of any one of embodiments 229 to 245, wherein the at least one engineered nucleic acid sequence comprises a heterologous coding sequence.

Embodiment 247. The mammalian cell population of embodiment 246, wherein the heterologous coding sequence is or comprises a heterologous gene and/or a heterologous gene segment.

Embodiment 248. The mammalian cell population of any one of embodiments 229 to 247, wherein the at least one engineered nucleic acid sequence comprises a heterologous regulatory element.

Embodiment 249. The mammalian cell population of embodiment 248, wherein the heterologous regulatory element is or comprises a heterologous promoter sequence and/or a heterologous enhancer sequence.

Embodiment 250. The mammalian cell population of embodiment 248, wherein the heterologous promoter sequence is or comprises a SV40 promoter, elongation factor (EF)-1 promotor, a cytomegalovirus (CMV) promoter, phosphoglycerate kinase (PGK)1 promoter, ubiquitin (Ubc) promoter, human beta actin promoter, tetracycline response element (TRE) promoter or a derivative thereof.

Embodiment 251. The mammalian cell population of any one of embodiments 229 to 250, wherein the at least one engineered nucleic acid sequence is or comprises an insertion, deletion, substitution, replacement or rearrangement of an endogenous coding sequence within the mammalian cell genome.

Embodiment 252. The mammalian cell population of embodiment 251, wherein the endogenous coding sequence is or comprises an endogenous gene or gene segment.

Embodiment 253. The mammalian cell population of any one of embodiments 229 to 252, wherein the at least one engineered nucleic acid sequence comprises an insertion, deletion, substitution, replacement or rearrangement of an endogenous regulatory element within the mammalian cell genome.

Embodiment 254. The mammalian cell population of embodiment 253, wherein the endogenous regulatory element is or comprises an endogenous promoter sequence and/or endogenous enhancer sequence.

Embodiment 255. The mammalian cell population of any one of embodiments 229 to 254, wherein the at least one engineered nucleic acid sequence comprises an insertion within the mammalian cell genome.

Embodiment 256. The mammalian cell population of any one of embodiments 229 to 255, wherein the at least one engineered nucleic acid sequence comprises an insertion of a viral or non-viral nucleic acid sequence into the mammalian cell genome.

Embodiment 257. The mammalian cell population of embodiment 255 or 256, wherein the insertion within the mammalian cell genome comprises a random insertion site.

Embodiment 258. The mammalian cell population of embodiment 257, wherein the random insertion site is random within a predetermined subset of genomic locations.

Embodiment 259. The mammalian cell population of embodiment 255 or 256, wherein the insertion within the mammalian cell genome comprises a predetermined insertion site.

Embodiment 260. The mammalian cell population of any one of embodiments 240 to 242, wherein the second engineered nucleic acid sequence is or comprises an insertion at a predetermined insertion site.

Embodiment 261. The mammalian cell population of embodiment 260, wherein the predetermined insertion site is rationally selected.

Embodiment 262. The mammalian cell population of embodiment 261, wherein the predetermined insertion site is rationally selected using machine learning.

Embodiment 263. The mammalian cell population of embodiment 262, wherein the predetermined insertion site is rationally selected using the sequence of the first engineered sequence or the location of the first engineered sequence in the mammalian cell genome.

Embodiment 263. The mammalian cell population of any one of embodiments 240 to 242, produced by the steps of introducing into the plurality of mammalian cells the first engineered nucleic acid sequence and first barcode sequence, and introducing into the plurality of mammalian cells the second engineered nucleic acid sequence and second barcode sequence, wherein the second engineered nucleic acid sequence is inserted at a predetermined site in the mammalian cell genome.

Embodiment 264. The mammalian cell population of any one of embodiments 229 to 263, wherein the at least one barcode sequence comprises a nucleic acid sequence that is about 5 to about 25 nucleotides.

Embodiment 265. The mammalian cell population of any one of embodiments 229 to 264, wherein the plurality of mammalian cells is or comprises human embryonic kidney (HEK) cells, Chinese hamster ovary (CHO) cells, HeLa cells, PER.C6 cells, HKB11 cells, CAP cells, Baby Hamster Kidney fibroblasts (BHK cells), Sp2/0 cells, NS0 cells, COS cells, Vero cells, or a derivative of any thereof.

Embodiment 266. The mammalian cell population of any one of embodiments 229 to 264, wherein the plurality of mammalian cells is or comprises HEK 293 cells, CHO cells, or a derivative thereof.

Embodiment 267. The mammalian cell population of any one of embodiments 229 to 266, wherein the viral vector is an adeno-associated virus (AAV) vector.

Embodiment 268. The mammalian cell population of embodiment 267, wherein the AAV vector comprises human AAV1 capsid proteins; human AAV2 capsid proteins; human AAV3b capsid proteins; human AAV4 capsid proteins; human AAV5 capsid proteins; human AAV6 capsid proteins; human AAV7 capsid proteins; human AAV8 capsid proteins; human AAV9 capsid proteins; human AAV10 capsid proteins; human AAV11 capsid proteins; human AAV12 capsid proteins; or human AAV13 capsid proteins.

Embodiment 269. The of mammalian cell population embodiment 267, wherein the AAV vector comprises human ancestral AAV capsid proteins.

Embodiment 270. The mammalian cell population of any one of embodiments 240 to 242, wherein the AAV vector comprises an AAV vector, wherein the AAV vector comprises a pair of inverted terminal repeats (ITRs) that are or comprise a human AAV1 ITR(s); human AAV2 ITR(s); human AAV3b ITR(s); human AAV4 ITR(s); human AAV5 ITR(s); human AAV6 ITR(s); human AAV7 ITR(s); human AAV8 ITR(s); human AAV9 ITR(s); human AAV10 ITR(s); human AAV11 ITR(s); human AAV12 ITR(s); or human AAV13 ITR(s).

Embodiment 271. The mammalian cell population of embodiment 267, wherein the AAV vector comprises bovine AAV (b-AAV) capsid proteins; canine AAV (CAAV) capsid proteins; mouse AAV1 capsid proteins; caprine AAV capsid proteins; rat AAV capsid proteins; or avian AAV (AAAV) capsid proteins.

Embodiment 272. The mammalian cell population of embodiment 267 or 271, wherein the AAV vector comprises an AAV vector, wherein the AAV vector comprises a pair of ITRs that are or comprise a bovine AAV (b-AAV) ITR(s); canine AAV (CAAV) ITR(s); mouse AAV1 ITR(s); caprine AAV ITR(s); rat AAV ITR(s); or avian AAV (AAAV) ITR(s).

Embodiment 273. The mammalian cell population of any one of embodiments 267 to 272, wherein at least one polynucleotide comprising one or more nucleic acid sequences essential for formation of a viral vectors comprises: an AAV Rep gene; an AAV Cap gene; one or more adenovirus helper genes; or a combination thereof.

Embodiment 274. The mammalian cell population of any one of embodiments 229 to 273, wherein each of the plurality of mammalian cells further comprises a transgene that is or comprises a reporter gene, a therapeutic gene, an immunogenic gene, a diagnostic gene, or a combination thereof.

Embodiment 275. The mammalian cell population of embodiment 274, wherein the plurality of mammalian cells produce a plurality of the viral vector comprising the transgene.

Embodiment 276. A mammalian cell population comprising a plurality of mammalian cells, wherein each of the plurality of mammalian cells individually comprises: (a) at least one engineered nucleic acid sequence, (b) at least one barcode sequence, and (c) at least one nucleic acid sequence comprising one or more elements essential for formation of an AAV vector selected from: an AAV Rep gene, an AAV Cap gene, one or more adenovirus helper genes, or a combination thereof, wherein the plurality of mammalian cells produce a plurality of the AAV vector.

Embodiment 277. A mammalian cell population comprising a plurality of mammalian cells suitable for production of an adeno-associated virus (AAV) vector, wherein each of the plurality of mammalian cells individually comprises: (a) at least one engineered nucleic acid sequence, (b) at least one barcode sequence, and (c) at least one nucleic acid sequence comprising one or more elements essential for formation of an AAV vector, wherein the plurality of mammalian cells produce the AAV vector.

Embodiment 278. A method comprising the steps of: (a) producing an AAV library comprising a plurality of AAV vectors from a library of mammalian cells comprising a plurality of mammalian cells, wherein each mammalian cell of the plurality individually comprises: at least one engineered nucleic acid sequence, at least one barcode sequence, and at least one nucleic acid sequence that expresses one or more elements essential for formation of an AAV vector, wherein each AAV vector comprises an AAV vector that comprises a barcode sequence that is identical to the at least one barcode sequence of the mammalian cells that produced the AAV vector; (b) detecting the one or more barcode sequences in the AAV library.

Embodiment 279. The method of embodiment 278, wherein the step of detecting barcodes comprises a step of sequencing the barcodes.

Embodiment 280. The method of embodiment 279, wherein the sequencing step comprises a next generation sequencing (NGS) step.

Embodiment 281. The method of any one of embodiments 278-280, further comprising identifying a mammalian cell producing an AAV vector based on the presence of a barcode in the AAV library.

Embodiment 282. A method of producing AAV vectors in a mammalian cell, comprising culturing a mammalian cell identified in embodiment 281, thereby producing AAV vectors.

Embodiment 283. A method of producing AAV vectors, comprising: culturing a population of mammalian cells as in any one of embodiments 229 to 279 under conditions so that the mammalian cells produce AAV vectors, wherein each AAV vector produced comprises an AAV vector comprising at least one barcode sequence that is identical to the at least one barcode sequence of the mammalian cell that produced the AAV vector.

Embodiment 284. The method of embodiment 282 to 283, further comprising isolating the AAV vectors.

Embodiment 285. The method of any one of embodiments 280 to 284, wherein the mammalian cell that produced the AAV vectors is a HEK cell or a CHO cell.

Embodiment 286. The method of any one of embodiments 280 to 285, wherein the method provides at least about $1 \times 10^3$ AAV vector vectors per mammalian cell.

Embodiment 287. The method of any one of embodiments 280 to 286, wherein the method provides at least about $1 \times 10^3$ AAV vector vectors per liter of culture.

Embodiment 288. An AAV vector produced by a method of any one of embodiments 282 to 287.

Embodiment 289. A method of producing AAV vectors in a mammalian cell, comprising culturing a mammalian cell identified in embodiment 281 under conditions, thereby producing AAV vectors.

Embodiment 290. A method of producing AAV vectors, comprising: culturing mammalian cells under conditions so that the mammalian cells produce AAV vectors, wherein the mammalian cells each individually comprise: at least one engineered nucleic acid sequence, at least one barcode sequence, and at least one polynucleotide comprising one or more nucleic acid sequences essential for formation of an AAV vector, and wherein each AAV vector comprises at least one barcode sequence that is identical to the at least one barcode sequence of the mammalian cell that produced the AAV vector.

Embodiment 291. The method of embodiment 290, further comprising isolating the AAV vectors.

Embodiment 292. The method of any one of embodiments 290 or 291, wherein the identified mammalian cell is a HEK cell or a CHO cell.

Embodiment 293. An AAV vector produced by a method of any one of embodiments 289 or 290.

Embodiment 294. A library of adeno-associated virus (AAV) vectors, comprising at least $1 \times 10^3$ AAV vectors, wherein each AAV vector comprises a barcode sequence suitable for identifying the AAV vector.

Embodiment 295. A library of adeno-associated virus (AAV) vectors, comprising at least $1 \times 10^3$ AAV vectors, wherein each AAV vector comprises a barcode sequence suitable for identifying a mammalian cell or mammalian clonal cell line that produced AAV the vector.

Embodiment 296. The library of embodiment 294 or 295, wherein the AAV vectors each comprise an AAV vector comprising a nucleic acid sequence encoding a transgene.

Embodiment 297. The library of any one of embodiments 294-296, wherein the AAV vectors are produced by a mammalian cell or mammalian clonal cell line.

Embodiment 298. A mammalian cell population comprising a plurality of mammalian cells, wherein each mammalian cell comprises: (a) at least one engineered nucleic acid sequence, (b) at least one barcode sequence, and (c) at least one polynucleotide comprising one or more nucleic acid sequences essential for formation of a viral vector, wherein the plurality of mammalian cells produce a plurality of the viral vector, wherein the plurality of mammalian cells comprise two or more subsets of mammalian cells, and wherein each subset of mammalian cells comprises at least one engineered nucleic acid sequence and at least one barcode sequence that are unique to the subset.

Embodiment 299. A method comprising the steps of (a) producing an AAV library comprising a plurality of AAV vectors from a library of mammalian cells comprising a plurality of mammalian cells, wherein each mammalian cell of the plurality individually comprises: at least one engineered nucleic acid sequence, at least one barcode sequence, and at least one nucleic acid sequence that expresses one or more elements essential for formation of an AAV vector, wherein the plurality of mammalian cells comprise two or more subsets of mammalian cells, and wherein each subset of mammalian cells comprises at least one engineered nucleic acid sequence and at least one barcode sequence that are unique to the subset, and wherein each AAV vector of the plurality comprises an AAV vector that comprises a barcode sequence that is identical to at least one barcode sequence of the mammalian cell that produced the AAV vector; (b) detecting the one or more barcode sequences in the AAV library.

Embodiment 300. The method of embodiment 299, further comprising determining an amount of each of the one or more barcode sequences in the AAV library.

Embodiment 301. The method of embodiment 300, further comprising comparing the amount of the one or more barcode sequences in the AAV library to a reference value.

Embodiment 302. The method of embodiment 299 or 300, further comprising determining an amount of at least two of the one or more barcode sequences in the AAV library.

Embodiment 303. The method of embodiment 302, further comprising comparing the amount of the least two of the one or more barcode sequences in the AAV library to each other.

Embodiment 304. The method of any one of embodiments 299 to 303, further comprising identifying a mammalian cell or mammalian clonal cell line producing an AAV vector based on the presence of a barcode in the AAV library.

Embodiment 305. A mammalian cell population comprising a plurality of mammalian cells that each individually comprise: (a) at least one engineered nucleic acid sequence, (b) a guide sequence, wherein the guide sequence is at least partially complementary to an engineered nucleic acid sequence, (c) at least one excising nucleic acid, and (d) at least one polynucleotide comprising one or more nucleic acid sequences essential for production of a viral vector, wherein the plurality of mammalian cells produce a plurality of the viral vector.

Embodiment 306. The mammalian cell population of embodiment 305, wherein the at least one excising nucleic acid encodes an RNA-guided endonuclease fused to a nuclear localization signal (NLS), and wherein the guide sequence comprises a guide RNA that directs the endonuclease to at least one targeted locus present in a mammalian cell.

Embodiment 307. The mammalian cell population of embodiment 305 or 306, wherein the at least one engineered nucleic acid sequence provides an increase in viral vector production under a manufacturing practice as compared to a reference cell population.

Embodiment 308. The mammalian cell population of any one of embodiments 305 to 307, wherein the at least one engineered nucleic acid sequence provides an increase in the produced viral vector under a then-current good manufacturing practice (cGMP).

Embodiment 309. The mammalian cell population of any one of embodiments 305 to 308, wherein the at least one engineered nucleic acid sequence provides an increase in the viability of the mammalian cell population relative to a reference cell population.

Embodiment 310. The mammalian cell population of any one of embodiments 305 to 309, wherein the at least one engineered nucleic acid sequence provides an increase in duration of viral vector production by the mammalian cell population relative to a reference cell population.

Embodiment 311 The mammalian cell population of any one of embodiments 305 to 310, wherein the at least one engineered nucleic acid sequence provides an increase in genomic stability of the mammalian cell population relative to a reference cell population.

Embodiment 312. The mammalian cell population of any one of embodiments 306 to 311, wherein the reference cell population is: (i) a population of comparable mammalian cells that do not include the at least one engineered nucleic acid sequence; or (ii) a population of standard cells capable of producing the viral vector.

Embodiment 313. The mammalian cell population of any one of embodiments 305 to 312, wherein the plurality of mammalian cells is or comprises human embryonic kidney (HEK) cells, Chinese hamster ovary (CHO) cells, HeLa cells, PER.C6 cells, HKB11 cells, CAP cells, Baby Hamster Kidney fibroblasts (BHK cells), Sp2/0 cells, NS0 cells, COS cells, Vero cells, or a derivative of any thereof.

Embodiment 314. The mammalian cell population of any one of embodiments 305 to 313, wherein the plurality of mammalian cells is or comprises HEK 293 cells, CHO cells, or a derivative thereof.

Embodiment 315. The mammalian cell population of any one of embodiments 305 to 314, wherein the at least one engineered nucleic acid sequence is or comprises an insertion, deletion, substitution, replacement or rearrangement of an endogenous coding sequence within the mammalian cell genome.

Embodiment 316. The mammalian cell population of embodiment 315, wherein the endogenous coding sequence is or comprises an endogenous gene or gene segment.

Embodiment 317. The mammalian cell population of any one of embodiments 305 to 316, wherein the at least one engineered nucleic acid sequence comprises an insertion, deletion, substitution, replacement or rearrangement of an endogenous regulatory element within the mammalian cell genome.

Embodiment 318. The mammalian cell population of embodiment 317, wherein the endogenous regulatory element is or comprises an endogenous promoter sequence and/or endogenous enhancer sequence.

Embodiment 319. The mammalian cell population of any one of embodiments 305 to 318, wherein the at least one engineered nucleic acid sequence consists of a single engineered nucleic acid sequence.

Embodiment 320. The mammalian cell population of any one of embodiments 305 to 319, wherein the at least one engineered nucleic acid sequence comprises a heterologous coding sequence.

Embodiment 321. The mammalian cell population of embodiment 320, wherein the heterologous coding sequence is or comprises a heterologous gene and/or a heterologous gene segment.

Embodiment 322. The mammalian cell population of any one of embodiments 305 to 319, wherein the at least one engineered nucleic acid sequence comprises a heterologous regulatory element.

Embodiment 323. The mammalian cell population of embodiment 322, wherein the heterologous regulatory element is or comprises a heterologous promoter sequence and/or a heterologous enhancer sequence.

Embodiment 324. The mammalian cell population of any one of embodiments 305 to 323, wherein the viral vector is an adeno-associated virus (AAV) vector.

Embodiment 325. The mammalian cell population of embodiment 324, wherein the AAV vector comprises human AAV1 capsid proteins; human AAV2 capsid proteins; human AAV3b capsid proteins; human AAV4 capsid proteins; human AAV5 capsid proteins; human AAV6 capsid proteins; human AAV7 capsid proteins; human AAV8 capsid proteins; human AAV9 capsid proteins; human AAV10 capsid proteins; human AAV11 capsid proteins; human AAV12 capsid proteins; or human AAV13 capsid proteins.

Embodiment 326. The of mammalian cell population embodiment 324, wherein the AAV vector comprises human ancestral AAV capsid proteins.

Embodiment 327. The mammalian cell population of any one of embodiments 324 to 326, wherein the AAV vector comprises an AAV vector, wherein the AAV vector comprises a pair of inverted terminal repeats (ITRs) that are or comprise a human AAV1 ITR(s); human AAV2 ITR(s); human AAV3b ITR(s); human AAV4 ITR(s); human AAV5 ITR(s); human AAV6 ITR(s); human AAV7 ITR(s); human AAV8 ITR(s); human AAV9 ITR(s); human AAV10 ITR(s); human AAV11 ITR(s); human AAV12 ITR(s); or human AAV13 ITR(s).

Embodiment 328. The mammalian cell population of embodiment 324, wherein the AAV vector comprises bovine AAV (b-AAV) capsid proteins; canine AAV (CAAV) capsid proteins; mouse AAV1 capsid proteins; caprine AAV capsid proteins; rat AAV capsid proteins; or avian AAV (AAAV) capsid proteins.

Embodiment 329. The mammalian cell population of embodiment 325 or 328, wherein the AAV vector comprises an AAV vector, wherein the AAV vector comprises a pair of ITRs that are or comprise a bovine AAV (b-AAV) ITR(s); canine AAV (CAAV) ITR(s); mouse AAV1 ITR(s); caprine AAV ITR(s); rat AAV ITR(s); or avian AAV (AAAV) ITR(s).

Embodiment 330. The mammalian cell population of any one of embodiments 324 to 329, wherein at least one polynucleotide comprising one or more nucleic acid sequences essential for formation of a viral vectors comprises: an AAV Rep gene, an AAV Cap gene, one or more adenovirus helper genes, or a combination thereof.

Embodiment 331. The mammalian cell population of any one of embodiments 305 to 330, wherein each of the plurality of mammalian cells further comprises a transgene that is or comprises a reporter gene, a therapeutic gene, an immunogenic gene, a diagnostic gene, or a combination thereof.

Embodiment 332. The mammalian cell population of embodiment 331, wherein the plurality of mammalian cells produce a plurality of the viral vector comprising the transgene.

The following examples are provided so as to describe to the skilled artisan how to make and use methods and compositions described herein, and are not intended to limit the scope of the present disclosure.

EXAMPLES

Example 1: CRISPR gRNA-Based Library Technique for Screening AAV Production, Genomically Integrated Using Lentiviral Vectors The present example describes a method of producing and screening a mammalian cell library to determine the level of production of an exemplary viral vector (e.g., in this example, AAV vectors) by specific cell perturbations (e.g., in cells containing specific library variants) within the library. Specifically, this example describes a method of linking individual viral vectors produced from the mammalian cell library to the specific cell variants from which they were derived, wherein the gRNA used to create the mammalian cell library is the identifier.

Example 1.1: Transfection and Construction of Mammalian Cell Library

The present example describes a method of generating an AAV vector-producing, mammalian cell library. An exemplary AAV vector host production cell line, for example 293T, can be modified through stable or transient expression of a CRISPR nuclease expression construct. For example, a CRISPR nuclease expression construct can be stably expressed by lentiviral integration a SpCas9 nuclease (293T-Cas9). A library of gRNA sequences (library variants) targeting genomic sequences, will be synthesized and cloned into a vector (e.g., a plasmid) between two AAV ITR sequences. The ITR-delimited sequence will itself be located on the nucleic acid downstream of a lentiviral 5' LTR and relevant lentiviral packaging sequences including Psi, and upstream of a lentiviral 3' LTR, suitable for 3rd-Generation lentiviral packaging of a transcribed RNA delimited by the LTRs and containing the AAV ITR sequences and gRNA expression cassette in transcribed RNA form. Such a construct with AAV ITRs positioned between lentiviral LTR and Psi sequences will be referred to here as AAV-in-*Lenti*. A schematic of an exemplary AAV-in-Lenti construct is depicted in FIG. 2. The AAV-in-*Lenti* plasmid may also contain a selectable marker gene, such as antibiotic resistance (e.g., puromycin resistance) or a fluorescent protein (e.g., GFP), enabling future selection or identification of mammalian cells containing the eventual integrated library construct. The gRNA library as cloned into the AAV-in-Lenti plasmid may be prepared as a purified plasmid pool for transfection into the 293T-Cas9 cells. This plasmid library can be transfected into 293T cells alongside a plasmid encoding a viral glycoprotein, for example the VSV-G protein, and either a $2^{nd}$ or $3^{rd}$ Generation lentiviral packaging plasmid(s) to provide, minimally, the lentiviral Gag Pol, Rev gene functions. AAV-in-Lenti library viral vectors will be collected from culture supernatant, filtered, and either concentrated or applied directly to the 293T-Cas9 cell line. Cells transduced with an AAV-in-Lenti library will be isolated via their selectable marker. Post-transduction, expression of the gRNA library per cell will be assumed to have resulted in gRNA-targeted cleavage and indel formation through the action of the stably expressed SpCas9 gene. The purified population of cells of an AAV-in-Lenti library can then be transfected with plasmid constructs necessary for production and packaging of recombinant AAV viral vectors (e.g., polynucleotides essential for formation of a viral vector), for example, pHelper and pAAV Rep-Cap. The functions present on these plasmids can direct replication of ITR-defined AAV vector genomes from the lentivirally-integrated ITR-in-Lenti sequence, and these ITR viral vector constructs will be packaged and released into AAV vectors. Using this AAV-in-Lenti method, and titering the lentivirally-packaged construct on 293T-Cas9 cells, enables control of an MOI such that each cell receives approximately one ITR-flanked gRNA library member sequence.

Example 1.2: Production and Harvesting of Viral Vectors

The present example describes a method of production and purification of viral vector produced from the mammalian cell library. Viral vector is produced using methods known in the art, for example, as described in Zolotukhin, et al., 1999 (*Gene Therapy* 6, pp. 973-985). For example, after transfection, media (DMEM w/Glutamax, Pen/Strep antibiotic, 5% FBS) is changed after 24 hours, and 50% media volume (500 mL) added after 72 hours. After 5 days, cells are lysed by adding NaCl to 150 mM and incubating for 2 hours at 37° C. The media-cell mixture is collected and allowed to sit overnight at 4° C. The supernatant is separated and filtered through a 0.22 µM filter (Corning 431098). 40% PEG-8000 in $dH_2O$ is added to the viral vector material to a final concentration of 8%, and incubated at 4° C. overnight. This material is spun at 4800 g for 20 minutes, the pellet is collected and dissolved in 7 mL PBS. The material is then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 1.3: NGS of Viral Vectors

The present example describes a method of sequencing the DNA contained within the purified AAV vectors, specifically a gRNA-encoding sequence, as an identifier. DNA is isolated from a pool of purified AAV vectors (e.g., the entire pool of AAV vectors, a pool of AAV vectors from a subset of selected cells or selected AAV vectors). The DNA can be purified using methods known in the art, such as alkaline lysis. The DNA is amplified using PCR from flanking primer sequences. The amplified product is purified, mixed with sequencing adapters (e.g., Illumina adapters) with homologous overhangs at 50:1 amplicon:adapter molar ratio, put into a GGA reaction (BsmBI and T4 ligase, NEB), and allowed to cycle 100× overnight (16C for 5 min then 37° C. for 5 min), conceptually similar to Velculescu, et al., 1995 (*Science* Vol. 270, Issue 5235, pp. 484-487). This material is then amplified to add Illumina adapters and indexes, and sequenced using the NextSeq platform. The gRNA sequences contained within the host cells production strain library will also be amplified and prepared for sequencing in the same way. The frequency of sequence reads for each gRNA is measured, and their relative abundances within the pool of all gRNAs determined. The relative abundance of gRNA sequences amplified from AAV vector-associated DNA will be compared to that of gRNA sequence abundance in the original host cell population. In this way, gRNA library variants which result in perturbations that direct changes on host cell biology and result in differential AAV vector production can be identified as they either enrich or de-enrich in the AAV vector DNA population in comparison to a reference host cell population.

The approach described herein also allows for iterative rounds of library screening, where gRNA sequences found to significantly enrich in the AAV vector population, and confirmed to introduce a perturbation in the cell towards a higher titer production of AAV vector can be introduced to host cells separately from the AAV-in-Lenti gRNA library, enabling combinations of mutations to be 'stacked' over successive rounds of screening and hit confirmation.

Figure 4:
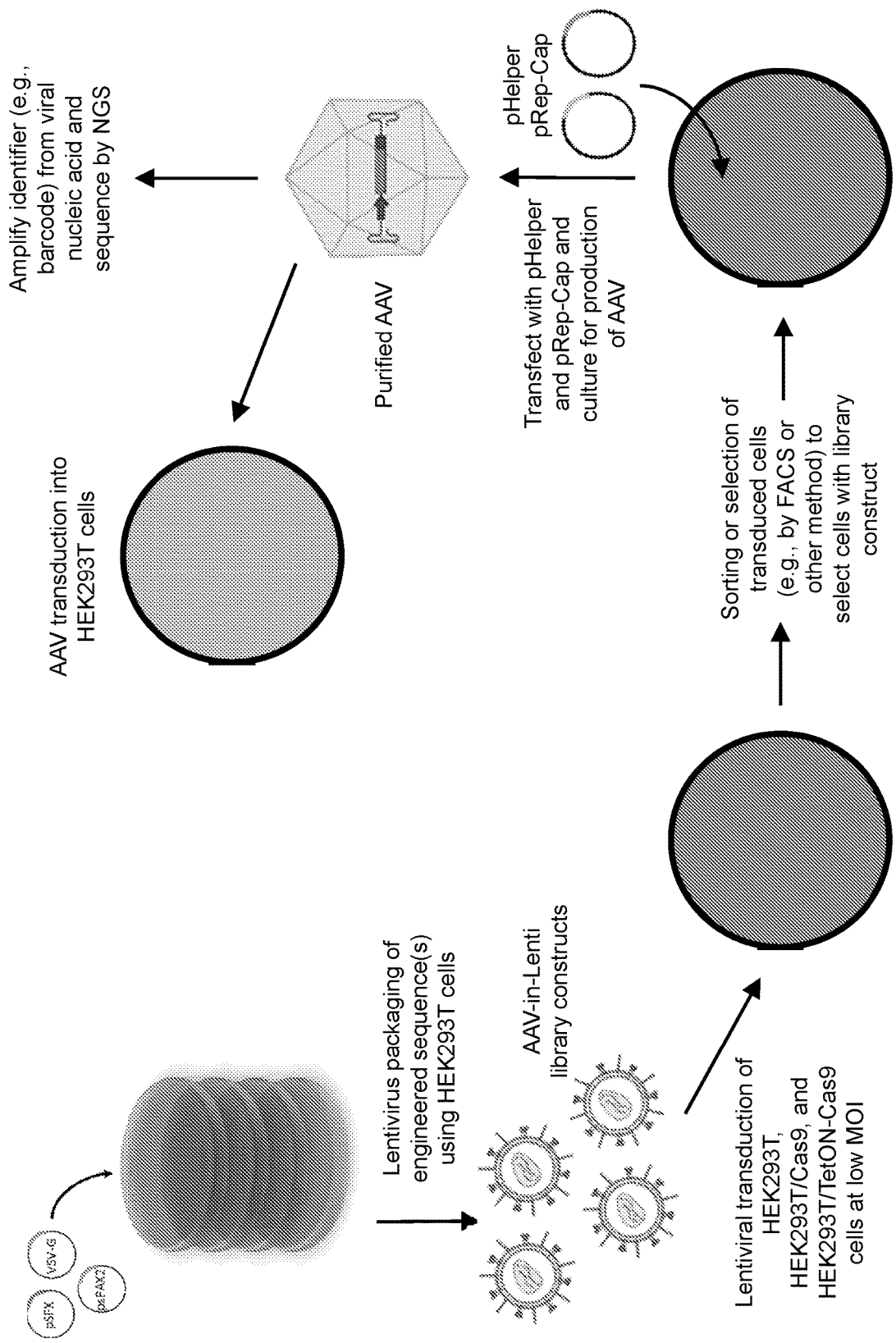
FIG. 4 depicts an exemplary scheme for generation of a mammalian cell library that expresses AAV viral vectors using an AAV-in-Lenti library of constructs that include an identifier.

Example 2: Barcoded CRISPR gRNA-Based Library Technique for Screening AAV Production, Genomically Integrated Using Lentiviral Vectors The present example describes a method of producing and screening a mammalian cell library to determine the level of production of an exemplary viral vector (e.g., AAV vectors) by specific cell perturbations (e.g., in cells containing specific library variants) within the library. Specifically, this example describes a method of linking individual viral vectors produced from the mammalian cell library to the specific cell variants from which they were derived, using a barcode as an identifier. A schematic overview of this method is provided as FIG. 4.

Example 2.1: Transfection and Construction of Mammalian Cell Library

The present example describes a method of generating exemplary AAV vector-producing mammalian cell libraries. An exemplary AAV vector host production cell line, for example HEK 293T, was modified to express a CRISPR nuclease expression construct, for example, Cas9. Cas9 was stably expressed in HEK 293T cells through stable lentiviral integration. HEK293T cells were generated that stably expressed Cas9 under the control of a constitutive promoter and also cell that express Cas9 under the control of an inducible promoter (e.g., a tetracycline-inducible promoter (TetON)). Successful gene editing was demonstrated using a model gRNA in both the mammalian cells that constitutively and inducibly express Cas9 (data not shown). Moreover, in the mammalian cells that express Cas9 under a TetON promoter, gene editing was dose-dependent editing with increasing concentrations of doxycycline, and no editing was observed in the absence of doxycycline (data not shown).

Exemplary libraries of gRNA sequences (library variants) targeting various genomic sequences, were synthesized and cloned into plasmids: a pilot library of 23 gRNAs was constructed and a larger screening library of 12,000 gRNAs.

Figure 5:
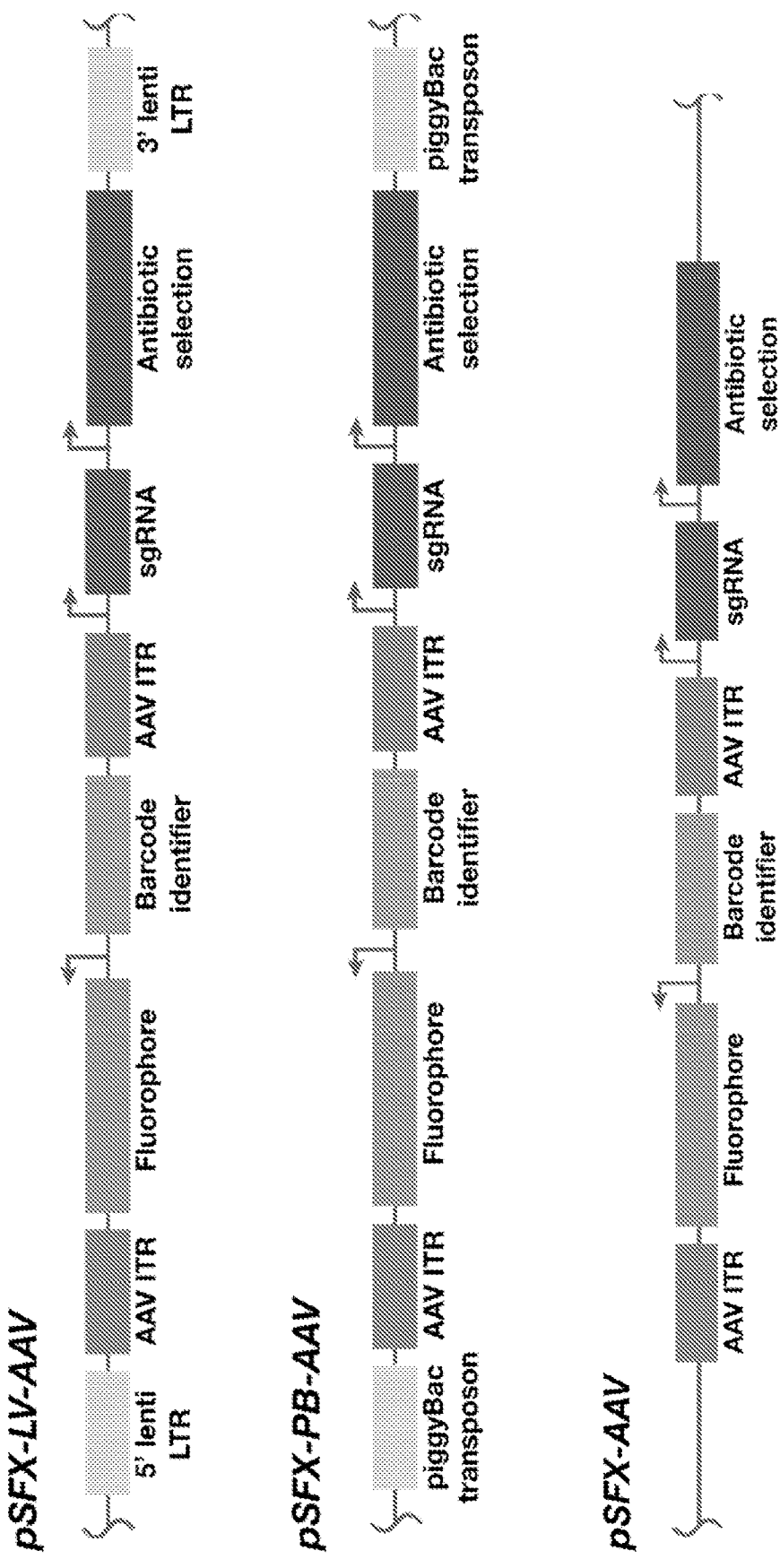
FIG. 5 depicts schematics of exemplary library constructs for use in methods of generating a mammalian cell library that expresses AAV viral vectors. pSFX-LV-AAV is an exemplary AAV-in-Lenti library construct; pSFX-PB-AAV is an exemplary AAV-in-Transposase library construct; and pSFX-AAV is an exemplary AAV construct for episomal expression.

Each library construct included a gRNA library variant positioned outside two AAV ITR sequences, and a corresponding barcode identifier sequence positioned between the two AAV ITR sequences. Associated pairing of a library variant (gRNA) with a barcode sequence pairing may be predetermined at the point of construct design and synthesis or may be randomly associated depending on specific cloning methods utilized, with gRNA:barcode pairings determined by NGS of the cloned library plasmid DNA. The ITR-delimited sequence will itself be located on the plasmid downstream of a cis-acting integration sequence such as lentiviral 5' LTR and relevant lentiviral packaging sequences including Psi, and upstream of a lentiviral 3' LTR, suitable for third generation lentiviral packaging of a transcribed RNA delimited by the LTRs and containing the AAV ITR sequences and gRNA expression cassette in transcribed RNA form. Such a library construct with AAV ITRs positioned between lentiviral LTR and Psi sequences will be referred to here as AAV-in-Lenti, and an exemplary schematic of such an AAV-in-Lenti construct is provided in FIG. 5, labeled pSFX-LV-AAV. AAV-in-Lenti plasmids were generated that also contain an exemplary selectable marker gene, an antibiotic resistance gene (e.g., puromycin resistance) and an exemplary AAV payload of a fluorescent protein gene (e.g., Green Fluorescent Protein), enabling future selection or identification of mammalian cells containing the integrated library construct and that produce AAV vectors.

An exemplary gRNA library as cloned into AAV-in-Lenti format was prepared as a purified plasmid pool for transfection into 293T-Cas9 cells. AAV-in-Lenti plasmid libraries of 23 gRNAs (pilot assay) and 12,000 gRNAs (screening assay) were transfected into 293T cells alongside a plasmid encoding a viral glycoprotein, for example the VSV-G protein, and either a second or third generation lentiviral packaging plasmid(s) to provide, minimally, the lentiviral Gag Pol, Rev gene functions. AAV-in-Lenti library viral vectors will be collected from culture supernatant, filtered, and either concentrated or applied directly to the 293T-Cas9 cell line. Cells transduced with the lentiviral-packaged AAV-in-Lenti library will be isolated via their selectable marker. Post-transduction, expression of the gRNA library per cell will be assumed to have resulted in gRNA-targeted cleavage and indel formation through the action of the stably expressed SpCas9 gene. The purified library population will then be transfected with plasmid constructs necessary for production and packaging of recombinant AAV viral vectors (e.g., polynucleotides essential for formation of a viral vector), for example pHelper and pAAV Rep-Cap. The functions present on these plasmids will direct replication of ITR-defined AAV vector genomes from the lentivirally-integrated ITR-in-Lenti sequence, and these ITR viral vector constructs will be packaged and released into AAV vectors. Using this AAV-in-Lenti method, and titering the lentivirally-packaged construct on 293T-Cas9 cells, enables control of an MOI such that each cell receives approximately one ITR-flanked gRNA library member sequence.

Example 2.2: Production and Harvesting of Viral Vectors

Viral vector was produced using methods known in the art, for example, as described above in Example 1.2, and in Zolotukhin, et al., 1999 (*Gene Therapy* 6, pp. 973-985).

Functionality of AAV purified from lentivirus-integrated, ITR-flanked template DNA was assessed. Purified AAV was transduced into HEK293T and green cells were visualized with fluorescence microscopy. AAV produced from a AAV-in-Lenti library was found to successfully transduce HEK293T cells (data not shown).

Example 2.3: NGS of Viral Vectors

Figure 6:
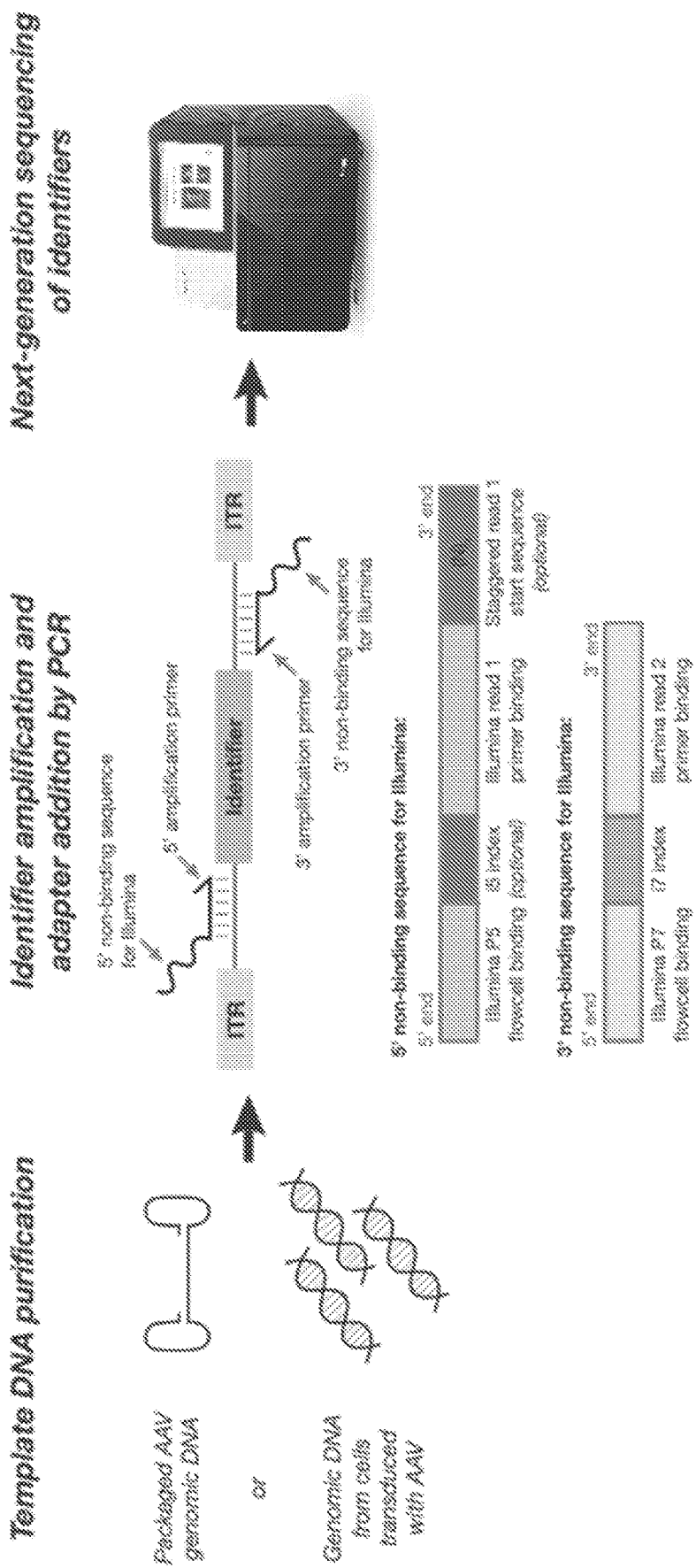
FIG. 6 depicts an exemplary schematic overview of sequencing viral vector nucleic acid, e.g., an identifier (e.g., barcode) sequence from viral vectors (e.g., AAV viral vectors) or cellular genomic DNA.

The present example describes a method of amplification and sequencing of DNA contained within purified AAV vectors, specifically the barcode sequences and library variants (e.g., gRNA). The present disclosure encompasses a recognition that the barcode sequences can identify the mammalian cell that produced the AAV vector, and the corresponding library variants of the mammalian cells. A schematic overview of this purification, amplification and sequencing is provided as FIG. 6. DNA was isolated, using methods known in the art as described in Example 1.3. The amplified product was purified, mixed with sequencing adapters (e.g., Illumina adapters) with homologous overhangs at 50:1 amplicon:adapter molar ratio, put into a GGA reaction (BsmBI and T4 ligase, NEB), and cycled 100× overnight (16° C. for 5 min then 37° C. for 5 min), as described above in Example 1.3. This material was then amplified to add Illumina adapters and indexes, and sequenced using the NextSeq platform. The gRNA sequences contained within the host cells production strain library were also amplified and sequenced using a substantially similar method. The frequency of sequence reads for each gRNA was measured, and their relative abundances within the pool of all gRNAs determined. The relative abundance of gRNA sequences amplified from AAV vector-associated DNA was compared to that of gRNA sequence abundance in the original host cell population. In this way, gRNA library variants which result in perturbations that direct changes on host cell biology and result in differential AAV vector production were identified as they either enrich or de-enrich in the AAV vector DNA population in comparison to the host cell population.

Figure 7:
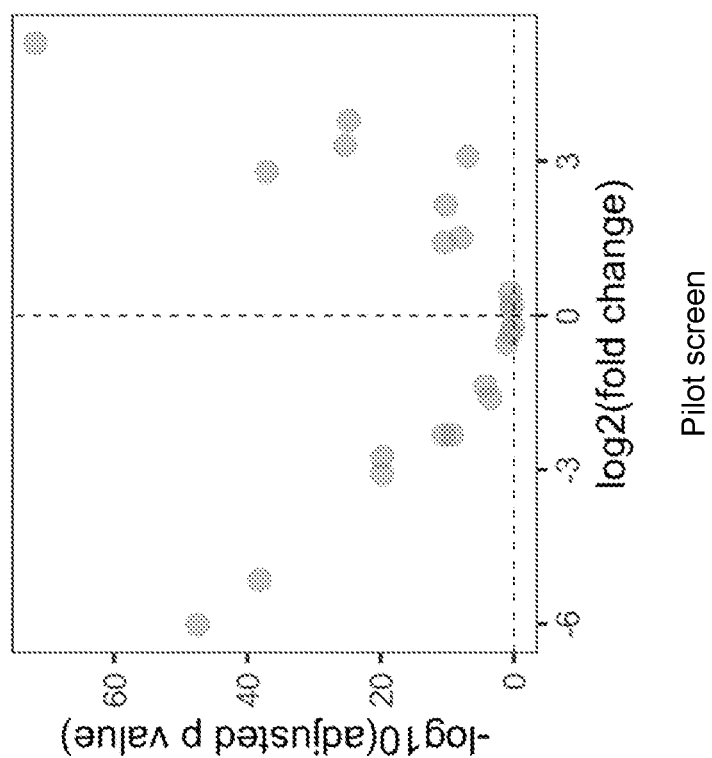
FIG. 7 depicts a plot of relative abundance of barcode identifiers in a pool of viral vector produced by an exemplary limited mammalian cell library generated using AAV-in-Lenti constructs for 23 gRNA library variants. Barcode abundance is relative to that of wild-type cells (that lack library variants). Each dot in the plot represents the score for a single gRNA library variant in the library; results are an average of three biological replicates.

Results of a screen of a pilot library of 23 gRNAs is provided in FIG. 7. Three biological replicates of AAV produced in Cas9-expressing cells were compared with three biological replicates of AAV produced in wild-type ("WT") cells. NGS data was aligned to the set of barcodes in the 23 pool using bowtie2 software. Langmead B, Salzberg S. "Fast gapped-read alignment with Bowtie 2." *Nature Methods.* 2012, 9:357-359. Relative barcode abundance was evaluated with the DESeq2 package for differential expression analysis. Love M I, Huber W, Anders S (2014). "Moderated estimation of fold change and dispersion for RNA-seq data with DESeq2." *Genome Biology,* 15, 550. The results in FIG. 7 demonstrate that the screening protocol, NGS sample preparation, sequencing, and data analysis pipeline were effective. Moreover, the results of the pilot screen suggest that several genes may be associated with increased or decreased AAV production with high statistical confidence (adjusted p values ~0.1).

Figure 8:
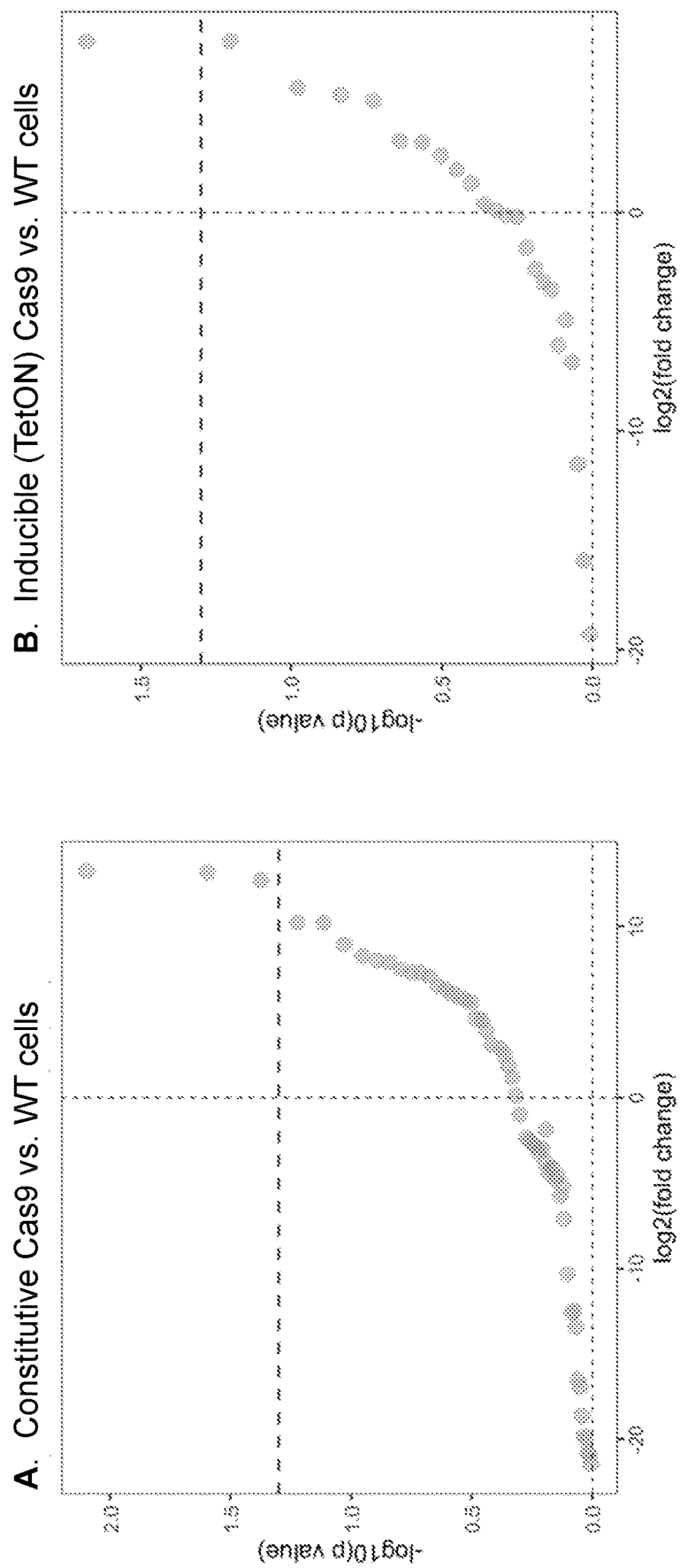
FIG. 8 depicts two plots of relative abundance of barcode identifiers from pools of viral vector produced by exemplary mammalian cell libraries generated using AAV-in-Lenti constructs for approximately 12,000 gRNA library variants. (A) provides a plot of relative abundance of barcode identifiers in a pool of viral vectors produced by a library of mammalian cells that constitutively express Cas9; (B) provides a plot of relative abundance of barcode identifiers in a pool of viral vector produced by a library of mammalian cells that inducibly express Cas9. Barcode abundance is relative to that of wild-type cells (that lack library variants). Each dot represents the scoring for a single gene in the library (calculated from 4 corresponding sgRNA scores); results are an average of three biological replicates.

Results of a screen of a library of 12,000 gRNAs is provided in FIG. 8. Three biological replicates of AAV produced in Cas9-expressing cells were compared with three biological replicates of AAV produced in WT cells. NGS data was aligned to the set of barcodes in the 12 pool using bowtie2 software, Langmead and Salzberg, supra. Relative barcode abundance was evaluated with the MAGeCK package and gene-level enrichment and significance (FDR) scores were calculated. Li, et al. "MAGeCK enables robust identification of essential genes from genome-scale CRISPR/Cas9 knockout screens." (2014) *Genome Biology* 15:554. Each point in FIG. 8 represents the scoring for a single gene in the library (calculated from 4 corresponding sgRNA scores). The results in FIG. 8 demonstrate that the screening protocol, NGS sample preparation, sequencing, and data analysis pipeline were effective for a large-scale screen. Moreover, the data demonstrate that barcodes can be used as a readout for identifying library variants associated with changes in AAV production, as numerous cell lines (and therefore associated gRNAs) were associated with increased or decreased AAV production.

The approach described in this example also allows for iterative rounds of library screening, where gRNA sequences found to significantly enrich in the AAV vector population, and confirmed to introduce a perturbation in the cell towards a higher titer production of AAV vector can be introduced to host cells separately from the AAV-in-Lenti gRNA library, enabling combinations of mutations to be 'stacked' over successive rounds of screening and hit confirmation.

Example 3: ORF-Based Library Technique for Screening Lentiviral Production, Genomically Integrated Using DNA Transposition The present example describes a method of producing and screening a mammalian cell library to determine the level of production of an exemplary viral vector (e.g., in this example, lentiviral vectors) by specific cell variants (e.g., containing specific library variants) within the library. Specifically, this example describes a method of linking individual viral vectors produced from the mammalian cell library to the specific cell variants from which they were derived, where a transgenic ORF used to create the mammalian cell library is the identifier.

Example 3.1: Generation of Mammalian Cell Library

The present example describes a method of generating a recombinant lentiviral vector producing, mammalian cell library within a host production cell line, for example 293T. A library of ORF sequences encoding protein gene products (with sequences designed to exclude cleavage by enzymes in downstream sequencing preparation steps, such as the BsmBI restriction enzyme) with expected biological function in the host cell line, will be synthesized and cloned into a lentiviral transfer plasmid downstream of the lentiviral 5' LTR and relevant lentiviral packaging sequences including Psi, and upstream of a lentiviral 3' LTR, suitable for $3^{rd}$ Generation lentiviral packaging of a transcribed RNA delimited by the LTRs. This LTR-defined segment will itself be positioned between DNA sequences which enable enzymatic integration of the DNA into the host cell genome, for example through use of the piggyBac transposase via flanking cognate inverted terminal repeats (ITRs) taken from the piggyBac DNA transposon system. Such a construct with lentiviral LTRs positioned between transposon ITRs will be referred to here as Lenti-in-Transposon. The Lenti-in-Transposon plasmid will also contain a selectable marker gene, such as Puromycin resistance or Green Fluorescent Protein, enabling future selection or identification of mammalian cells containing the eventual integrated library construct. The ORF library as cloned into the Lenti-in-Transposon plasmid will be prepared as a purified plasmid pool for transfection into the 293T cells. This plasmid library will be transfected into 293T cells alongside a transposase enzyme expression plasmid (expressing the trans-acting integration sequence) to drive enzymatic integration into random locations within the host genome. Genomically-modified library cells produced following this transfection will be isolated via continued exposure to a selectable agent such as puromycin or through fluorescent cell sorting on a fluorescent marker gene such as GFP. The library population of stable clones isolated in this manner will then be transfected with plasmid constructs necessary for production and packaging of recombinant lentiviral vectors (e.g., polynucleotides essential for formation of a viral vector), such as plasmids encoding a viral glycoprotein, for example the VSV-G protein, and either a second or third generation lentiviral packaging plasmid(s) to provide, minimally, the lentiviral Gag Pol, Rev gene functions. The functions present on these plasmids will direct production of LTR-defined lentiviral vector genomes from the transposon-integrated Lenti-in-Transposon sequence, and these lentiviral vector RNAs will be packaged and released into lentiviral vectors. Using this Lenti-in-Transposon method will enable low-copy-number integration of library members per cell such that the large excess of non-integrated transfected plasmid DNA is depleted over the course of selection of the stable library population.

Example 3.2: Production and Harvesting of Viral Vectors

The present example describes a method of production and purification of viral vector produced from the mammalian cell library. Virus is produced using methods known in the art, for example, as described in Zolotukhin, et al., 1999 (*Gene Therapy* 6, pp. 973-985). For example, after transfection, media (DMEM w/Glutamax, Pen/Strep antibiotic, 5% FBS) is changed after 24 hours, and 50% media volume (500 mL) added after 48 hours. After 3 days, culture supernatant is collected and filtered through a 0.45 um filter (Corning 431098). 40% PEG-8000 in $dH_2O$ is added to the viral vector material to a final concentration of 8%, and incubated at 4 C overnight. This material is spun at 1500 g for 45 minutes, the pellet is collected and dissolved.

Example 3.3: NGS of Viral Vectors

The present example describes a method of sequencing the purified lentiviral vector RNA, specifically the ORF-encoding sequence. RNA is isolated en masse, from the entire pool of purified lentiviral vectors. The RNA is purified using alkaline lysis. The RNA is reverse transcribed into cDNA using a universal primer reverse sequence with a binding site downstream of the ORFs. This cDNA is then subjected to PCR using universal forward and reverse primers flanking the ORF sequences. The amplified products of PCR are purified, mixed with Illumina adapters with homologous overhangs at 50:1 amplicon:adapter molar ratio, put into a GGA reaction (BsmBI and T4 ligase, NEB), and allowed to cycle 100× overnight (16° C. for 5 min then 37° C. for 5 min), conceptually similar to Velculescu, et al., 1995 (*Science* Vol. 270, Issue 5235, pp. 484-487). This material is then amplified to add Illumina adapters and indexes, and sequenced using the NextSeq platform. The ORF sequences contained within the host cells production strain library as integrated DNA will also be amplified by PCR and prepared for sequencing in the same way. The ORFs will be identified per-read via reference of the partial terminal ORF sequences obtained from each read Illumina read to their known full-length sequences. The frequency of each is thus measured, and their relative abundances within the pool of all ORFs determined. The relative abundance of ORFs amplified from lentiviral vector-associated RNA will be compared to that of ORF sequence abundance in the original host cell population. In this way, ORF library variants which result in perturbations that direct changes on host cell biology and result in differential lentiviral vector production can be identified as they either enrich or deenrich in the lentiviral population in comparison to the host cell population.

The approach described in this example also allows for iterative rounds of library screening, where ORF sequences found to significantly enrich in the lentiviral population, and confirmed to introduce a perturbation in the cell towards a higher titer production of lentiviral vectors can be introduced into host cells separately from the Lenti-in-Transposon ORF library, enabling combinations of mutations to be 'stacked' over successive rounds of screening and hit confirmation.

Figure 9:
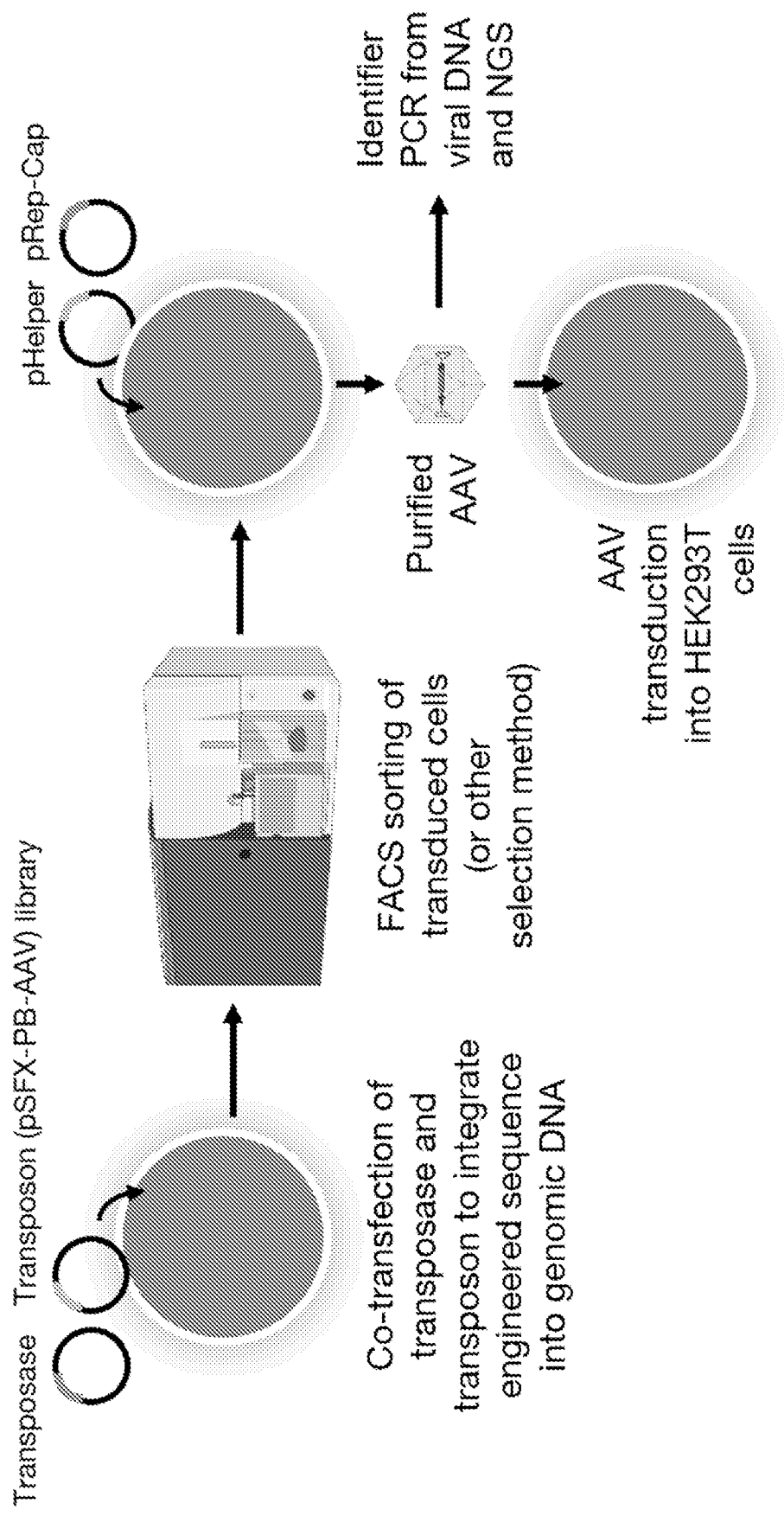
FIG. 9 depicts an exemplary scheme for generation of a mammalian cell library that expresses AAV viral vectors using an AAV-in-Transposase library of constructs that include an identifier.

Example 4: Barcoded CRISPR gRNA-Based Library Technique for Screening AAV Production, Genomically Integrated Using DNA Transposition The present example describes a method of producing and screening a mammalian cell library to determine the level of production of an exemplary viral vector (e.g., AAV vectors) by specific library variants) within the library. Specifically, this example describes construction of an exemplary library of mammalian cells that use a barcoded identifier with a CRISPR gRNA-based library that was integrated into the mammalian cell genomes by DNA transposition. This example also provides a method of linking individual viral vectors produced from said mammalian cell library to the specific cell variants from which they were derived. A schematic overview of this method is provided as FIG. 9.

Example 4.1: Generation of Mammalian Cell Library

The present example describes a method of generating a recombinant AAV vector producing, mammalian cell library within a host production cell line, for example 293T. An AAV vector host production cell line, for example 293T, was modified through stable lentiviral integration of a CRISPR nuclease expression construct, for example, Cas9, as described above in Example 2.1. A library of gRNA sequences (library variants) targeting genomic sequences, was synthesized and cloned into plasmids at a position outside the two AAV ITR sequences, with a corresponding barcode identifier sequence positioned between the two AAV ITR sequences. This ITR-defined segment was positioned between DNA sequences which enable enzymatic integration of the DNA into the host cell genome, for example through use of the piggyBac transposase via flanking cognate inverted terminal repeats (transposon ITRs) taken from the piggyBac DNA transposon system. Such a construct with AAV ITRs positioned between transposon ITRs will be referred to here as AAV-in-Transposon; an exemplary schematic of such an AAV-in-Transposon construct is provided in FIG. 5, labeled pSFX-PB-AAV. The AAV-in-Transposon plasmid also contained an exemplary selectable marker gene, an antibiotic resistance gene (e.g., puromycin resistance) and an exemplary AAV payload of a fluorescent protein gene (e.g., Green Fluorescent Protein), enabling future selection or identification of mammalian cells containing the integrated library construct and that produce AAV vectors. An exemplary barcoded gRNA library as cloned into the AAV-in-Transposon plasmid was prepared as a purified plasmid pool for transfection into the 293T cells. AAV-in-Transposon plasmid libraries of 23 gRNAs (pilot assay) and 12,000 gRNAs (screening assay) were generated. These plasmid libraries were transfected into 293T cells alongside a transposase enzyme expression plasmid (expressing the trans-acting integration sequence) to drive enzymatic integration into random locations within the host genome.

Genomically-modified library cells produced following this transfection were isolated via continued exposure to a selectable agent such as puromycin or through fluorescent cell sorting on a fluorescent marker gene such as GFP. Both HEK293T cells constitutively-expressing Cas9 and HEK293T expressing inducible TetON-Cas9 were transduced with AAV-in-Transposon plasmids. Fluorescent cells were visualized with fluorescence microscopy and fluorescent cells were observed at all transposase:transposon ratios, indicating successful integration.

The purified cell library population was then transfected with plasmid constructs necessary for production and packaging of recombinant AAV viral vectors (e.g., polynucleotides essential for formation of a viral vector), for example pHelper and pAAV Rep-Cap. The functions present on these plasmids direct replication of ITR-defined AAV vector genomes from the genomically-integrated AAV-in-Transposon sequence, and these ITR viral vector constructs are packaged and released into AAV vectors.

Transposon copy number was measured by qPCR relative to a plasmid standard; genomic copy numbers initially ranged from 3-8 depending on the ratio of transposon to transposase (data not shown). The AAV titer obtained from the sorted populations was directly proportional to the GFP expression level of the sorted populations.

The ratio of transfected transposase:transposon plasmids was optimized such that the copy number of transposon-integrated cells is lower than previously observed in order that most cells receive only approximately 1 genetic perturbation (1 gRNA library variant/barcode pair from the library). Plasmid with cis-acting transposons was co-transfected with plasmid containing trans-acting sequences coding for piggyBac transposase at various transposase:transposon ratios to obtain a lower copy number. The copy number increased as the relative amount of transposon plasmid was increased, with successful identification of an optimized transposase:transposon ratio to achieve approximately 1 copy per cell (data not shown).

This example demonstrate the successful optimization of the ratio of transfected transposase:transposon plasmids such that most cells receive only 1 genetic perturbation (1 sgRNA:barcode pair from the library). Accordingly, this example demonstrates that an exemplary AAV-in-Transposon method enables low-copy-number integration of library variants per cell, such that the large excess of non-integrated transfected plasmid DNA is depleted over the course of selection of the stable library population.

Example 4.2: Production and Harvesting of Viral Vectors

The present example describes a method of production and purification of viral vector produced from the mammalian cell library. Viral vector was produced using methods known in the art, for example, as described in Zolotukhin, et al., 1999 (*Gene Therapy* 6, pp. 973-985). For example, after transfection, media (DMEM w/Glutamax, Pen/Strep antibiotic, 5% FBS) was changed after 24 hours, and 50% media volume (500 mL) added after 72 hours. After 5 days, cells were lysed by adding NaCl to 150 mM and incubating for 2 hours at 37° C. The media-cell mixture was collected and allowed to sit overnight at 4° C. The supernatant was separated and filtered through a 0.22 µM filter (Corning 431098). 40% PEG-8000 in $dH_2O$ was added to the viral vector material to a final concentration of 8%, and incubated at 4° C. overnight. This material was spun at 4800 g for 20 minutes, the pellet was collected and dissolved in 7 mL PBS. The material was then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Functionality of AAV purified from transposase-integrated, ITR-flanked template DNA was assessed. Purified AAV was transduced into HEK293T and green cells were visualized with fluorescence microscopy. AAV produced from a AAV-in-Transposon library was found to successfully transduce HEK293T cells (data not shown).

Example 4.3: NGS of Viral Vectors

The present example describes a method of sequencing the DNA contained within the purified AAV vectors, specifically the barcode sequence corresponding to a library gRNA. A schematic overview of this purification, amplification and sequencing is provided as FIG. 6. DNA was isolated using methods known in the art as described in Example 1.3. The DNA is amplified using PCR from flanking primer sequences. The amplified product was purified, mixed with Illumina adapters with homologous overhangs at 50:1 amplicon:adapter molar ratio, put into a GGA reaction (BsmBI and T4 ligase, NEB), and allowed to cycle 100× overnight (16C for 5 min then 37C for 5 min), conceptually similar to Velculescu, et al., 1995 (*Science* Vol. 270, Issue 5235, pp. 484-487). This material was then amplified to add Illumina adapters and indexes, and sequenced using the NextSeq platform. The gRNA sequences contained within the host cells production strain library will also be amplified and prepared for sequencing in the same way. The frequency of sequence reads for each gRNA was measured, and their relative abundances within the pool of all gRNAs determined. The relative abundance of gRNA sequences was amplified from AAV vector-associated DNA will be compared to that of gRNA sequence abundance in the original host cell population. In this way, gRNA library variants which result in perturbations that direct changes on host cell biology and result in differential AAV vector production can be identified as they either enrich or deenrich in the AAV vector DNA population in comparison to the host cell population.

Figure 10:
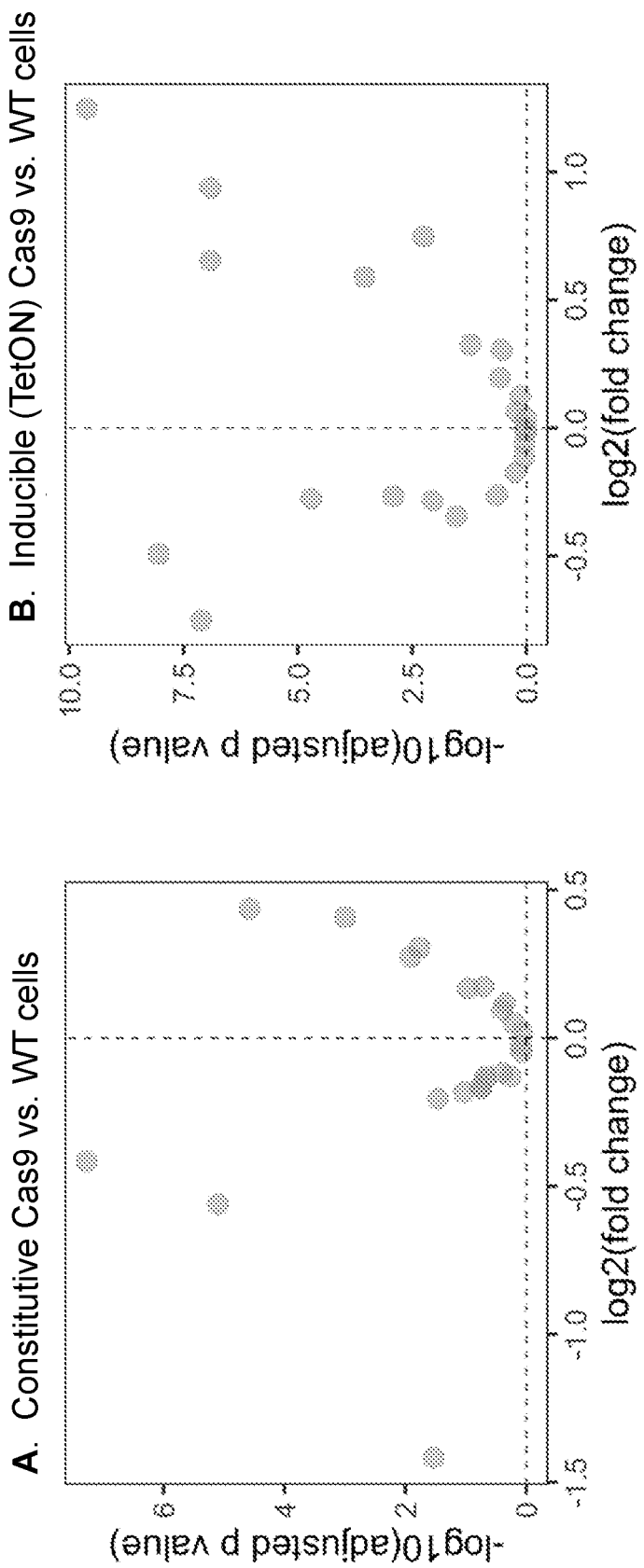
FIG. 10 depicts two plots of relative abundance of barcode identifiers from pools of viral vector produced by exemplary mammalian cell libraries generated using AAV-in-Transposase constructs for 23 gRNA library variants. (A) provides a plot relative abundance of barcode identifiers in a pool of viral vectors produced by a library of mammalian cells that constitutively express Cas9; (B) provides a plot of relative abundance of barcode identifiers in a pool of viral vector produced by a library of mammalian cells that inducibly express Cas9. Barcode abundance is relative to that of wild-type cells (that lack library variants). Each dot in the plot represents the score for a single gRNA library variant in the library; results are an average of three biological replicates.

Results of a screen of a pilot library of 23 gRNAs is provided in FIG. 10. Three biological replicates of AAV produced in Cas9-expressing cells were compared with three biological replicates of AAV produced in wild-type ("WT") cells. Separately, three biological replicates of AAV produced in cells expressing Cas9 under the control of a tetracycline-inducible promoter ("TetON") were compared with three biological replicates of AAV produced in wild-type ("WT") cells. NGS data was aligned to the set of barcodes in the 23 pool using bowtie2 software. Langmead B, Salzberg S. "Fast gapped-read alignment with Bowtie 2." *Nature Methods.* 2012, 9:357-359. Relative barcode abundance was evaluated with the DESeq2 package for differential expression analysis. Love M I, Huber W, Anders S (2014). "Moderated estimation of fold change and dispersion for RNA-seq data with DESeq2." *Genome Biology,* 15, 550. The results in FIG. 10 demonstrate that the screening protocol, NGS sample preparation, sequencing, and data analysis pipeline were effective. Moreover, the results of the pilot screen suggest that several genes may be associated with increased or decreased AAV production with high statistical confidence (adjusted p values ~0.1).

Figure 11:
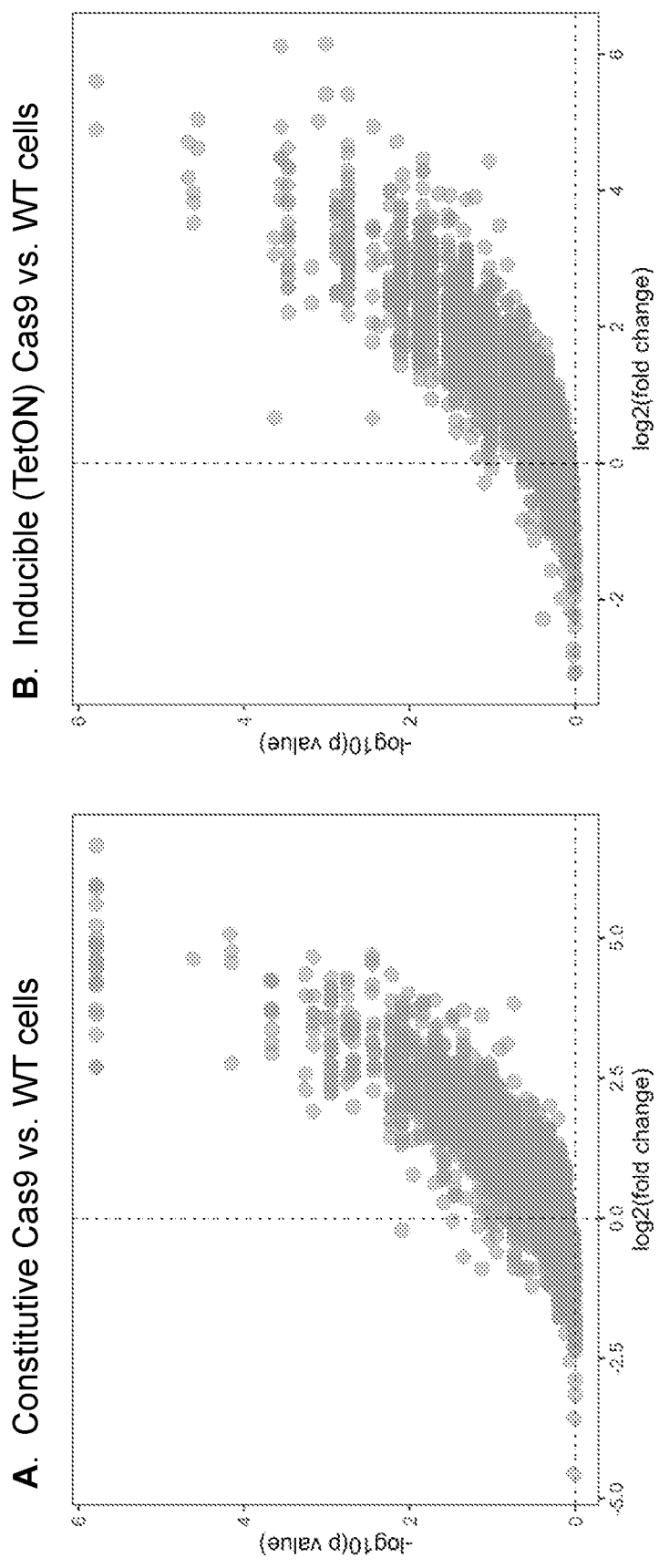
FIG. 11 depicts two plots of relative abundance of barcode identifiers from pools of viral vector produced by exemplary mammalian cell libraries generated using AAV-in-Transposase constructs for approximately 12,000 gRNA library variants. (A) provides a plot relative abundance of barcode identifiers in a pool of viral vector produced by a library of mammalian cells that constitutively express Cas9; (B) provides a plot of relative abundance of barcode identifiers in a pool of viral vector produced by a library of mammalian cells that inducibly express Cas9. Barcode abundance is relative to that of wild-type cells (that lack library variants). Each dot represents the scoring for a single gene in the library (calculated from 4 corresponding sgRNA scores); results are an average of three biological replicates.

Results of a screen of a library of 12,000 gRNAs is provided in FIG. 11. Three biological replicates of AAV produced in Cas9-expressing cells were compared with three biological replicates of AAV produced in WT cells. NGS data was aligned to the set of barcodes in the 12,000 pool using bowtie2 software, Langmead and Salzberg, supra. Relative barcode abundance was evaluated with the MAGeCK package and gene-level enrichment and significance (FDR) scores were calculated. Li, et al. "MAGeCK enables robust identification of essential genes from genome-scale CRISPR/Cas9 knockout screens." (2014) *Genome Biology* 15:554. Each point in FIG. 11 represents the scoring for a single gene in the library (calculated from 4 corresponding sgRNA scores). The results in FIG. 11 demonstrate that the screening protocol, NGS sample preparation, sequencing, and data analysis pipeline were effective for a large-scale screen. Moreover, the data demonstrate that barcodes can be used as a readout for identifying library variants associated with changes in AAV production, as numerous cell lines (and therefore associated gRNAs) were associated with increased or decreased AAV production.

Thus, this example confirms that library construction using various integration methods (e.g., lentiviral integration and transposon-mediate integration) are both effective.

The approach described in this example also allows for iterative rounds of library screening, where gRNA sequences found to significantly enrich in the AAV vector population, and confirmed to introduce a perturbation in the cell towards a higher titer production of AAV vector can be introduced to host cells separately from the AAV-in-Lenti gRNA library, enabling combinations of mutations to be 'stacked' over successive rounds of screening and hit confirmation.

Example 5: Barcoded ORF-Based Library Technique for Screening AAV Production, Genomically Integrated Via Targeted Nuclease Cleavage The present example describes a method of producing and screening a mammalian cell library to determine the level of production of an exemplary viral vector (e.g., in this example, AAV vectors) by specific cell variants (e.g., containing specific library variants) within the library. Specifically, this example describes a method of linking individual viral vectors produced from the mammalian cell library to the specific cell variants from which they were derived, wherein each transgenic ORF library variant used to create the mammalian cell library is paired with a DNA barcode, which is the identifier.

Example 5.1: Generation of Mammalian Cell Library

The present example describes a method of generating a recombinant AAV vector-producing, mammalian cell library within a host production cell line, for example 293T. A library of ORF sequences (library variants) encoding protein gene products with expected biological function in the host cell line will be synthesized and cloned into a plasmid alongside a DNA barcode sequence. This ORF:DNA barcode sequence pairing may be predetermined at the point of construct design and synthesis or may be randomly associated depending on specific cloning methods utilized, with ORF:barcode pairings determined by NGS of the cloned library plasmid DNA. This library will be constructed such that the barcode sequence is located between two AAV ITR sequences, with the corresponding ORF and ORF expression regulatory sequences such as promoter and poly-A signal, located outside of the ITR-defined region. The entire contiguous sequence of ITR-delimited region and the ORF-expression unit will be flanked upstream and downstream by sequences sufficient to function as homology arms (cis-acting integration sequences) for nuclease-stimulated homologous-recombination-based targeted integration into a host cell genomic locus such as the AAVS1 locus. Such a construct with AAV ITRs positioned between AAVS1 homology arms will be referred to here as AAV-in-Locus. The AAV-in-Locus plasmid will also contain a selectable marker gene, such as Puromycin resistance or Green Fluorescent Protein, enabling future selection or identification of mammalian cells containing the eventual integrated library construct. The barcoded ORF library as cloned into the AAV-in-Locus plasmid will be prepared as a purified plasmid pool for transfection into the 293T cells. This plasmid library will be transfected into 293T cells alongside a plasmid encoding SpCas9 nuclease and a gRNA targeting the AAVS1 locus. Genomically-modified library cells produced following this transfection will be isolated via continued exposure to a selectable agent such as puromycin or through fluorescent cell sorting on a fluorescent marker gene such as GFP. The library population of stable clones isolated in this manner will then be transfected with plasmid constructs necessary for production and packaging of recombinant AAV vectors (e.g., polynucleotides essential for formation of a viral vector), for example pHelper and pAAV Rep-Cap. The functions present on these plasmids will direct replication of ITR-defined AAV vector genomes from the AAVS1-integrated ITR-in-Locus sequence, and these ITR vector DNAs will be packaged and released into AAV vectors. Using this AAV-in-Locus method, will enable control of per-cell library member copy number by restricting possible on-target integration events to just the copies of the AAVS1 locus present within the host cell sister chromatids.

Example 5.2: Production and Harvesting of Viral Vectors

The present example describes a method of production and purification of viral vector produced from the mammalian cell library. Viral vector is produced as described previously in Zolotukhin, et al., 1999 (*Gene Therapy* 6, pp. 973-985). Briefly, after transfection, media (DMEM w/Glutamax, Pen/Strep antibiotic, 5% FBS) is changed after 24 hours, and 50% media volume (500 mL) added after 72 hours. After 5 days, cells are lysed by adding NaCl to 150 mM and incubating for 2 hours at 37 C. The media-cell mixture is collected and allowed to sit overnight at 4° C. The supernatant is separated and filtered through a 0.22 µM filter (Corning 431098). 40% PEG-8000 in $dH_2O$ is added to the viral vector material to a final concentration of 8%, and incubated at 4° C. overnight. This material is spun at 4800 g for 20 minutes, the pellet is collected and dissolved in 7 mL PBS. The material is then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 5.3: NGS of Viral Vectors

The present example describes a method of sequencing the DNA contained within the purified AAV vectors, specifically the Barcode sequence. DNA is isolated en masse, from the entire pool of purified AAV viral vectors. The DNA is purified using alkaline lysis. The DNA is amplified using PCR from flanking primer sequences. The amplified product is purified, mixed with Illumina adapters with homologous overhangs at 50:1 amplicon:adapter molar ratio, put into a GGA reaction (BsmBI and T4 ligase, NEB), and allowed to cycle 100× overnight (16C for 5 min then 37° C. for 5 min), conceptually similar to Velculescu, et al., 1995 (*Science* Vol. 270, Issue 5235, pp. 484-487). This material is then amplified to add Illumina adapters and indexes, and sequenced using the NextSeq platform. The Barcode sequences contained within the host cells production strain library will also be amplified and prepared for sequencing in the same way. The frequency of sequence reads for each barcode is measured, and their relative abundances within the pool of all barcodes determined. The relative abundance of barcode sequences amplified from AAV vector-associated DNA will be compared to that of barcode sequence abundance in the original host cell population. As each barcode has a known association with a specific ORF library member, ORF library variants which result in perturbations that direct changes on host cell biology and result in differential AAV vector production can be identified as their associated barcodes either enrich or deenrich in the AAV vector DNA population in comparison to the host cell population.

The approach described in this example also allows for iterative rounds of library screening, where ORF sequences with barcodes found to significantly enrich in the AAV population, and confirmed to introduce a perturbation in the cell towards a higher titer production of AAV vector can be introduced to host cells separately from the AAV-in-Locus barcoded ORF library, enabling combinations of mutations to be 'stacked' over successive rounds of screening and hit confirmation.

Example 6: Barcoded ORF-Based Library Technique for Screening AAV Production on Episomal Plasmid DNA The present example describes a method of producing and screening a mammalian cell library to determine the level of production of an exemplary viral vector (e.g, in this example, AAV vectors) by specific cell variants (e.g., containing specific library variants) within the library. Specifically, this example describes a method of linking individual viral vectors produced from the mammalian cell library to the specific cell variants from which they were derived, wherein each transgenic ORF library variant used to create the mammalian cell library is paired with a DNA barcode, which is the identifier.

Example 6.1: Generation of Mammalian Cell Library

The present example describes a method of generating a recombinant AAV vector-producing, mammalian cell library within a host production cell line, for example, 293T. A library of ORF sequences (library variants) encoding protein gene products with expected biological function in the host cell line will be synthesized and cloned into a plasmid alongside a DNA barcode sequence. This ORF:DNA barcode sequence pairing may be predetermined at the point of construct design and synthesis or may be randomly associated depending on specific cloning methods utilized, with ORF:barcode pairings determined by NGS of the cloned library plasmid DNA. This library will be constructed such that the barcode sequence is located between two AAV ITR sequences and will be transcribed into a poly-A-tailed mRNA transcript, wherein this transcript is an ITR-flanked transcriptional unit or a transcriptional unit which spans an intervening ITR sequence. The corresponding ORF and ORF expression regulatory sequences such as promoter and poly-A signal, will be located outside of the ITR-defined region. The entire contiguous sequence of ITR-delimited region and the ORF-expression unit will be contained within a circular plasmid DNA backbone. Such a construct with AAV-on-plasmid will also contain a selectable marker gene, such as Puromycin resistance or Green Fluorescent Protein, enabling future selection or identification of mammalian cells containing the plasmid construct as well as an SV40 origin of replication facilitating retention of the plasmids within transfected cells over subsequent passage of the culture. The barcoded ORF library as cloned into the AAV-on-plasmid will be prepared as a purified plasmid pool for transfection into the 293T cells. The library population of cells transfected in this manner will then be transfected with plasmid constructs necessary for production and packaging of recombinant AAV vectors (e.g., polynucleotides essential for formation of a viral vector), for example pHelper and pAAV Rep-Cap. The functions present on these plasmids will direct replication of ITR-defined AAV vector genomes from the ITR-on-Plasmid sequence, and these ITR vector DNAs will be packaged and released into AAV vectors. Transfection of cells at low efficiency will limit the number of unique plasmids per cell, with SV40 origin-dependent replication within 293T cells enabling retention of low-copy transfections over the course of library cell purification steps via the plasmid-borne selectable marker. Additionally, inclusion of the barcode within an express mRNA transcript will facilitate deconvolution of per-cell, multi-copy plasmid library member identity through, first, limiting detectable library members to those plasmids actually functioning within the host cell nucleus and not retained elsewhere in the cell (such as endosomes or cytoplasm) and secondly by facilitating per-cell multiplex plasmid library member identification through capture of barcode sequences through use of established single-cell barcoding and RNA sequencing methods (such as 10× Genomics). Use of this AAV-on-Plasmid method will limit the problem of number of multiplex library members per host cell, while facilitating deconvolution of multi-copy per-cell identity. These per-cell combinatorial library identities can then be correlated with AAV vector-enriching barcodes to confidently identify hits from within the multiplexed library population.

Example 6.2: Production and Harvesting of Viral Vectors

The present example describes a method of production and purification of viral vector produced from the mammalian cell library. Viral vector is produced as described previously in Zolotukhin, et al., 1999 (*Gene Therapy* 6, pp. 973-985). Briefly, after transfection, media (DMEM w/Glutamax, Pen/Strep antibiotic, 5% FBS) is changed after 24 hours, and 50% media volume (500 mL) added after 72 hours. After 5 days, cells are lysed by adding NaCl to 150 mM and incubating for 2 hours at 37° C. The media-cell mixture is collected and allowed to sit overnight at 4° C. The supernatant is separated and filtered through a 0.22 µM filter (Corning 431098). 40% PEG-8000 in $dH_2O$ is added to the viral vector material to a final concentration of 8%, and incubated at 4° C. overnight. This material is spun at 4800 g for 20 minutes, the pellet is collected and dissolved in 7 mL PBS. The material is then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 6.3: NGS of Viral Vectors and Per Cell Library Member Representation The present example describes a method of sequencing the DNA contained within the purified AAV vectors, specifically the barcode sequence. DNA is isolated en masse, from the entire pool of purified AAV viral vectors. The DNA is purified using alkaline lysis. The DNA is amplified using PCR from flanking primer sequences. The amplified product is purified, mixed with Illumina adapters with homologous overhangs at 50:1 amplicon:adapter molar ratio, put into a GGA reaction (BsmBI and T4 ligase, NEB), and allowed to cycle 100× overnight (16° C. for 5 min then 37° C. for 5 min), conceptually similar to Velculescu, et al., 1995 (*Science* Vol. 270, Issue 5235, pp. 484-487). This material is then amplified to add Illumina adapters and indexes, and sequenced using the NextSeq platform. The barcode sequences contained within the host cells production strain library will also be amplified and prepared for sequencing in the same way. The frequency of sequence reads for each barcode is measured, and their relative abundances within the pool of all barcodes determined. The relative abundance of barcode sequences amplified from AAV vector-associated DNA will be compared to that of barcode sequence abundance in the original host cell population. As each barcode has a known association with a specific ORF library variant, ORF library variants which result in perturbations that direct changes on host cell biology and result in differential AAV vector production can be identified as their associated barcodes either enrich or deenrich in the AAV vector DNA population in comparison to the host cell population. With sufficiently high-fold coverage of the cell library and sequencing depth, truly enriched hits will be identified within the inherently multiplexed transfected plasmid library. Additionally, to simplify the problem of hit identification from within a multiplex transfected library, the producer population can be subjected to single cell sequencing. Producer cells will be individually labeled during reverse transcription of the cellular mRNA (10× Genomics), appending a cell identity sequence to cellular mRNAs thereby tagging all barcodes contained within the cell library population. The cell identity sequence-tagged barcoded cDNAs can then be specifically amplified by PCR and these amplicons prepared for NGS by Illumina as described above. Sequencing of these amplicons will reveal the per-cell library member combinations present within the cell library population, allowing hits, single or combinatorial, versus falsely-enriching 'hitchhikers' to be discerned.

The approach described in this example also allows for iterative rounds of library screening, where ORF sequences with barcodes found to significantly enrich in the AAV vector population, and confirmed to introduce a perturbation in the cell towards a higher titer production of AAV vector can be introduced to host cells separately from the AAV-on-Plasmid barcoded ORF library, enabling combinations of mutations to be 'stacked' over successive rounds of screening and hit confirmation.

Figure 12:
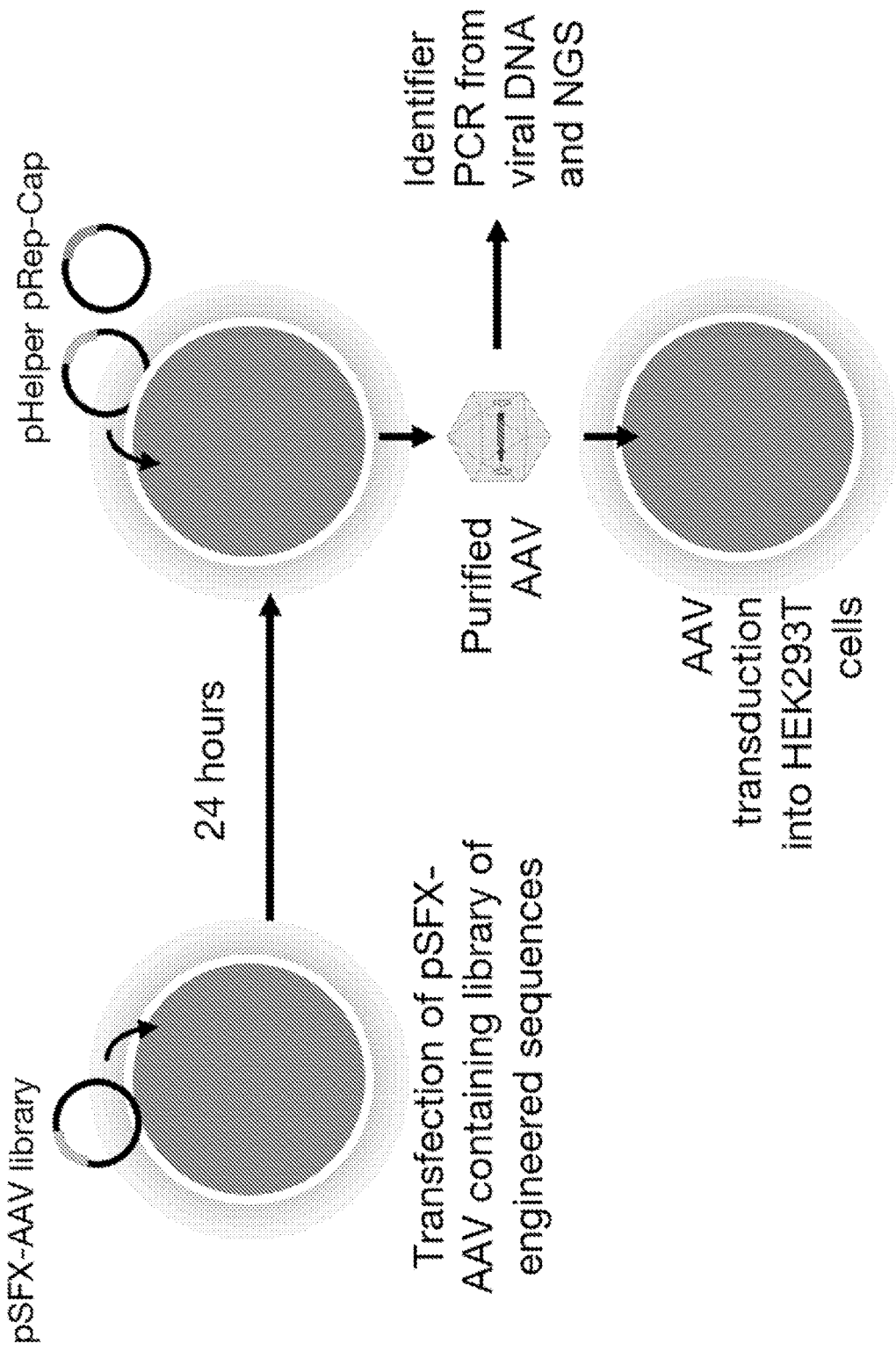
FIG. 12 depicts an exemplary scheme for generation of a mammalian cell library that expresses AAV viral vectors using an episomal library of constructs that include an identifier.

Example 7: Barcoded CRISPR gRNA-Based Library Technique for Screening AAV Production on Episomal Plasmid DNA The present example describes a method of producing and screening a mammalian cell library to determine the level of production of an exemplary viral vector (e.g., in this example, AAV vectors) by specific cell variants (e.g., containing specific library variants) within the library. Specifically, this example describes a method of linking individual viral vectors produced from the mammalian cell library to the specific cell variants from which they were derived, wherein each transgenic gRNA library variant used to create the mammalian cell library was paired with a DNA barcode, which is the identifier. A schematic overview of this method is provided as FIG. 12.

Example 7.1: Generation of Mammalian Cell Library

The present example describes a method of generating a recombinant AAV vector-producing, mammalian cell library within a host production cell line, for example 293T. A library of barcoded CRISPR gRNA sequences (library variants) encoding protein gene products with expected biological function in the host cell line was synthesized and cloned into a plasmid alongside a DNA barcode sequence. This gRNA:DNA barcode sequence pairing may be predetermined at the point of construct design and synthesis or may be randomly associated depending on specific cloning methods utilized, with gRNA:barcode pairings determined by NGS of the cloned library plasmid DNA. This library was constructed such that the barcode sequence is located between two AAV ITR sequences. The corresponding gRNA and gRNA expression regulatory sequences such as a promoter, will be located outside of the ITR-defined region. The entire contiguous sequence of ITR-delimited region and the gRNA-expression unit will be contained within a circular plasmid DNA backbone, an exemplary schematic of such an episomal construct is provided in FIG. 5, labeled pSFX-AAV. Such an AAV-on-plasmid construct also contains an exemplary selectable marker gene, an antibiotic resistance gene (e.g., puromycin resistance) and an exemplary AAV payload of a fluorescent protein gene (e.g., Green Fluorescent Protein), enabling future selection or identification of mammalian cells containing the integrated library construct and that produce AAV vectors, as well as an SV40 origin of replication facilitating retention of the plasmids within transfected cells over subsequent passage of the culture. The barcoded gRNA library as cloned into the AAV-on-plasmid was prepared as a purified plasmid pool for transfection into the 293T cells. The library population of cells transfected in this manner was then transfected with plasmid constructs necessary for production and packaging of recombinant AAV vectors (e.g., polynucleotides essential for formation of a viral vector), for example pHelper and pAAV Rep-Cap. The functions present on these plasmids direct replication of ITR-defined AAV vector genomes from the ITR-on-Plasmid sequence, and these ITR vector DNAs are be packaged and released into AAV vectors. Transfection of cells at low efficiency can limit the number of unique plasmids per cell, with SV40 origin-dependent replication within 293T cells enabling retention of low-copy transfections over the course of library cell purification steps via the plasmid-borne selectable marker. Additionally, inclusion of the barcode within an express mRNA transcript facilitates deconvolution of per-cell, multi-copy plasmid library member identity through, first, limiting detectable library members to those plasmids actually functioning within the host cell nucleus and not retained elsewhere in the cell (such as endosomes or cytoplasm) and secondly by facilitating per-cell multiplex plasmid library member identification through capture of barcode sequences through use of established single-cell barcoding and RNA sequencing methods (such as 10× Genomics). Use of this AAV-on-Plasmid method limits the number of multiplex library members per host cell while also facilitating deconvolution of multi-copy per-cell identity. These per-cell combinatorial library identities are then correlated with AAV vector-enriching barcodes to confidently identify hits from within the multiplexed library population.

Example 7.2: Production and Harvesting of Viral Vectors

The present example describes a method of production and purification of viral vector produced from the mammalian cell library. Viral vector is produced as described previously in Zolotukhin, et al., 1999 (*Gene Therapy* 6, pp. 973-985). Briefly, after transfection, media (DMEM w/Glutamax, Pen/Strep antibiotic, 5% FBS) is changed after 24 hours, and 50% media volume (500 mL) added after 72 hours. After 5 days, cells were lysed by adding NaCl to 150 mM and incubating for 2 hours at 37° C. The media-cell mixture was collected and allowed to sit overnight at 4° C. The supernatant is separated and filtered through a 0.22 μM filter (Corning 431098). 40% PEG-8000 in dH$_2$O was added to the viral vector material to a final concentration of 8%, and incubated at 4° C. overnight. This material was spun at 4800 g for 20 minutes, the pellet collected and dissolved in 7 mL PBS. The material was then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 7.3: NGS of Viral Vectors and Per Cell Library Member Representation The present example describes a method of sequencing the DNA contained within the purified AAV vectors, specifically the barcode sequence. DNA was isolated en masse, from the entire pool of purified AAV viral vectors. The DNA was purified using alkaline lysis. The DNA was amplified using PCR from flanking primer sequences. The amplified product was purified, mixed with Illumina adapters with homologous overhangs at 50:1 amplicon:adapter molar ratio, put into a GGA reaction (BsmBI and T4 ligase, NEB), and allowed to cycle 100× overnight (16C for 5 min then 37C for 5 min), conceptually similar to Velculescu, et al., 1995 (*Science* Vol. 270, Issue 5235, pp. 484-487). This material was then amplified to add Illumina adapters and indexes, and sequenced using the NextSeq platform. The barcode sequences contained within the host cells production strain library were also amplified and prepared for sequencing in the same way. The frequency of sequence reads for each barcode was measured, and their relative abundances within the pool of all barcodes determined. The relative abundance of barcode sequences amplified from AAV vector-associated DNA was compared to that of barcode sequence abundance in the original host cell population, as well as to transfected cells that do not express Cas9 and therefore are not genomically-modified. As each barcode has a known association with a specific gRNA library variant, gRNA library variants that result in perturbations that direct changes on host cell biology and result in differential AAV vector production can be identified as their associated barcodes either enrich or de-enrich in the AAV vector DNA population in comparison to the host cell population and/or AAV isolated from cells that do not express Cas9 (WT cells). With sufficiently high-fold coverage of the cell library and sequencing depth, truly enriched hits can be identified within the inherently multiplexed transfected plasmid library. Additionally, to simplify the problem of hit identification from within a multiplex transfected library, the producer population can be subjected to single cell sequencing. Producer cells will be individually labeled during reverse transcription of the cellular mRNA (10× Genomics), appending a cell identity sequence to cellular mRNAs thereby tagging all barcodes contained within the cell library population. The cell identity sequence-tagged barcoded cDNAs can then be specifically amplified by PCR and these amplicons prepared for NGS by Illumina as described above. Sequencing of these amplicons will reveal the per-cell library member combinations present within the cell library population, allowing hits, single or combinatorial, versus falsely-enriching 'hitchhikers' to be discerned.

Figure 13:
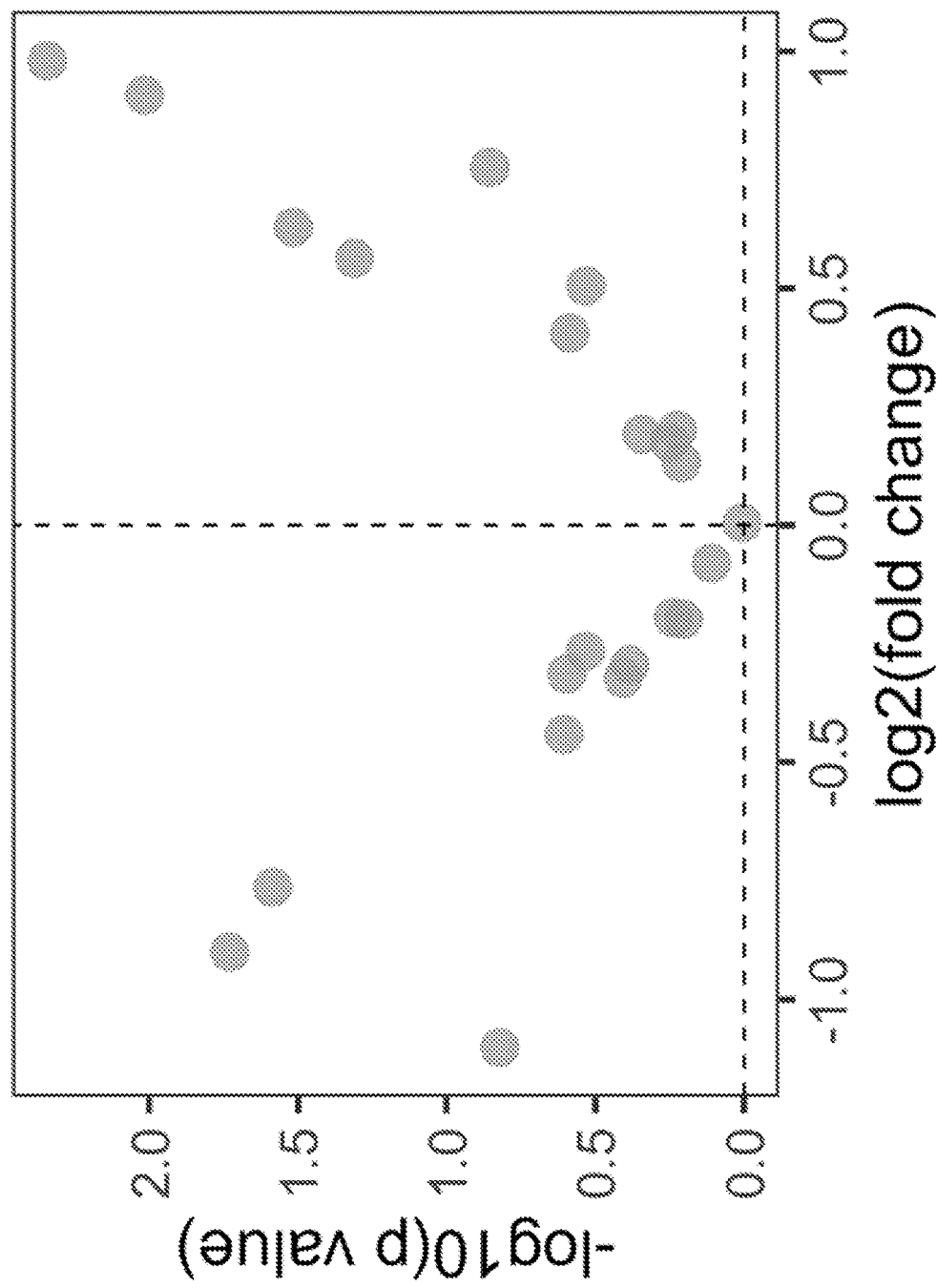
FIG. 13 depicts a plot of relative abundance of barcode identifiers in a pool of viral vector produced by an exemplary limited mammalian cell library generated using episomal AAV library constructs for 23 gRNA library variants. Barcode abundance is relative to that of wild-type cells (that lack library variants). Each dot in the plot represents the score for a single gRNA library variant in the library; results are an average of three biological replicates.

Results of a screen of a pilot library of 23 gRNAs is provided in FIG. 13. Three biological replicates of AAV produced in Cas9-expressing cells were compared with three biological replicates of AAV produced in wild-type ("WT") cells. NGS data was aligned to the set of barcodes in the 23 pool using bowtie2 software. Langmead B, Salzberg S. "Fast gapped-read alignment with Bowtie 2." *Nature Methods.* 2012, 9:357-359. Relative barcode abundance was evaluated with the DESeq2 package for differential expression analysis. Love M I, Huber W, Anders S (2014). "Moderated estimation of fold change and dispersion for RNA-seq data with DESeq2." *Genome Biology,* 15, 550. The results in FIG. 13 demonstrate that the screening protocol, NGS sample preparation, sequencing, and data analysis pipeline were effective. Moreover, the results of the pilot screen suggest that several genes may be associated with increased or decreased AAV production with high statistical confidence (adjusted p values ~0.1).

Figure 14:
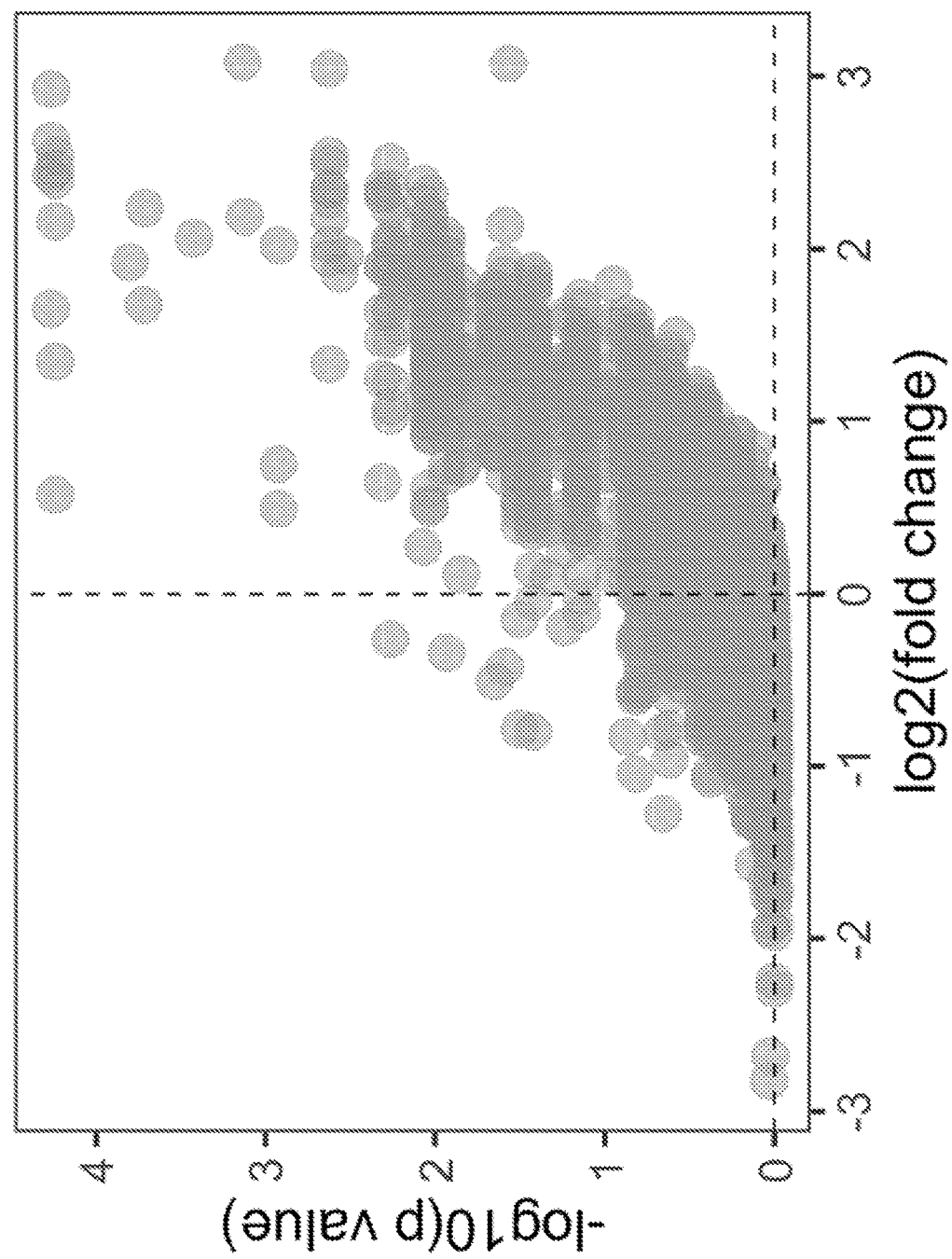
FIG. 14 depicts a plot of relative abundance of barcode identifiers from a pool of viral vector produced by exemplary mammalian cell libraries generated using episomal AAV library constructs for approximately 12,000 gRNA library variants. Barcode abundance is relative to that of wild-type cells (that lack library variants). Each dot represents the scoring for a single gene in the library (calculated from 4 corresponding sgRNA scores); results are an average of three biological replicates.

Results of a screen of a library of 12,000 gRNAs is provided in FIG. 14. Three biological replicates of AAV produced in Cas9-expressing cells were compared with three biological replicates of AAV produced in WT cells. NGS data was aligned to the set of barcodes in the 12,000 barcode pool using bowtie2 software, Langmead and Salzberg, supra. Relative barcode abundance was evaluated with the MAGeCK package and gene-level enrichment and significance (FDR) scores were calculated. Li, et al. "MAGeCK enables robust identification of essential genes from genome-scale CRISPR/Cas9 knockout screens." (2014) *Genome Biology* 15:554. Each point in FIG. 14 represents the scoring for a single gene in the library (calculated from 4 corresponding sgRNA scores). The results in FIG. 14 demonstrate that the screening protocol, NGS sample preparation, sequencing, and data analysis pipeline were effective for a large-scale screen. Moreover, the data demonstrate that barcodes can be used as a readout for identifying library variants associated with changes in AAV production, as numerous cell lines (and therefore associated gRNAs) were associated with increased or decreased AAV production.

The pooled VectorSelect screen identified hundreds of genes associated with enhanced AAV production, and we selected 14 to verify independently. Thus, this example confirms that library construction using various integration methods (e.g., lentiviral integration and transposon-mediate integration) are both effective. Based on the screen data, we delivered the best-performing sgRNA for each of the 14 genes as a ribonucleoprotein (RNP) complex with Cas9 to HEK293T cells via reverse transfection with CRISPRMax reagent. Each sgRNA was delivered independently, generating separate groups of modified cells and an unmodified group as a reference sample (WT). We allowed gene-edited cells to recover for 8 days after RNP delivery, then seeded an equal number of cells from each cell group and produced AAV by triple transfecting an AAV transfer plasmid (pTransfer), a helper plasmid (pHelper), and a plasmid with the AAV2 rep and cap genes (pRepCap). A negative control group was also included that was made by transfecting only pTransfer into unmodified cells (WT-RepCap).

AAV production was performed in biological triplicate for all groups of edited cells. AAV was harvested using a commercially available AAV2Pro purification kit (e.g., from Takara), then treated with DNase I to remove non-encapsulated DNA. The number of AAV vector genomes in the purified product was measured using ddPCR with an EvaGreen-based protocol that used primers targeting the AAV ITR regions.

Figure 15:
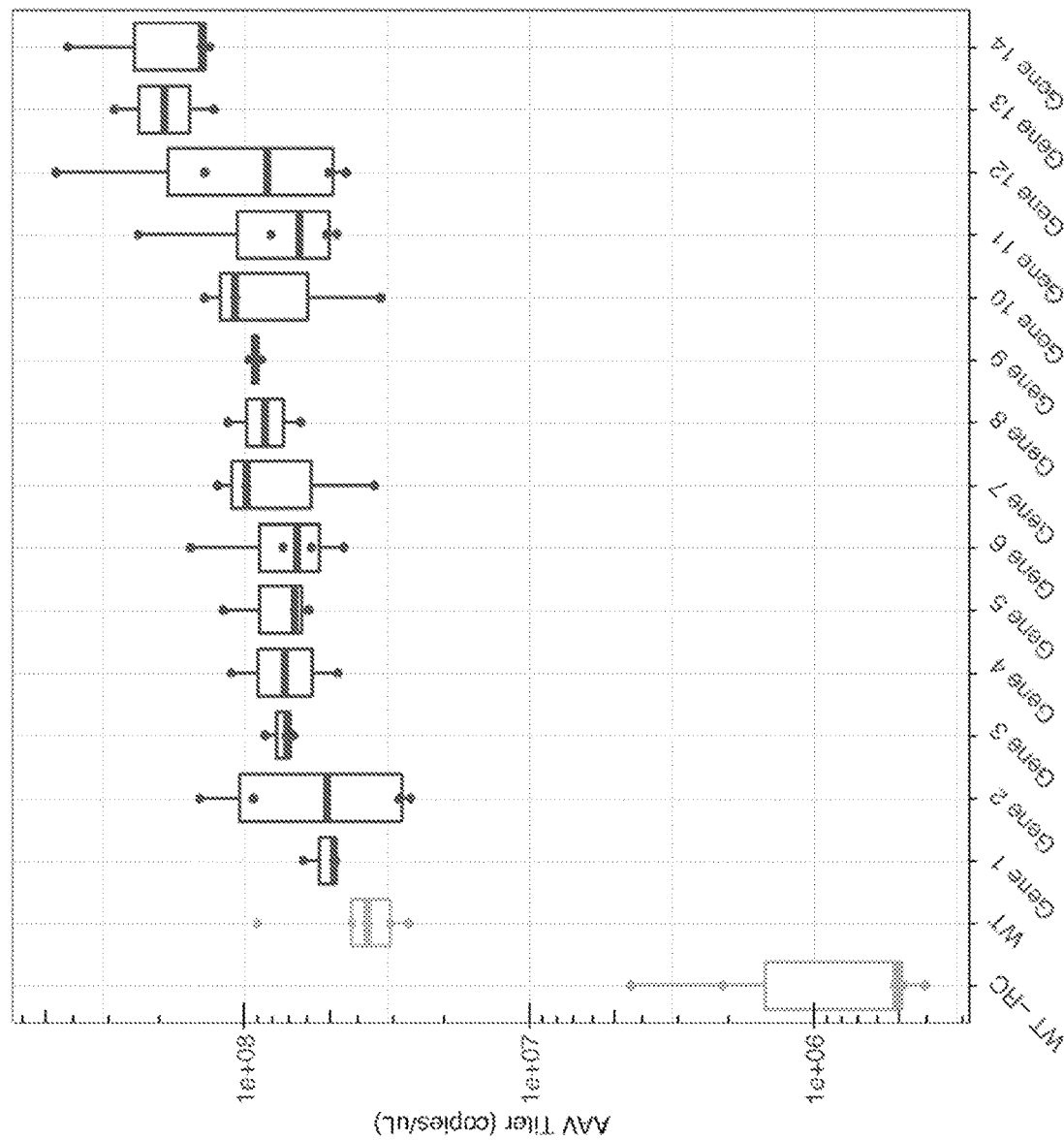
FIG. 15 depicts a plot of viral vector production, specifically AAV, capabilities of mammalian cells (HEK293T) that have been engineered to include a library variant identified by an exemplary method described herein. Y-axis provides AAV titer in copies per L and x-axis provides different engineered cells. Walking along the x-axis from the left to right, first is a sample of wild-type mammalian cells that lack Rep/Cap (negative control), followed by wild-type mammalian cells, and then 14 different mammalian cells that have each been engineered in a single gene identified from a screen described herein, Genes 1 to 14. AAV titer was improved compared to wild-type cells for several genes, with an approximately 10× increase observed for Gene 13 and Gene 14

Vector genome quantification by ddPCR for each cell group is shown in FIG. 15. The results indicate that AAV was successfully produced in all groups as measured by a large difference in signal relative to the -RepCap group (negative control), which should not produce AAV and provides a measure of background signal in the assay. A key takeaway from this data is that all 14 gene knockout groups had increased AAV production relative to the unmodified HEK293T cell group, in some cases by nearly 10-fold (genes 13 and 14). This confirms the results of the VectorSelect high-throughput pooled screen and validates the platform's ability to rapidly identify candidate cell perturbations that have a high likelihood of validating when tested independently in more traditional low-throughput, parallel screening assays.

The approach described in this example also allows for iterative rounds of library screening, where gRNA sequences with barcodes found to significantly enrich in the AAV vector population, and confirmed to introduce a perturbation in the cell towards a higher titer production of AAV vector can be introduced to host cells separately from the AAV-on-Plasmid barcoded gRNA library, enabling combinations of mutations to be 'stacked' over successive rounds of screening and hit confirmation.

Example 8: Multiplex gRNA Library Technique for Screening AAV Production, Genomically Integrated Via Lentiviral Vectors The present example describes a method of producing and screening a mammalian cell library to determine the level of production of an exemplary viral vector (e.g., in this example, AAV vectors) by specific cell variants within the library (e.g., containing specific library variants). Specifically, this example describes a method of linking individual viral vectors produced from a multiplex gRNA genome-edited mammalian cell library to the specific cell variants from which they were derived, wherein a DNA and RNA-encoded barcode is the identifier.

Example 8.1: Generation of Mammalian Cell Library

The present example describes a method of generating an AAV-producing, mammalian cell library. An AAV host production cell line, for example 293T, will be modified through stable lentiviral integration of a CRISPR nuclease expression construct, for example the SpCas9 nuclease (293T-Cas9). A library of gRNA sequences (library variants) targeting genomic sequences, will be synthesized and cloned into a lentiviral vector plasmid such that the gRNA-encoding sequence is also contained within a poly-A-tailed mRNA transcript originating from the lentiviral vector. Separately, a barcode sequence to function as an identifier will be cloned between two AAV ITR sequences and placed within the vector such that the identifier is contained within a poly-A-tailed mRNA transcript. This ITR-flanked identifier will itself be flanked itself be located on the plasmid downstream of a lentiviral 5' LTR and relevant lentiviral packaging sequences including Psi, and upstream of a lentiviral 3' LTR, suitable for $3^{rd}$ Generation lentiviral packaging of a transcribed RNA delimited by the LTRs and containing the AAV ITR sequences in transcribed RNA form. Such a construct with AAV ITRs positioned between Lentiviral LTR and Psi sequences will be referred to here as AAV-in-Lenti. The AAV-in-*Lenti* plasmid will also contain a selectable marker gene, such as Puromycin resistance or Green Fluorescent Protein, enabling future selection or identification of mammalian cells containing the eventual integrated library construct. The lentiviral gRNA library and the barcoded AAV-in-Lenti plasmid libraries will be separately transfected into 293T cells alongside a plasmid encoding a viral glycoprotein, for example the VSV-G protein, and either a $2^{nd}$ or $3^{rd}$ Generation lentiviral packaging plasmid(s) to provide, minimally, the lentiviral Gag Pol, Rev gene functions (e.g., polynucleotides essential for formation of a viral vector). Lentiviral vectors produced following this transfection will be collected from culture supernatant, filtered, and either concentrated or applied directly to the 293T-Cas9 cell line. Cells will first be transduced at high efficiency to drive multi-copy integration of separate gRNA library variants. Achievement of the desired average per-cell library variant number in the cell library will be determined by qPCR of the cell library gDNA. Subsequently, this multi-copy gRNA library population will be transduced at single-copy efficiency with the identifier-containing AAV-in-Lenti barcode library and selected to establish a per-cell barcoded multiplex gRNA cell library.

Expression of the gRNAs per cell will be assumed to have resulted in gRNA-targeted cleavage and indel formation through the action of the stably expressed SpCas9 gene. The purified library population will then be transfected with plasmid constructs necessary for production and packaging of recombinant AAV vectors, for example pHelper and pAAV Rep-Cap. The functions present on these plasmids will direct replication of ITR-defined AAV vector genomes from the lentivirally-integrated ITR-in-Lenti sequence, and these ITR vector DNAs will be packaged and released into AAV vectors.

Example 8.2: Production and Harvesting of Viral Vectors

The present example describes a method of production and purification of viral vector produced from the mammalian cell library. Viral vector is produced as described previously in Zolotukhin, et al., 1999 (*Gene Therapy* 6, pp. 973-985). Briefly, after transfection, media (DMEM w/Glutamax, Pen/Strep antibiotic, 5% FBS) is changed after 24 hours, and 50% media volume (500 mL) added after 72 hours. After 5 days, cells are lysed by adding NaCl to 150 mM and incubating for 2 hours at 37° C. The media-cell mixture is collected and allowed to sit overnight at 4° C. The supernatant is separated and filtered through a 0.22 µM filter (Corning 431098). 40% PEG-8000 in $dH_2O$ is added to the viral vector material to a final concentration of 8%, and incubated at 4° C. overnight. This material is spun at 4800 g for 20 minutes, the pellet is collected and dissolved in 7 mL PBS. The material is then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 8.3: NGS of Viral Vectors and Per-Cell Library Member Representation The present example describes a method of sequencing the DNA contained within the purified AAV vectors, specifically the Barcode sequence. DNA is isolated en masse, from the entire pool of purified AAV viral vectors. The DNA is purified using alkaline lysis. The DNA is amplified using PCR from flanking primer sequences. The amplified product is purified, mixed with Illumina adapters with homologous overhangs at 50:1 amplicon:adapter molar ratio, put into a GGA reaction (BsmBI and T4 ligase, NEB), and allowed to cycle 100×overnight (16° C. for 5 min then 37° C. for 5 min), conceptually similar to Velculescu, et al., 1995 (*Science* Vol. 270, Issue 5235, pp. 484-487). This material is then amplified to add Illumina adapters and indexes, and sequenced using the NextSeq platform. The Barcode sequences contained within the host cells production strain library will also be amplified and prepared for sequencing in the same way. The frequency of sequence reads for each barcode is measured, and their relative abundances within the pool of all barcodes determined. The relative abundance of barcode sequences amplified from AAV vector-associated DNA will be compared to that of barcode sequence abundance in the original host cell population. To connect vector identifiers to producer cell genotype (that is, combinatorial gRNA identities), the producer population will be subjected to single cell RNA labeling during reverse transcription of the cellular mRNA (10×genomics), appending a cell identity sequence on mRNAs and thereby tagging all ITR-flanked barcodes and gRNAs (as each is designed to be contained, whether in sense or antisense orientation, within a poly-A-tailed mRNA transcript) contained on a per-cell basis across the cell library population. The cell identity sequence-tagged barcoded cDNAs can then be specifically amplified by PCR and these amplicons prepared for NGS (Illumina) as described above. Sequencing of these amplicons will reveal the per-cell library member combinations present within the cell library population, allowing true hits, whether due to single or combinatorial gRNA-driven indels, versus falsely-enriching 'hitchhikers' to be discerned.

The approach described in this example facilitates combinatorial library generation and iterative rounds of library screening, as library members and ITR-flanked identifiers are discontiguous, library composition and per-cell copy-number can be tuned over successive rounds without need to re-clone complex multi-gRNA-encoding DNA constructs. Clonal genotypes tied to viral vector production phenotypes through use of single-cell RNA sequencing methods, granting maximal flexibility on DNA library construction.

Example 9: CRISPR gRNA-Based Library Technique for Screening AAV Production on Episomal Plasmid DNA with Viral Infection and Re-Amplification The present example describes a method of producing and screening a mammalian cell library to determine the level of production of an exemplary viral vector (e.g., in this example, AAV vectors) by specific cell perturbations (e.g., in cells containing specific library variants) within the library. Specifically, this example describes a method of linking individual viral vectors produced from the mammalian cell library to the specific cell variants from which they were derived, wherein the gRNA used to create the mammalian cell library is the identifier. In this example, viral vectors are generated in two sequential Mammalian Cell Libraries. This provides a method for accurately identifying the effects of engineered sequences delivered at high copy number in Mammalian Cell Library 1 through an additional low-copy number selection step in Mammalian Cell Library 2.

Example 9.1: Generation of Mammalian Cell Library 1

The present example describes a method of generating a first recombinant AAV vector-producing, mammalian cell library within a host production cell line, for example 293T. A library of barcoded CRISPR gRNA sequences (library variants) encoding protein gene products with expected biological function in the host cell line will be synthesized and cloned into a plasmid alongside a DNA barcode sequence. This gRNA:DNA barcode sequence pairing may be predetermined at the point of construct design and synthesis or may be randomly associated depending on specific cloning methods utilized, with gRNA:barcode pairings determined by NGS of the cloned library plasmid DNA. This library will be constructed such that the barcode sequence is located between two AAV ITR sequences. The corresponding gRNA and gRNA expression regulatory sequences (such as, e.g., a promoter), will be located outside of the ITR-defined region. The entire contiguous sequence of ITR-delimited region and the gRNA-expression unit will be contained within a circular plasmid DNA backbone, an exemplary schematic of such an episomal construct is provided in FIG. 5, labeled pSFX-AAV. Such a construct with AAV-on-plasmid also contains an exemplary selectable marker gene, an antibiotic resistance gene (e.g., puromycin resistance) and an exemplary AAV payload of a fluorescent protein gene (e.g., Green Fluorescent Protein), enabling future selection or identification of mammalian cells containing the integrated library construct and that produce AAV vectors, as well as an SV40 origin of replication facilitating retention of the plasmids within transfected cells over subsequent passage of the culture. The barcoded gRNA library as cloned into the AAV-on-plasmid is prepared as a purified plasmid pool for transfection into the 293T cells. The library population of cells transfected in this manner will then be transfected with plasmid constructs necessary for production and packaging of recombinant AAV vectors (e.g., polynucleotides essential for formation of a viral vector), for example pHelper and pAAV Rep-Cap. The functions present on these plasmids direct replication of ITR-defined AAV vector genomes from the ITR-on-Plasmid sequence, and these ITR vector DNAs are be packaged and released into AAV vectors.

Example 9.2: Production and Harvesting of Viral Vectors

The present example describes a method of production and purification of viral vector produced from Mammalian Cell Library 1. Viral vector is produced as described previously in Zolotukhin, et al., 1999 (*Gene Therapy* 6, pp. 973-985). Briefly, after transfection, media (DMEM w/Glutamax, Pen/Strep antibiotic, 5% FBS) is changed after 24 hours, and 50% media volume (500 mL) added after 72 hours. After 5 days, cells are lysed by adding NaCl to 150 mM and incubating for 2 hours at 37° C. The media-cell mixture is collected and allowed to sit overnight at 4° C. The supernatant is separated and filtered through a 0.22 μM filter (Corning 431098). 40% PEG-8000 in $dH_2O$ is added to the viral vector material to a final concentration of 8%, and incubated at 4 C overnight. This material is spun at 4800 g for 20 minutes, the pellet is collected and dissolved in 7 mL PBS. The material is then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 9.3: Generation of Mammalian Cell Library 2 Through Viral Infection, and Re-Amplification and Harvesting of Viral Vectors Viral vectors purified from Mammalian Cell Library 1 will be used to infect the host production line such as HEK293T, or a variant of this cell line expressing Cas9 nuclease or a derivative. These cells will not have been previously modified with any engineered sequence. Transduction of the viral vector payload containing the gRNA library variants into this cell population will generate a second mammalian cell library, Mammalian Cell Library 2. Mammalian Cell Library 2 cells that express Cas9 will be modified by the set of transduced gRNA library variants that were derived from cells in Mammalian Cell Library 1 that produced high levels of virus, thus amplifying the gRNAs in Mammalian Cell Library 1 whose effects are truly associated with improved viral titer.

The library population of cells generated in this manner will then be transfected with plasmid constructs necessary for production and packaging of recombinant AAV vectors (e.g., polynucleotides essential for formation of a viral vector), for example pHelper and pAAV Rep-Cap. The functions present on these plasmids direct replication of ITR-defined AAV vector genomes from the ITR-on-Plasmid sequence, and these ITR vector DNAs are be packaged and released into AAV vectors.

Use of this sequential Mammalian Cell Library method provides a way to deconvolute the effects of multi-copy delivery of engineered sequences that results from episomal delivery. Infecting a second cell population with the virus produced by Mammalian Cell Library 1 can be performed under controlled conditions such that most cell members only receive one copy of the gRNA library per cell. Control of copy number in this second Mammalian cell library will lead to more robust identification of gRNAs affecting AAV production compared to Mammalian Cell Library 1, because Mammalian Cell Library 1 was constructed by episomal transfection and likely contains many cells that received multiple engineered sequences.

Per-cell library identities are then correlated with AAV vector-enriching barcodes to confidently identify hits from within the multiplexed library population.

Example 9.4: Production and Harvesting of Viral Vectors

The present example describes a method of production and purification of viral vector produced from Mammalian Cell Library 2. Viral vector is produced as described previously in Zolotukhin, et al., 1999 (*Gene Therapy* 6, pp. 973-985). Briefly, after transfection, media (DMEM w/Glutamax, Pen/Strep antibiotic, 5% FBS) is changed after 24 hours, and 50% media volume (500 mL) added after 72 hours. After 5 days, cells are lysed by adding NaCl to 150 mM and incubating for 2 hours at 37° C. The media-cell mixture is collected and allowed to sit overnight at 4° C. The supernatant is separated and filtered through a 0.22 µM filter (Corning 431098). 40% PEG-8000 in $dH_2O$ is added to the viral vector material to a final concentration of 8%, and incubated at 4° C. overnight. This material is spun at 4800 g for 20 minutes, the pellet is collected and dissolved in 7 mL PBS. The material is then subjected to iodixanol gradient purification, as described previously in Zolotukhin, et al., 1999 (*Gene Therapy* 6, pp. 973-985), concentrated using a spin concentrator (Millipore UFC910024), and frozen at −80° C.

Example 9.5: NGS of Viral Vectors and Per Cell Library Member Representation The present example describes a method of sequencing the DNA contained within the purified AAV vectors, specifically the barcode sequence. DNA is isolated en masse, from the entire pool of purified AAV viral vectors. The DNA is purified using alkaline lysis. The DNA is amplified using PCR from flanking primer sequences. The amplified product is purified, mixed with Illumina adapters with homologous overhangs at 50:1 amplicon:adapter molar ratio, put into a GGA reaction (BsmBI and T4 ligase, NEB), and allowed to cycle 100× overnight (16° C. for 5 min then 37° C. for 5 min), conceptually similar to Velculescu, et al., 1995 (*Science* Vol. 270, Issue 5235, pp. 484-487). This material is then amplified to add Illumina adapters and indexes, and sequenced using the NextSeq platform. The barcode sequences contained within the host cells production strain library will also be amplified and prepared for sequencing in the same way. The frequency of sequence reads for each barcode is measured, and their relative abundances within the pool of all barcodes determined. The relative abundance of barcode sequences amplified from AAV vector-associated DNA will be compared to that of barcode sequence abundance in the original host cell population, as well as to transfected cells that do not express Cas9 and therefore are not genomically-modified. As each barcode has a known association with a specific gRNA library variant, gRNA library variants which result in perturbations that direct changes on host cell biology and result in differential AAV vector production can be identified as their associated barcodes either enrich or de-enrich in the AAV vector DNA population in comparison to the host cell population and/or AAV isolated from cells that do not express Cas9 (WT cells). With sufficiently high-fold coverage of the cell library and sequencing depth, truly enriched hits will be identified within the inherently multiplexed transfected plasmid library. Additionally, to simplify the problem of hit identification from within a multiplex transfected library, the producer population can be subjected to single cell sequencing. Producer cells will be individually labeled during reverse transcription of the cellular mRNA (10× Genomics), appending a cell identity sequence to cellular mRNAs thereby tagging all barcodes contained within the cell library population. The cell identity sequence-tagged barcoded cDNAs can then be specifically amplified by PCR and these amplicons prepared for NGS by Illumina as described above. Sequencing of these amplicons will reveal the per-cell library member combinations present within the cell library population, allowing hits, single or combinatorial, versus falsely-enriching 'hitchhikers' to be discerned.

EQUIVALENTS

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

The invention claimed is:
1. A method, comprising:
   a. producing a plurality of adeno-associated viral (AAV) vectors from a library of mammalian cells, wherein the library of mammalian cells comprises a plurality of mammalian cells, wherein each mammalian cell in the plurality of mammalian cells individually comprises:
      (i) a nucleic acid sequence comprising a barcode, two functional AAV ITR sequences and a pair of cis-acting integration sequences, wherein the barcode is positioned between the AAV ITR sequences which are flanked by the cis-acting integration sequences, and wherein the nucleic acid sequence is integrated into the genome of the mammalian cell based on the cis-acting integration sequences, so that AAV vectors produced by the mammalian cell include the barcode;
      (ii) one or more library variants that result in one or more perturbations, wherein at least one library variant comprises a guide RNA (gRNA), and each mammalian cell of the plurality includes a different one or more library variants;

(iii) an RNA-guided nuclease, and
(iv) one or more nucleic acid sequences essential for production of AAV vectors,
wherein the barcode in each mammalian cell is unique to that mammalian cell relative to other mammalian cells in the plurality and identifies the one or more library variants; and b. detecting the barcodes of the plurality of AAV vectors, so that the particular mammalian cell that produced a particular AAV vector is identified, and the one or more library variants in that mammalian cell is also identified.

2. The method of claim 1, wherein abundance of the barcode correlates with a level production or secretion of AAV vectors by the mammalian cell.

3. The method of claim 1, wherein the cis-acting integration sequences are or comprise viral repeat sequences derived from lentivirus.

4. The method of claim 1, wherein the cis-acting integration sequences are or comprise transposase recognition sites.

5. The method of claim 1, further comprising a step of determining a relative abundance of a particular barcode relative to one or more other barcodes present in the plurality of AAV vectors produced from the library of mammalian cells.

6. The method of claim 1, wherein the one or more perturbations is associated with an increase in AAV production relative to a reference mammalian cell that lacks the one or more perturbations, AAV secretion relative to such reference mammalian cell, or both.

7. The method of claim 1, wherein at least one library variant is integrated into the mammalian genome positioned between the pair of cis-acting integration sequences.

8. The method of claim 1, wherein one or two copies of the nucleic acid sequence of (i) is integrated in the genome of the mammalian cell.

9. The method of claim 1, wherein the two functional AAV ITR sequences comprise human AAV1 ITRs, human AAV2 ITRs, human AAV3b ITRs, human AAV4 ITRs, human AAV5 ITRs, human AAV6 ITRs, human AAV7 ITRs, human AAV8 ITRs, human AAV9 ITRs, human AAV10 ITRs, human AAV11 ITRs, human AAV12 ITRs, or human AAV13 ITRs.

10. The method of claim 1, wherein the two functional AAV ITR sequences comprise bovine AAV (b-AAV) ITRs, canine AAV (CAAV) ITRs, mouse AAV1 ITRs, caprine AAV ITRs, rat AAV ITRs, or avian AAV (AAAV) ITRs.

11. The method of claim 1, wherein the one or more nucleic acid sequences essential for the production of an AAV vector comprise (a) an AAV Rep gene, (b) an AAV Cap gene, (c) one or more AAV helper genes; or (d) any combination thereof.

12. The method of claim 11, wherein the one or more sequences essential for the production of an AAV vector comprise an AAV Cap gene encoding a human AAV1 capsid protein, a human AAV2 capsid protein, a human AAV3b capsid protein, a human AAV4 capsid protein, a human AAV5 capsid protein, a human AAV6 capsid protein, a human AAV7 capsid protein, a human AAV8 capsid protein, a human AAV9 capsid protein, a human AAV10 capsid protein, a human AAV11 capsid protein, a human AAV12 capsid protein, or a human AAV13 capsid protein.

13. The method of claim 1, wherein each of the one or more perturbations comprises an insertion, a deletion, a substitution, a replacement, an epigenetic modification, or a rearrangement of an endogenous genomic coding sequence.

14. The method of claim 1, wherein the one or more library variants comprise at least two library variants, wherein the at least two library variants comprise at least one unique gene, at least one unique ORF, at least one unique gRNA sequence, at least one unique non-coding nucleic acid, any combination thereof, or a plurality thereof.

15. The method of claim 1, wherein the method further comprises single cell sequencing.

16. The method of claim 1, wherein the cis-acting integration sequences are or comprise recombinase recognition sites.

17. The method of claim 4, wherein the transposase that recognizes the transposase recognition sites is a PiggyBac transposase or a derivative thereof, a Sleepingbeauty transposase or a derivative thereof, a Tn5 transposase or a derivative thereof.

18. The method of claim 1, wherein the method comprises introducing (i), (ii), (iii), and (iv) into the mammalian cell.

19. The method of claim 1, wherein the method produces a plurality of AAV vectors comprising at least one improved feature compared to a plurality of AAV vectors produced by a mammalian cell that lacks the one or more perturbations.

20. The method of claim 19, wherein the at least one improved feature comprises:
(a) an altered ability to transfer viral nucleic acid,
(b) an altered AAV therapeutic activity, or
(c) a decrease in percentage of AAV vectors that are nonfunctional.

* * * * *